US012552791B2

(12) United States Patent
Meng et al.

(10) Patent No.: US 12,552,791 B2
(45) Date of Patent: Feb. 17, 2026

(54) HETEROCYCLIC GLP-1 AGONISTS

(71) Applicant: Gasherbrum Bio, Inc., South San Francisco, CA (US)

(72) Inventors: Qinghua Meng, Shanghai (CN); Andrew Jennings, Shanghai (CN); Hui Lei, Shanghai (CN); Xichen Lin, Shanghai (CN)

(73) Assignee: Gasherbrum Bio, Inc., South San Francisco, CA (US)

( * ) Notice: Subject to any disclaimer, the term of this patent is extended or adjusted under 35 U.S.C. 154(b) by 0 days.

(21) Appl. No.: 19/083,274

(22) Filed: Mar. 18, 2025

(65) Prior Publication Data

US 2025/0214999 A1 Jul. 3, 2025

Related U.S. Application Data

(63) Continuation of application No. 17/921,964, filed as application No. PCT/CN2021/090645 on Apr. 28, 2021, now abandoned.

(30) Foreign Application Priority Data

Apr. 29, 2020 (WO) ................ PCT/CN2020/087776
Jul. 30, 2020 (WO) ................ PCT/CN2020/105865

(51) Int. Cl.
*C07D 471/04* (2006.01)
*C07D 405/14* (2006.01)

(52) U.S. Cl.
CPC ......... *C07D 471/04* (2013.01); *C07D 405/14* (2013.01)

(58) Field of Classification Search
CPC ............................ C07D 471/04; C07D 405/14
USPC .......................................................... 514/303
See application file for complete search history.

(56) References Cited

U.S. PATENT DOCUMENTS

| | | | |
|---|---|---|---|
| 11,897,851 | B2 | 2/2024 | Meng et al. |
| 11,926,626 | B2 | 3/2024 | Meng et al. |
| 12,221,442 | B2 | 2/2025 | Meng et al. |
| 2008/0280933 | A1 | 11/2008 | Efremov et al. |
| 2018/0170908 | A1 | 6/2018 | Aspnes et al. |
| 2019/0276465 | A1 | 9/2019 | Xu |
| 2019/0382384 | A1 | 12/2019 | Aspnes et al. |
| 2019/0382387 | A1 | 12/2019 | Aspnes et al. |
| 2023/0071840 | A1 | 3/2023 | Meng et al. |
| 2023/0107793 | A1 | 4/2023 | Meng et al. |
| 2023/0165846 | A1 | 6/2023 | Meng et al. |
| 2023/0192633 | A1 | 6/2023 | Meng et al. |
| 2023/0391760 | A1 | 12/2023 | Meng et al. |
| 2024/0083886 | A1 | 3/2024 | Meng et al. |
| 2024/0246962 | A1 | 7/2024 | Meng et al. |
| 2024/0376061 | A1 | 11/2024 | Meng et al. |
| 2025/0109148 | A1 | 4/2025 | Huang et al. |
| 2025/0115606 | A1 | 4/2025 | Meng et al. |
| 2025/0145596 | A1 | 5/2025 | Meng et al. |
| 2025/0177362 | A1 | 6/2025 | Meng et al. |
| 2025/0206757 | A1 | 6/2025 | Lei et al. |
| 2025/0250269 | A1 | 8/2025 | Lin et al. |

FOREIGN PATENT DOCUMENTS

| | | | |
|---|---|---|---|
| CN | 108017636 | | 5/2018 |
| CN | 108430998 | | 8/2018 |
| CN | 109790161 | | 5/2019 |
| CN | 110325530 | | 10/2019 |
| CN | 112533674 | A | 3/2021 |
| CN | 113480534 | | 10/2021 |
| CN | 113493447 | | 10/2021 |
| CN | 113773310 | | 12/2021 |
| CN | 113801136 | | 12/2021 |
| CN | 113816948 | | 12/2021 |
| CN | 113831337 | | 12/2021 |
| CN | 114591296 | | 6/2022 |
| CN | 114591308 | | 6/2022 |
| CN | 114634510 | | 6/2022 |
| CN | 114716423 | | 7/2022 |
| CN | 114761395 | A | 7/2022 |
| CN | 114763352 | | 7/2022 |
| CN | 114907351 | | 8/2022 |
| CN | 115594669 | A | 1/2023 |
| CN | 115884969 | A | 3/2023 |
| WO | WO 2004/026305 | | 4/2004 |
| WO | WO 2005/002503 | A2 | 1/2005 |
| WO | WO 2006/102610 | | 9/2006 |
| WO | WO 2007/146122 | | 12/2007 |
| WO | WO 2008/137770 | A1 | 11/2008 |
| WO | WO 2008/153701 | | 12/2008 |
| WO | WO 2009/143039 | A2 | 11/2009 |

(Continued)

OTHER PUBLICATIONS

Database Registry Chemical Abstracts Service; Sep. 21, 2008, Anonymous: "1-Ethyl-2-[[[5-[[5-(3-thienyl)-2H-tetrazol-2-yl]methyl]-1, 3, 4-oxadiazol-2-yl]thio]methyl]-1H-benzimidazole-5-carboxylic acid" Database accession No. 1051103-45-7.

(Continued)

*Primary Examiner* — Kahsay Habte
(74) *Attorney, Agent, or Firm* — Sheppard Mullin Richter & Hampton LLP

(57) ABSTRACT

This disclosure relates to GLP-1 agonists of Formula (I): including pharmaceutically acceptable salts and solvates thereof, and pharmaceutical compositions including the same.

(I)

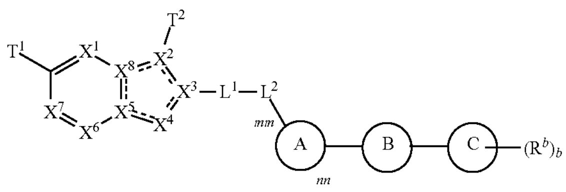

27 Claims, No Drawings

(56) References Cited

FOREIGN PATENT DOCUMENTS

WO WO 2010/065674 A1 6/2010
WO WO-2011/068821 6/2011
WO WO 2016/084816 A 2/2016
WO WO 2018/056453 A1 3/2018
WO WO 2018/085148 A1 5/2018
WO WO-2018/109607 6/2018
WO WO 2018/157857 A1 9/2018
WO WO-2019/239319 12/2019
WO WO-2019/239371 12/2019
WO WO-2020/103815 5/2020
WO WO-2020/207474 10/2020
WO WO-2020/234726 11/2020
WO WO-2020/263695 12/2020
WO WO-2021/018023 2/2021
WO WO-2021/081207 4/2021
WO WO-2021/096284 5/2021
WO WO-2021/096304 5/2021
WO WO-2021/112538 6/2021
WO WO-2021/154796 8/2021
WO WO-2021/160127 8/2021
WO WO-2021/187886 9/2021
WO WO-2021/197464 10/2021
WO WO-2021/219019 11/2021
WO WO-2021/244645 12/2021
WO WO-2021/249492 12/2021
WO WO-2021/254470 12/2021
WO WO 2021/259309 A1 12/2021
WO WO-2022/007979 1/2022
WO WO-2022/028572 2/2022
WO WO-2022/031994 2/2022
WO WO-2022/040600 2/2022
WO WO-2022/042691 3/2022
WO WO 2022/048665 A1 3/2022
WO WO-2022/068772 4/2022
WO WO-2022/078152 4/2022
WO WO-2022/078380 4/2022
WO WO-2022/078407 4/2022
WO WO-2022/109182 5/2022
WO WO-2022/111624 6/2022
WO WO-2022/135572 6/2022
WO WO-2022/165076 8/2022
WO WO-2022/192428 9/2022
WO WO-2022/192430 9/2022
WO WO-2022/199458 9/2022
WO WO-2022/199661 9/2022
WO WO-2022/202864 9/2022
WO WO-2022/216094 10/2022
WO WO-2022/219495 10/2022
WO WO 2022/228490 A1 11/2022
WO WO 2023/138684 A1 7/2023
WO WO 2023/151574 A1 8/2023
WO WO 2023/151575 A1 8/2023
WO WO 2023/179542 A1 9/2023
WO WO 2023/198140 A1 10/2023
WO WO 2024/045208 A1 3/2024

OTHER PUBLICATIONS

International Search Report and Written Opinion for PCT/CN2021/090645 dated Jul. 30, 2021, 10 pages.

ACS STN. RN 1290110-76-7, 1228633-44-0, 1228554-41-3. STN Registry. May 4, 2011, 2 pages.

"GLP-1 Receptor Agonists," The Johns Hopkins Patient Guide to Diabetes, Hopkinsdiabetesinfo.org/medications-for-type-2-diabetes-glp-1-agonists/. Retrieved May 15, 2023, 2 pages.

Castro, "GLP-1 Agonists: Diabetes drugs and weight loss," Mayo Clinic. Mayoclinic.org/diseaes-conditions/type-2-diabetes/expert-answers/byetta/faq-20057955, Jun. 29, 2022, 2 pages.

HETEROCYCLIC GLP-1 AGONISTS

CROSS REFERENCE TO RELATED APPLICATIONS

This application is a Continuation of U.S. patent application Ser. No. 17/921,964, filed Oct. 27, 2022, which is a U.S. National Stage Application under 35 U.S.C. § 371 of International Patent Application No. PCT/CN2021/090645, filed on Apr. 28, 2021, which claims the benefit of International Patent Application No. PCT/CN2020/105865, filed on Jul. 30, 2020, and International Patent Application No. PCT/CN2020/087776, filed on Apr. 29, 2020, each of which is incorporated herein by reference in its entirety.

TECHNICAL FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take anti-diabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

Accordingly, provided herein are compounds of Formula I:

Formula I

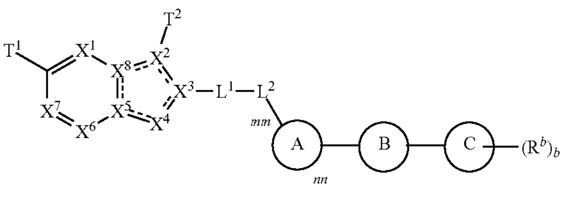

or a pharmaceutically acceptable salt or solvate thereof, wherein:

 indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;

$T^1$ is C(=O) OH or a carboxylic acid bioisostere;

$T^2$ is a $(C_1$-$C_6)$alkyl optionally substituted with $(C_1$-$C_6)$ alkoxy, $(C_1$-$C_6)$haloalkoxy, $(C_3$-$C_6)$ cycloalkyl, 3- to 6-membered heterocycloalkyl, phenyl, or 5- to 6-membered heteroaryl, wherein each of the $(C_3$-$C_6)$ cycloalkyl, 3- to 6-membered heterocycloalkyl, phenyl, or 5- to 6-membered heteroaryl is optionally substituted with 1-4 $R^X$;

each $R^X$ is independently selected from the group consisting of OH, SH, CN, $NO_2$, halogen, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$ cyanoalkyl, $(C_1$-$C_6)$ hydroxyalkyl, $(C_1$-$C_6)$ alkoxy, $(C_1$-$C_6)$haloalkoxy, $(C_3$-$C_6)$ cycloalkyl, amino, $(C_1$-$C_6)$alkylamino, and di$(C_1$-$C_6)$alkylamino;

$L^1$ is a bond or $(C_1$-$C_3)$alkylene which is optionally substituted with 1-3 $R^L$;

$L^2$ is a bond, —O—, —S(O)$O_2$—, or —NH—;

each $R^L$ is independently selected from the group consisting of: halogen, $(C_1$-$C_3)$alkyl, and $(C_1$-$C_3)$haloalkyl; or a pair of $R^L$ on the same or on adjacent carbon atoms, taken together with the atom(s) to which each is attached, forms a $(C_3$-$C_6)$ cycloalkyl ring;

Ring A is selected from the group consisting of:

phenylene optionally substituted with 1-4 $R^Y$;

5- to 6-membered heteroarylene optionally substituted with 1-3 $R^Y$;

partially unsaturated monocyclic $(C_5$-$C_8)$ cycloalkylene optionally substituted with 1-4 $R^Y$;

partially unsaturated monocyclic 5- to 8-membered heterocycloalkylene optionally substituted with 1-4 $R^Y$;

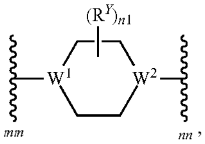

wherein n1 is 0, 1, or 2; $W^1$ is $CR^{Y1}$ or N; and $W^2$ is $CR^{Y2}$ or N; and

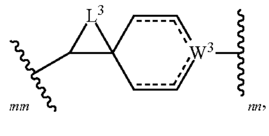

wherein $W^3$ is C, $CR^{Y3}$, or N, $L^3$ is $(C_1$-$C_3)$alkylene, and each  is independently a single bond or a double bond, as allowed by valence;

wherein mm represents the point of attachment to $L^2$, and nn represents the point of attachment to Ring B; and each occurrence of $R^Y$ is independently selected from the group consisting of halogen, cyano, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y1}$, $R^{Y2}$, and $R^{Y3}$ are each independently selected from the group consisting of hydrogen, halogen, cyano, —OH, $(C_1-C_6)$alkyl, $(C_1-C_3)$haloalkyl, $(C_1-C_3)$alkoxy, and $(C_1-C_3)$haloalkoxy; or when $W^1$ is $CR^{Y1}$ and $W^2$ is $CR^{Y2}$, the $R^{Y1}$ and $R^{Y2}$ groups taken together can form $(C_1-C_4)$alkylene, wherein one of the $CH_2$ units of the $(C_1-C_4)$alkylene is optionally replaced by a heteroatom selected from the group consisting of O, S, NH, and $N(C_{1-3})$alkyl;

Ring B is selected from the group consisting of (B-I) and (B-II):

(B-I)

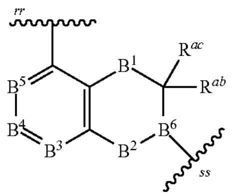

and (B-II)

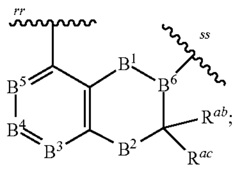

wherein rr represents the point of attachment to Ring A; and ss represents the point of attachment to Ring C;

$B^1$ and $B^2$ are independently selected from the group consisting of:—O—, —$NR^N$—, and —$C(R^1)_2$—;

$B^6$ is N or $CR^{aa}$;

each $R^1$ is independently selected from the group consisting of: hydrogen, $(C_1-C_6)$alkyl, $(C_1-C_6)$haloalkyl, and halogen;

$R^N$ is selected from the group consisting of: hydrogen, $(C_1-C_6)$alkyl, $(C_1-C_6)$haloalkyl, C(=O) $(C_1-C_6)$alkyl, $S(O)_2$ $(C_1-C_6)$alkyl, and C(=O) $O(C_1-C_6)$alkyl;

$B^3$, $B^4$, and $B^5$ are independently selected from the group consisting of CH, $CR^a$, and N;

each $R^a$ is independently selected from the group consisting of: halogen, $(C_1-C_6)$alkyl, $(C_1-C_3)$alkyl$(C_3-C_6)$ cycloalkyl, $(C_1-C_3)$alkyl(3- to 5-membered heterocycloalkyl), —$C(O)NR^2R^3$, and $(C_1-C_6)$ fluoroalkyl;

each $R^2$ and $R^3$ is independently selected from the group consisting of H and $(C_1-C_6)$alkyl;

$R^{aa}$, $R^{ab}$, and $R^{ac}$ are each independently selected from the group consisting of H, $(C_1-C_6)$alkyl, and $(C_1-C_6)$ haloalkyl;

Ring C is selected from the group consisting of phenyl, 5- to 6-membered heteroaryl, $(C_3-C_6)$ cycloalkyl, $(C_5-C_{10})$ bicycloalkyl, 5- to 10-membered bicycloheteroaryl, and 3- to 6-membered heterocycloalkyl;

each $R^b$ is independently selected from the group consisting of $(C_1-C_6)$alkyl, $(C_1-C_6)$haloalkyl, $(C_1-C_6)$alkoxy, halogen, $(C_3-C_6)$ cycloalkyl, and CN; and b is an integer selected from 0-3.

Also provided herein are pharmaceutical compositions comprising a compound of Formula I, or a pharmaceutically acceptable salt or solvate thereof, and a pharmaceutically acceptable excipient.

Also provided herein are methods for treating type 2 diabetes mellitus in a patient in need thereof, the methods comprising administering to the patient a therapeutically effective amount of a compound of Formula I, or a pharmaceutically acceptable salt or solvate thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula I, or a pharmaceutically acceptable salt or solvate thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula I, or a pharmaceutically acceptable salt or solvate thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin Alc (HbAlc), fasting plasma glucose, non-fasting plasma glucose, or any combination thereof. In some embodiments, the level of HbAlc is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 $kg/m^2$. In some embodiments, the patient has a BMI greater than or about 30 $kg/m^2$.

In some embodiments, the methods for the treatment of type 2 diabetes mellitus comprise a reduction in fasting plasma glucose levels. In some embodiments, the fasting plasma glucose levels are reduced to about or below 100 mg/dL. In some embodiments, the methods for the treatment of type 2 diabetes mellitus comprise a reduction in HbAlc levels. In some embodiments, the HbAlc levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 $kg/m^2$.

In some embodiments, the compound of Formula I, or a pharmaceutically acceptable salt or solvate thereof, or a pharmaceutical composition thereof, is administered orally.

In some embodiments, the methods of treatment for type 2 diabetes mellitus further comprise administering an additional therapy or therapeutic agent to the patient. In some embodiments, the additional therapy or therapeutic agent is selected from the group consisting of an anti-diabetic agent, an anti-obesity agent, a GLP-1 receptor agonist, an agent to treat non-alcoholic steatohepatitis (NASH), gastric electrical stimulation, dietary monitoring, physical activity, or any combinations thereof. In some embodiments, the anti-diabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the antiobesity agent is selected from the group consisting of neuropeptide Y receptor type 2 ($NPYR^2$) agonist, a $NPYR^1$ or $NPYR^5$ antagonist, a human proislet peptide (HIP), a cannabinoid receptor type 1 (CBIR) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, or any combinations thereof. In some embodiments, the compound of Formula I, or a pharmaceutically acceptable salt or solvate thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula I, or a pharmaceutically acceptable salt or solvate thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, nonalcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the invention will be apparent from the following detailed description and figures, and from the claims.

DETAILED DESCRIPTION

Provided herein are heterocyclic GLP-1 agonists for use in the management of T2DM and other conditions where activation of GLP-1 activity is useful.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "halo" or "halogen" means-F (sometimes referred to herein as "fluoro" or "fluoros"), —Cl (sometimes referred to herein as "chloro" or "chloros"), —Br (sometimes referred to herein as "bromo" or "bromos"), and —I (sometimes referred to herein as "iodo" or "iodos").

As used herein, the term "alkyl" refers to saturated linear or branched-chain monovalent hydrocarbon radicals, containing the indicated number of carbon atoms.

For example, "($C_1$-$C_6$)alkyl" refers to saturated linear or branched-chain monovalent hydrocarbon radicals of one to six carbon atoms. Non-limiting examples of alkyl include methyl, ethyl, 1-propyl, isopropyl, 1-butyl, isobutyl, sec-butyl, tert-butyl, 2-methyl-2-propyl, pentyl, neopentyl, and hexyl.

As used herein, the term "alkylene" refers to a divalent alkyl containing the indicated number of carbon atoms. For example, "($C_1$-$C_3$)alkylene" refers to a divalent alkyl having one to three carbon atoms (e.g., $—CH_2—$, $—CH(CH_3)—$, $—CH_2CH_2—$, or $—CH_2CH_2CH_2—$). Similarly, the terms "cycloalkylene", "heterocycloalkylene", "arylene", and "heteroarylene" mean divalent cycloalkyl, heterocycloalkyl, aryl, and heteroaryl, respectively.

As used herein, the term "alkenyl" refers to a linear or branched monounsaturated hydrocarbon chain, containing the indicated number of carbon atoms. For example, "($C_2$-$C_6$)alkenyl" refers a linear or branched mono unsaturated hydrocarbon chain of two to six carbon atoms. Non-limiting examples of alkenyl include ethenyl, propenyl, butenyl, or pentenyl.

As used herein, the term "alkynyl" refers to a linear or branched di-unsaturated hydrocarbon chain, containing the indicated number of carbon atoms. For example, "($C_2$-$C_6$) alkynyl" refers to a linear or branched di-unsaturated hydrocarbon chain having two to six carbon atoms. Non-limiting examples of alkynyl include ethynyl, propynyl, butynyl, or pentynyl.

As used herein, the term "cycloalkyl" refers to a saturated or partially unsaturated cyclic hydrocarbon, containing the indicated number of carbon atoms. For example, "($C_3$-$C_6$) cycloalkyl" refers to a saturated or partially unsaturated cyclic hydrocarbon having three to six ring carbon atoms. Non-limiting examples of cycloalkyl include cyclopropyl, cyclobutyl, cyclopentyl, and cyclohexyl. Cycloalkyl may be partially unsaturated. Non-limiting examples of partially unsaturated cycloalkyl include cyclohexenyl, cyclopentenyl, cycloheptenyl, cyclooctenyl, and the like. Cycloalkyl may include multiple fused and/or bridged rings. Non-limiting examples of fused/bridged cycloalkyl includes: bicyclo[1.1.0]butane, bicyclo[2.1.0]pentane, bicyclo[2.1.1]hexane, bicyclo[1.1.1]pentane, bicyclo[3.2.0]heptane, bicyclo[3.1.0]hexane, bicyclo[4.1.0]heptane, bicyclo[4.2.0]octane, bicyclo[2.2.1]heptane, bicyclo[3.1.1]heptane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

As used herein, the term "heterocycloalkyl" refers to a mon-, bi-, tri-, or polycyclic nonaromatic ring system containing indicated number of ring atoms (e.g., 3-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, the heteroatoms selected from O, N, S, or S(O)1-2 (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyl groups include piperazinyl, pyrrolidinyl, dioxanyl, morpholinyl, tetrahydrofuranyl, and the like. Heterocycloalkyl groups may be partially unsaturated. Non-limiting examples of partially unsaturated heterocycloalkyl include dihydropyrrolyl, dihydropyridinyl, tetrahydropyridinyl, dihydrofuranyl, dihydropyranyl, and the like. Heterocycloalkyl may include multiple fused and bridged rings. Non-limiting examples of fused/bridged heteorocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocycloalkyl also includes spirocyclic rings (e.g., spirocyclic bicycle wherein two rings are connected through just one atom). Non-limiting examples of spirocyclic heterocycloalkyl include 2-azaspiro[2.2]pentane, 4-azaspiro[2.5]octane, 1-azaspiro[3.5]nonane, 7-azaspiro[3.5]nonane, 2-2-azaspiro[3.5]nonane, azaspiro[4.4]nonane, azaspiro[4.5]decane 6-azaspiro[2.6]nonane, 1,7-diazaspiro[4.5]decane, 7-2,5-diazaspiro[3.6]decane, 4-oxaspiro[2.5]octane, 3-azaspiro[5.5]undecane, 2-oxaspiro[2.2]pentane, oxaspiro[3.5]nonane, oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, the term "aryl" refers to a mono-, bi-, tri- or polycyclic hydrocarbon group containing the indicated numbers of carbon atoms, wherein at least one ring in the system is aromatic (e.g., $C_6$ monocyclic, $C_{10}$ bicyclic, or $C_{14}$ tricyclic aromatic ring system). Examples of aryl groups include phenyl, naphthyl, tetrahydronaphthyl, and the like.

As used herein, the term "heteroaryl" refers to a mono-, bi-, tri- or polycyclic group having indicated numbers of ring atoms (e.g., 5-6 ring atoms; e.g., 5, 6, 9, 10, or 14 ring atoms); and having 6, 10, or 14 pi electrons shared in a cyclic array; wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others.

As used herein, the term "haloalkyl" refers to an alkyl radical as defined herein, wherein one or more hydrogen atoms is replaced with one or more halogen atoms. Non-limiting examples include fluoromethyl, difluoromethyl, trifluoromethyl, 2-fluoroethyl, 2,2-difluoroethyl, 2,2,2-trifluoroethyl, chloromethyl, dichloromethyl, chloroethyl, trichloroethyl, bromomethyl, and iodomethyl.

As used herein, the term "alkoxy" refers to an—O-alkyl radical, wherein the radical is on the oxygen atom. For example, "$C_1$-6 alkoxy" refers to an —O—($C_1$-6 alkyl) radical, wherein the radical is on the oxygen atom. Examples of alkoxy include methoxy, ethoxy, propoxy, isopropoxy, butoxy and tert-butoxy. Accordingly, as used herein, the term "haloalkoxy" refers to an —O-haloalkyl radical, wherein the radical is on the oxygen atom.

As used herein, "- - -" indicates an optional single or double bond, as allowed by valence. As used herein, "~" indicates the point of attachment to the parent molecule.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

As used herein, when a ring is described as being "aromatic", it means the ring has a continuous, delocalized x-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like. When a ring system comprising at least two rings is described as "aromatic", it means the ring system comprises one or more aromatic ring(s). Accordingly, when a ring system comprising at least two rings is described as "non-aromatic", none of the constituent rings of the ring system is aromatic.

As used herein, when a ring is described as being "partially unsaturated", it means the ring has one or more additional degrees of unsaturation (in addition to the degree of unsaturation attributed to the ring itself; e.g., one or more double bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like. When a ring system comprising at least two rings is described as "partially unsaturated", it means the ring system comprises one or more partially unsaturated ring(s), provided that none of the constituent rings of the ring system is aromatic.

As used herein, the term "carboxylic acid bioisostere" means a group which has chemical and physical similarities producing broadly similar biological properties to a carboxylic acid (see Lipinski, Annual Reports in Medicinal Chemistry, 1986,21, p283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 25 "Bioisosteric Replacement And Development Of Lead Compounds In Drug Design"; Graham, Theochem, 1995, 343, pages 105-109 "Theoretical Studies Applied To Drug Design: ab initio Electronic Distributions In Bioisosteres"). Examples of suitable carboxylic acid bioisostere include: sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucosedependent insulin secretion; suppress inappropriately elevated glucagon levels, both in fasting and postprandial states; and slow gastric emptying. Karla et al., Glucagonlike peptide-1 receptor agonists in the treatment of type 2 diabetes: Past, present, and future, *Indian J Endocrinol Metab.* 2016 March-Apr; 20 (2): 254-267. GLP-1 RAs have been shown to treat type 2 diabetes. Examples of GLP-1 RAs include, but are not limited to, albiglutide (TANZEUM®), dulaglutide (LY2189265, TRULICITY®), efpeglenatide, exenatide (BYETTA®, BYDUREON®, Exendin-4), liraglutide (VICTOZA®, NN2211), lixisenatide (LYXUMIAR), semaglutide (OZEMPIC®), tirzepatide, ZP2929, NNC0113-0987, BPI-3016, and TT401. See, also, for example, additional GLP-1 receptor agonists described in U.S. Pat. Nos. 10,370,426; 10,308,700; 10, 259,823; 10,208,019;

9,920,106; 9,839,664; 8,129,343; 8,536,122; 7,919,598; 6,414,126; 6,628,343; RE45313; and International Publication Nos. WO 2019/239319; WO 2019/239371; WO 2020/103815; WO 2020/207474; WO20202/34726; WO2020/044266; WO2020117987; and WO2020263695.

The term "pharmaceutically acceptable" as used herein indicates that the compound, or salt or composition thereof is compatible chemically and/or toxicologically with the other ingredients comprising a formulation and/or the patient being treated therewith.

The term "therapeutic compound" as used herein is meant to include, without limitation, all compounds of Formula I, or pharmaceutically acceptable salts or solvates thereof (e.g., a compound of any one of Formulas IA, IB, IB-1, IC, ID, IE, and IE-1, or a pharmaceutically acceptable salt or solvate thereof), and all compositions (e.g., pharmaceutical compositions) wherein a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is a component of the composition.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof)) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009.

The term "pharmaceutical composition" refers to a mixture of a compound of Formula I, or a pharmaceutically acceptable salt or solvate thereof (e.g., a compound of any one of Formulas IA, IB, IB-1, IC, ID, IE, and IE-1 or a pharmaceutically acceptable salt or solvate thereof) as described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing", as used herein, is the prevention of the onset, recurrence or spread, in whole or in part, of the disease or condition as described herein, or a symptom thereof.

The terms "subject", "patient" or "individual", as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the patient is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination of the invention.

The term "pharmaceutical combination", as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulation", as used herein, refers to a regulation or an adjustment (e.g., increase or decrease) and can include, for example agonism, partial agonism or antagonism.

Compounds Accordingly, provided herein are compounds of Formula I:

Formula I

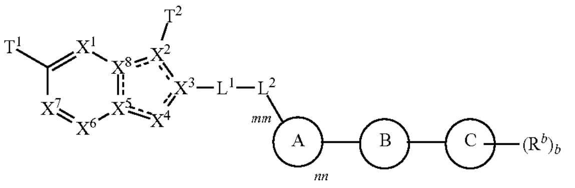

or a pharmaceutically acceptable salt or solvate thereof, wherein:

- ⁄⁄ indicates an optional single or double bond, as allowed by valence;
- each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;
- $T^1$ is C(═O) OH or a carboxylic acid bioisostere;
- $T^2$ is a ($C_1$-$C_6$)alkyl optionally substituted with ($C_1$-$C_6$) alkoxy, ($C_1$-$C_6$)haloalkoxy, ($C_3$-$C_6$) cycloalkyl, 3- to 6-membered heterocycloalkyl, phenyl, or 5- to 6-membered heteroaryl, wherein each of the ($C_3$-$C_6$) cycloalkyl, 3- to 6-membered heterocycloalkyl, phenyl, or 5- to 6-membered heteroaryl is optionally substituted with 1-4 $R^X$;
- each $R^x$ is independently selected from the group consisting of OH, SH, CN, $NO_2$, halogen, ($C_1$-$C_6$)alkyl, ($C_2$-$C_6$)alkenyl, ($C_2$-$C_6$)alkynyl, ($C_1$-$C_6$)haloalkyl, ($C_1$-$C_6$) cyanoalkyl, ($C_1$-$C_6$) hydroxyalkyl, ($C_1$-$C_6$) alkoxy, ($C_1$-$C_6$)haloalkoxy, ($C_3$-$C_6$) cycloalkyl, amino, ($C_1$-$C_6$)alkylamino, and di($C_1$-$C_6$)alkylamino;
- $L^1$ is a bond or ($C_1$-$C_3$)alkylene which is optionally substituted with 1-3 $R^L$;
- $L^2$ is a bond, —O—, —S(O) 0-2-, or —NH—;
- each $R^L$ is independently selected from the group consisting of: halogen, ($C_1$-$C_3$)alkyl, and ($C_1$-$C_3$)haloalkyl; or
- a pair of $R^L$ on the same or on adjacent carbon atoms, taken together with the atom(s) to which each is attached, forms a ($C_3$-$C_6$) cycloalkyl ring;
- Ring A is selected from the group consisting of:
- phenylene optionally substituted with 1-4 $R^Y$;
- 5- to 6-membered heteroarylene optionally substituted with 1-3 $R^Y$;
- partially unsaturated monocyclic ($C_5$-$C_8$) cycloalkylene optionally substituted with 1-4 $R^Y$;
- partially unsaturated monocyclic 5- to 8-membered heterocycloalkylene optionally substituted with 1-4 $R^Y$;

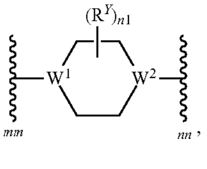

wherein n1 is 0, 1, or 2; $W^1$ is $CR^{Y1}$ or N; and $W^2$ is $CR^{Y2}$ or N; and

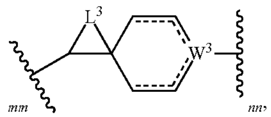

wherein $W^3$ is C, $CR^{Y3}$, or N, $L^3$ is ($C_1$-$C_3$)alkylene, and each ═══ is independently a single bond or a double bond, as allowed by valence;

- wherein mm represents the point of attachment to $L^2$, and nn represents the point of attachment to Ring B; and
- each occurrence of $R^Y$ is independently selected from the group consisting of halogen, cyano, —OH, oxo, ($C_1$-$C_6$)alkyl, ($C_1$-$C_3$)haloalkyl, ($C_1$-$C_3$)alkoxy, and ($C_1$-$C_3$)haloalkoxy;
- $R^{Y1}$, $R^{Y2}$, and $R^{Y3}$ are each independently selected from the group consisting of hydrogen, halogen, cyano, —OH, ($C_1$-$C_6$)alkyl, ($C_1$-$C_3$)haloalkyl, ($C_1$-$C_3$)alkoxy, and ($C_1$-$C_3$)haloalkoxy; or when $W^1$ is $CR^{Y1}$ and $W^2$ is $CR^{Y2}$, the $R^{Y1}$ and $R^{Y2}$ groups taken together can form ($C_1$-$C_4$)alkylene, wherein one of the $CH_2$ units of the ($C_1$-$C_4$)alkylene is optionally replaced by a heteroatom selected from the group consisting of O, S, NH, and N($C_1$-3)alkyl;
- Ring B is selected from the group consisting of (B—I) and (B-II):

(B-I)

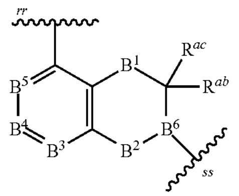

and (B-II)

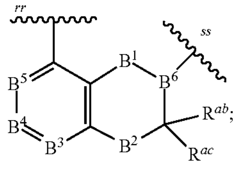

- wherein rr represents the point of attachment to Ring A; and ss represents the point of attachment to Ring C;
- $B^1$ and $B^2$ are independently selected from the group consisting of:—O—, —$NR^N$—, and —$C(R^1)_2$—;
- $B^6$ is N or $CR^{aa}$;
- each $R^1$ is independently selected from the group consisting of: hydrogen, ($C_1$-$C_6$)alkyl, ($C_1$-$C_6$)haloalkyl, and halogen;
- $R^N$ is selected from the group consisting of: hydrogen, ($C_1$-$C_6$)alkyl, ($C_1$-$C_6$)haloalkyl, C(═O) ($C_1$-$C_6$)alkyl, $S(O)_2$ ($C_1$-$C_6$)alkyl, and C(═O) O($C_1$-$C_6$)alkyl;
- $B^3$, $B^4$, and $B^5$ are independently selected from the group consisting of CH, $CR^a$, and N;
- each $R^a$ is independently selected from the group consisting of: halogen, ($C_1$-$C_6$)alkyl, ($C_1$-$C_3$)alkyl($C_3$-$C_6$) cycloalkyl, ($C_1$-$C_3$)alkyl(3- to 5-membered heterocycloalkyl), —C(O)$NR^2R^3$, and ($C_1$-$C_6$) fluoroalkyl;
- each $R^2$ and $R^3$ is independently selected from the group consisting of H and ($C_1$-$C_6$)alkyl;
- $R^{aa}$; $R^{ab}$, and $R^{ac}$ are each independently selected from the group consisting of H, ($C_1$-$C_6$)alkyl, and ($C_1$-$C_6$) haloalkyl;

Ring C is selected from the group consisting of phenyl, 5- to 6-membered heteroaryl, ($C_3$-$C_6$) cycloalkyl, ($C_5$-$C_{10}$) bicycloalkyl, 5- to 10-membered bicycloheteroaryl, and 3- to 6-membered heterocycloalkyl;

each $R^b$ is independently selected from the group consisting of ($C_1$-$C_6$)alkyl, ($C_1$-$C_6$)haloalkyl, ($C_1$-$C_6$)alkoxy, halogen, ($C_3$-$C_6$) cycloalkyl, and CN; and b is an integer selected from 0-3.

In some embodiments, provided herein are compounds of Formula I:

Formula I

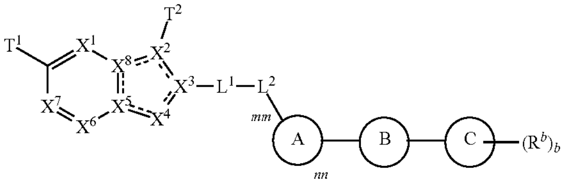

or a pharmaceutically acceptable salt or solvate thereof, wherein:

--- indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;

$T^1$ is C(═O) OH or a carboxylic acid bioisostere;

$T^2$ is a ($C_1$-$C_6$)alkyl optionally substituted with ($C_3$-$C_6$) cycloalkyl, 3- to 6-membered heterocycloalkyl, phenyl, or 5- to 6-membered heteroaryl, wherein each of the ($C_3$-$C_6$) cycloalkyl, 3- to 6-membered heterocycloalkyl, phenyl, or 5- to 6-membered heteroaryl is optionally substituted with 1-4 $R^X$;

each $R^X$ is independently selected from the group consisting of OH, SH, CN, $NO_2$, halogen, ($C_1$-$C_6$)alkyl, ($C_2$-$C_6$)alkenyl, ($C_2$-$C_6$)alkynyl, ($C_1$-$C_6$)haloalkyl, ($C_1$-$C_6$) cyanoalkyl, ($C_1$-$C_6$) hydroxyalkyl, ($C_1$-$C_6$) alkoxy, ($C_1$-$C_6$)haloalkoxy, ($C_3$-$C_6$) cycloalkyl, amino, ($C_1$-$C_6$)alkylamino, and di($C_1$-$C_6$)alkylamino;

$L^1$ is a bond or ($C_1$-$C_3$)alkylene which is optionally substituted with 1-3$R^X$;

$L^2$ is a bond, —O—, —S(O) 0-2-, or —NH—;

each $R^L$ is independently selected from the group consisting of: halogen, ($C_1$-$C_3$)alkyl, and ($C_1$-$C_3$)haloalkyl; or a pair of $R^L$ on the same or on adjacent carbon atoms, taken together with the atom(s) to which each is attached, forms a ($C_3$-$C_6$) cycloalkyl ring;

Ring A is selected from the group consisting of:

phenylene optionally substituted with 1-4 $R^Y$; 5- to 6-membered heteroarylene optionally substituted with 1-3 $R^Y$;

partially unsaturated monocyclic ($C_5$-$C_8$) cycloalkylene optionally substituted with 1-4 $R^Y$;

partially unsaturated monocyclic 5- to 8-membered heterocycloalkylene optionally substituted with 1-4 $R^Y$;

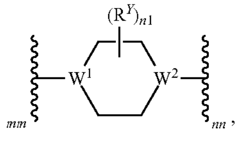

wherein n1 is 0, 1, or 2; $W^1$ is $CR^{Y1}$ or N; and $W^2$ is $CR^{Y2}$ or N; and

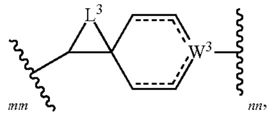

wherein $W^3$ is C, $CR^{Y3}$, or N, $L^3$ is ($C_1$-$C_3$)alkylene, and each ═══ is independently a single bond or a double bond, as allowed by valence;

wherein mm represents the point of attachment to $L^2$, and nn represents the point of attachment to Ring B; and each occurrence of $R^Y$ is independently selected from the group consisting of halogen, cyano, —OH, oxo, ($C_1$-$C_6$)alkyl, ($C_1$-$C_3$)haloalkyl, ($C_1$-$C_3$)alkoxy, and ($C_1$-$C_3$)haloalkoxy;

$R^{Y1}$, $R^{Y2}$, and $R^{Y3}$ are each independently selected from the group consisting of hydrogen, halogen, cyano, —OH, ($C_1$-$C_6$)alkyl, ($C_1$-$C_3$)haloalkyl, ($C_1$-$C_3$)alkoxy, and ($C_1$-$C_3$)haloalkoxy; or when $W^1$ is $CR^{Y1}$ and $W^2$ is $CR^{Y2}$, the $R^{Y1}$ and $R^{Y2}$ groups taken together can form ($C_1$-$C_4$)alkylene, wherein one of the $CH_2$ units of the ($C_1$-$C_4$)alkylene is optionally replaced by a heteroatom selected from the group consisting of O, S, NH, and N($C_1$-3)alkyl;

Ring B is selected from the group consisting of (B-Ia) and (B-IIa):

(B-Ia)

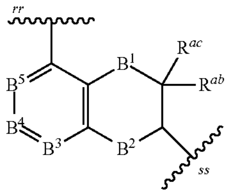

and (B-IIa)

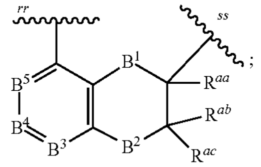

wherein rr represents the point of attachment to Ring A; and ss represents the point of attachment to Ring C;

$B^1$ and $B^2$ are independently selected from the group consisting of:—O—, —$NR^N$—, and —C($R^1$)$_2$—;

each $R^1$ is independently selected from the group consisting of: hydrogen, ($C_1$-$C_6$)alkyl, ($C_1$-$C_6$)haloalkyl, and halogen;

$R^N$ is selected from the group consisting of: hydrogen, ($C_1$-$C_6$)alkyl, ($C_1$-$C_6$)haloalkyl, C(═O) ($C_1$-$C_6$)alkyl, $S(O)_2$ ($C_1$-$C_6$)alkyl, and C(═O) O($C_1$-$C_6$)alkyl;

$B^3$, $B^4$, and $B^5$ are independently selected from the group consisting of CH, $CR^a$, and N;

each $R^a$ is independently selected from the group consisting of: halogen, ($C_1$-$C_6$)alkyl, ($C_1$-$C_3$)alkyl($C_3$-$C_6$) cycloalkyl, ($C_1$-$C_3$)alkyl(3- to 5-membered heterocycloalkyl), —C(O)$NR^2R^3$, and ($C_1$-$C_6$) fluoroalkyl;

each $R^2$ and $R^3$ is independently selected from the group consisting of H and ($C_1$-$C_6$)alkyl;

$R^{aa}$; $R^{ab}$, and $R^{ac}$ are each independently selected from the group consisting of H, $(C_1$-$C_6)$alkyl, and $(C_1$-$C_6)$ haloalkyl;

Ring C is selected from the group consisting of phenyl, 5- to 6-membered heteroaryl, $(C_3$-$C_6)$ cycloalkyl, $(C_5$-$C_{10})$ bicycloalkyl, 5- to 10-membered bicycloheteroaryl, and 3- to 6-membered heterocycloalkyl;

each $R^b$ is independently selected from the group consisting of $(C_1$-$C_6)$alkyl, $(C_1$-$C_6)$alkoxy, halogen, $(C_3$-$C_6)$ cycloalkyl, and CN; and b is an integer selected from 0-3.

In another aspect, provided herein is a compound of Formula IA:

Formula IA

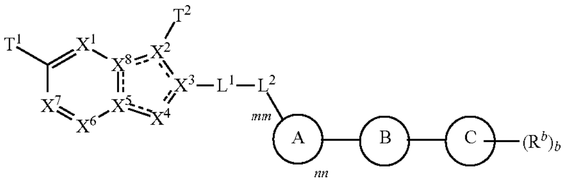

or a pharmaceutically acceptable salt or solvate thereof, wherein: ⸌⸍ indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^1$, and $X^8$ are N;

$T^1$ is C(═O) OH or a carboxylic acid bioisostere;

$T^2$ is a $(C_1$-$C_6)$alkyl optionally substituted with $(C_1$-$C_6)$ alkoxy, $(C_1$-$C_6)$haloalkoxy, $(C_3$-$C_6)$ cycloalkyl, 3- to 6-membered heterocycloalkyl, phenyl, or 5- to 6-membered heteroaryl, wherein each of the $(C_3$-$C_6)$ cycloalkyl, 3- to 6-membered heterocycloalkyl, phenyl, or 5- to 6-membered heteroaryl is optionally substituted with 1-4 $R^Y$;

each $R^x$ is independently selected from the group consisting of OH, SH, CN, $NO_2$, halogen, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$ cyanoalkyl, $(C_1$-$C_6)$ hydroxyalkyl, $(C_1$-$C_6)$ alkoxy, $(C_1$-$C_6)$haloalkoxy, $(C_3$-$C_6)$ cycloalkyl, amino, $(C_1$-$C_6)$alkylamino, and di$(C_1$-$C_6)$alkylamino;

$L^1$ is a bond or $(C_1$-$C_3)$alkylene which is optionally substituted with 1-3 $R^L$;

$L^2$ is a bond, —O—, —S(O) 0-2-, or —NH—;

each $R^L$ is independently selected from the group consisting of: halogen, $(C_1$-$C_3)$alkyl, and $(C_1$-$C_3)$haloalkyl; or a pair of $R^L$ on the same or on adjacent carbon atoms, taken together with the atom(s) to which each is attached, forms a $(C_3$-$C_6)$ cycloalkyl ring;

Ring A is selected from the group consisting of:

phenylene optionally substituted with 1-4 $R^Y$;

5- to 6-membered heteroarylene optionally substituted with 1-3 $R^Y$;

partially unsaturated monocyclic $(C_5$-$C_8)$ cycloalkylene optionally substituted with 1-4 $R^Y$;

partially unsaturated monocyclic 5- to 8-membered heterocycloalkylene optionally substituted with 1-4 $R^Y$;

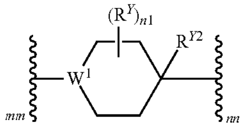,
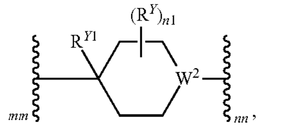,
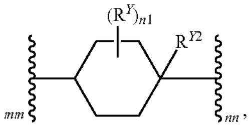, or
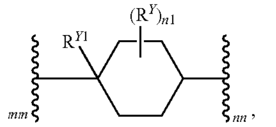, wherein n1 is 0, 1, or 2; $W^1$ is $CR^{Y1}$ or N; and $W^2$ is $CR^{Y2}$ or N; and

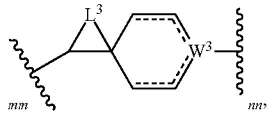

wherein $W^3$ is C, $CR^{Y3}$, or N, $L^3$ is $(C_1$-$C_3)$alkylene, and each ═ is independently a single bond or a double bond, as allowed by valence, provided that (1) the ring containing $W^3$ is partially unsaturated, or (2) $L^3$ is $(C_2$-$C_3)$alkylene;

wherein mm represents the point of attachment to $L^2$, and nn represents the point of attachment to Ring B; and each occurrence of $R^Y$ is independently selected from the group consisting of halogen, cyano, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y3}$ is selected from the group consisting of hydrogen, halogen, cyano, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y1}$ and $R^{Y2}$ are independently selected from the group consisting of halogen, cyano, —OH, $(C_1$-$C_6)$alkyl, $(C_1$-$C_3)$haloalkyl, $(C_1$-$C_3)$alkoxy, and $(C_1$-$C_3)$haloalkoxy; or $R^{Y1}$ and $R^{Y2}$ groups taken together form $(C_1$-$C_4)$alkylene, wherein one of the $CH_2$ units of the $(C_1$-$C_4)$alkylene is optionally replaced by a heteroatom selected from the group consisting of O, S, NH, and $N(C_1$-3)alkyl;

Ring B is selected from the group consisting of (B—I) and (B-II):

(B-I)

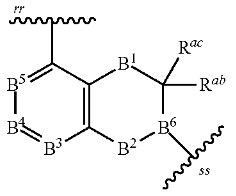

and (B-II)

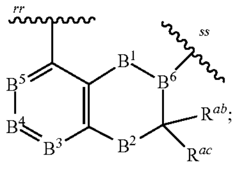

wherein rr represents the point of attachment to Ring A; and ss represents the point of attachment to Ring C;

$B^1$ and $B^2$ are independently selected from the group consisting of: —O—, —$NR^N$, and —$C(R^1)_2$—;

$B^6$ is N or $CR^{aa}$;

each $R^1$ is independently selected from the group consisting of: hydrogen, $(C_1$-$C_6)$alkyl, $(C_1$-$C_6)$haloalkyl, and halogen;

$R^N$ is selected from the group consisting of: hydrogen, $(C_1$-$C_6)$alkyl, $(C_1$-$C_6)$haloalkyl, C(=O) $(C_1$-$C_6)$alkyl, $S(O)_2$ $(C_1$-$C_6)$alkyl, and C(=O) O$(C_1$-$C_6)$alkyl;

$B^3$, $B^4$, and $B^5$ are independently selected from the group consisting of CH, $CR^a$, and N;

each $R^a$ is independently selected from the group consisting of: halogen, $(C_1$-$C_6)$alkyl, $(C_1$-$C_3)$alkyl$(C_3$-$C_6)$ cycloalkyl, $(C_1$-$C_3)$alkyl(3- to 5-membered heterocycloalkyl), —$C(O)NR^2R^3$, and $(C_1$-$C_6)$ fluoroalkyl;

each $R^2$ and $R^3$ is independently selected from the group consisting of H and $(C_1$-$C_6)$alkyl;

$R^{aa}$; $R^{ab}$, and $R^{ac}$ are each independently selected from the group consisting of H, $(C_1$-$C_6)$alkyl, and $(C_1$-$C_6)$ haloalkyl;

Ring C is selected from the group consisting of phenyl, 5- to 6-membered heteroaryl, $(C_3$-$C_6)$ cycloalkyl, $(C_5$-$C_{10})$ bicycloalkyl, 5- to 10-membered bicycloheteroaryl, and 3- to 6-membered heterocycloalkyl;

each $R^b$ is independently selected from the group consisting of $(C_1$-$C_6)$alkyl, $(C_1$-$C_6)$haloalkyl, $(C_1$-$C_6)$alkoxy, halogen, $(C_3$-$C_6)$ cycloalkyl, and CN; and b is an integer selected from 0-3.

In some embodiments, provided herein is a compound of Formula IA:

Formula IA

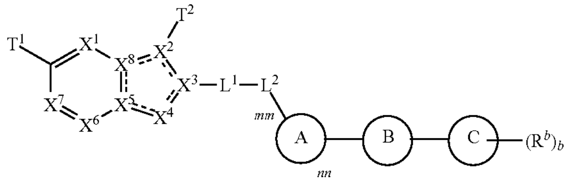

or a pharmaceutically acceptable salt or solvate thereof, wherein:

⁄⁄ indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;

$T^1$ is C(=O) OH or a carboxylic acid bioisostere;

$T^2$ is a $(C_1$-$C_6)$alkyl optionally substituted with $(C_3$-$C_6)$ cycloalkyl, 3- to 6-membered heterocycloalkyl, phenyl, or 5- to 6-membered heteroaryl, wherein each of the $(C_3$-$C_6)$ cycloalkyl, 3- to 6-membered heterocycloalkyl, phenyl, or 5- to 6-membered heteroaryl is optionally substituted with 1-4 $R^X$;

each $R^x$ is independently selected from the group consisting of OH, SH, CN, $NO_2$, halogen, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$ cyanoalkyl, $(C_1$-$C_6)$ hydroxyalkyl, $(C_1$-$C_6)$ alkoxy, $(C_1$-$C_6)$haloalkoxy, $(C_3$-$C_6)$ cycloalkyl, amino, $(C_1$-$C_6)$alkylamino, and di$(C_1$-$C_6)$alkylamino;

$L^1$ is a bond or $(C_1$-$C_3)$alkylene which is optionally substituted with 1-3 $R^Y$, $L^2$ is a bond, —O—, —S(O) 0-2-, or —NH—;

each R' is independently selected from the group consisting of: halogen, $(C_1$-$C_3)$alkyl, and $(C_1$-$C_3)$haloalkyl; or a pair of $R^L$ on the same or on adjacent carbon atoms, taken together with the atom(s) to which each is attached, forms a $(C_3$-$C_6)$ cycloalkyl ring;

Ring A is selected from the group consisting of:

phenylene optionally substituted with 1-4 $R^Y$;

5- to 6-membered heteroarylene optionally substituted with 1-3 $R^Y$;

partially unsaturated monocyclic $(C_5$-$C_8)$ cycloalkylene optionally substituted with 1-4 $R^Y$;

partially unsaturated monocyclic 5- to 8-membered heterocycloalkylene optionally substituted with 1-4 $R^Y$;

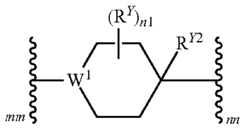,

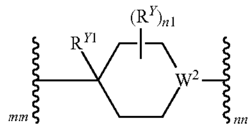,

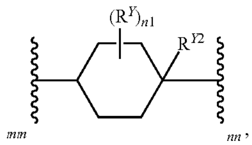, or

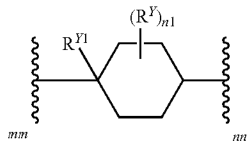, wherein n1 is 0, 1, or 2; $W^1$ is $CR^{Y1}$ or N; and $W^2$ is $CR^{Y2}$ or N; and

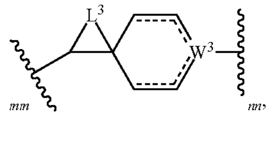

wherein $W^3$ is C, $CR^{Y3}$, or N, $L^3$ is $(C_1$-$C_3)$alkylene, and each ⩶ is independently a single bond or a double bond, as allowed by valence, provided that (1) the ring containing $W^3$ is partially unsaturated, or (2) $L^3$ is $(C_2$-$C_3)$alkylene;

wherein mm represents the point of attachment to $L^2$, and nn represents the point of attachment to Ring B; and each occurrence of $R^Y$ is independently selected from the group consisting of halogen, cyano, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y3}$ is selected from the group consisting of hydrogen, halogen, cyano, —OH, oxo, $(C_1$-$C_6)$alkyl, $(C_1$-$C_3)$haloalkyl, $(C_1$-$C_3)$alkoxy, and $(C_1$-$C_3)$haloalkoxy;

$R^{Y1}$ and $R^{Y2}$ are independently selected from the group consisting of halogen, cyano, —OH, $(C_1$-$C_6)$alkyl, $(C_1$-$C_3)$haloalkyl, $(C_1$-$C_3)$alkoxy, and $(C_1$-$C_3)$haloalkoxy; or $R^{Y1}$ and $R^{Y2}$ groups taken together form $(C_1$-$C_4)$alkylene, wherein one of the $CH_2$ units of the $(C_1$-$C_4)$alkylene is optionally replaced by a heteroatom selected from the group consisting of O, S, NH, and N$(C_1$-3)alkyl;

Ring B is selected from the group consisting of (B-Ia) and (B-IIa):

(B-Ia)

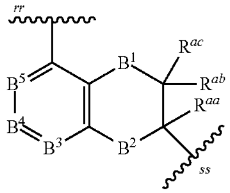

and (B-IIa)

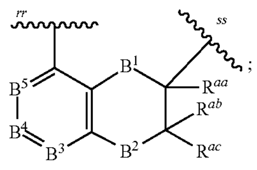

;

wherein rr represents the point of attachment to Ring A; and ss represents the point of attachment to Ring C;

$B^1$ and $B^2$ are independently selected from the group consisting of:—O—, —$NR^N$, and —$C(R^1)_2$—;

each $R^1$ is independently selected from the group consisting of: hydrogen, $(C_1-C_6)$alkyl, $(C_1-C_6)$haloalkyl, and halogen;

$R^N$ is selected from the group consisting of: hydrogen, $(C_1-C_6)$alkyl, $(C_1-C_6)$haloalkyl, C(═O) $(C_1-C_6)$alkyl, $S(O)_2$ $(C_1-C_6)$alkyl, and C(═O) O$(C_1-C_6)$alkyl;

$B^3$, $B^4$, and $B^5$ are independently selected from the group consisting of CH, $CR^a$, and N;

each $R^a$ is independently selected from the group consisting of: halogen, $(C_1-C_6)$alkyl, $(C_1-C_3)$alkyl$(C_3-C_6)$ cycloalkyl, $(C_1-C_3)$alkyl(3- to 5-membered heterocycloalkyl), —$C(O)NR^2R^3$, and $(C_1-C_6)$ fluoroalkyl;

each $R^2$ and $R^3$ is independently selected from the group consisting of H and $(C_1-C_6)$alkyl;

$R^{aa}$; $R^{ab}$, and $R^{ac}$ are each independently selected from the group consisting of H, $(C_1-C_6)$alkyl, and $(C_1-C_6)$ haloalkyl;

Ring C is selected from the group consisting of phenyl, 5- to 6-membered heteroaryl, $(C_3-C_6)$ cycloalkyl, $(C_5-C_{10})$ bicycloalkyl, 5- to 10-membered bicycloheteroaryl, and 3- to 6-membered heterocycloalkyl;

each $R^b$ is independently selected from the group consisting of $(C_1-C_6)$alkyl, $(C_1-C_6)$alkoxy, halogen, $(C_3-C_6)$ cycloalkyl, and CN; and b is an integer selected from 0-3.

Embodiments can include any one or more of the features delineated below and/or in the claims.

In some embodiments of Formulas I or IA, $X^8$ is C; and $X^5$ is C.

In some embodiments of Formulas I or IA, $X^3$ is C.

In some embodiments of Formulas I or IA, $X^2$ is N.

In some embodiments of Formulas I or IA, $X^4$ is N.

In some embodiments of Formulas I or IA, $X^3$ is C; $X^2$ is N; and $X^4$ is N.

In some embodiments of Formulas I or IA, $X^7$ is CH.

In some embodiments of Formulas I or IA, $X^8$ is C; $X^5$ is C; and $X^7$ is CH. In some embodiments of Formulas I or IA, $X^8$, $X^5$, and $X^3$ are C; $X^2$ and $X^4$ are N; $X^1$ is CH; and $X^1$ and $X^6$ are independently CH or N. For example, $X^1$ and $X^6$ are both CH. As another non-limiting example, $X^1$ is N; and $X^6$ is CH. As yet another non-limiting example, $X^1$ is CH; and $X^6$ is N.

In some embodiments of Formulas I or IA, $X^8$, $X^5$, and $X^3$ are C; $X^7$ and $X^6$ are CH; $X^1$ is N; and $X^2$ and $X^4$ is N.

In some embodiments of Formulas I or IA, $X^8$, $X^5$, and $X^3$ are C; $X^7$, ×6, and $X^1$ are CH; and $X^2$ and $X^4$ is N.

In some embodiments of Formulas I or IA, the

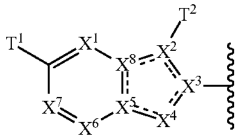

moiety has the formula:

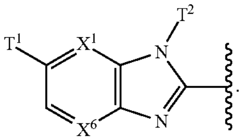

In some embodiments of Formulas I or IA, the

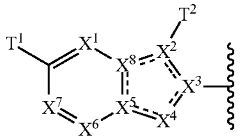

moiety has the formula:

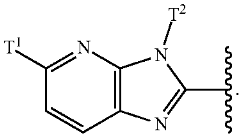

In some embodiments of Formulas I or IA, the

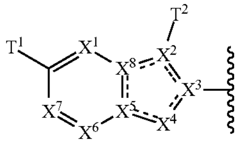

moiety has the formula:

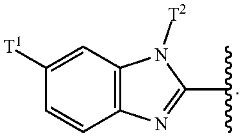

In some embodiments of Formulas I or IA, $T^1$ is C(═O) OH.

In some embodiments of Formulas I or IA, $T^1$ is a carboxylic acid bioisostere. In some embodiments of Formulas I or IA (when $T^1$ is a carboxylic acid bioisostere), $T^1$ is a 5-membered heteroaryl including from 2-4 heteroatoms each independently selected from the group consisting of N, O, and S, wherein the heteroaryl is optionally substituted with from 1-4 substituents each independently selected from the group consisting of hydroxy, $(C_1-C_6)$alkyl, $(C_1-C_6)$ haloalkyl, and halogen.

In some embodiments of Formulas I or IA, $T^1$ is tetrazolyl, which is optionally substituted with from 1-2 substituents each independently selected from the group consisting of hydroxy, $(C_1-C_6)$alkyl, $(C_1-C_6)$haloalkyl, and halogen. For example, $T^1$ is selected from the group consisting of:

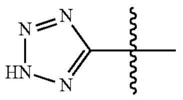
and
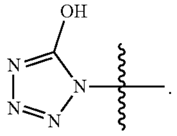

In some embodiments of Formulas I or IA, $T^1$ is triazolyl or oxadiazolyl, which is optionally substituted with from 1-2 substituents each independently selected from $(C_1-C_6)$alkyl and hydroxy. For example, $T^1$ is

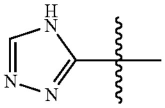
or
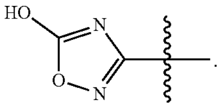

In some embodiments of Formulas I or IA, T is a ring (e.g., a 4-6 membered ring, e.g., a 5-membered ring) including from 0-3 heteroatoms each independently selected from the group consisting of N, O, and S, wherein the ring is substituted with from 1-2 oxo and further optionally substituted from 1-2 substituent each independently selected from the group consisting of hydroxy, $(C_1-C_6)$alkyl, $(C_1-C_6)$ haloalkyl, and halogen. For example, $T^1$ is

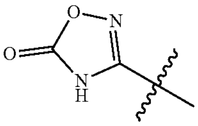
or
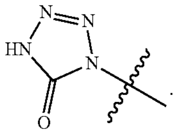

In some embodiments of Formulas I or IA, $T^1$ is $(C_1-C_6)$ alkyl which is substituted with from 1-3 hydroxy and further optionally substituted with from 1-10 fluoro. In certain of these embodiments, $T^1$ is $(C_1-C_6)$alkyl which is substituted with from 1-3 hydroxy and further substituted with from 1-10 fluoro. For example, $T^1$ is

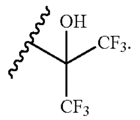

In some embodiments of Formulas I or IA, $T^1$ is C(=O)NHS(O)$_2$ $(C_1-C_4)$alkyl. For example, $T^1$ is C(=O)NHS(O)$_2$Me.

In some embodiments of Formulas I or IA, T' is selected from the group consisting of the following:

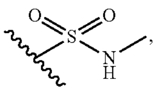
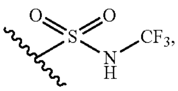
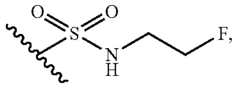
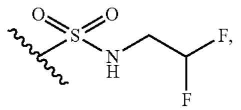
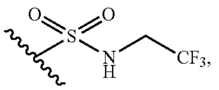
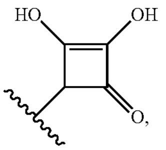
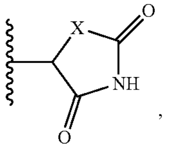
X = O, S
,
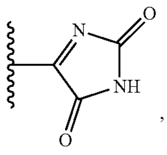
,
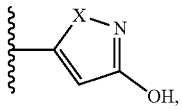
X = O, S, NMe
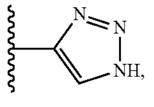
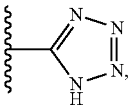
and
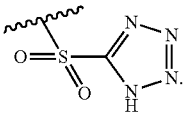

In some embodiments of Formulas I or IA, $T^2$ is $(C_1-C_3)$ alkyl which is substituted with $(C_1-C_6)$alkoxy, $(C_3-C_6)$ cycloalkyl, 3- to 6-membered heterocycloalkyl, phenyl, or 5- to 6-membered heteroaryl.

In some embodiments of Formulas I or IA, $T^2$ is $(C_1-C_3)$ alkyl which is substituted with $(C_3-C_6)$ cycloalkyl, 3- to 6-membered heterocycloalkyl, phenyl, or 5- to 6-membered heteroaryl.

In some embodiments of Formulas I or IA, $T^2$ is $(C_1-C_3)$ alkyl which is substituted with $(C_3-C_6)$ cycloalkyl or 3- to 6-membered heterocycloalkyl.

In some embodiments of Formulas I or IA, $T^2$ is $(C_1-C_3)$ alkyl which is substituted with 3- to 6-membered heterocycloalkyl.

In some embodiments of Formulas I or IA, $T^2$ is $(C_1-C_3)$ alkyl which is substituted with 4- to 6-membered heterocycloalkyl.

In some embodiments of Formulas I or IA, $T^2$ is $(C_1-C_3)$ alkyl which is substituted with oxetanyl.

In some embodiments of Formulas I or IA, $T^2$ is

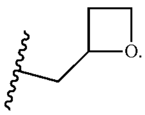 [SMILES: *CC1CCO1]

In some embodiments of Formulas I or IA, $T^2$ is

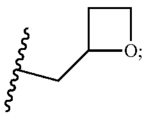 [SMILES: *CC1CCO1]

and the stereogenic center of $T^2$ has (S)-configuration.

In some embodiments of Formulas I or IA, $T^2$ is

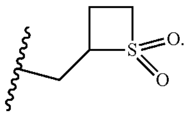 [SMILES: *CC1CCS1(=O)=O]

In some embodiments of Formulas I or IA, $T^2$ is $(C_1\text{-}C_3)$ alkyl which is substituted with $(C_1\text{-}C_6)$alkoxy. In some embodiments, $T^2$ is $(C_1\text{-}C_3)$alkyl which is substituted with $(C_1\text{-}C_3)$alkoxy. In some embodiments, $T^2$ is $(C_2\text{-}C_3)$alkyl which is substituted with $(C_1\text{-}C_3)$alkoxy. As a non-limiting example, $T^2$ is $CH_2CH_2OCH_3$.

As a non-limiting example, the

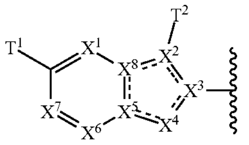

moiety can be:

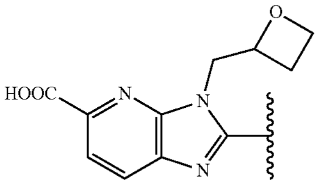

(e.g.,

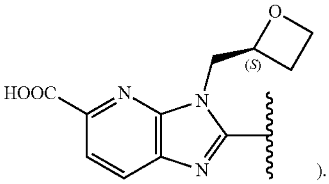

).

As another non-limiting example, the

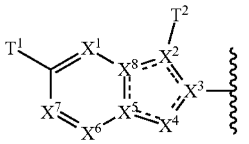

moiety can be:

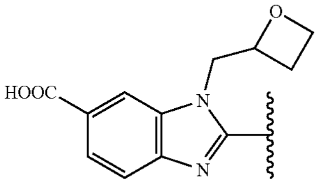

-continued (e.g.,

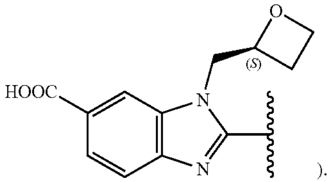

).

In some embodiments of Formulas I or IA, $L^2$ is a bond.

In some embodiments of Formulas I or IA, $L^1$ is $CH_2$.

In some embodiments of Formulas I or IA, $L^1$ is $CH_2$; and $L^2$ is a bond.

In some embodiments of Formula I, Ring A is

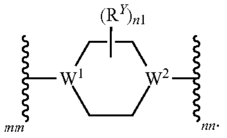

In some embodiments, $W^1$ is N. In some embodiments, $W^2$ is $CR^{Y2}$. In some embodiments, $R^{Y2}$ is hydrogen. In some embodiments, $W^2$ is N. In some embodiments, n1 is 0. In some embodiments, n1 is 1.

In some embodiments of Formula I, Ring A is

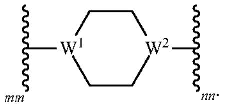

In some embodiments, $W^1$ is N. In some embodiments, $W^2$ is $CR^{Y2}$. In some embodiments, $R^{Y2}$ is hydrogen. In some embodiments, $W^2$ is N.

As a non-limiting example, Ring A can be

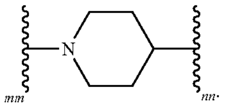

As another non-limiting example, Ring A can be

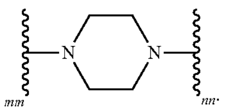

In some embodiments of Formula I, Ring A is

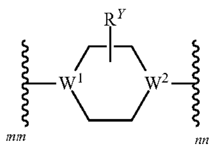

(e.g.,

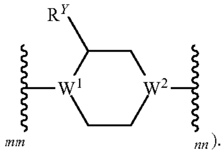

).

In some embodiments, $W^1$ is N. In some embodiments, $W^2$ is $CR^{Y2}$. In some embodiments, $R^Y$ is $(C_1$-$C_3)$alkyl such as methyl.

As a non-limiting example of the foregoing embodiments, Ring A can be

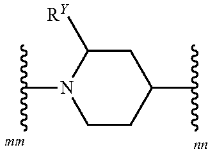 (e.g., 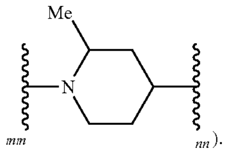).

For avoidance of doubt, when Ring A is $W^1$ is

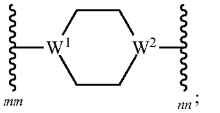;

$CR^{Y1}$; $W^2$ is $CR^{Y2}$; and $R^{Y1}$ and $R^{Y2}$ groups taken together form $(C_1$-$C_4)$alkylene as defined herein, then Ring A is a bridged bicyclic ring system.

In some embodiments of Formula IA, Ring A is selected from the group consisting of:

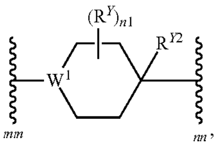, 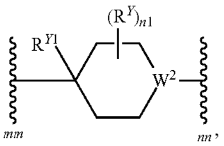, 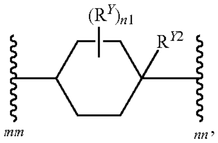, and 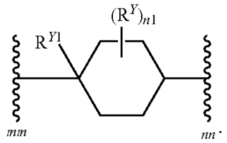.

In some of these embodiments, n1 is 0.

In some embodiments of Formulas I or IA, Ring A is selected from the group consisting of:

phenylene optionally substituted with 1-4 $R^Y$; and 5- to 6-membered heteroarylene optionally substituted with 1-3 $R^Y$.

In some embodiments of Formulas I or IA, Ring A is selected from the group consisting of:

phenylene optionally substituted with 1-4 $R^Y$; and 6-membered heteroarylene optionally substituted with 1-3 $R^Y$; and mm is para or meta to nn.

In some embodiments of Formulas I or IA, Ring A is phenylene optionally substituted with 1-2 $R^Y$; and mm is para or meta to nn. In some embodiments, Ring A is 1,4-phenylene which is optionally substituted with 1-2 $R^Y$. As a non-limiting example of the foregoing embodiments, Ring A can be:

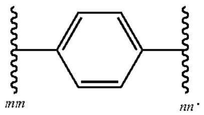.

In some embodiments of Formulas I or IA, Ring A is selected from the group consisting of:

partially unsaturated monocyclic $(C_5$-$C_8)$ cycloalkylene optionally substituted with 1-4 $R^Y$; and partially unsaturated monocyclic 5- to 8-membered heterocycloalkylene optionally substituted with 1-4 $R^Y$.

In some embodiments of Formulas I or IA, Ring A is selected from the group consisting of:

partially unsaturated monocyclic $C_6$ cycloalkylene optionally substituted with 1-4 $R^Y$; and partially unsaturated monocyclic 6-membered heterocycloalkylene optionally substituted with 1-4 $R^Y$; and mm is para to nn.

In some embodiments of Formula I, $L^1$ is $CH_2$; $L^2$ is a bond; and Ring A is

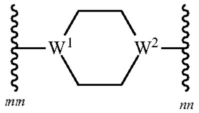 or 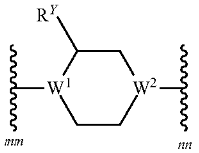

(e.g., 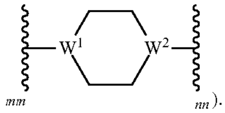).

As a non-limiting example of the foregoing embodiments, Ring A can be

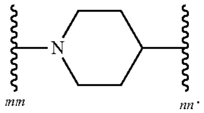.

As another non-limiting example, Ring A can be

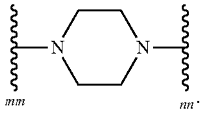.

As yet another non-limiting example, Ring A can be

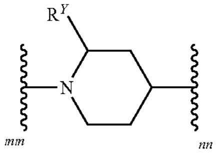

(e.g., $R^Y$ is $(C_1$-$C_3)$alkyl such as methyl).

In some embodiments of Formulas I or IA, $L^1$ is $CH_2$; $L^2$ is a bond; and Ring A is selected from the group consisting of:

phenylene optionally substituted with 1-4 $R^Y$; and 6-membered heteroarylene optionally substituted with 1-3 $R^Y$; and mm is para or meta to nn.

In some embodiments of Formulas I or IA, Ring A is phenylene optionally substituted with 1-2 $R^Y$; and mm is para or meta to nn. As a non-limiting example of the foregoing embodiments, Ring A can be

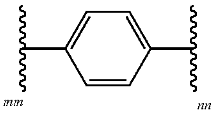 or 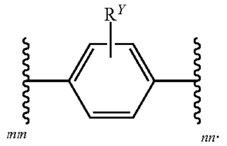

In some embodiments of Formulas I or IA, $B^6$ is $CR^{aa}$. In some embodiments of Formulas I or IA, $B^6$ is N.

In some embodiments of Formulas I or IA, $B^1$ is —O—. In some embodiments of Formulas I or IA, $B^1$ is $—C(R^1)_2—$(e.g., $—CH_2—$). In some embodiments of Formulas I or IA, $B^1$ is $—N(R^N)—$(e.g., NH).

In some embodiments of Formulas I or IA, $B^2$ is —O—. In some embodiments of Formulas I or IA, $B^2$ is $—C(R^1)_2—$(e.g., $—CH_2—$). In some embodiments of Formulas I or IA, $B^2$ is $—N(R^N)—$(e.g., NH).

In some embodiments of Formulas I or IA, $R^1$ is hydrogen. In some embodiments of Formulas I or IA, $R^1$ is $(C_1\text{-}C_6)$alkyl. In some embodiments of Formulas I or IA, $R^1$ is $(C_1\text{-}C_6)$haloalkyl. In some embodiments of Formulas I or IA, $R^1$ is halogen.

In some embodiments of Formulas I or IA, $R^N$ is hydrgeon. In some embodiments of Formulas I or IA, $R^N$ is $(C_1\text{-}C_6)$alkyl. In some embodiments of Formulas I or IA, $R^N$ is $(C_1\text{-}C_6)$haloalkyl. In some embodiments of Formulas I or IA, $R^N$ is C(═O) $(C_1\text{-}C_6)$alkyl. In some embodiments of Formulas I or IA, $R^N$ is C(═O) $O(C_1\text{-}C_6)$alkyl. In some embodiments of Formulas I or IA, $R^N$ is $S(O)_2$ $(C_1\text{-}C_6)$alkyl.

In some embodiments of Formulas I or IA, Ring B is (B-Ia)

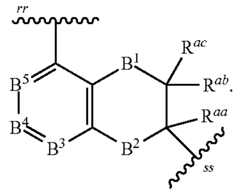

In some embodiments of Formulas I or IA, Ring B is (B-IIa)

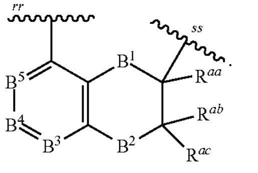

In some embodiments of Formulas I or IA, $B^1$ is —O—; and $B^2$ is —O—.

In some embodiments of Formulas I or IA, $B^1$ is —O—; and $B^2$ is $—NR^N—$(e.g., —NH—).

In some embodiments of Formulas I or IA,$B^1$ is —O—; and $B^2$ is $—C(R^1)_2—$. For example, $B^1$ can be—O—; and $B^2$ can be$—CH_2—$.

In some embodiments of Formulas I or IA, $B^1$ is $—C(R^1)_2—$; and $B^2$ is —O—. For example, $B^1$ can be$—CH_2—$; and $B^2$ can be—O—.

In some embodiments of Formulas I or IA, Ring B is (B-Ia)

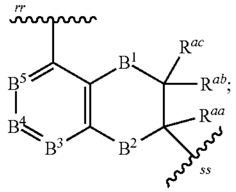

$B^1$ is —O—; and $B^2$ is —O—.

In some embodiments of Formulas I or IA, Ring B is, (B-IIa)

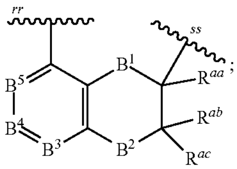

$B^1$ is —O—; and $B^2$ is —O—.

In some embodiments of Formulas I or IA, Ring B is (B-Ib)

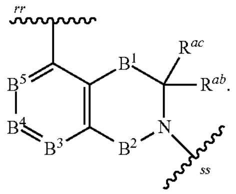

In some embodiments of Formulas I or IA, $B^1$ is $—C(R^1)_2—$(e.g., $—CH_2—$). In some embodiments of Formulas I or IA, $B^2$ is $—C(R^1)_2—$(e.g., $—CH_2—$).

In some embodiments of Formulas I or IA, $R^{aa}$ is H. In some embodiments of Formulas I or IA, $R^{aa}$ is $(C_1\text{-}C_6)$alkyl. As a non-limiting example of the foregoing embodiments, $R^{aa}$ can be methyl. In some embodiments of Formulas I or IA, $R^{ab}$ is H. In some embodiments of Formulas I or IA, $R^{ac}$ is H.

In some embodiments of Formulas I or IA, $R^{aa}$ is H; $R^{ab}$ is H; and $R^{ac}$ is H. In some embodiments of Formulas I or IA, $R^{aa}$ is $(C_1\text{-}C_3)$alkyl (e.g., methyl); $R^{ab}$ is H; and $R^{ac}$ is H.

In some embodiments of Formulas I or IA, $B^3$ is CH. In some embodiments of Formulas I or IA, $B^3$ is $CR^a$. In some embodiments of Formulas I or IA, $B^3$ is N.

In some embodiments of Formulas I or IA, $B^4$ is CH. In some embodiments of Formulas I or IA, $B^4$ is $CR^a$. In some embodiments of Formulas I or IA, $B^4$ is N. In some embodiments of Formulas I or IA, $B^5$ is CH. In some embodiments of Formulas I or IA, $B^5$ is $CR^a$. In some embodiments of Formulas I or IA, $B^5$ is N.

In some embodiments of Formulas I or IA, $B^3$, $B^4$, and $B^5$ are independently CH or $CR^a$. In some embodiments of Formulas I or IA, $B^3$, $B^4$, and $B^5$ are CH.

In some embodiments of Formulas I or IA, $B^1$ is —O—; $B^2$ is —O—; and $B^3$, $B^4$, and $B^5$ are independently CH or $CR^a$. In some embodiments, $B^3$, $B^4$, and $B^5$ are CH. In some embodiments, $R^{aa}$ is H; $R^{ab}$ is H; and $R^{ac}$ is H. In some embodiments, $B^6$ is $CR^{aa}$. In some embodiments, $R^{aa}$ is $(C_1\text{-}C_3)$alkyl (e.g., methyl); $R^{ab}$ is H; and $R^{ac}$ is H.

In some embodiments of Formulas I or IA, $B^1$ is —O—; $B^2$ is —$NR^N$_(e.g., —NH—); and $B^3$, $B^4$, and $B^5$ are independently CH or $CR^a$. In some embodiments, $B^3$, $B^4$, and $B^5$ are CH. In some embodiments, $R^{aa}$ is H; $R^{ab}$ is H; and $R^{ac}$ is H. In some embodiments, $B^6$ is $CR^{aa}$. In some embodiments, $R^{aa}$ is $(C_1\text{-}C_3)$alkyl (e.g., methyl); $R^{ab}$ is H; and $R^{ac}$ is H.

In some embodiments of Formulas I or IA, $B^1$ is —O—; $B^2$ is —$CH_2$—; and $B^3$, $B^4$, and $B^5$ are independently CH or $CR^a$. In some embodiments, $B^3$, $B^4$, and $B^5$ are CH. In some embodiments, $R^{aa}$ is H; $R^{ab}$ is H; and $R^{ac}$ is H. In some embodiments, $B^6$ is $CR^{aa}$. In some embodiments, $R^{aa}$ is $(C_1\text{-}C_3)$alkyl (e.g., methyl); $R^{ab}$ is H; and $R^{ac}$ is H.

In some embodiments of Formulas I or IA, $B^1$ is —$CH_2$—; $B^2$ is —O—; and $B^3$, $B^4$, and $B^5$ are independently CH or $CR^a$. In some embodiments, $B^3$, $B^4$, and $B^5$ are CH.

In some embodiments, $R^{aa}$ is H; $R^{ab}$ is H; and $R^{ac}$ is H. In some embodiments, $B^6$ is $CR^{aa}$. In some embodiments, $R^{aa}$ is $(C_1\text{-}C_3)$alkyl (e.g., methyl); $R^{ab}$ is H; and $R^{ac}$ is H.

In some embodiments of Formulas I or IA, $B^1$ and $B^2$ are—O—; and $B^3$, $B^4$, and $B^5$ are CH. In some embodiments of Formulas I or IA, one of $B^1$ and $B^2$ is —$CH_2$—; the other one of $B^1$ and $B^2$ is —O—; and $B^3$, $B^4$, and $B^5$ are CH. In some embodiments, $B^6$ is $CR^{aa}$. In some embodiments, $R^{aa}$ is H; $R^{ab}$ is H; and $R^{ac}$ is H. In some embodiments, $R^{aa}$ is $(C_1\text{-}C_3)$alkyl (e.g., methyl); $R^{ab}$ is H; and $R^{ac}$ is H.

In some embodiments of Formulas I or IA, Ring B is (B-Ia); and the carbon atom to which $R^{aa}$ and $B^2$ are both attached has (S)-configuration. In some embodiments of Formulas I or IA, Ring B is (B-Ia); and the carbon atom to which $R^{aa}$ and $B^2$ are both attached has (R)-configuration.

In some embodiments of Formulas I or IA, Ring B is (B-II); $B^6$ is $CR^{aa}$, and the carbon atom to which $R^{aa}$ and $B^1$ are both attached has (S)-configuration.

In some embodiments of Formulas I or IA, Ring B is (B-II); $B^6$ is $CR^{aa}$, and the carbon atom to which $R^{aa}$ and $B^1$ are both attached has (R)-configuration.

In some embodiments of Formulas I or IA, Ring B is (B-Ia)

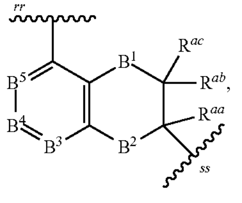

wherein: $B^3$, $B^4$, and $B^5$ are each CH; $B^1$ and $B^2$ are each —O—; $R^{ac}$ and $R^{ab}$ are each H; and $R^{aa}$ is H or $(C_1\text{-}C_3)$alkyl (e.g., H or methyl). In some embodiments, the carbon atom to which $R^{aa}$ and $B^2$ are both attached has (R)-configuration. In some embodiments, the carbon atom to which $R^{aa}$ and $B^2$ are both attached has (S)-configuration. In some embodiments, $R^{aa}$ is H. In some embodiments, $R^{aa}$ is methyl.

In some embodiments of Formula I or IA, Ring B is (B-IIa)

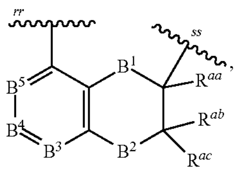

wherein $B^3$, $B^4$, and $B^5$ are each CH; $B^1$ and $B^2$ are each —O—; $R^{ac}$ and $R^{ab}$ are each H; and $R^{aa}$ is H or $(C_1\text{-}C_3)$ alkyl. In some embodiments, the carbon atom to which $R^{aa}$ and $B^1$ are both attached has (S)-configuration. In some embodiments, the carbon atom to which $R^{aa}$ and $B^1$ are both attached has (R)-configuration. In some embodiments, $R^{aa}$ is H. In some embodiments, $R^{aa}$ is methyl.

In some embodiments of Formula I or IA, Ring B is selected from the group consisting of:

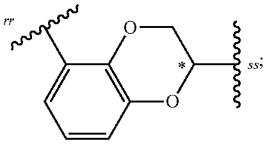

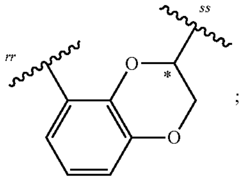

; and

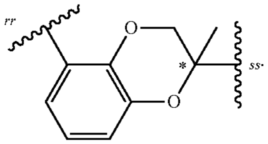

In some embodiments, the carbon atom marked with * has (R)-configuration. In some embodiments, the carbon atom marked with * has (S)-configuration.

In some embodiments of Formulas I or IA, Ring C is selected from the group consisting of: phenyl, 5- to 6-membered heteroaryl, and 5- to 10-membered bicycloheteroaryl.

In some embodiments of Formulas I or IA, Ring C is phenyl.

In some embodiments of Formulas I or IA, b is 1-3.

In some embodiments of Formulas I or IA, b is 2.

In some embodiments of Formulas I or IA, b is 1.

In some embodiments of Formulas I or IA, b is 0.

In some embodiments of Formulas I or IA, Ring C is phenyl; and b is 2.

In some embodiments of Formulas I or IA,

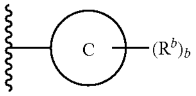

is

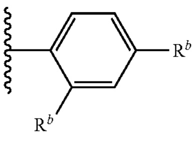

-continued

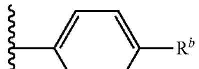

(e.g., 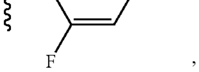 , such as

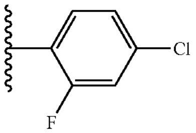 or 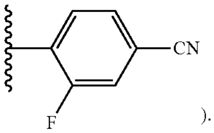 ).

In some embodiments of Formulas I or IA,

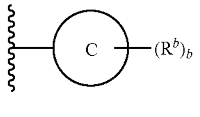 is 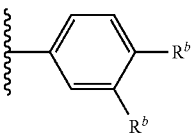

(e.g., 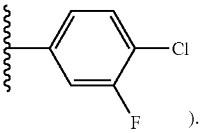 ).

In some embodiments of Formulas I or IA, Ring C is phenyl; and b is 1.

In some embodiments of Formulas I or IA,

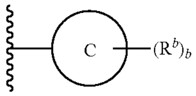 is 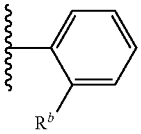

(e.g., 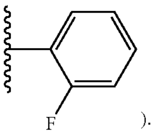 ).

In some embodiments of Formulas I or IA,

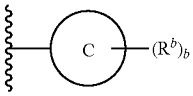 is 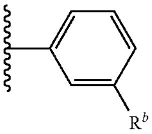

(e.g., 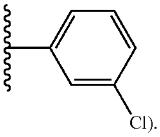).

In some embodiments of Formulas I or IA,

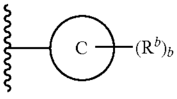 is 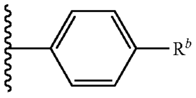

(e.g., 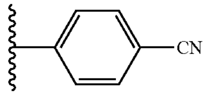 , 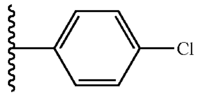 , 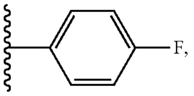 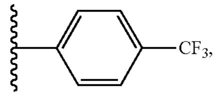 or 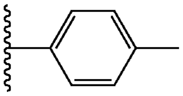 ).

In some embodiments of Formulas I or IA, Ring C is phenyl; and b is 0.

In some embodiments of Formulas I or IA, each occurrence of $R^b$ is independently selected from the group consisting of: $(C_1-C_6)$alkyl, $(C_1-C_6)$haloalkyl, $(C_1-C_6)$alkoxy, halogen, and CN.

In some embodiments of Formulas I or IA, each occurrence of $R^b$ is independently selected from the group consisting of: $(C_1-C_6)$alkyl, $(C_1-C_6)$alkoxy, halogen, and CN.

In some embodiments of Formulas I or IA, each occurrence of $R^b$ is independently selected from the group consisting of —F, —Cl, —$CH_3$, —$CF_3$, and CN.

In some embodiments of Formulas I or IA, each occurrence of $R^b$ is independently selected from the group consisting of —F, —Cl, and CN.

In some embodiments of Formulas I or IA, the compound is a compound of Formula IB:

Formula IB

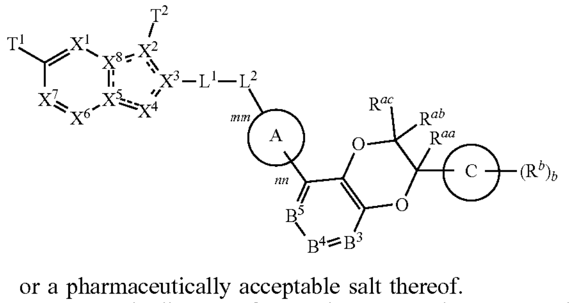

or a pharmaceutically acceptable salt thereof.

In some embodiments of Formulas I or IA, the compound is a compound of Formula IC:

Formula IC

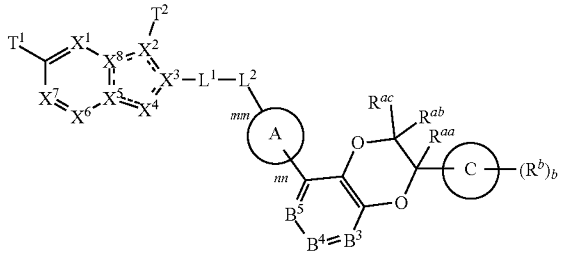

or a pharmaceutically acceptable salt thereof.

In some embodiments of Formulas I or IA, the compound is a compound of Formula ID:

Formula ID

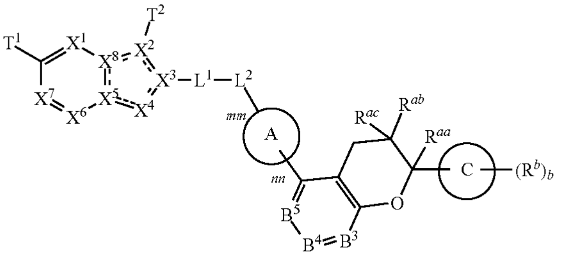

or a pharmaceutically acceptable salt thereof.

In some embodiments of Formulas I or IA, the compound is a compound of Formula IE:

Formula IE

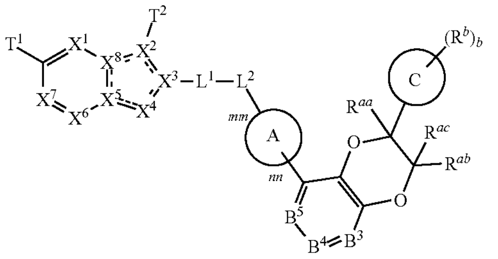

or a pharmaceutically acceptable salt thereof.

In Formulas IB, IC, ID, and IE, $T^1$, $T^2$, $X^1$, $X^2$, $X^3$, $X^4$, $X^3$, $X^6$, $X^1$, $X^8$, $L^1$, $L^2$, Ring A (including mm and nn), $B^3$, $B^4$, $B^5$, $R^{aa}$; $R^{ab}$, $R^{ac}$, Ring C, $R^b$, and b can be as defined for Formulas I or IA anywhere herein.

In some embodiments of Formulas IB, IC, ID, or IE, $B^3$, $B^4$, and $B^5$ are independently selected from the group consisting of CH and $CR^a$.

In some embodiments of Formulas IB, IC, ID, or IE, $B^3$, $B^4$, and $B^5$ are CH.

In some embodiments of Formulas IB, IC, ID, or IE, $R^{aa}$ is H; and $R^{ab}$ and $R^{ac}$ are H.

In some embodiments of Formulas IB, IC, ID, or IE, $R^{aa}$ is ($C_1$-$C_3$)alkyl (e.g., methyl); and $R^{ab}$ and $R^{ac}$ are H.

In some embodiments of Formulas IB, IC, ID, or IE, $X^8$, $X^5$, and $X^3$ are C; $X^2$ and $X^4$ are N; $X^7$ is CH; and $X^1$ and $X^6$ are independently CH or N. In some embodiments of Formulas IB, IC, ID, or IE, $X^1$ is N; and $X^6$ is CH. In some embodiments of Formulas IB, IC, ID, or IE, $X^1$ is CH; and $X^6$ is CH. In some embodiments of Formulas IB, IC, ID, or IE, $X^1$ is CH; and $X^6$ is N.

In some embodiments of Formulas IB, IC, ID, or IE, $T^1$ is C(=O) OH.

In some embodiments of Formulas IB, IC, ID, or IE, $T^2$ is ($C_1$-$C_3$)alkyl which is substituted with 4- to 6-membered heterocycloalkyl. In some embodiments of Formulas IB, IC, ID, or IE, $T^2$ is ($C_1$-$C_3$)alkyl which is substituted with oxetanyl. As a non-limiting example of the foregoing embodiments, $T^2$ can be

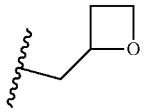

(for example, the stereogenic center in $T^2$ can have (S)-configuration).

In some embodiments of Formulas IB, IC, ID, or IE, $T^2$ is

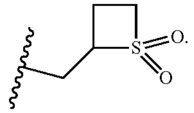

In some embodiments of Formulas IB, IC, ID, or IE, $T^2$ is ($C_1$-$C_3$)alkyl which is substituted with ($C_1$-$C_6$)alkoxy. In some embodiments, $T^2$ is ($C_1$-$C_3$)alkyl which is substituted with ($C_1$-$C_3$)alkoxy. In some embodiments, $T^2$ is ($C_2$-$C_3$) alkyl which is substituted with ($C_1$-$C_3$)alkoxy. As a non-limiting example, $T^2$ is $CH_2CH_2OCH_3$.

In some embodiments of Formulas IB, IC, ID, or IE, $L^2$ is a bond.

In some embodiments of Formulas IB, IC, ID, or IE, $L^1$ is $CH_2$.

In some embodiments of Formulas IB, IC, ID, or IE, $L^1$ is $CH_2$; and $L^2$ is a bond.

In some embodiments of Formulas IB, IC, ID, or IE, Ring A is

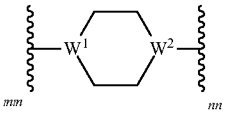
or
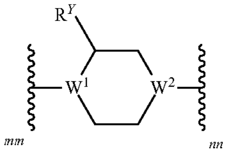

(e.g.,
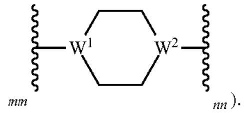
).

In some embodiments, $W^1$ is N. In some embodiments, $W^2$ is $CR^{Y2}$. In some embodiments, $R^{Y2}$ is hydrogen.

In some embodiments, $W^2$ is N. As a non-limiting example, Ring A can be

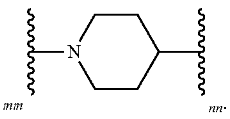

As another non-limiting example, Ring A can be

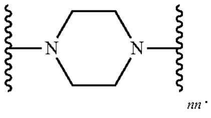

As yet another non-limiting example, Ring A can be

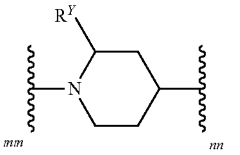

$C_3$)alkyl).

(e.g., $R^Y$ is ($C_1$—In some embodiments of Formulas IB, IC, ID, or IE, Ring A is selected from the group consisting of:

phenylene optionally substituted with 1-4 $R^Y$;

5- to 6-membered heteroarylene optionally substituted with 1-3 $R^Y$;

partially unsaturated monocyclic ($C_5$-$C_8$) cycloalkylene optionally substituted with 1-4 $R^Y$;

partially unsaturated monocyclic 5- to 8-membered heterocycloalkylene optionally substituted with 1-4 $R^Y$;

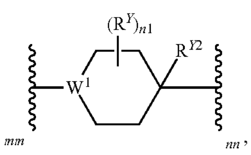, 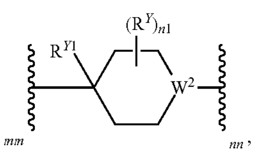, 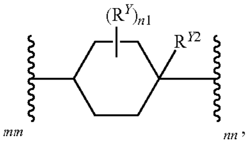, or 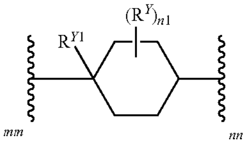, wherein n1 is 0, 1, or 2; $W^1$ is $CR^{Y1}$ or N; and $W^2$ is $CR^{Y2}$ or N; and

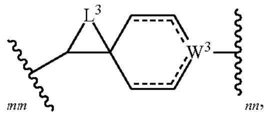

wherein $W^3$ is C, $CR^{Y3}$, or N, $L^3$ is ($C_1$-$C_3$)alkylene, and each ═══ is independently a single bond or a double bond, as allowed by valence, provided that (1) the ring containing $W^3$ is partially unsaturated, or (2) $L^3$ is ($C_2$-$C_3$)alkylene;

wherein mm represents the point of attachment to $L^2$, and nn represents the point of attachment to Ring B; and each occurrence of $R^Y$ is independently selected from the group consisting of halogen, cyano, —OH, oxo, ($C_1$-$C_6$)alkyl, ($C_1$-$C_3$)haloalkyl, ($C_1$-$C_3$)alkoxy, and ($C_1$-$C_3$)haloalkoxy;

$R^{Y3}$ is selected from the group consisting of hydrogen, halogen, cyano, —OH, oxo, ($C_1$-$C_6$)alkyl, ($C_1$-$C_3$)haloalkyl, ($C_1$-$C_3$)alkoxy, and ($C_1$-$C_3$)haloalkoxy;

$R^{Y1}$ and $R^{Y2}$ are independently selected from the group consisting of halogen, cyano, —OH, ($C_1$-$C_6$)alkyl, ($C_1$-$C_3$)haloalkyl, ($C_1$-$C_3$)alkoxy, and ($C_1$-$C_3$)haloalkoxy; or $R^{Y1}$ and $R^{Y2}$ groups taken together form ($C_1$-$C_4$)alkylene, wherein one of the $CH_2$ units of the ($C_1$-$C_4$)alkylene is optionally replaced by a heteroatom selected from the group consisting of O, S, NH, and N($C_1$-3)alkyl.

In some embodiments of Formulas IB, IC, ID, or IE, Ring A is selected from the group consisting of:

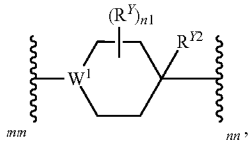, 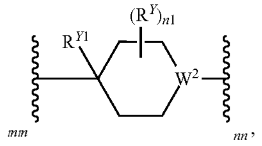, 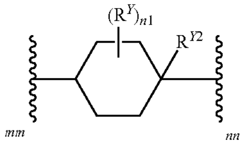, and 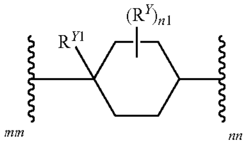, wherein n1 is 0, 1, or 2; $W^1$ is $CR^{Y1}$ or N, and $W^2$ is $CR^{Y2}$ or N; and $R^{Y1}$ and $R^{Y2}$ are independently selected from the group consisting of halogen, cyano, —OH, ($C_1$-$C_6$)alkyl, ($C_1$-$C_3$)haloalkyl, ($C_1$-$C_3$)alkoxy, and ($C_1$-$C_3$)haloalkoxy; or $R^{Y1}$ and $R^{Y2}$ groups taken together form ($C_1$-$C_4$)alkylene, wherein one of the $CH_2$ units of the ($C_1$-$C_4$)alkylene is optionally replaced by a heteroatom selected from the group consisting of O, S, NH, and N($C_1$-3)alkyl. In some embodiments, n1 is 0.

In some of these embodiments, Ring A is selected from the group consisting of:

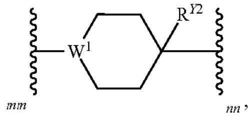, 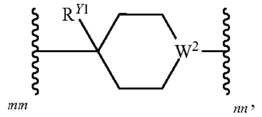, 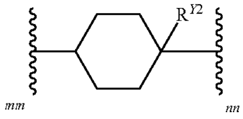, and 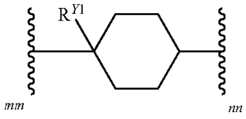.

In some embodiments of Formulas IB, IC, ID, or IE, Ring A is

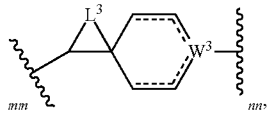

wherein $W^3$ is C, $CR^{Y3}$, or N, $L^3$ is ($C_1$-$C_3$)alkylene, and each ═══ is independently a single bond or a double bond, as allowed by valence, provided that (1) the ring containing $W^3$ is partially unsaturated, or (2) $L^3$ is ($C_2$-$C_3$)alkylene;

In some embodiments of Formulas IB, IC, ID, or IE, Ring A is selected from the group consisting of:

phenylene optionally substituted with 1-4 $R^Y$; and 5- to 6-membered heteroarylene optionally substituted with 1-3 $R^Y$.

In some embodiments of Formulas IB, IC, ID, or IE, Ring A is selected from the group consisting of:

phenylene optionally substituted with 1-4 $R^Y$; and 6-membered heteroarylene optionally substituted with 1-3 $R^Y$; and mm is para or meta to nn.

In some embodiments of Formulas IB, IC, ID, or IE, Ring A is phenylene optionally substituted with 1-2 $R^Y$; and mm is para or meta to nn. In some embodiments, Ring A is 1,4-phenylene which is optionally substituted with 1-2 $R^Y$. As a non-limiting example of the foregoing embodiments, Ring A is:

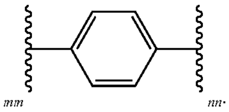

In some embodiments of Formulas IB, IC, ID, or IE, Ring A is selected from the group consisting of:

partially unsaturated monocyclic ($C_5$-$C_8$) cycloalkylene optionally substituted with 1-4 $R^Y$; and partially unsaturated monocyclic 5- to 8-membered heterocycloalkylene optionally substituted with 1-4 $R^Y$.

In some embodiments of Formulas IB, IC, ID, or IE, Ring A is selected from the group consisting of:

partially unsaturated monocyclic $C_6$ cycloalkylene optionally substituted with 1-4 $R^Y$; and partially unsaturated monocyclic 6-membered heterocycloalkylene optionally substituted with 1-4 $R^Y$. In some embodiments, mm is para to nn.

In some embodiments of Formulas IB, IC, ID, or IE, $L^1$ is $CH_2$; $L^2$ is a bond; and Ring A is

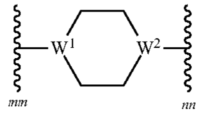

or

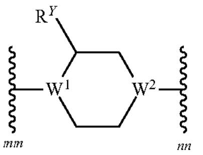

(e.g.,

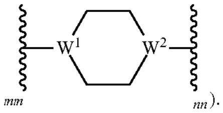

).

As a non-limiting example of the foregoing embodiments, Ring A can be

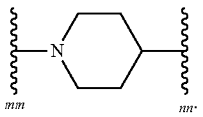 [SMILES: *C1CCN(*)CC1]

As another non-limiting example, Ring A can be

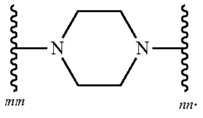

As yet another nonlimiting example, Ring A can be

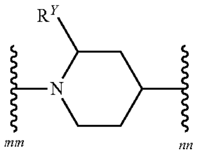

(e.g., $R^Y$ is ($C_1$-$C_3$)alkyl).

In some embodiments of Formulas IB, IC, ID, or IE, $L^1$ is $CH_2$; $L^1$ is a bond; and Ring A is selected from the group consisting of:

phenylene optionally substituted with 1-4 $R^Y$; and 5- to 6-membered heteroarylene optionally substituted with 1-3 $R^Y$.

In some of these embodiments, mm is meta or para to nn. In some embodiments, Ring A is phenylene optionally substituted with 1-2 $R^Y$; and mm is meta or para to nn. In some embodiments, Ring A is 1,4-phenylene optionally substituted with 1-2 $R^Y$. As a non-limiting example of the foregoing embodiments, Ring A can be

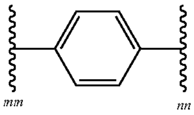

or

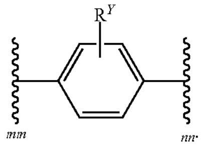

In some embodiments of Formulas IB, IC, ID, or IE, Ring C is phenyl.

In some embodiments of Formulas IB, IC, ID, or IE, b is 1-3.

In some embodiments of Formulas IB, IC, ID, or IE, b is 2.

In some embodiments of Formulas IB, IC, ID, or IE, b is 1.

In some embodiments of Formulas IB, IC, ID, or IE, b is 0.

In some embodiments of Formulas IB, IC, ID, or IE, Ring C is phenyl; and b is 2.

In some embodiments of Formulas IB, IC, ID, or IE,

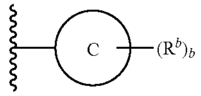

is

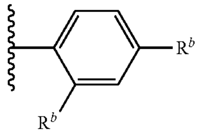

(e.g.,

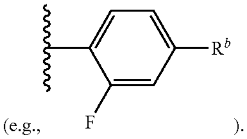

).

For example,

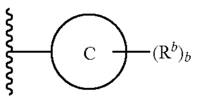

can be

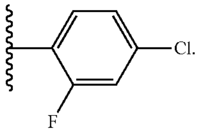 [SMILES: *c1ccc(Cl)cc1F]

As another non-limiting example,

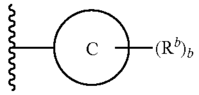

can be

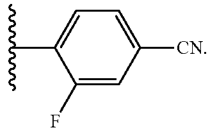 [SMILES: *c1ccc(C#N)cc1F]

In some embodiments of Formulas IB, IC, ID, or IE,

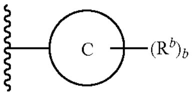
is
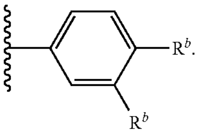

For example,

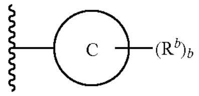

can be

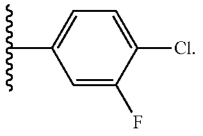 [SMILES: *c1ccc(Cl)c(F)c1]

In some embodiments of Formulas IB, IC, ID, or IE, Ring C is phenyl; and b is 1.

In some embodiments of Formulas IB, IC, ID, or IE,

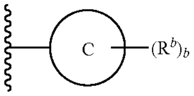
is
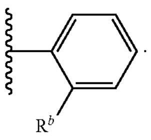

For example,

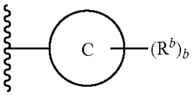

can be

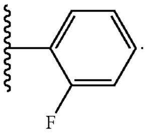

In some embodiments of Formulas IB, IC, ID, or IE,

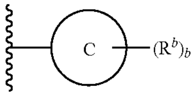
is
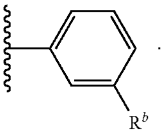

For example,

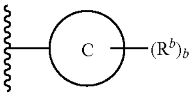

can be

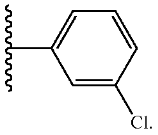 [SMILES: *c1cccc(Cl)c1]

In some embodiments of Formulas IB, IC, ID, or IE,

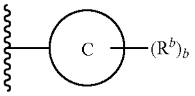
is
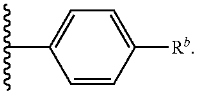

For example,

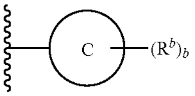

can be

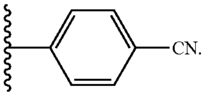 [SMILES: *c1ccc(C#N)cc1]

As another non-limiting example,

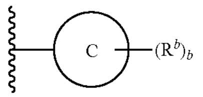

can be

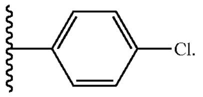 [SMILES: *c1ccc(Cl)cc1]

As another non-limiting example,

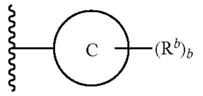

can be

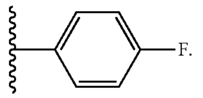 [SMILES: *c1ccc(F)cc1]

As another non-limiting example,

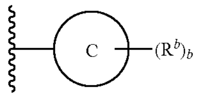

can be

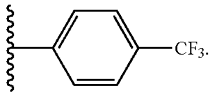 [SMILES: *c1ccc(C(F)(F)F)cc1]

In some embodiments of Formulas IB, IC, ID, or IE, Ring C is phenyl; and b is 0.

In some embodiments of Formulas IB, IC, ID, or IE, each occurrence of $R^b$ is independently selected from the group consisting of: $(C_1-C_6)$alkyl, $(C_1-C_6)$haloalkyl, $(C_1-C_6)$ alkoxy, halogen, and CN.

In some embodiments of Formulas IB, IC, ID, or IE, each occurrence of $R^b$ is independently selected from the group consisting of: $(C_1-C_6)$alkyl, $(C_1-C_6)$alkoxy, halogen, and CN.

In some embodiments of Formulas IB, IC, ID, or IE, each occurrence of $R^b$ is independently selected from the group consisting of —F, —Cl, —$CH_3$, —$CF_3$, and CN.

In some embodiments of Formulas IB, IC, ID, or IE, each occurrence of $R^b$ is independently selected from the group consisting of —F, —Cl, and CN.

In some embodiments of Formulas IB, IC, ID, or IE, the carbon atom to which $R^{aa}$ and Ring C are both attached has (S)-configuration. In some embodiments of Formulas IB, IC, ID, or IE, the carbon atom to which $R^{aa}$ and Ring C are both attached has (R)-configuration.

In some embodiments, the compound of Formula I is a compound of Formula IB-1:

Formula IB-1

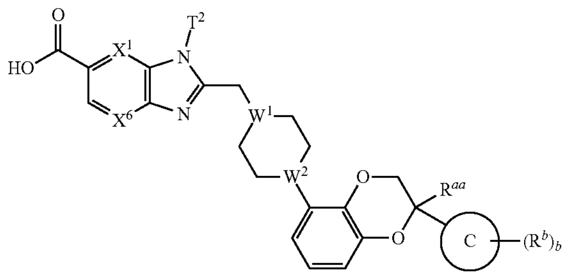

or a pharmaceutically acceptable salt thereof, wherein:

$X^1$ and $X^6$ are independently N or CH;

$T^2$ is $(C_1-C_3)$alkyl substituted with $(C_1-C_6)$alkoxy, $(C_1-C_6)$haloalkoxy, $(C_3-C_6)$ cycloalkyl, 3- to 6-membered heterocycloalkyl, phenyl, or 5- to 6-membered heteroaryl, wherein each of the $(C_3-C_6)$ cycloalkyl, 3- to 6-membered heterocycloalkyl, phenyl, or 5- to 6-membered heteroaryl is optionally substituted with 1-4 substituents each independently selected from the group consisting of: halogen, CN, and $(C_1-C_6)$alkyl;

$W^1$ and $W^2$ are independently N or CH;

$R^{aa}$ is H or $(C_1-C_3)$alkyl;

Ring C is selected from the group consisting of: phenyl and 6-membered heteroaryl;

b is 0, 1, or 2; and each occurrence of $R^b$ is independently selected from the group consisting of: $(C_1-C_6)$alkyl, $(C_1-C_6)$haloalkyl, $(C_1-C_6)$alkoxy, halogen, and CN.

In some embodiments of Formula IB-1:

$X^6$ is CH;

$X^1$ is N or CH;

$T^2$ is $(C_1-C_3)$alkyl substituted with 3- to 6-membered heterocycloalkyl;

Ring C is selected from the group consisting of: phenyl and 6-membered heteroaryl; and b is 1 or 2.

In some embodiments of Formula IB-1:

$X^6$ is CH; $X^1$ is N or CH;

$T^2$ is $(C_1-C_3)$alkyl substituted with oxetanyl;

$W^1$ is N; $W^2$ is CH;

$R^{aa}$ is H or methyl;

Ring C is phenyl;

b is 1 or 2; and each occurrence of $R^b$ is independently selected from the group consisting of —F, —$C_1$, —$CH_3$, —$CF_3$, and CN.

In some embodiments of Formula IB-1:

$X^6$ is CH; $X^1$ is N;

$T^2$ is

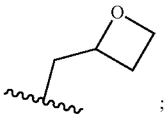 [SMILES: *CC1CCO1]

;

$W^1$ is N; $W^2$ is CH $R^{aa}$ is H or methyl;

Ring C is

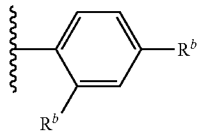

or

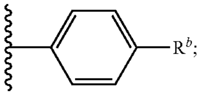

and each occurrence of $R^b$ is independently selected from the group consisting of —F, —$C_1$, —$CH_3$, —$CF_3$, and CN.

In some embodiments of Formula IB-1, the carbon atom to which $R^{aa}$ is attached has (R)-configuration.

In some embodiments of Formula IB-1, the carbon atom to which $R^{aa}$ is attached has (S)-configuration.

In some embodiments, the compound of Formula I is a compound of Formula IE-1:

Formula IE-1

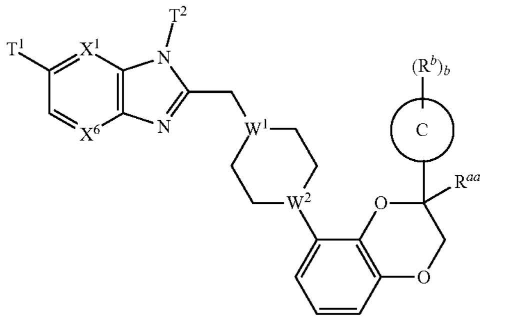

or a pharmaceutically acceptable salt thereof, wherein:

$X^1$ and $X^6$ are independently N or CH;

$T^2$ is ($C_1$-$C_3$)alkyl substituted with ($C_1$-$C_6$)alkoxy, ($C_1$-$C_6$)haloalkoxy, ($C_3$-$C_6$) cycloalkyl, 3- to 6-membered heterocycloalkyl, phenyl, or 5- to 6-membered heteroaryl, wherein each of the ($C_3$-$C_6$) cycloalkyl, 3- to 6-membered heterocycloalkyl, phenyl, or 5- to 6-membered heteroaryl is optionally substituted with 1-4 substituents each independently selected from the group consisting of: halogen, CN, and ($C_1$-$C_6$)alkyl;

$W^1$ and $W^2$ are independently N or CH;

$R^{aa}$ is H or ($C_1$-$C_3$)alkyl;

Ring C is selected from the group consisting of: phenyl and 6-membered heteroaryl;

b is 0, 1, or 2; and each occurrence of $R^b$ is independently selected from the group consisting of: ($C_1$-$C_6$)alkyl, ($C_1$-$C_6$)haloalkyl, ($C_1$-$C_6$)alkoxy, halogen, and CN.

In some embodiments of Formula IE-1:

$X^6$ is CH;

$X^1$ is N or CH;

$T^2$ is ($C_1$-$C_3$)alkyl substituted with 3- to 6-membered heterocycloalkyl;

Ring C is selected from the group consisting of: phenyl and 6-membered heteroaryl; and b is 1 or 2.

In some embodiments of Formula IE-1:

$X^6$ is CH; $X^1$ is N or CH;

$T^2$ is ($C_1$-$C_3$)alkyl substituted with oxetanyl;

$W^1$ is N; $W^2$ is CH;

$R^{aa}$ is H or methyl;

Ring C is phenyl;

b is 1 or 2; and each occurrence of $R^b$ is independently selected from the group consisting of —F, —$C_1$, —$CH_3$, —$CF_3$, and CN.

In some embodiments of Formula IE-1:

$X^6$ is CH; $X^1$ is N;

$T^2$ is

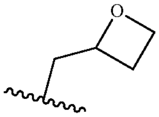

;

$W^1$ is N; $W^2$ is CH $R^{aa}$ is H or methyl;

Ring C is

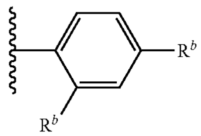

or

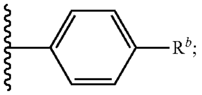

and each occurrence of $R^b$ is independently selected from the group consisting of —F, —$C_1$, —$CH_3$, —$CF_3$, and CN.

In some embodiments of Formula IE-1, the carbon atom to which $R^{aa}$ is attached has (R)-configuration.

In some embodiments of Formula IE-1, the carbon atom to which $R^{aa}$ is attached has (S)-configuration.

In some embodiments, the compound is selected from the group consisting of the compounds in Table $C_1$ or a pharmaceutically acceptable salt or solvate thereof.

TABLE C1
| Compound No. | Structure |
|---|---|
| 101 | 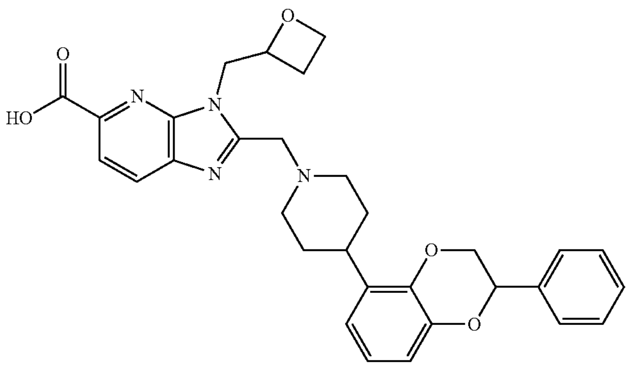 [SMILES: O=C(O)c1ccc2nc(CN3CCC(c4cccc5c4OCC(c4ccccc4)O5)CC3)n(CC3CCO3)c2n1] |
| 102 | 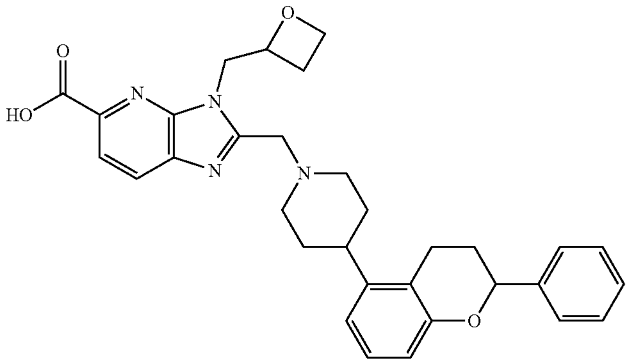 [SMILES: O=C(O)c1ccc2nc(CN3CCC(c4cccc5c4CCC(c4ccccc4)O5)CC3)n(CC3CCO3)c2n1] |
| 103 | 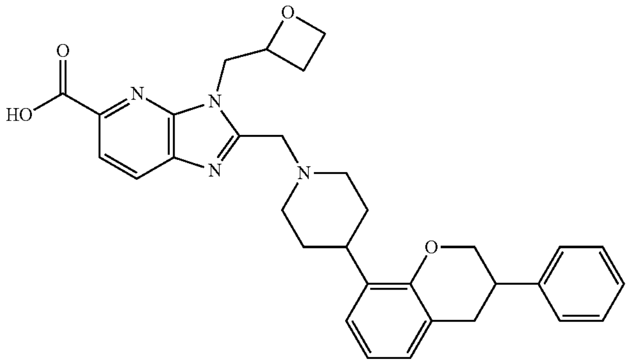 [SMILES: O=C(O)c1ccc2nc(CN3CCC(c4cccc5c4OCC(c4ccccc4)C5)CC3)n(CC3CCO3)c2n1] |
| 104 | 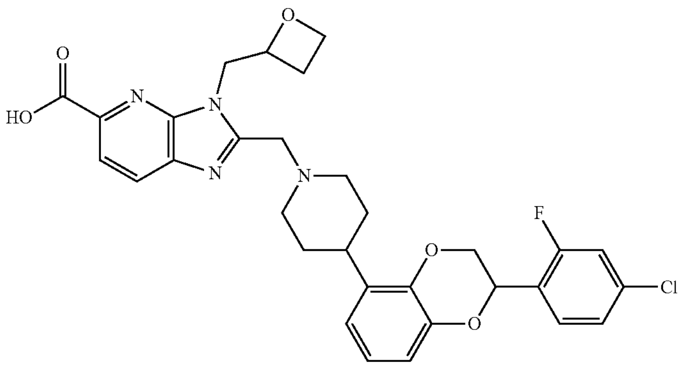 [SMILES: O=C(O)c1ccc2nc(CN3CCC(c4cccc5c4OCC(c4ccc(Cl)cc4F)O5)CC3)n(CC3CCO3)c2n1] |

TABLE C1-continued
| Compound No. | Structure |
|---|---|
| 105 | 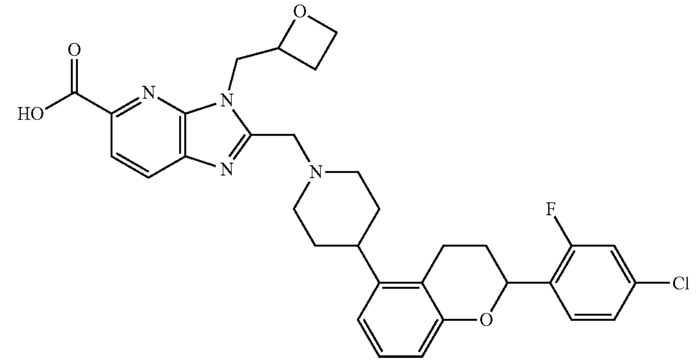 [SMILES: O=C(O)c1ccc2nc(CN3CCC(c4cccc5c4CCC(c4ccc(Cl)cc4F)O5)CC3)n(CC3CCO3)c2n1] |
| 106 | 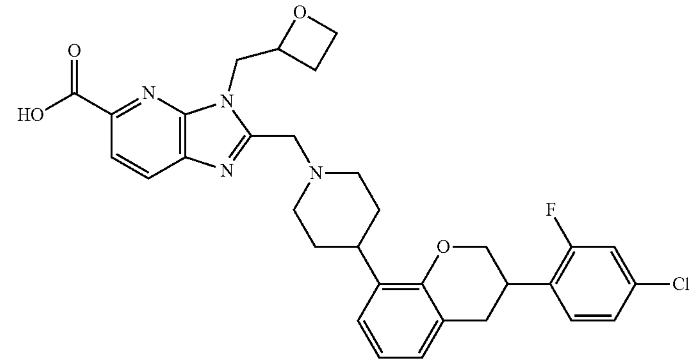 [SMILES: O=C(O)c1ccc2nc(CN3CCC(c4cccc5c4OCC(c4ccc(Cl)cc4F)C5)CC3)n(CC3CCO3)c2n1] |
| 107 | 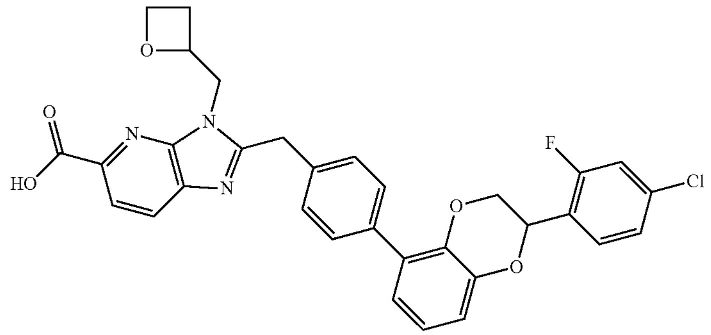 [SMILES: O=C(O)c1ccc2nc(Cc3ccc(-c4cccc5c4OCC(c4ccc(Cl)cc4F)O5)cc3)n(CC3CCO3)c2n1] |
| 108 | 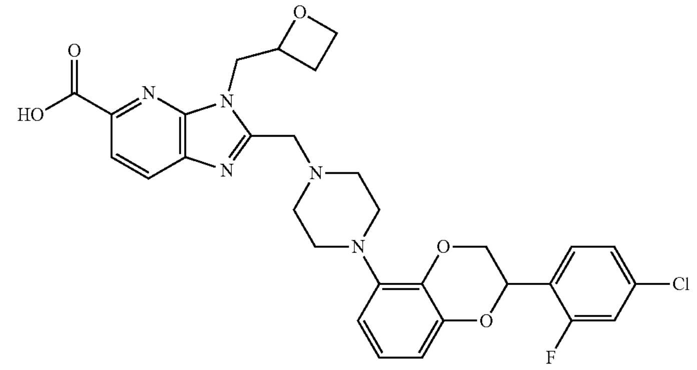 [SMILES: O=C(O)c1ccc2nc(CN3CCN(c4cccc5c4OCC(c4ccc(Cl)cc4F)O5)CC3)n(CC3CCO3)c2n1] |

TABLE C1-continued
| Compound No. | Structure |
|---|---|
| 109 | 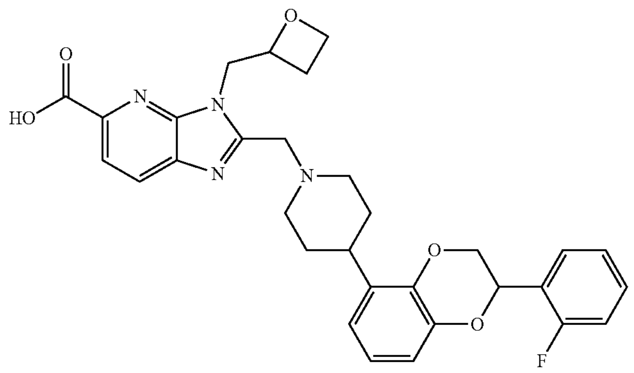 [SMILES: O=C(O)c1ccc2nc(CN3CCC(c4cccc5c4OCC(c4ccccc4F)O5)CC3)n(CC3CCO3)c2n1] |
| 110 | 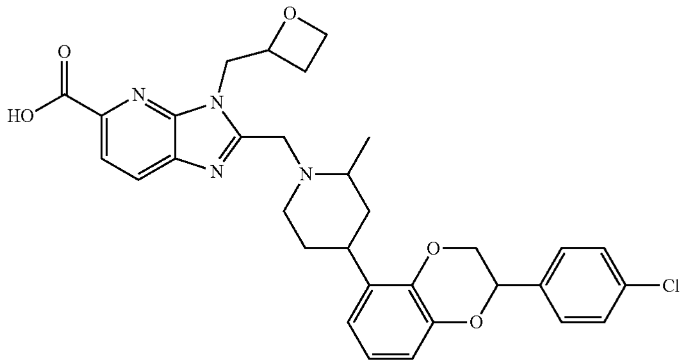 [SMILES: CC1CC(c2cccc3c2OCC(c2ccc(Cl)cc2)O3)CCN1Cc1nc2ccc(C(=O)O)nc2n1CC1CCO1] |
| 111 | 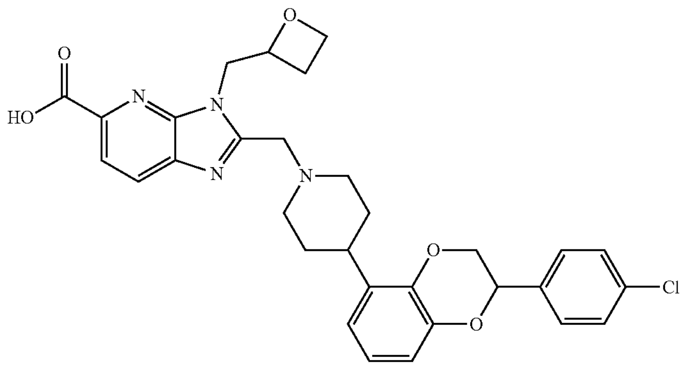 [SMILES: O=C(O)c1ccc2nc(CN3CCC(c4cccc5c4OCC(c4ccc(Cl)cc4)O5)CC3)n(CC3CCO3)c2n1] |
| 112 | 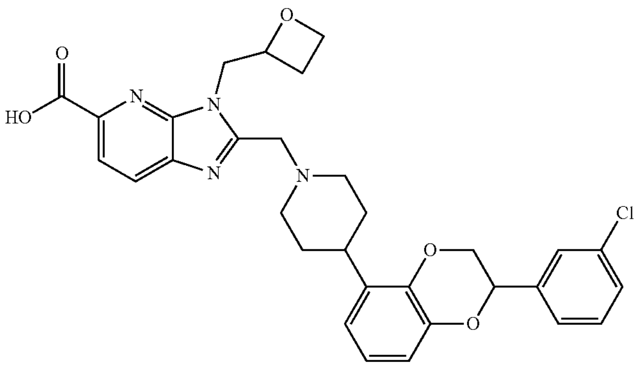 [SMILES: O=C(O)c1ccc2nc(CN3CCC(c4cccc5c4OCC(c4cccc(Cl)c4)O5)CC3)n(CC3CCO3)c2n1] |

TABLE C1-continued
| Compound No. | Structure |
| --- | --- |
| 113 | 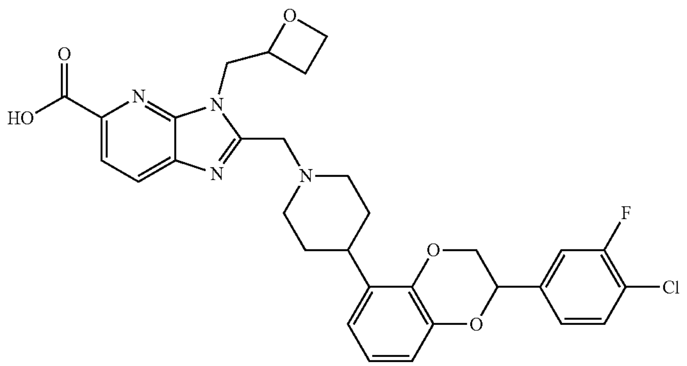 [SMILES: O=C(O)c1ccc2nc(CN3CCC(c4cccc5c4OCC(c4ccc(Cl)c(F)c4)O5)CC3)n(CC3CCO3)c2n1] |
| 114 | 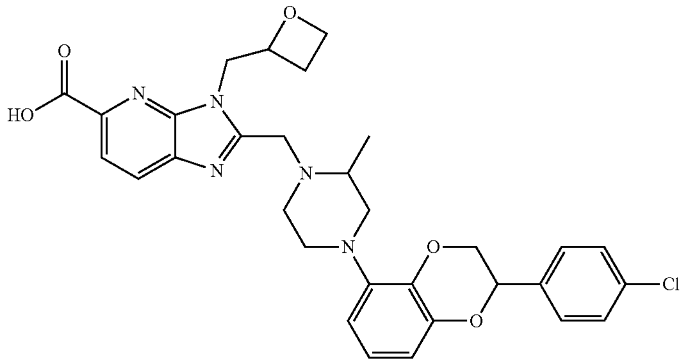 [SMILES: CC1CN(c2cccc3c2OCC(c2ccc(Cl)cc2)O3)CCN1Cc1nc2ccc(C(=O)O)nc2n1CC1CCO1] |
| 115 | 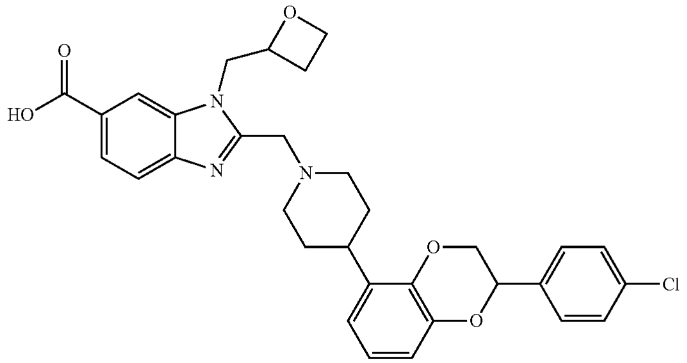 [SMILES: O=C(O)c1ccc2nc(CN3CCC(c4cccc5c4OCC(c4ccc(Cl)cc4)O5)CC3)n(CC3CCO3)c2c1] |
| 116 | 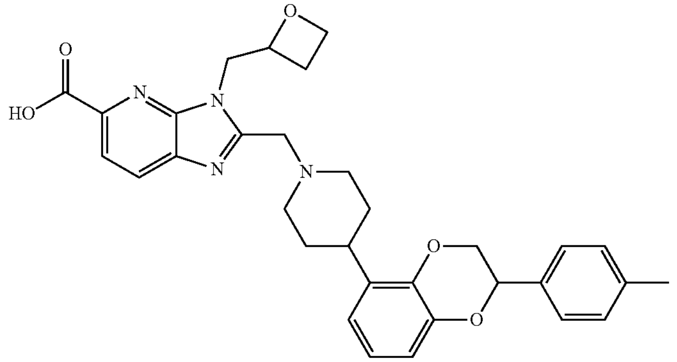 [SMILES: Cc1ccc(C2COc3c(cccc3C3CCN(Cc4nc5ccc(C(=O)O)nc5n4CC4CCO4)CC3)O2)cc1] |

TABLE C1-continued
| Compound No. | Structure |
| --- | --- |
| 117 | 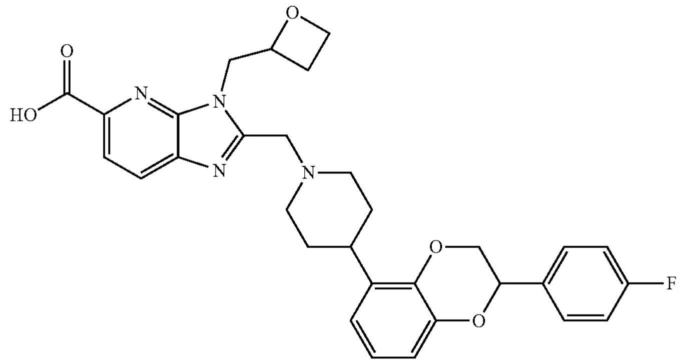 [SMILES: O=C(O)c1ccc2nc(CN3CCC(c4cccc5c4OCC(c4ccc(F)cc4)O5)CC3)n(CC3CCO3)c2n1] |
| 118 | 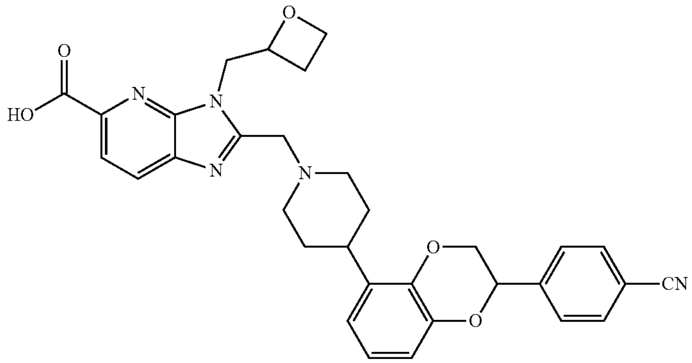 [SMILES: N#Cc1ccc(C2COc3c(cccc3C3CCN(Cc4nc5ccc(C(=O)O)nc5n4CC4CCO4)CC3)O2)cc1] |
| 119 | 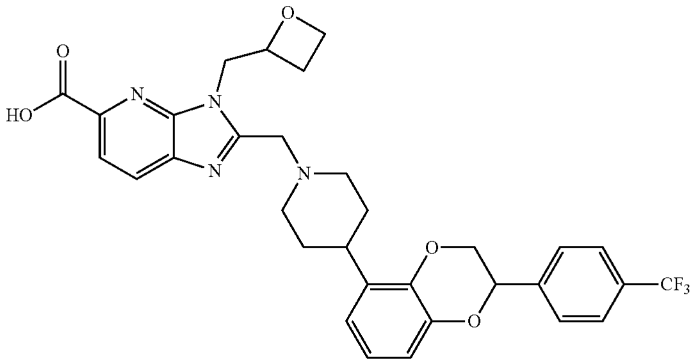 [SMILES: O=C(O)c1ccc2nc(CN3CCC(c4cccc5c4OCC(c4ccc(C(F)(F)F)cc4)O5)CC3)n(CC3CCO3)c2n1] |
| 120 | 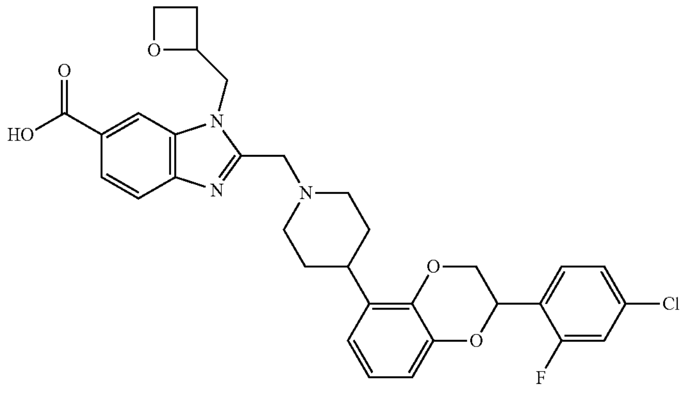 [SMILES: O=C(O)c1ccc2nc(CN3CCC(c4cccc5c4OCC(c4ccc(Cl)cc4F)O5)CC3)n(CC3CCO3)c2c1] |

TABLE C1-continued
| Compound No. | Structure |
|---|---|
| 121 | 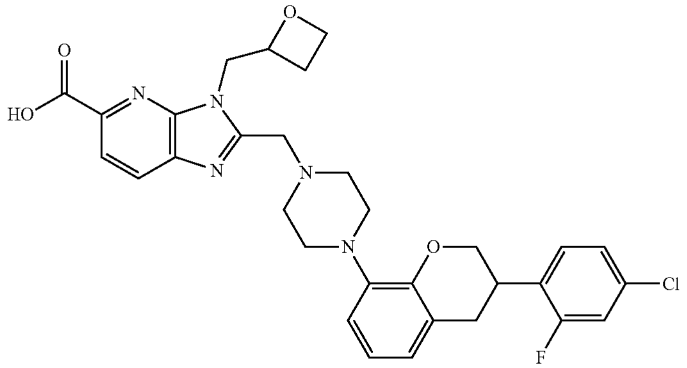 [SMILES: O=C(O)c1ccc2nc(CN3CCN(c4cccc5c4OCC(c4ccc(Cl)cc4F)C5)CC3)n(CC3CCO3)c2n1] |
| 122 | 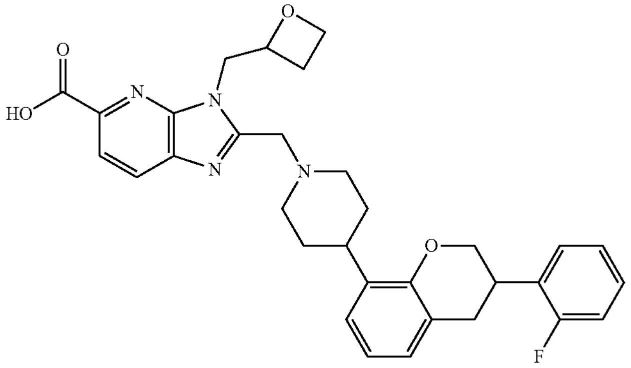 [SMILES: O=C(O)c1ccc2nc(CN3CCC(c4cccc5c4OCC(c4ccccc4F)C5)CC3)n(CC3CCO3)c2n1] |
| 123 | 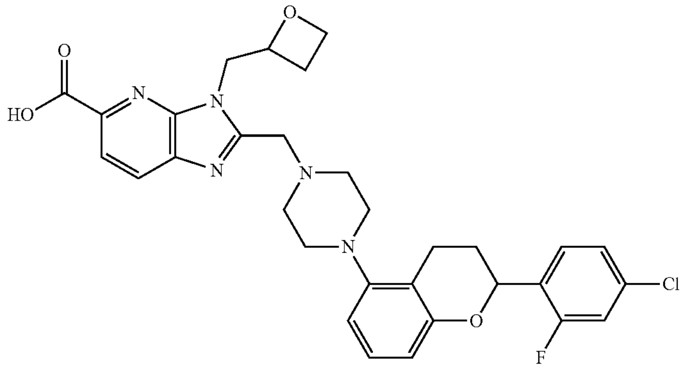 [SMILES: O=C(O)c1ccc2nc(CN3CCN(c4cccc5c4CCC(c4ccc(Cl)cc4F)O5)CC3)n(CC3CCO3)c2n1] |
| 124 | 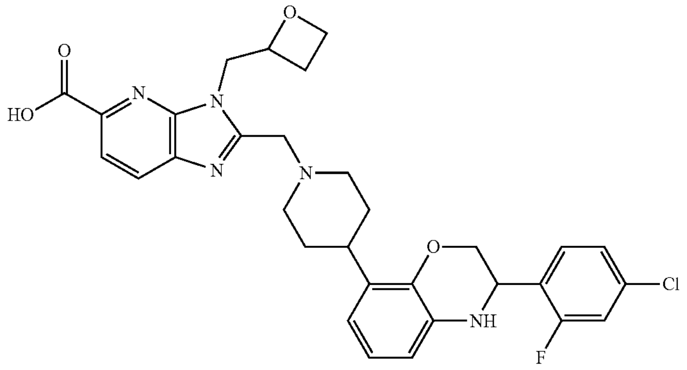 [SMILES: O=C(O)c1ccc2nc(CN3CCC(c4cccc5c4OCC(c4ccc(Cl)cc4F)N5)CC3)n(CC3CCO3)c2n1] |

TABLE C1-continued
| Compound No. | Structure |
| --- | --- |
| 125 | 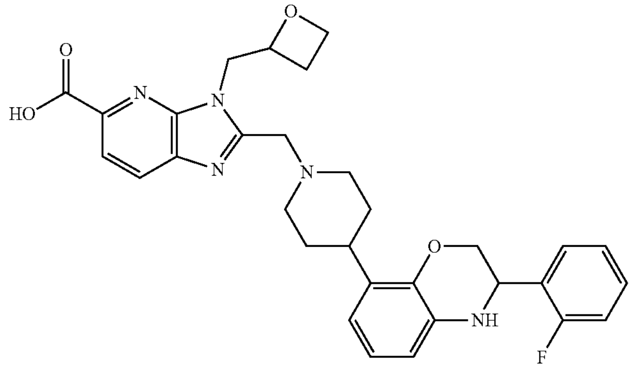 [SMILES: O=C(O)c1ccc2nc(CN3CCC(c4cccc5c4OCC(c4ccccc4F)N5)CC3)n(CC3CCO3)c2n1] |
| 126 | 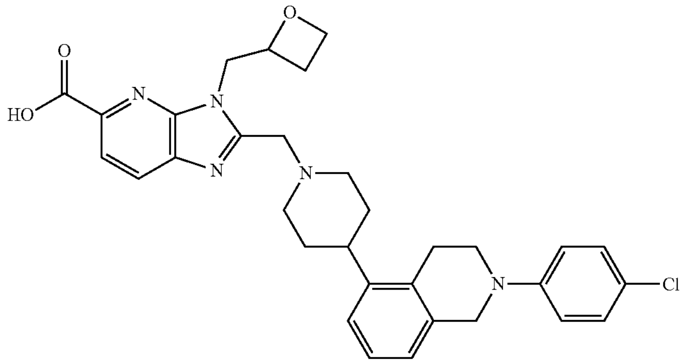 [SMILES: O=C(O)c1ccc2nc(CN3CCC(c4cccc5c4CCN(c4ccc(Cl)cc4)C5)CC3)n(CC3CCO3)c2n1] |
| 127 | 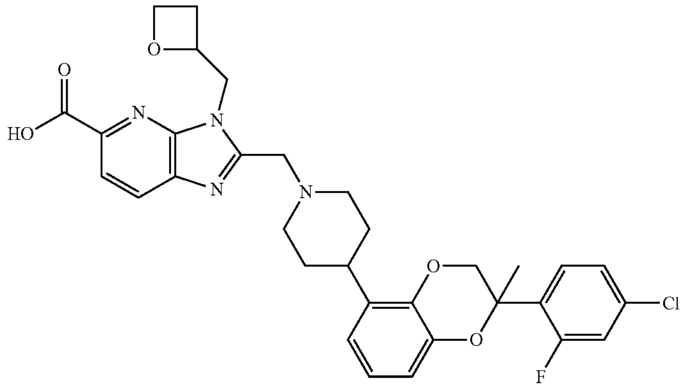 [SMILES: CC1(c2ccc(Cl)cc2F)COc2c(cccc2C2CCN(Cc3nc4ccc(C(=O)O)nc4n3CC3CCO3)CC2)O1] |
| 128 | 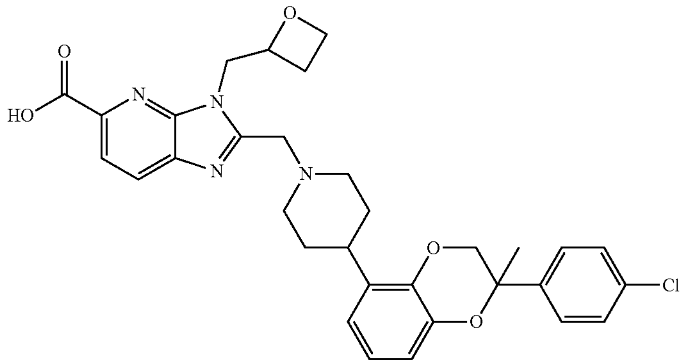 [SMILES: CC1(c2ccc(Cl)cc2)COc2c(cccc2C2CCN(Cc3nc4ccc(C(=O)O)nc4n3CC3CCO3)CC2)O1] |

TABLE C1-continued
| Compound No. | Structure |
|---|---|
| 129 | 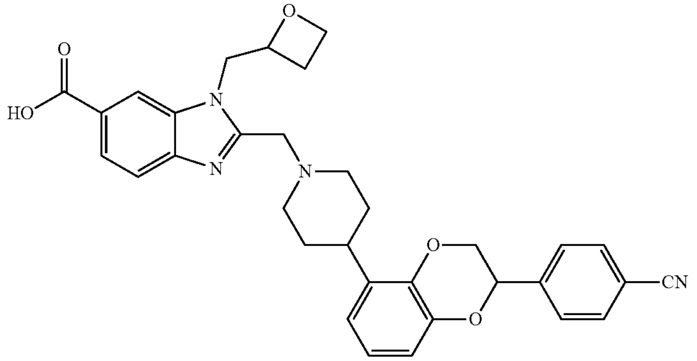 [SMILES: N#Cc1ccc(C2COc3c(cccc3C3CCN(Cc4nc5ccc(C(=O)O)cc5n4CC4CCO4)CC3)O2)cc1] |
| 130 | 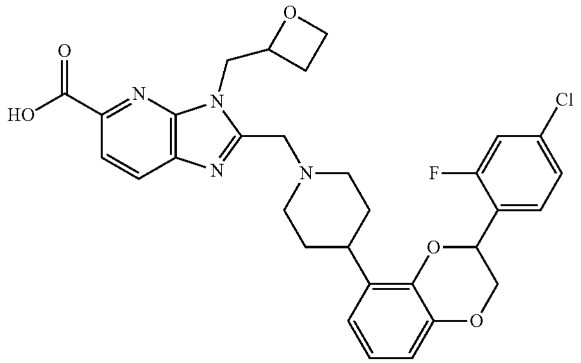 [SMILES: O=C(O)c1ccc2nc(CN3CCC(c4cccc5c4OC(c4ccc(Cl)cc4F)CO5)CC3)n(CC3CCO3)c2n1] |
In some embodiments, the compound is selected from the group consisting of the compounds in Table $C_2$ or a pharmaceutically acceptable salt or solvate thereof.
TABLE C2
| Compound No. | Structure |
|---|---|
| 101a | 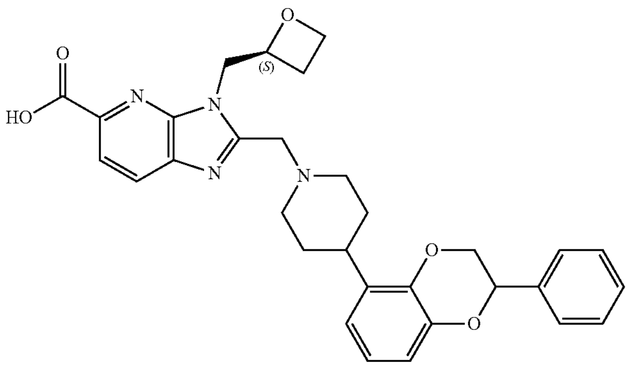 |

TABLE C2-continued
| Compound No. | Structure |
|---|---|
| 102a | 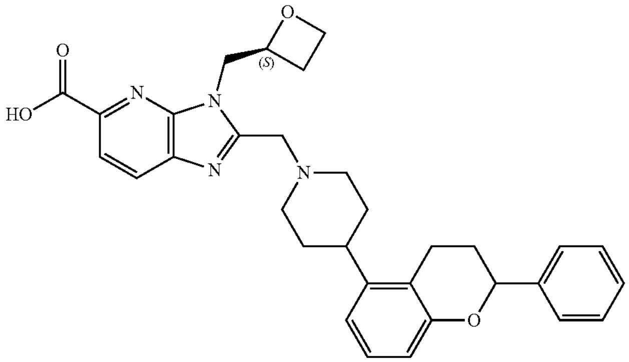 |
| 103a | 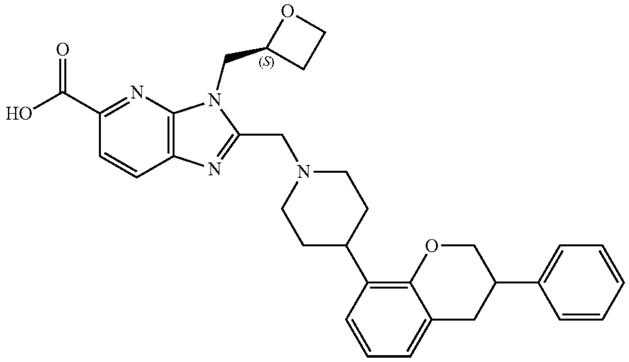 |
| 104a | 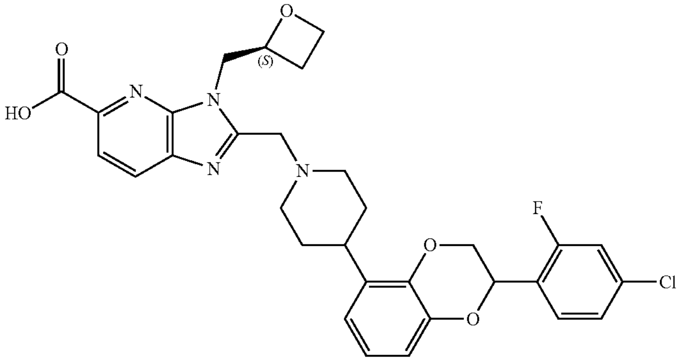 |
| 104b | 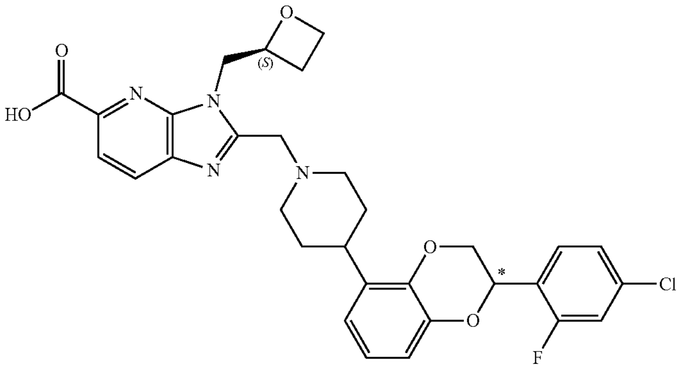<br>Diastereomer 1 |

TABLE C2-continued
| Compound No. | Structure |
| --- | --- |
| 104c | 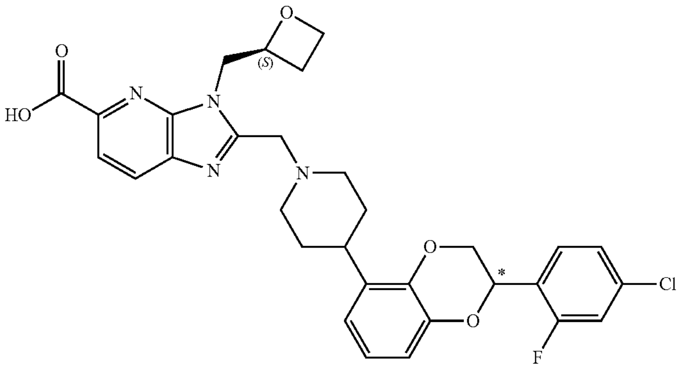 Diastereomer 2 |
| 105a | 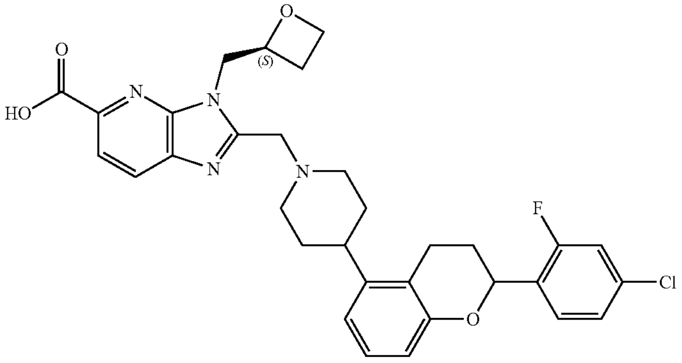 |
| 106a | 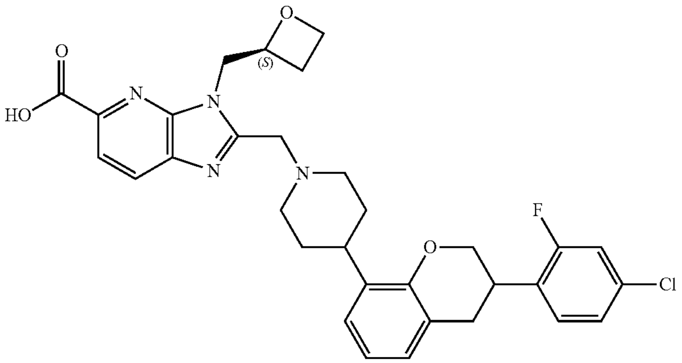 |
| 107a | 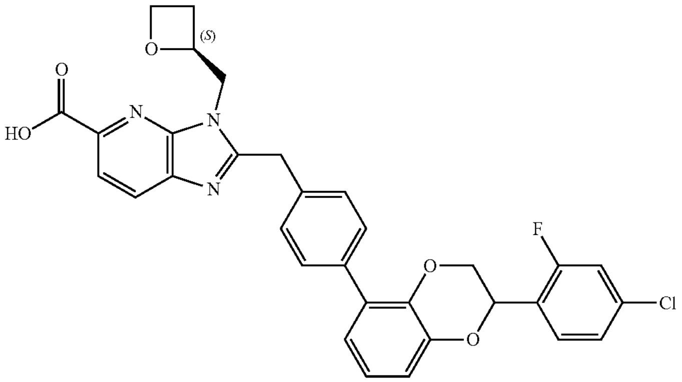 |

TABLE C2-continued
| Compound No. | Structure |
|---|---|
| 108a | 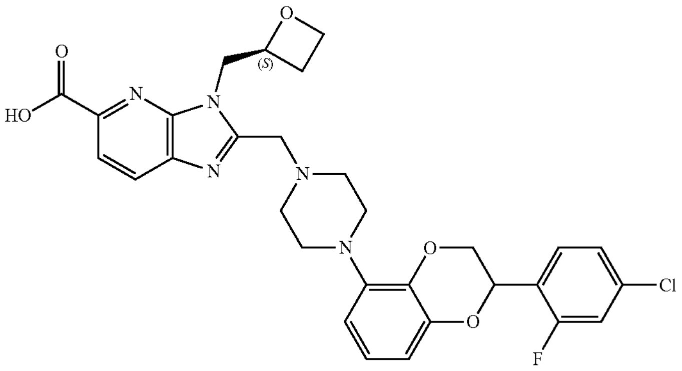 |
| 109a | 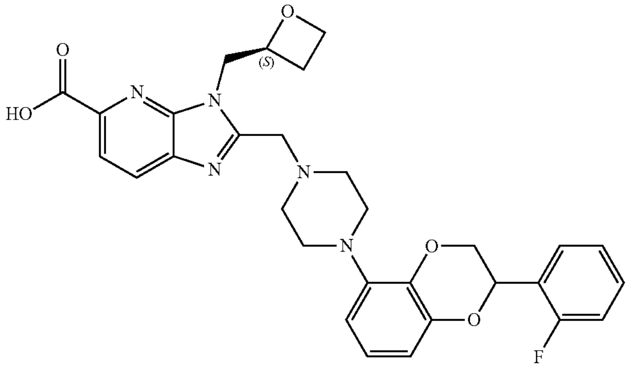 |
| 110a | 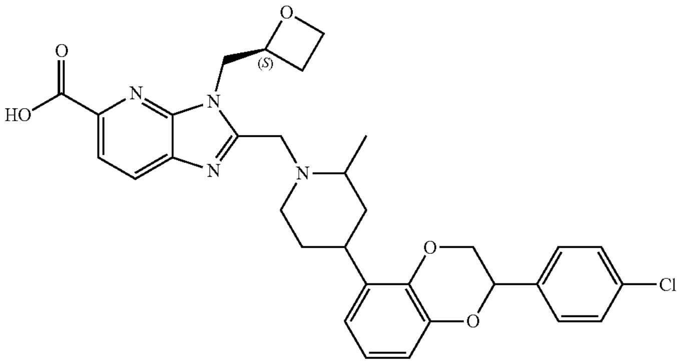 |
| 111a | 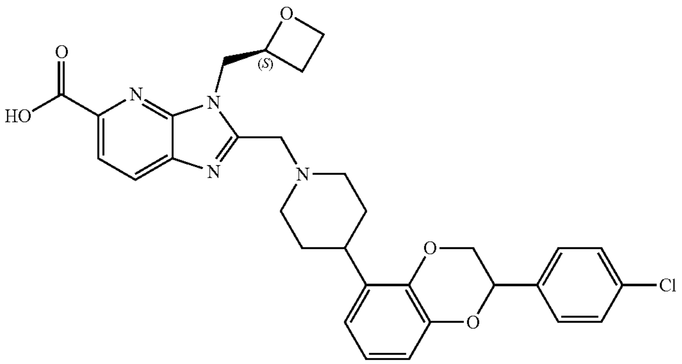 |

TABLE C2-continued
| Compound No. | Structure |
| --- | --- |
| 111b | 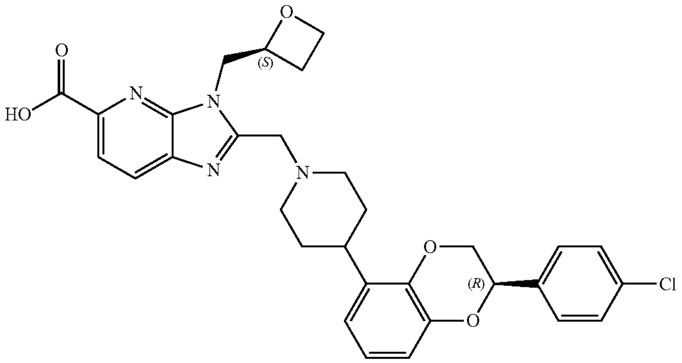 |
| 111c | 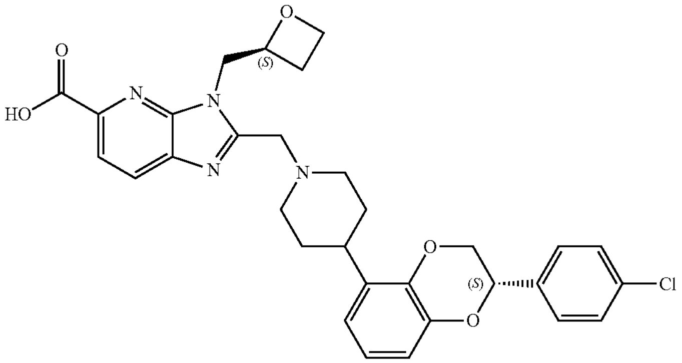 |
| 112a | 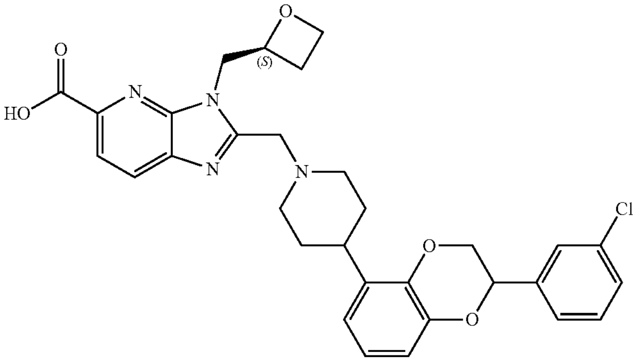 |
| 113a | 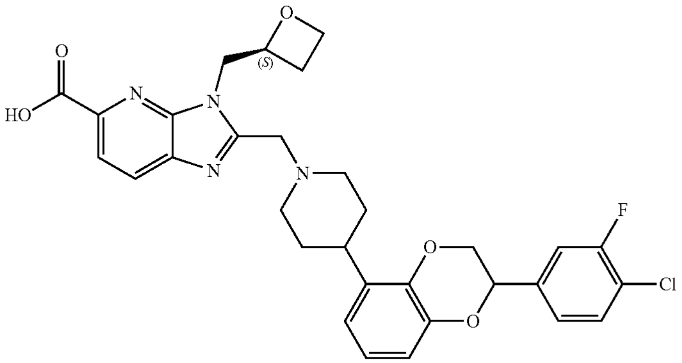 |

TABLE C2-continued
| Compound No. | Structure |
|---|---|
| 114a | 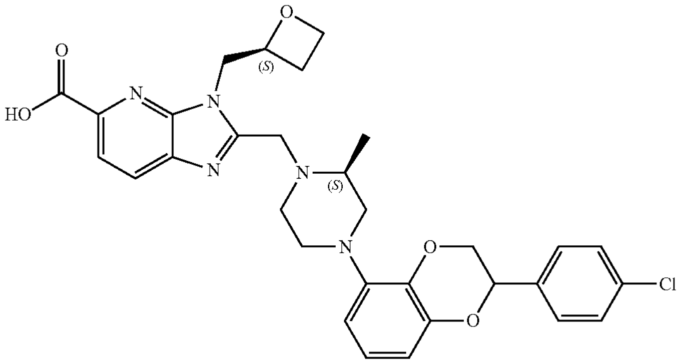 |
| 115a | 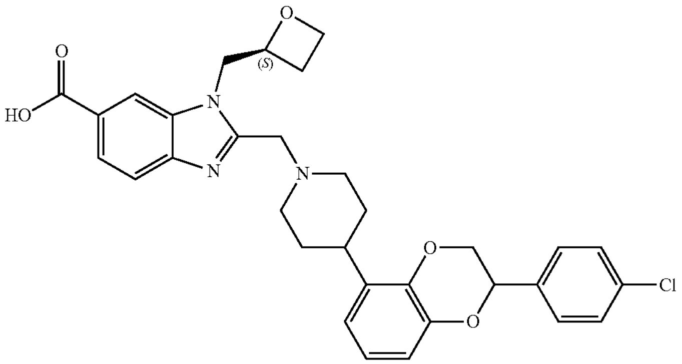 |
| 116a | 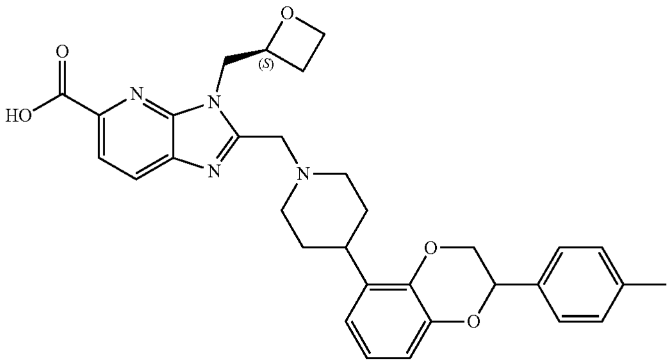 |
| 117a | 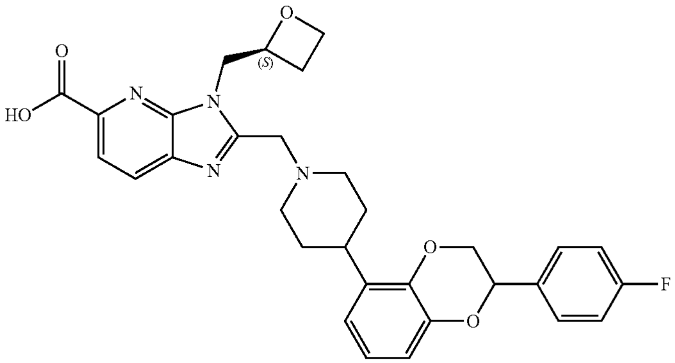 |

TABLE C2-continued
| Compound No. | Structure |
| --- | --- |
| 118a | 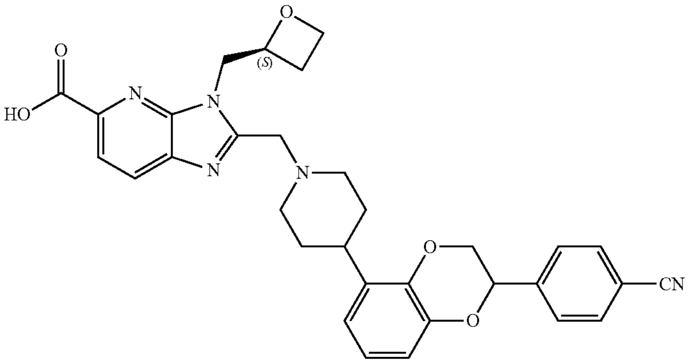 |
| 118b | 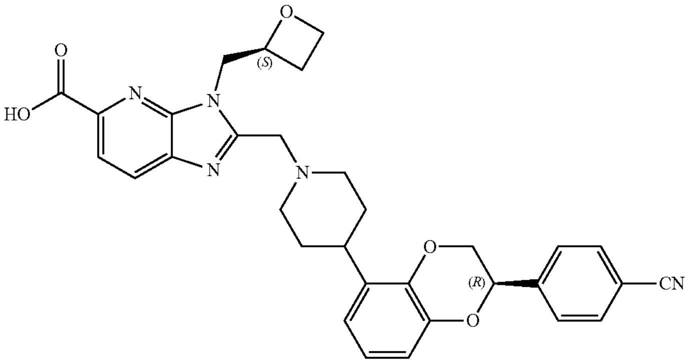 |
| 118c | 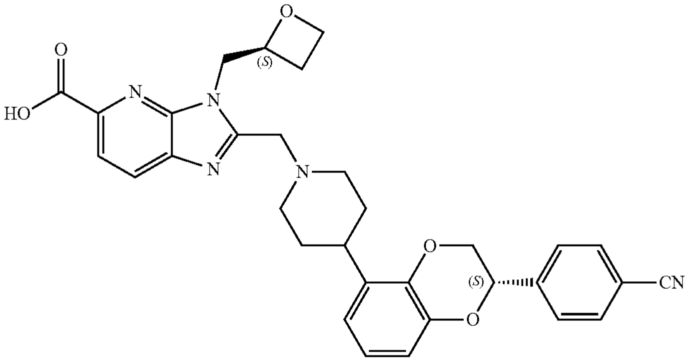 |
| 119a | 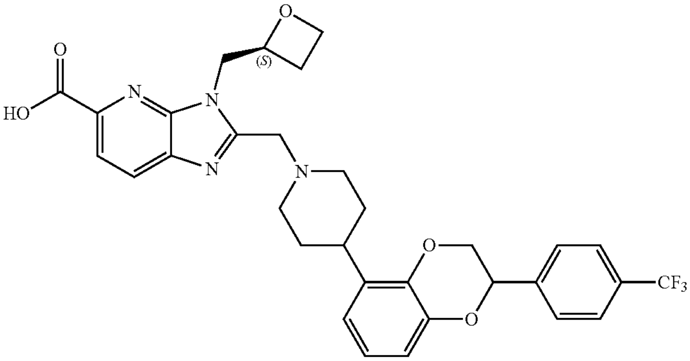 |

TABLE C2-continued
| Compound No. | Structure |
|---|---|
| 120a | 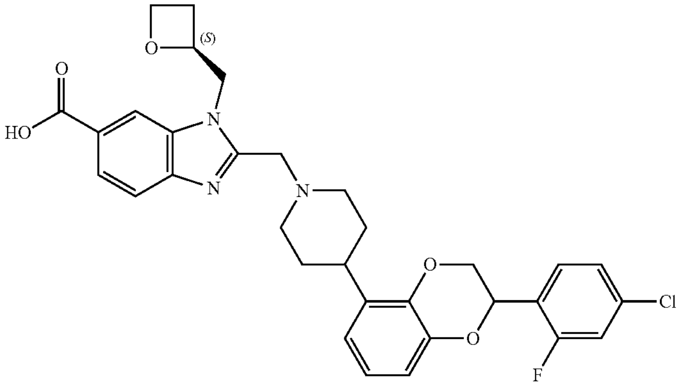 |
| 120b | 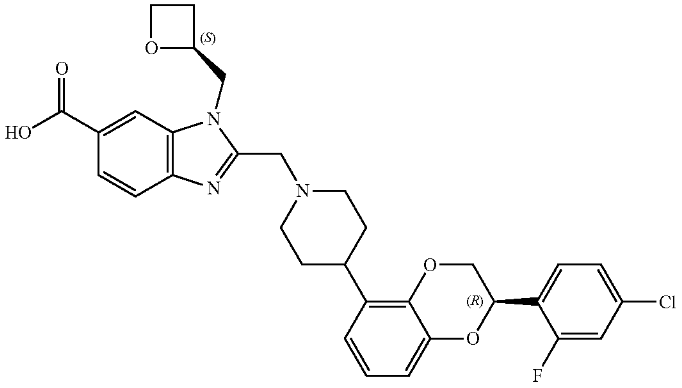 |
| 120c | 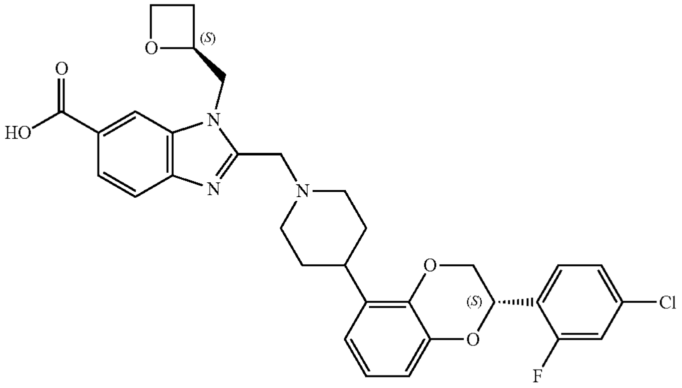 |
| 121a | 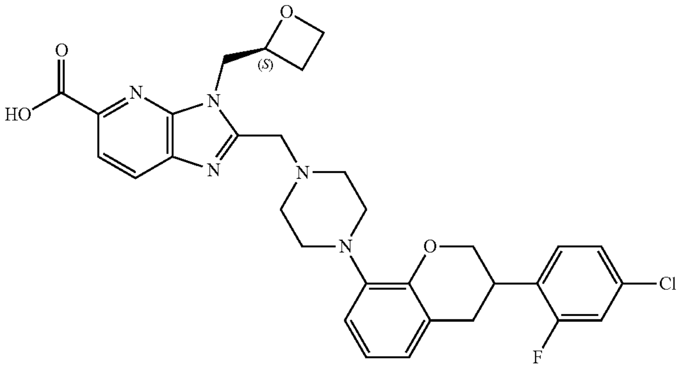 |

TABLE C2-continued
| Compound No. | Structure |
|---|---|
| 122a | 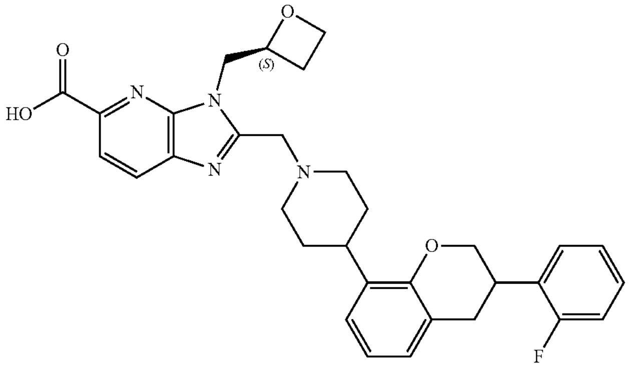 |
| 123a | 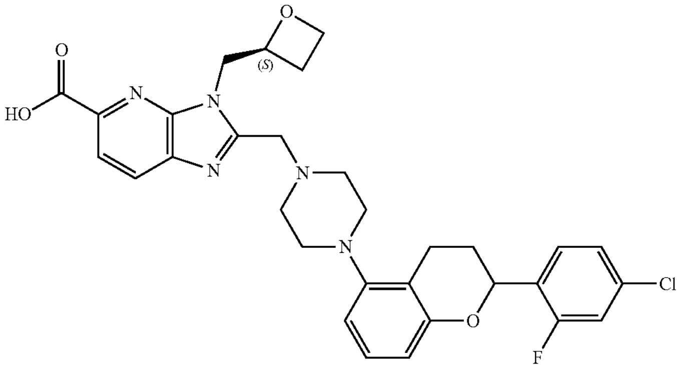 |
| 124a | 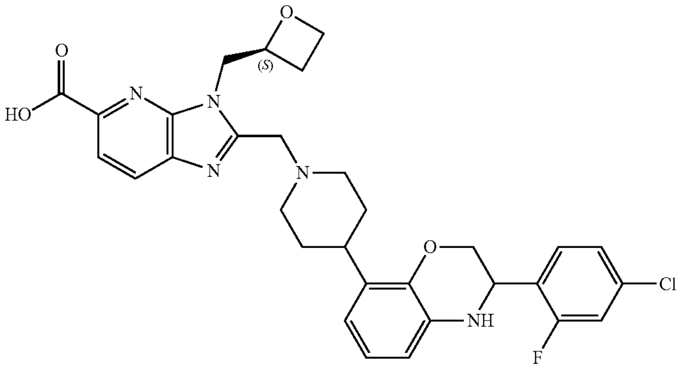 |
| 125a | 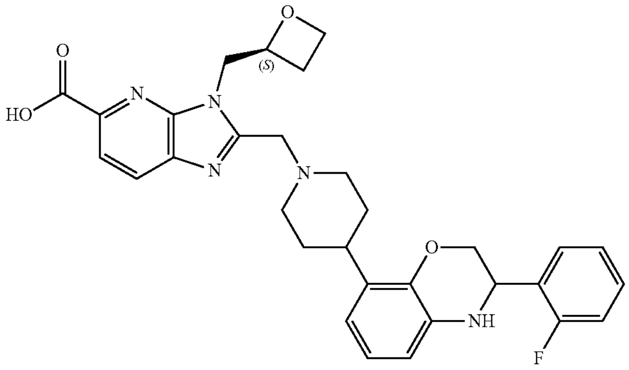 |

TABLE C2-continued
| Compound No. | Structure |
|---|---|
| 126a | 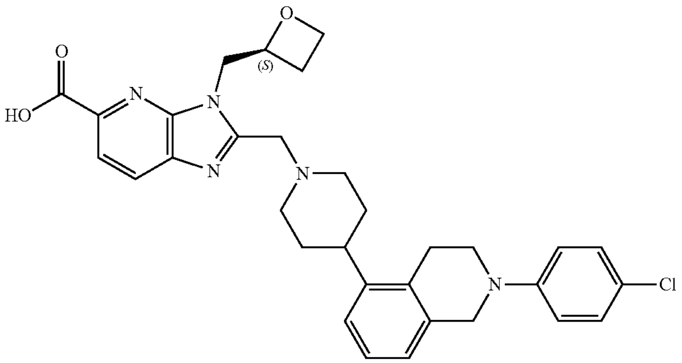 |
| 127a | 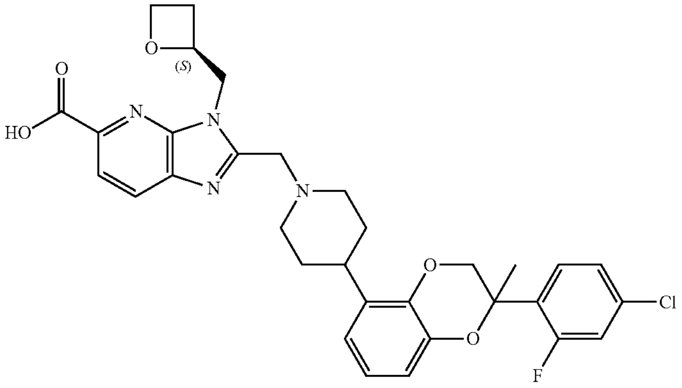 |
| 128a | 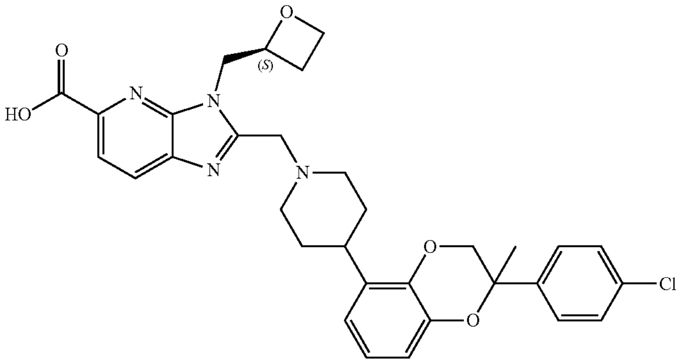 |
| 129a | 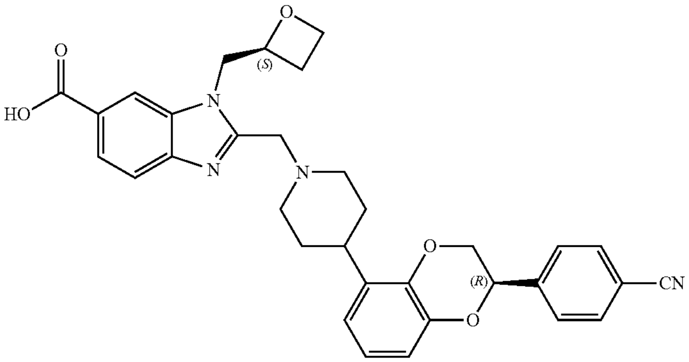 |

TABLE C2-continued

| Compound No. | Structure |
|---|---|
| 130a | 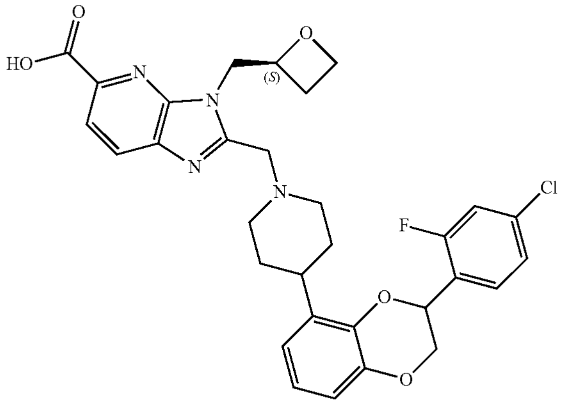 |
| 130b | 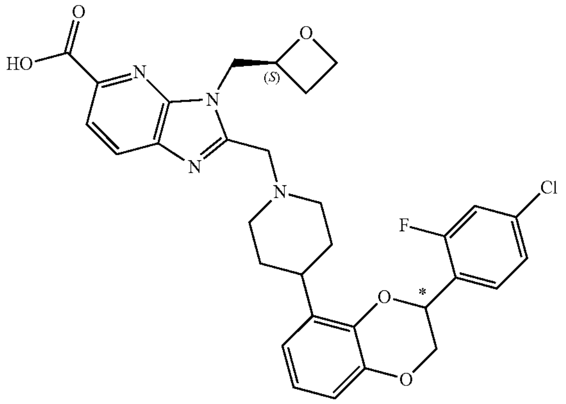 Diastereomer 1 |
| 130c | 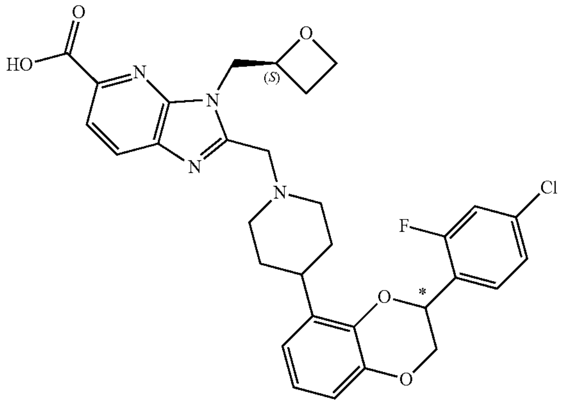 Diastereomer 2 |

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

Pharmaceutical Compositions and Administration

When employed as pharmaceuticals, the compounds of Formula I, including pharmaceutically acceptable salts or solvates thereof can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, or a pharmaceutically acceptable salt or solvate thereof, in combination with one or more pharmaceutically acceptable excipients (carriers). For example, a pharmaceutical composition prepared using a compound of Formula I, or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, or a pharmaceutically acceptable salt or solvate thereof with a pharmaceutically acceptable excipient. Pharmaceutical compositions containing a compound of Formula I, or a pharmaceutically acceptable salt or solvate thereof as the active ingredient can be prepared by intimately mixing the compound of Formula I, or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non- toxic excipient may be prepared. The contemplated compositions may contain 0.001%- 100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22nd Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein or a pharmaceutical composition thereof is formulated for ocular administration. In some embodiments, ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments, the dosage for a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), is determined based on a multiple factors including, but not limited to, type, age, weight, sex, medical condition of the patient, severity of the medical condition of the patient, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein is administered as a dosage of about 100 mg/Kg.

In some embodiments, the foregoing dosages of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is administered to a patient for a period of time followed by a separate period of time where administration of the compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is stopped. In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is administered for a first period and a second period following the first period, with administration stopped during the second period, followed by a third period where administration of the compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) is started and then a fourth period following the third period where administration is stopped. For example, the period of administration of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), is orally administered to the patient one or more times per day (e.g., one time per day, two times per day, three times per day, four times per day per day or a single daily dose).

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), is administered by parenteral administration to the patient one or more times per day (e.g., 1 to 4 timesone time per day, two times per day, three times per day, four times per day or a single daily dose).

In some embodiments, a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), is administered by parenteral administration to the patient weekly.

Methods of Treatment

In some embodiments, this disclosure features methods for treating a patient (e.g., a human) having a disease, disorder, or condition in which modulation of GLP1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), or a pharmaceutical composition as disclosed herein.

In some embodiments, the disease, disorder, or condition includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity (including hypothalamic obesity and monogenic obesity), weight gain from use of other agents idiopathic intracranial hypertension, Wolfram syndrome, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, kidney disease (e.g., acute kidney disorder, tubular dysfunction, proinflammatory changes to the proximal tubules), adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), nonalcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to type 2 diabetes mellitus, early onset type 2 diabetes mellitus, obesity, idiopathic intracranial hypertension, Wolfram syndrome, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of a reduction of blood glucose levels (e.g., reduce blood glucose levels), a reduction of blood hemoglobin Alc (HbAlc) levels, a promotion of insulin synthesis, a stimulation of insulin secretion, an increase in the mass of B-cells, a modulation of gastric acid secretion, a modulation of gastric emptying, a decrease in the body mass index (BMI), and/or a decrease in glucagon production (e.g., level). In some embodiments, the compounds and pharmaceutical compositions and methods for treating a patient described herein can reduce blood glucose levels, reduce blood hemoglobin Alc (HbAlc) levels, promote insulin synthesis, stimulate insulin secretion, increase the mass of β-cells, modulate gastric acid secretion, modulate gastric emptying, decrease the body mass index (BMI), decrease glucagon production (e.g., level), or any combination thereof. In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt or solvate thereof (e.g., a compound of any one of Formulas IA, IB, IB-1, IC, ID, IE, and IE-1, or a pharmaceutically acceptable salt or solvate thereof), or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease or disorder is obesity and conditions, diseases or disorders that are associated with or related to obesity. Nonlimiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, urine incontinence, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Nonlimiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt or solvate thereof (e.g., a compound of any one of a compound of any one of Formulas IA, IB, IB-1, IC, ID, IE, and IE-1, or a pharmaceutically acceptable salt or solvate thereof, or a pharmaceutically acceptable salt or solvate thereof) or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt or solvate thereof (e.g., a compound of any one of a compound of any one of Formulas IA, IB, IB-1, IC, ID, IE, and IE-1, or a pharmaceutically acceptable salt or solvate thereof, or a pharmaceutically acceptable salt or solvate thereof), or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt or solvate thereof (e.g., a compound of any one of a compound of any one of Formulas IA, IB, IB-1, IC, ID, IE, and IE-1, or a pharmaceutically acceptable salt or solvate thereof, or a pharmaceutically acceptable salt or solvate thereof), or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbAlc levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI. In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dl indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbAlc levels of about 5% to about 95% indicates treatment of type 2 diabetes mellitus. In some embodiments, a reduction in HbAlc levels of about 15% to about 80% indicates treatment of type 2 diabetes mellitus. In some embodiments, a reduction in HbAlc levels of about 25% to about 60% indicates treatment of type 2 diabetes mellitus. In some embodiments, reduction in HbAlc levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include prediabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, hyperlipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and can ultimately lead to cirrhosis (Skelly et al., *J Hepatol* 2001; 35:195-9; Chitturi et al., *Hepatology* 2002; 35 (2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., *J Gastroenterol Hepatol* 2002; 17 Suppl: S186-90).

Other non-limiting examples of disorders in metabolically important tissues include joint disorders (e.g., osteoarthritis, secondary osteoarthritis), steatosis (e.g. in the liver); fibrosis (e.g., in the liver); cirrhosis (e.g., in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease or disorder is a neurological disorder (e.g., neurodegenerative disorder) or a psychiatric disorder. Non-limiting examples of neurological disorders include idiopathic intracranial hypertension (IIH), brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., U.S. Publication No. 20060275288A1.

In some embodiments, the condition, disease or disorder is idiopathic intracranial hypertension. Idiopathic intracranial hypertension is characterized by increased intracranial pressure and papilloedema. See, e.g., Virdee et al. *Ophthalmol Ther.* 2020; 9 (4): 767-781. In some embodiments, the compounds and pharmaceutical compositions and methods described herein reduce cerebrospinal fluid secretion in a patient with idiopathic intracranial hypertension. In some embodiments, the compounds and pharmaceutical compositions and methods described herein reduce intracranial pressure in a patient with idiopathic intracranial hypertension. In some embodiments, the compounds and pharmaceutical compositions and methods described herein reduce one or more symptoms in a patient with idiopathic intracranial hypertension. Symptoms of idiopathic intracranial hypertension can include severe headaches and visual impairment. In some embodiments, the patient with idiopathic intracranial hypertension is female. In some embodiments, the patient with idiopathic intracranial hypertension is about 20 to about 30 years old. In some embodiments, the patient with idiopathic intracranial hypertension is obese.

In some embodiments, the condition, disease or disorder is Wolfram syndrome. Wolfram syndrome is caused by biallelic mutations of the Wolframin E R transmembrane glycoprotein (Wfs1) gene. See, e.g., Seppa et al. *Sci Rep* 9, 15742 (2019). Wolfram syndrome can first appear as diabetes mellitus, followed by optic nerve atrophy, deafness, and symptoms of neurodegeneration. Patients with Wolfram syndrome can have symptoms of ataxia, sleep apnea, dysphagia, hearing loss, and loss of taste due to brainstem atrophy. In some embodiments, the compounds and pharmaceutical compositions and methods described herein reduce neuroinflammation in a patient with Wolfram syndrome. In some embodiments, the neuroinflammation is reduced in the inferior olive in the patient. In some embodiments, the compounds and pharmaceutical compositions and methods described herein reduce retinal ganglion cell death in a patient with Wolfram syndrome. In some embodiments, the compounds and pharmaceutical compositions and methods described herein reduce axonal degeneration in a patient with Wolfram syndrome. In some embodiments, the compounds and pharmaceutical compositions and methods described herein reduce one or more symptoms (e.g., any of the symptoms described herein) in a patient with Wolfram syndrome.

Non-limiting examples of psychiatric disorders include drugdependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., U.S. Publication No. 20120021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., U.S. Publication No. 20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking. In some embodiments, the weight gain is induced by the use of steroids or antipsychotics.

In some embodiments, the condition, disease or disorder is an eating disorder, such as hyperphagia, binge eating, bulimia, compulsive eating, or syndromic obesity such as Prader-Willi and Bardet-Biedl syndromes.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like Creative protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary nonpolyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the condition, disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamicpituitary-gonadal axis diseases include, but are not limited to, hypogonadism, polycystic ovary syndrome, hypothyroidism, hypopituitarism, sexual dysfunction, and Cushing's disease.

In some embodiments, the condition, disease or disorder associated with diabetes is related to the hypothalamic-pituitary-gonadal axis.

Pulmonary Disease

In some embodiments, the condition, disease or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the condition, disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of Formula I (e.g., a compound of any one of Formulas IA, IB, IB-1, IC, ID, IE, and IE-1 or a pharmaceutically acceptable salt or solvate thereof, or a pharmaceutically acceptable salt or solvate thereof), or a pharmaceutically acceptable salt or solvate thereof as described herein can be administered in combination with one or more additional therapeutic agents. Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, and therapeutic agents for dysuria.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), peptide YY or an analogue thereof, cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498, naltrexone), orexin receptor antagonists, melanocortin 4 receptor agonists, 11β-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCOA carboxylase (ACC) inhibitors (e.g., compounds described in WO 2020/234726, WO 2020/044266, and U.S. Pat. No. 8,859,577), stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin), empagliflozin, canagliflozin, ipragliflozin, tofogliflozin, sergliflozin etabonate, remogliflozin etabonate, or ertugliflozin), SGLT-1 inhibitors, MCR-4 agonists, monoamine reuptake inhibitors, melanocytestimulating hormone analogs, 5HT2c agonists, galanin antagonists, anorectic agents (such as a bombesin agonist), thyromimetic agents, dehydroepiandrosterone or analogs thereof, human agoutirelated protein (AGRP) inhibitors, neuromedin U agonists, NFK inhibitors (e.g., HE3286), PPAR agonists (e.g., GFT-505, DRF-11605, gemfibrozil, fenofibrate, balaglitazone, ciglitazone, darglitazone, englitazone, isaglitazone, pioglitazone, rosiglitazone, CLX-0940, GW-1536, GW-1 929, GW-2433, KRP-297, L-796449, $LR^{90}$, MK-0767, and SB-21 9994), phosphotyrosine phosphatase inhibitors (e.g., sodium vanadate, trodusquemin), $GPR^{119}$ agonists (e.g., PSN-821, MBX-2982, APD597, compounds described in WO 2010/140092, WO 2010/128425, WO 2010/128414, WO 2010/106457), glucokinase activators (e.g., piragliatin, AZD-1656, AZD6370, TTP-355, TTP-399, TTP547, $ARR^{Y403}$, MK-0599, TAK-329, AZD5658 or GKM001 compounds described in WO 2010/103437, WO 2010/103438, WO 2010/013161, WO 2007/122482, WO 2006/112549, WO 2007/028135, WO 2008/047821, WO 2008/050821, WO 2008/136428 and WO 2008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), melanocortin receptor 4 agonist (e.g., setmelanotide), melanin concentrating hormone receptor 1 antagonist, serotonergic agents (e.g. sibutramine, lorcaserin), farnesoid X receptor (FXR) agonist (e.g., obeticholic acid, tropifexor, cilofexor, LY2562175, Met409, TERN-101, EDP305, compounds described in WO 2020/234726 and WO 2020/044266), phentermine, zonisamide, norepinephrine/dopamine reuptake inhibitor (e.g., buproprion), GDF-15 analog, methionine aminopeptidase 2 (MetAP2) inhibitor (e.g., beloranib or ZGN-1061), diethylpropion, phendimetrazine, benzphetamine, fibroblast growth factor receptor (FGFR) modulator, biotin, a MAS receptor modulator, glucagon receptor agonist, CCKa agonists (e.g., compounds described in WO 2005/116034 and U.S. Publication No. 2005/0287100), and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, glimepiride, tolbutamide, glibenclamide, gliclazide, acetohexamide, glyclopyramide, glybuzole, glyburide, glipizide), thiazolidinedione agents (e.g. rosiglitazone, lobeglitazone, troglitazone, balaglitazone, rivoglitazone, lobeglitazone or pioglitazone), glitazars (e.g., aleglitazar, chiglitazar, saroglitazar, muraglitazar, tesaglitazar), SGLT2 inhibitors (e.g., JNJ-28431754, dapagliflozin, AVE2268, TS-033, YM543, TA-7284, ASP1941, $THR^{1474}$, TS-071, ISIS388626, LX4211, remogliflozin, empagliflozin, canagliflozin, ipragliflozin, tofogliflozin, sergliflozin etabonate, remogliflozin etabonate, ertugliflozin, compounds described in WO 2010/023594), $GPR^{40}$ agonists (e.g., a $FFAR^1$/FFA1 agonist, e.g. fasiglifam), aglucosidase inhibitors (e.g., adiposin, camiglibose, pradimicin-Q, salbostatin, voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-IR agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, anagliptin (SK-0403), teneligliptin, omarigliptin, BI1356, GRC8200, MP-513, PF-00734200, PHX1149, ALS2-0426, TA-6666, TS-021, KRP104, trelagliptin).

In some embodiments, the one or more additional therapeutic agents include those useful, for example, for treating NAFL and NASH. Non-limiting examples include FXR agonists (e.g., obeticholic acid), PF-05221304, PPAR a/8 agonists (e.g., elafibranor), a synthetic fatty acid-bile conjugate (e.g., aramchol), an anti-lysyl oxidase homologue 2 (LOXL2) monoclonal antibody (e.g., simtuzumab), a caspase inhibitor (e.g., emricasan), a MAPK5 inhibitor (e.g., GS-4997), a galectin 3 inhibitor (e.g., GR-MD-02), a fibroblast growth factor 21 (FGF21) (e.g., BMS-986036), a niacin analogue (e.g., ARJ 3037MO), a leukotriene D4 (LTD4) receptor antagonist (e.g., tipelukast), an acetyl-CoA carboxylase (ACC) inhibitor (e.g., NDI 010976 and compounds described in WO 2009/144554, WO 2003/072197, WO 2009/144555, and WO 2008/065508), a ketohexokinase (KHK) inhibitor (e.g., compounds described in WO 2020/234726), an apoptosis signal-regulating kinase 1 (ASK1) inhibitor, an ileal bile acid transporter (IBAT) inhibitor, a dual antagonist of chemokine receptor 2 ($CCR^2$) and $CCR^5$ (e.g., cenicriviroc), diacylglyceryl acyltransferase 2 (DGAT2) inhibitor (e.g., compounds described in WO 2020/234726 and U.S. Publication No. 20180051012), a CB1 receptor antagonist, an anti-CBIR antibody, glycyrrhizin, schisandra extract, ascorbic acid, glutathione, silymarin, lipoic acid, and d-alphatocopherol, ascorbic acid, glutathione, vitamin B-complex, glitazones/thiazolidinediones (e.g., troglitazone, rosiglitazone, pioglitazone, balaglitazone, rivoglitazone, lobeglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO 2001/14372 (e.g., 4-(4-chlorophenyl)-2-(2-methyl-1-imidazolyl)-5-[3-(2-methylphenoxyl) propyl] oxazole), compounds described in WO 2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and @-3 fatty acid preparations (e.g., ω-3-fatty acid ethyl esters 90).

In some embodiments, the one or more additional therapeutic agents include those useful, for example, as antihypertensive agents. Non-limiting examples include angiotensin converting enzyme inhibitors (e.g., captopril, zofenopril, fbsinopril, enalapril, ceranopril, cilazopril, delapril, pentopril, quinapril, ramipril, lisinopril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol). Further nonlimiting examples of antihypertensive agents include: diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone), alpha adrenergic blockers, beta adrenergic blockers, calcium channel blockers (e.g., diltiazem, verapamil, nifedipine and amlodipine), vasodilators (e.g., hydralazine), renin inhibitors, AT-1 receptor antagonists (e.g., losartan, irbesartan, valsartan), ET receptor antagonists (e.g., sitaxsentan, atrsentan, compounds disclosed in U.S. Pat. Nos. 5,612,359 and 6,043,265), dual ET/AII antagonist (e.g., compounds disclosed in WO 2000/01389), neutral endopeptidase (NEP) inhibitors, If channel blocker ivabradinand, vasopepsidase inhibitors (dual NEP-ACE inhibitors) (e.g., gemopatrilat and nitrates).

In some embodiments, the one or more additional therapeutic agents include those useful, for example, as diuretics. Non-limiting examples include_xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as antithrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran, boroarginine derivatives, boropeptides, heparins, hirudin, and melagatran), FXa inhibitors (e.g., rivaroxaban, apixaban, edoxaban, YM150, compounds described in WO 2002/06234, WO 2004/048363, WO 2005/030740, WO 2005/058823, and WO 2005/113504) thrombolytic agents (e.g., anistreplase, streptokinase, tenecteplase (TNK), lanoteplase (nPA), urokinase, tisokinase, alteplase, nateplase, monteplase, pamiteplase, factor VIIa inhibitors, PAI-1 inhibitors, alpha2-antiplasmin inhibitors, and anisoylated plasminogen streptokinase activator complex), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin $B^1$ and vitamin $B^{12}$. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of antiinflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-COA reductase inhibitors (statins, e.g. rosuvastatin, pravastatin, pitavastatin, lovastatin, atorvastatin, simvastatin, fluvastatin, itavastatin, ZD-4522), HMG-COA synthase inhibitors, cholesterol-lowering agents, bile acid sequestrants (e.g., cholestyramine, questran, colestipol, and colesevelam), cholesterol absorption inhibitors (e.g. plant sterols such as phytosterols), cholesteryl ester transfer protein (CETP) inhibitors, inhibitors of the ileal bile acid transport system (IBAT inhibitors), diacylglyceryl acyltransferase 1 (DGAT1) inhibitors (e.g., AZD7687, LCQ908, compounds described in WO 2009/016462, WO 2010/086820), monoacylglycerol O-acyltransferase inhibitors, aamylase inhibitors (e.g., tendamistat, trestatin, AL-3688), α-glucoside hydrolase inhibitors, SIRT-1 activators, c-Jun N-terminal kinase (JNK) inhibitors, a VPAC2 receptor agonist, $TGR^5$ receptor modulators (e.g., compounds described in), GPBARI receptor modulators, $GPR^{120}$ modulators, high affinity nicotinic acid receptor (HM74A) activators, carnitine palmitoyl transferase enzyme inhibitors, mineralocorticoid receptor inhibitors, inhibitors of TORC2, fatty acid synthetase inhibitors, serine palmitoyl transferase inhibitors, $GPR^{81}$ modulators, $GPR^{39}$ modulators, $GPR^{43}$ modulators, $GPR^{41}$ modulators, $GPR^{105}$ modulators, Kv1.3 modulators, retinol binding protein 4 modulators, somatostain receptor modulators, PDHK2 modulators, PDHK4 modulators, MAP4K4 inhibitors, IL1 family modulators (e.g., ILI beta modulators), ACAT inhibitors, MTP inhibitors (e.g., diriotapide, mitratapide, and implitapide), lipooxygenase inhibitors, PCSK9 modulators (e.g., alirocumab and evolocumab), RXRalpha modulators, cysteamine, cystamine, an RNA antisense construct to inhibit protein tyrosine phosphatase PTPRU, vitamin B complex, pentraxin proteins, a protein tyrosine phosphatase-1 B (PTP-1 B) inhibitor (e.g., trodusquemine, hyrtiosal extract, and compounds described by Zhang et al. *Drug Discovery Today.* 2007, 12 (9-10): 373-381), ezitimbe, betaine, pentoxifylline, alpha delta-9 desaturase, BCKDK inhibitors, branched-chain alpha keto acid dehydrogenase kinase (BCBK) inhibitors, PNPLA3 inhibitors, FGF1 9 analogs, SCD1 inhibitors, bile acid binding resins, nicotinic acid (niacin) and analogues thereof, antioxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone, spironolactone), centrally acting adrenergic drugs, such as central alpha agonists (e.g. clonidine), diuretic agents (e.g. furosemide, torsemide, bemetanide, ethacrynic acid, thiazide-type diuretics (e.g., chlorothiazide, hydrochlorothiazide, benzthiazide, hydroflumethiazide, bendroflumethiazide, methychlorthiazide, polythiazide, trichlormethiazide, indapamide), phthalimidine-type diuretics (e.g., chlorthalidone, metolazone), quinazoline-type diuretics (e.g., quinethazone), potassium-sparing diuretics (e.g., triamterene and amiloride), thyroid receptor agonists (e.g., compounds described in WO 2020/117987), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin), non-steroidal anti-inflammatory drugs (NSAIDS), thromboxane-A2-receptor antagonists (e.g., ifetroban), thromboxane-A2-synthetase inhibitors, PDE inhibitors (e.g., Pletal, dipyridamole)), antagonists of purinergic receptors (e.g., P2Y1 and P2Y12), adenosine diphosphate (ADP) receptor inhibitors (e.g. clopidogrel), phosphodiesterase inhibitors (e.g. cilostazol), glycoprotein IIB/IIA inhibitors (e.g. tirofiban, eptifibatide, and abcixima), adenosine reuptake inhibitors (e.g. dipyridamole), noradrenergic agents (e.g. phentermine), serotonergic agents (e.g. sibutramine, lorcaserin), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in WO 2007/013694, WO 2007/018314, WO 2008/093639 and WO 2008/099794, $GPR^{40}$ agonists (e.g., fasiglifam or a hydrate thereof, compounds described in WO 2004/041266, WO 2004/106276, WO 2005/063729, WO 2005/063725, WO 2005/087710, WO 2005/095338, WO 2007/013689 and WO 2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-$\alpha$, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor a (PPARa), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., $K^+$ channel openers, mexiletine, propafenone, metoprolol, atenolol, carvadiol, propranolol, sotalol, dofetilide, amiodarone, azimilide, ibutilide, ditiazem, and verapamil), acetylcholine receptor ligands (e.g., ABT-594), endothelin receptor antagonists (e.g., ABT-627), narcotic analgesics (e.g., morphine), a2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-$\beta$), immunomodulators (e.g., glatiramer), TNF-binding proteins (e.g., circulating receptors), immunosupressants (e.g., mycophenolate), metaglidasen, AMG-131, balaglitazone, MBX-2044, rivoglitazone, aleglitazar, chiglitazar, saroglitazar, muraglitazar, tesaglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide, piroxicam, NO donating agents (e.g., organonitrates), NO promoting agents (e.g., phosphodiesterase inhibitors).

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin Alc (HbAlc), fasting plasma glucose, non-fasting plasma glucose, or any combination thereof. In some embodiments, the level of HbAlc is about 6.5% to about 24.0%. In some embodiments, the level of HbAlc is greater than or about 6.5%. In some embodiments, the level of HbAlc is greater than or about 8.0%. In some embodiments, the level of HbAlc is greater than or about 10.0%. In some embodiments, the level of HbAlc is greater than or about 12.0%. In some embodiments, the level of HbAlc is greater than or about 14.0%. In some embodiments, the level of HbAlc is greater than or about 16.0%. In some embodiments, the level of HbAlc is greater than or about 18.0%. In some embodiments, the level of HbAlc is greater than or about 20.0%. In some embodiments, the level of HbAlc is greater than or about 22.0%. In some embodiments, the level of HbAlc is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 $kg/m^2$ to greater than or about 100 $kg/m^2$. In some embodiments, the BMI of the patient is greater than or about 30 $kg/m^2$ to greater than or about 90 $kg/m^2$. In some embodiments, the BMI of the patient is greater than or about 40 $kg/m^2$ to greater than or about 80 $kg/m^2$. In some embodiments, the BMI of the patient is greater than or about 50 $kg/m^2$ to greater than or about 70 $kg/m^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W. B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

EXAMPLES

The invention is further described in the following examples, which do not limit the scope of the invention described in the claims.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. H chemical shifts are reported in 8 values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Example 1

3-((S)-oxetan-2-ylmethyl)-2-((4-(2-phenyl-2,3-dihydrobenzo[b][1,4]dioxin-5-yl) piperidin-1-yl)methyl)-3H-imidazo[4,5-b]pyridine-5-carboxylic acid (Compound 101a)

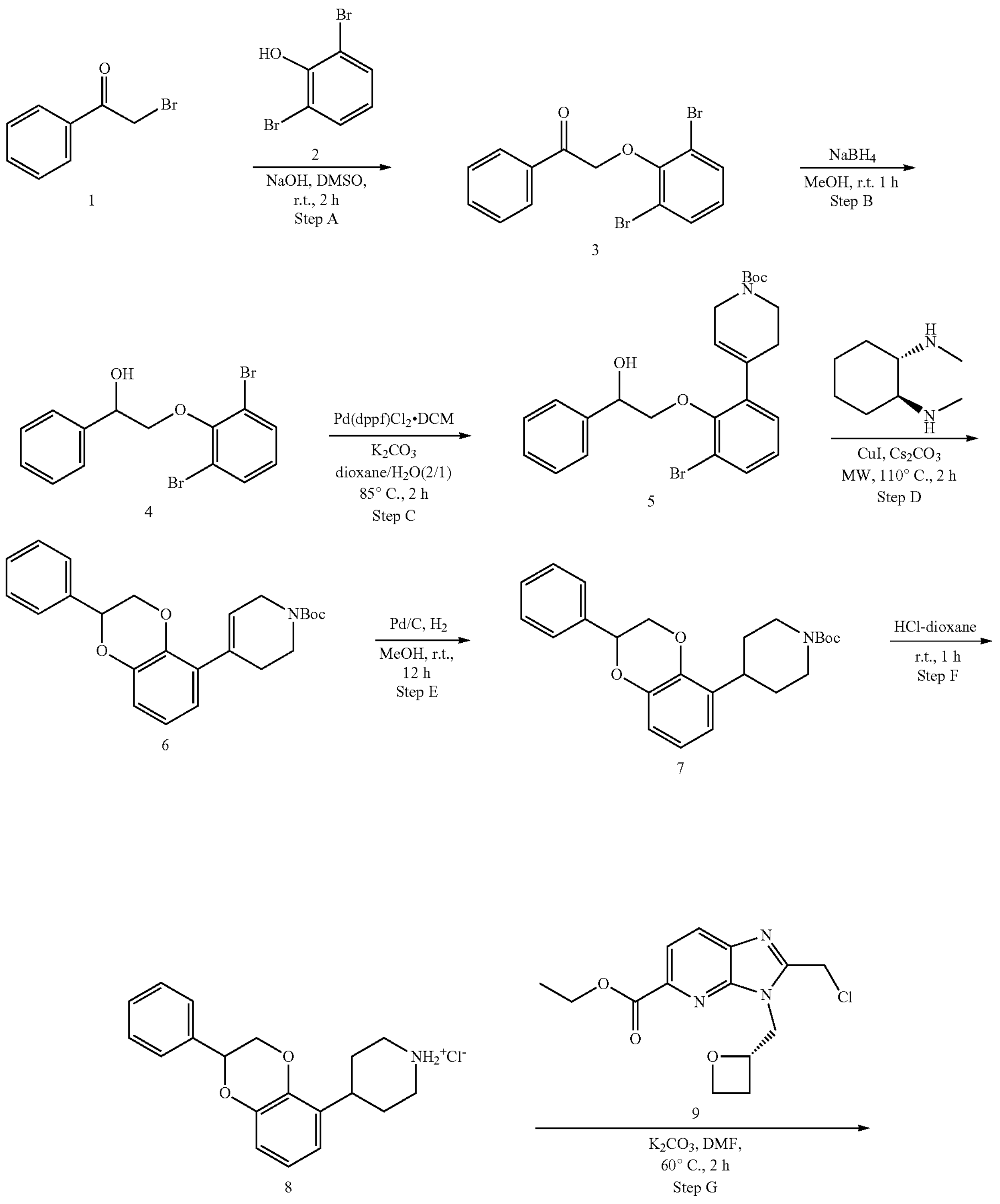

-continued

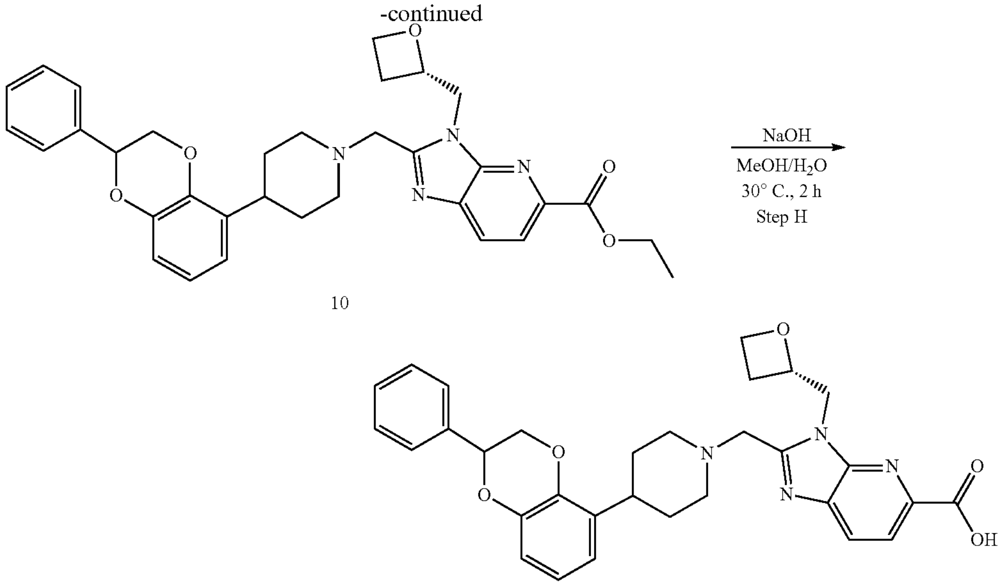

10

Example 1

Step A: 2-(2,6-Dibromophenoxy)-1-Phenylethanone

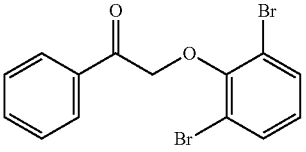 [SMILES: O=C(COc1c(Br)cccc1Br)c1ccccc1]

To a solution of 2-bromo-1-phenylethanone (3.90 g, 19.8 mmol, 1.1 equiv) and 2,6-dibromophenol (4.50 g, 18.0 mmol, 1.0 equiv) in DMSO (30 mL) was added NaOH (870 mg, 19.8 mmol, 1.1 equiv). The resulting mixture was stirred at room temperature for 2 hours under $N_2$ atmosphere. The reaction mixture was diluted with water (60 mL) and extracted with ethyl ether (3×80 mL). The combined organic phase was washed with brine (30 mL), dried over anhydrous $Na_2SO_4$ and concentrated. The residue was purified by flash chromatography (eluted with PE/EtOAc=10/1) to afford the title compound 2-(2,6-dibromophenoxy)-1-phenylethanone as a white solid (3.50 g, 53% yield).

$^1$H NMR (400 MHZ, $CDCl_3$) δ ppm 8.01-8.03 (m, 2H), 7.59-7.64 (m, 1H), 7.48-7.55 (m, 4H), 6.93 (t, J=8.0 Hz, 1H), 5.28 (s, 2H).

Step B: 2-(2,6-dibromophenoxy)-1-phenylethan-1-ol

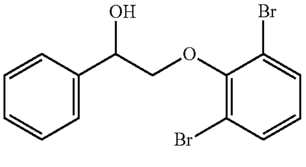 [SMILES: OC(COc1c(Br)cccc1Br)c1ccccc1]

To a solution of 2-(2,6-dibromophenoxy)-1-phenylethanone (3.50 g, 9.41 mmol, 1.0 equiv) in MeOH (100 mL) was added $NaBH_4$ (712 mg, 18.8 mmol, 2.0 equiv). The resulting mixture was stirred at room temperature for 1 hour. The reaction mixture was quenched with water (10 mL) and MeOH was evaporated. The resulting mixture was extracted with DCM (3×80 mL). The combined organic phase was washed with brine (30 mL), dried over anhydrous $Na_2SO_4$ and concentrated to afford the crude title compound 2-(2,6-dibromophenoxy)-1-phenylethan-1-ol as a white solid (2.80 g, 80% yield). The crude was used directly in next step without purification.

$^1$H NMR (400 MHZ, DMSO-$d_6$) δ ppm 7.65 (d, J=8.0 Hz, 2H), 7.44-7.46 (m, 2H), 7.34-7.37 (m, 2H), 7.26-7.30 (m, 1H), 7.02 (t, J=8.0 Hz, 1H), 5.69 (d, J=4.0 Hz, 1H), 4.08 (dd, J=9.2, 7.2 Hz, 1H), 3.95 (dd, J=9.2, 4.8 Hz, 1H).

Step C: tert-butyl 4-(3-bromo-2-(2-hydroxy-2-phenylethoxy)phenyl)-5,6-dihydropyridine-1 (2H)-carboxylate

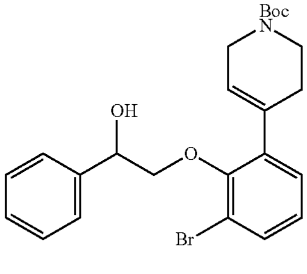 [SMILES: CC(C)(C)OC(=O)N1CC=C(c2cccc(Br)c2OCC(O)c2ccccc2)CC1]

A mixture of 2-(2,6-dibromophenoxy)-1-phenylethan-1-ol (1.45 g, 3.90 mmol, 1.0 equiv), tert-butyl 4-(4,4,5,5-tetramethyl-1,3,2-dioxaborolan-2-yl)-5,6-dihydropyridine-1 (2H)-carboxylate (1.20 g, 3.90 mmol, 1.0 equiv), Pd(dppf) $Cl_2$·DCM (320 mg, 0.390 mmol, 0.1 equiv) and $K_2CO_3$ (1.6 g, 11.7 mmol, 3.0 equiv) in dioxane/$H_2O$ (15 mL/7 mL) was stirred at 85° C. for 2 hours under $N_2$ atmosphere. The reaction mixture was filtered through celite and extracted with EtOAc (3×30 mL). The combined organic phase was washed with brine (20 mL), dried over anhydrous $Na_2SO_4$ and concentrated. The residue was purified by flash chromatography (eluted with PE/EtOAc=10/1) to afford the title compound tertbutyl 4-(3-bromo-2-(2-hydroxy-2-phenylethoxy)phenyl)-5,6-dihydropyridine-1 (2H)carboxylate as a colorless oil (850 mg, 46% yield).

$^1$H NMR (400 MHZ, $CDCl_3$) δ ppm 7.47 (dd, J=8.0, 1.6 Hz, 1H), 7.26-7.40 (m, 5H), 7.09 (dd, J=8.0, 1.6 Hz, 1H), 6.96 (t, J=8.0 Hz, 1H), 5.80 (s, 1H), 5.07 (d, J=8.0 Hz, 1H), 4.00-4.02 (m, 3H), 3.86-3.91 (m, 1H), 3.56 (t, J=4.0 Hz, 2H), 3.17 (d, J=1.6 Hz, 1H), 2.43 (d, J=8.0 Hz, 2H), 1.50 (s, 9H).

Step D: tert-butyl 4-(2-phenyl-2,3-dihydrobenzo[b][1,4]dioxin-5-yl)-5,6-dihydropyridine-1 (2H)-carboxylate

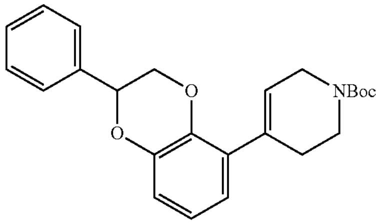

A mixture of tert-butyl 4-(3-bromo-2-(2-hydroxy-2-phenylethoxy)phenyl)-5,6-dihydropyridine-1 (2H)-carboxylate (850 mg, 1.80 mmol, 1.0 equiv), CuI (684 mg, 3.60 mmol, 2.0 equiv), (1S,2S)—N1,N2-dimethylcyclohexane-1,2-diamine (511 mg, 3.60 mmol, 2.0 equiv) and $Cs_2CO_3$ (1.76 g, 5.40 mmol, 3.0 equiv) in DMF (10 mL) was stirred at 110° C. via microwave irradiation for 2 hours under $N_2$ atmosphere. The reaction mixture was diluted with water (20 mL) and extracted with EtOAc (3×30 mL). The combined organic phase was washed with brine (30 mL), dried over anhydrous $Na_2SO_4$ and concentrated. The residue was purified by flash chromatography (eluted with PE/EtOAc=10/1) to afford the title compound tertbutyl 4-(2-phenyl-2,3-dihydrobenzo[b][1,4]dioxin-5-yl)-5,6-dihydropyridine-1 (2H) carboxylate as a colorless oil (280 mg, 39% yield).

$^1$H NMR (400 MHZ, $CDCl_3$) δ ppm 7.29-7.37 (m, 5H), 6.85 (dd, J=8.0, 2.0 Hz, 1H), 6.77 (t, J=8.0 Hz, 1H), 6.70 (dd, J=8.0, 2.0 Hz, 1H), 5.76 (s, 1H), 5.04 (dd, J=8.0, 2.4 Hz, 1H), 4.31 (dd, J=12.0, 2.4 Hz, 1H), 3.98 (d, J=2.0 Hz, 2H), 3.93 (dd, J=8.0, 2.4 Hz, 1H), 3.52-3.57 (m, 2H), 2.45 (s, 2H), 1.42 (s, 9H).

Step E: tert-butyl 4-(2-phenyl-2,3-dihydrobenzo[b][1,4]dioxin-5-yl)piperidine-1-carboxylate

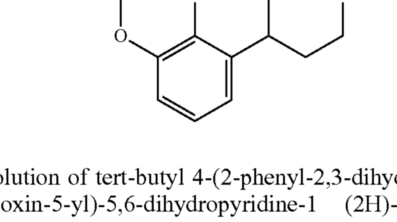

To a solution of tert-butyl 4-(2-phenyl-2,3-dihydrobenzo[b][1,4]dioxin-5-yl)-5,6-dihydropyridine-1 (2H)-carboxylate (280 mg, 0.710 mmol, 1.0 equiv) in MeOH (15 mL) was added Pd/C (28.0 mg, 10% wt) under $N_2$. The resulting mixture was degassed and refilled with $H_2$ for three times. Then the mixture was stirred at room temperature for 12 hours under $H_2$ atmosphere. The reaction mixture was filtered through celite and concentrated to afford the title compound tert-butyl 4-(2-phenyl-2,3-dihydrobenzo[b][1,4]dioxin-5-yl)piperidine-1-carboxylate as a white solid (260 mg, 93% yield). The title compound was used in next step directly without purification.

$^1$H NMR (400 MHZ, $CDCl_3$) δ ppm 7.37-7.43 (m, 5H), 6.83-6.88 (m, 2H), 6.76 (dd, J=8.0, 2.4 Hz, 1H), 5.11 (dd, J=8.0, 2.4 Hz, 1H), 4.40 (dd, J=11.6, 2.4 Hz, 1H), 4.24 (d, J=13.2 Hz, 2H), 4.00 (dd, J=11.2, 8.8 Hz, 1H), 3.05 (tt, J=12.0, 3.2 Hz, 1H), 2.82 (tt, J=12.8, 2.8 Hz, 1H), 1.77-1.86 (m, 2H), 1.55-1.68 (m, 2H), 1.48 (d, J=9.0 Hz, 9H).

Step F: 4-(2-phenyl-2,3-dihydrobenzo[b][1,4]dioxin-5-yl)piperidine hydrochloride

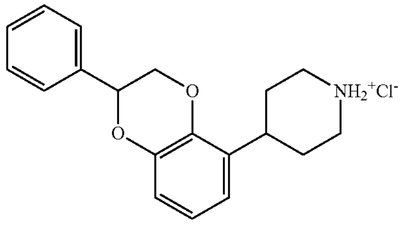

A solution of tert-butyl 4-(2-phenyl-2,3-dihydrobenzo[b][1,4]dioxin-5-yl)piperidine-1-carboxylate (260 mg, 0.66 mmol, 1.0 equiv) in HCl-dioxane solution (4M, 10 mL) was stirred at room temperature for 1 hour. The reaction mixture was concentrated to dryness to afford the title compound 4-(2-phenyl-2,3-dihydrobenzo[b][1,4]dioxin-5-yl) piperidine (220 mg, 100% yield) as a white solid.

LC-MS: m/z 296.1 $(M+H)^+$.

Step G: ethyl 3-((S)-oxetan-2-ylmethyl)-2-((4-(2-phenyl-2,3-dihydrobenzo[b][1,4]dioxin-5-yl)piperidin-1-yl)methyl)-3H-imidazo[4,5-b]pyridine-5-carboxylate

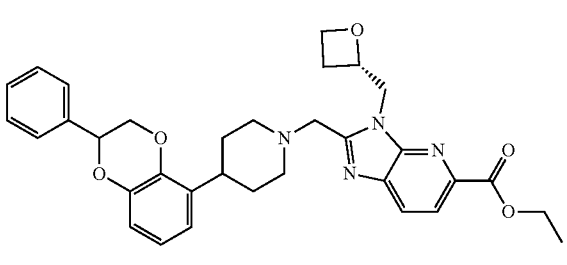 [SMILES: CCOC(=O)c1ccc2nc(CN3CCC(c4cccc5c4OCC(c4ccccc4)O5)CC3)n(C[C@@H]3CCO3)c2n1]

A mixture of 4-(2-phenyl-2,3-dihydrobenzo[b][1,4]dioxin-5-yl)piperidine hydrochloride (66.0 mg, 0.200 mmol, 1.0 equiv), (S)-ethyl 2-(chloromethyl)-3-(oxetan-2-ylmethyl)-3H-imidazo[4,5-b]pyridine-5-carboxylate (62.0 mg, 0.200 mmol, 1.0 equiv) and $K_2CO_3$ (55.0 mg, 0.400 mmol, 2.0 equiv) in DMF (2 mL) was stirred at 60° C. for 2 hours. The reaction mixture was diluted with water (10 mL) and extracted with EtOAc (3×10 mL). The combined organic phase was washed with brine (10 mL), dried over anhydrous $Na_2SO_4$ and concentrated. The residue was purified by flash chromatography (eluted with DCM/MeOH=50/1) to afford the title compound ethyl 3-((S)-oxetan-2-ylmethyl)-2-((4-(2-phenyl-2,3-dihydrobenzo[b][1,4]dioxin-5-yl) piperidin-1-yl)methyl)-3H-imidazo[4,5-b]pyridine-5-carboxylate as a colorless gum (40.0 mg, 35% yield).

LC-MS: m/z 569.1 $(M+H)^+$.

Step H: 3-((S)-oxetan-2-ylmethyl)-2-((4-(2-phenyl-2,3-dihydrobenzo[b][1,4]dioxin-5-yl) piperidin-1-yl) methyl)-3H-imidazo[4,5-b]pyridine-5-carboxylic acid

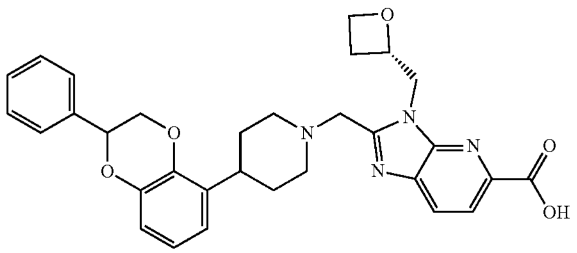

To a solution of ethyl 3-((S)-oxetan-2-ylmethyl)-2-((4-(2-phenyl-2,3-dihydrobenzo[b][1,4]dioxin-5-yl)piperidin-1-yl) methyl)-3H-imidazo[4,5-b]pyridine-5-carboxylate (40.0 mg, 0.0700 mmol, 1.0 equiv) in $MeOH/H_2O$ (3 mL/0.3 mL) was added NaOH (28.0 mg, 0.700 mmol, 10.0 equiv). The resulting mixture was stirred at 30° C. for 2 hours. Then the reaction mixture was adjusted to pH=5~ 7 with HCOOH and concentrated. The residue was purified by prep-HPLC to afford the title compound 3-((S)-oxetan-2-ylmethyl)-2-((4-(2-phenyl-2,3-dihydrobenzo[b][1,4]dioxin-5-yl)piperidin-1-yl)methyl)-3H-imidazo[4,5-b]pyridine-5-carboxylic acid as a white solid (22.0 mg, 58% yield).

$^1H$ NMR (400 MHZ, $CDCl_3$) δ ppm 8.21 (d, J=8.0 Hz, 1H), 8.17 (d, J=8.4 Hz, 1H), 7.36-7.43 (m, 5H), 6.79-6.88 (m, 3H), 5.25-5.27 (m, 1H), 5.11 (dd, J=8.0, 2.4 Hz, 1H), 4.98 (dd, J=16.0, 8.0 Hz, 1H), 4.85 (dd, J=16.0, 4.0 Hz, 1H), 4.63 (dd, J=16.0, 8.0 Hz, 1H), 4.39-4.43 (m, 2H), 4.05-4.16 (m, 2H), 4.00 (dd, J=11.4, 9.0 Hz, 1H), 2.93-3.07 (m, 3H), 2.74-2.82 (m, 1H), 2.35-2.53 (m, 3H), 1.71-1.89 (m, 4H). LC-MS: m/z 541.1 $(M+H)^+$.

Example 2

2-((4-(2-(4-Chloro-2-fluorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylic acid Compound 104a

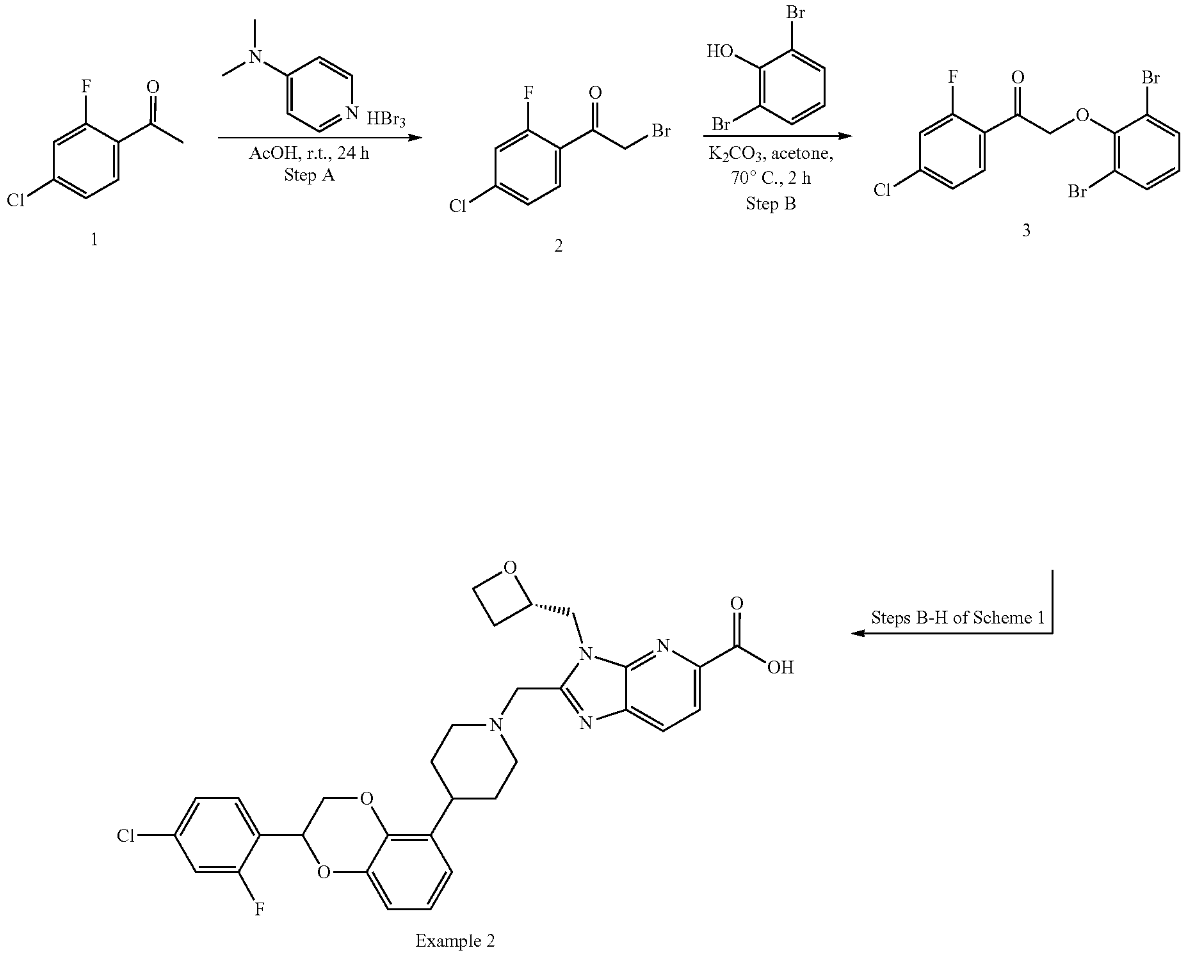

Example 2

Step A: 2-bromo-1-(4-chloro-2-fluorophenyl) ethanone

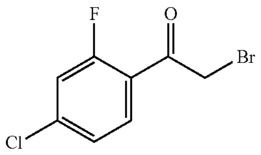 [SMILES: O=C(CBr)c1ccc(Cl)cc1F]

To a solution of 1-(4-chloro-2-fluorophenyl) ethanone (8.50 g, 49.4 mmol, 1.0 equiv) in acetic acid (150 mL) was added 4-(dimethylamino)pyridine tribromide (19.7 g, 54.3 mmol, 1.1 equiv). The resulting mixture was stirred at room temperature for 24 hours. Water (150 mL) was added and the mixture was stirred for 30 minutes. The precipitate was collected by filtration, washed with water, and dried in vacuo to afford the title compound 2-bromo-1-(4-chloro-2-fluorophenyl) ethenone as a white solid (10.0 g, 81% yield).

$^1$H NMR (400 MHZ, $CDCl_3$) δ ppm 7.94 (t, J=8.0 Hz, 1H), 7.67 (dd, J=11.2, 2.0 Hz, 1H), 7.47 (dd, J=8.0, 2.0 Hz, 1H), 4.84 (d, J=2.0 Hz, 2H).

Step B: 1-(4-chloro-2-fluorophenyl)-2-(2,6-dibromophenoxy) ethanone

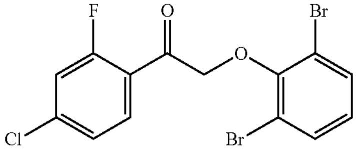 [SMILES: O=C(COc1c(Br)cccc1Br)c1ccc(Cl)cc1F]

A suspension of compound 2-bromo-1-(4-chloro-2-fluorophenyl) ethanone (10.0 g, 40.0 mmol, 1.1 equiv), 2,6-dibromophenol (9.10 g, 36.4 mmol, 1.0 equiv) and $K_2CO_3$ (5.50 g, 40.0 mmol, 1.1 equiv) in acetone (150 mL) was stirred at 70° C. for 2 hours.

The reaction mixture was filtered and the filtrate was concentrated. The residue was purified by flash chromatography (eluted with PE/EtOAc=10/1) to afford the title compound 1-(4-chloro-2-fluorophenyl)-2-(2,6-dibromophenoxy) ethanone as a white solid (8.00 g, 48% yield).

$^1$H NMR (400 MHZ, $CDCl_3$) δ ppm 8.07 (t, J=8.0 Hz, 1H), 7.53 (d, J=8.0 Hz, 2H), 7.31 (dd, J=8.4, 2.0 Hz, 1H), 7.21 (dd, J=10.8, 2.0 Hz, 1H), 6.92 (t, J=8.0 Hz, 1H), 5.19 (d, J=3.6 Hz, 2H).

2-((4-(2-(4-Chloro-2-fluorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylic acid Compound 104a

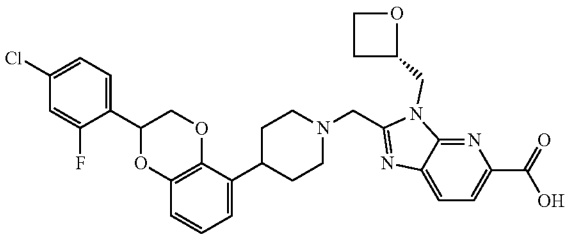 [SMILES: O=C(O)c1ccc2nc(CN3CCC(c4cccc5c4OCC(c4ccc(Cl)cc4F)O5)CC3)n(C[C@@H]3CCO3)c2n1]

Following the procedure of Example 1 (step B to step H in Scheme 1), Example 2 (Compound 104a) was synthesized from 1-(4-chloro-2-fluorophenyl)-2-(2,6-dibromophenoxy) ethanone obtained in step B.

$^1$H NMR (400 MHZ, $CDCl_3$) δ ppm 8.18 (d, J=8.4 Hz, 1H), 8.15 (d, J=8.4 Hz, 2H), 7.45 (t, J=8.0 Hz, 1H), 7.20 (dd, J=8.0, 1.6 Hz, 1H), 7.14 (dd, J=8.0, 1.6 Hz, 1H), 6.80-6.85 (m, 3H), 5.39 (dd, J=8.0, 1.6 Hz, 1H), 5.24-5.25 (m, 1H), 4.99 (dd, J=14.8, 6.0 Hz, 1H), 4.86 (d, J=14.0 Hz, 2H), 4.60 (dd, J=14.4, 7.6 Hz, 1H), 4.44 (dd, J=11.2, 2.0 Hz), 4.36-4.41 (m, 1H), 4.12-4.22 (m, 2H), 3.94 (dd, J=12.0, 8.0 Hz, 1H), 3.15 (t, J=12.0 Hz, 2H), 2.94-3.00 (m, 1H), 2.69-2.78 (m, 1H), 2.45-2.48 (m, 3H), 1.83-1.92 (m, 4H). LC-MS: m/z 593.2 $(M+H)^+$.

The (R)- and (S)-isomers of Compound 104a were obtained via chiral separation and chiral center was confirmed via chiral synthesis.

Chiral Separation condition:

Column: ChiralPak AD-H Daicel chemical Industries, Ltd, 250*30 mm I.D., 5 um

Mobile phase A: Supercritical $CO_2$, Mobile phase B: Ethanol (0.1% $NH_3H_2O$)

A:B=60:40 at 50 ml/min

Column Temp: 38° C.

Nozzle Pressure: 100Bar;

Wavelength: 220 nm 2-((4-((R)-2-(4-chloro-2-fluorophenyl)-2,3-dihydrobenzo[b][1,4]dioxin-5-yl) piperidin-1-yl)methyl)-3-(((S)-oxetan-2-yl)methyl)-3H-imidazo[4,5-b]pyridine-5-carboxylic acid (Compound 104b)

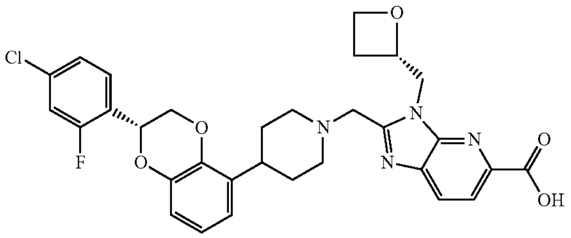 [SMILES: O=C(O)c1ccc2nc(CN3CCC(c4cccc5c4OC[C@@H](c4ccc(Cl)cc4F)O5)CC3)n(C[C@@H]3CCO3)c2n1]

$^1$H NMR (400 MHZ, $CDCl_3$) δ ppm 8.20 (dd, J=13.2, 8.0 Hz, 2H), 7.46 (t, J=8.0 Hz, 1H), 7.21 (dd, J=8.4, 2.0 Hz, 1H), 7.15 (dd, J=10.0, 2.0 Hz, 1H), 6.81-6.87 (m, 3H), 5.40 (dd, J=8.4, 2.0 Hz, 1H), 5.23-5.28 (m, 1H), 4.97 (dd, J=14.8, 6.4 Hz, 1H), 4.84 (dd, J=15.2, 3.6 Hz, 1H), 4.65 (q, J=6.8 Hz, 1H), 4.39-4.47 (m, 2H), 4.11 (dd, J=18.4, 14.0 Hz, 2H), 3.94 (dd, J=11.2, 8.4 Hz, 1H), 2.93-3.09 (m, 3H), 2.75-2.82 (m, 1H), 2.39-2.53 (m, 3H), 1.77-1.92 (m, 4H). LC-MS: m/z 593.2 $(M+H)^+$.

2-((4-((S)-2-(4-chloro-2-fluorophenyl)-2,3-dihydrobenzo[b][1,4]dioxin-5-yl) piperidin-1-yl)methyl)-3-(((S)-oxetan-2-yl)methyl)-3H-imidazo[4,5-b]pyridine-5-carboxylic acid (Compound 104c)

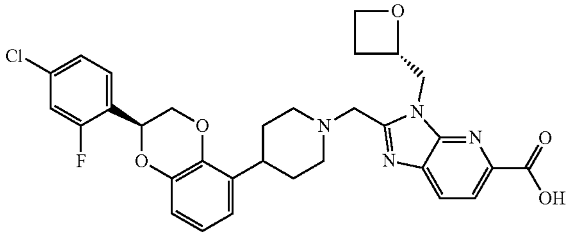 [SMILES: O=C(O)c1ccc2nc(CN3CCC(c4cccc5c4OC[C@H](c4ccc(Cl)cc4F)O5)CC3)n(C[C@@H]3CCO3)c2n1]

$^1$H NMR (400 MHZ, $CDCl_3$) δ ppm 8.19 (dd, J=13.2, 8.0 Hz, 2H), 7.46 (t, J=8.0 Hz, 1H), 7.20 (dd, J=8.4, 2.0 Hz, 1H), 7.15 (dd, J=10.0, 2.0 Hz, 1H), 6.80-6.87 (m, 3H), 5.40 (dd, J=8.4, 2.0 Hz, 1H), 5.25-5.27 (m, 1H), 4.96 (dd, J=14.8, 6.0 Hz, 1H), 4.84 (dd, J=14.4, 3.2 Hz, 1H), 4.64 (q, J=7.2 Hz, 1H), 4.38-4.47 (m, 2H), 4.10 (s, 2H), 3.95 (dd, J=11.2, 8.4 Hz, 1H), 2.92-3.06 (m, 3H), 2.75-2.84 (m, 1H), 2.35-2.51 (m, 3H), 1.73-1.89 (m, 4H). LC-MS: m/z 593.2 $(M+H)^+$.

Example 3

2-[[4-[2-(4-chloro-2-fluoro-phenyl)-2,3-dihydro-1,4-benzodioxin-5-yl]phenyl]methyl]-3-(oxetan-2-ylmethyl)imidazo[4,5-b]pyridine-5-carboxylic acid (Compound 107a)

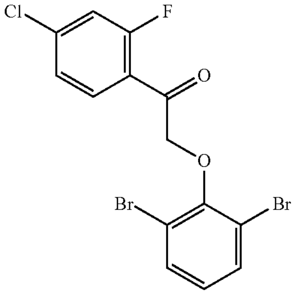

1

$NaBH_4$
MeOH
Step A

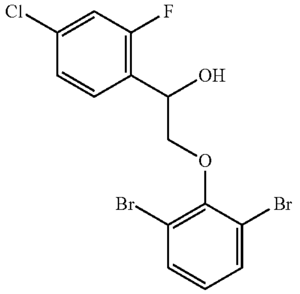

2

CuI, $Cs_2CO_3$
1,10-Phenanthroline, toluene
Step B

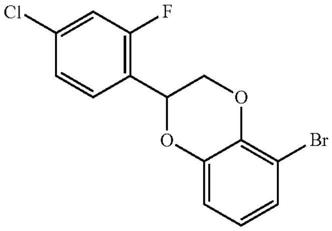

3

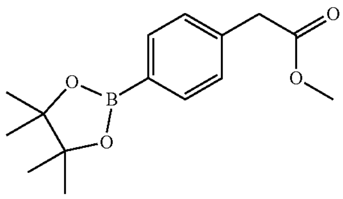

4

Pd(dppf)$Cl_2$, $K_2CO_3$, dioxane, $H_2O$ 80° C., 1 h
Step C

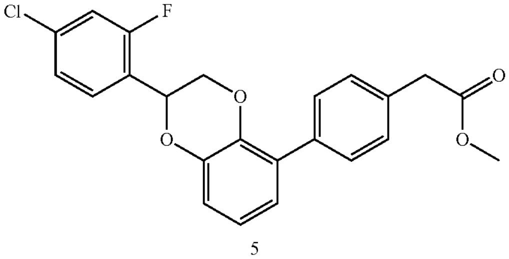

5

LiOH
MeOH/THF, $H_2O$
15° C., 16 h
Step D

-continued
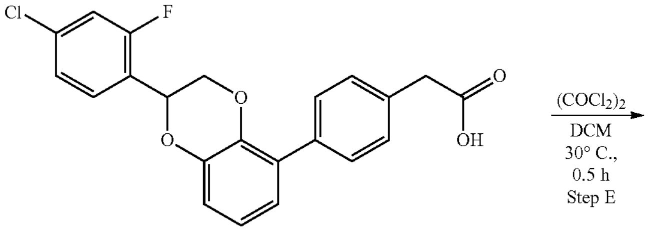
6
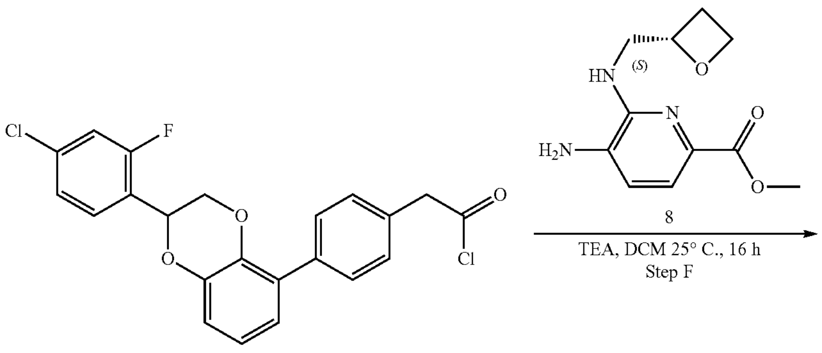
7
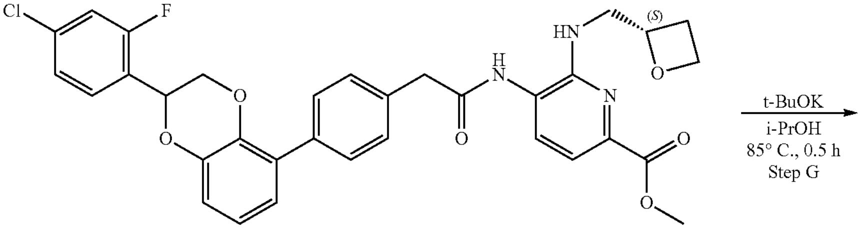
9
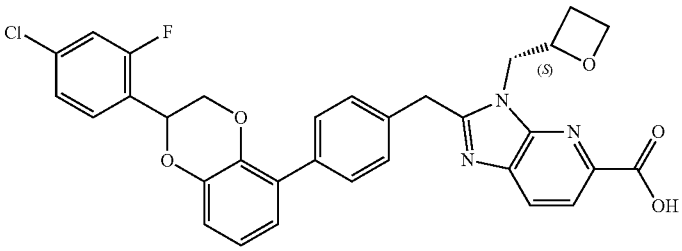
Example 3
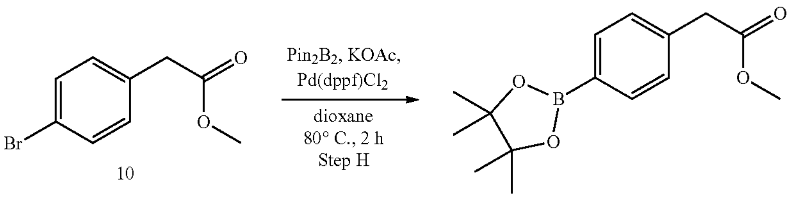
10
4

Step A 1-(4-chloro-2-fluoro-phenyl)-2-(2,6-dibromophenoxy) ethanol

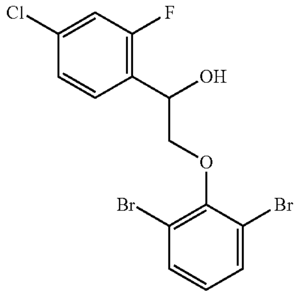 [SMILES: OC(COc1c(Br)cccc1Br)c1ccc(Cl)cc1F]

To a solution of 1-(4-chloro-2-fluoro-phenyl)-2-(2,6-dibromophenoxy) ethanone (16.2 g, 38.35 mmol) in EtOH (200 mL) was added $NaBH_4$ (2.90 g, 76.69 mmol) and stirred 25° C. for 2 h. TLC showed that the starting material was consumed completely. The mixture was quenched by addition water (150 mL) and concentrated to provide a brown mixture. The mixture was extracted with EtOAc (150 mL*2). The combined organic layers were dried over anhydrous $Na_2SO_4$, filtered, and concentrated to give 1-(4-chloro-2-fluoro-phenyl)-2-(2,6-dibromophenoxy) ethanol (16.0 g, crude) as a white solid.

$^1$H NMR (400 MHZ, DMSO-$d_6$) δ ppm 7.60-7.67 (m, 3H) 7.29-7.42 (m, 2H) 7.02 (t, J=8.0 Hz, 1H) 5.94 (d, J=5.2 Hz, 1H) 5.25-5.33 (m, 1H)$_4$.06-4.13 (m, 1H) 3.93-4.02 (m, 1H).

Step B 5-bromo-2-(4-chloro-2-fluoro-phenyl)-2,3-dihydro-1,4-benzodioxine

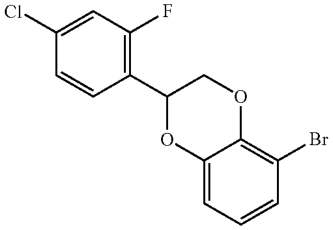 [SMILES: Fc1cc(Cl)ccc1C1COc2c(Br)cccc2O1]

To a solution of 1-(4-chloro-2-fluoro-phenyl)-2-(2,6-dibromophenoxy) ethanol (16.0 g, 37.69 mmol) in toluene (300 mL) was added 1,10-phenanthroline (1.36 g, 7.54 mmol), CuI (717.85 mg, 3.77 mmol) and $Cs_2CO_3$ (36.84 g, 113.08 mmol). The mixture was stirred at 100° C. for 16 h. TLC showed that the starting material was consumed completely. The mixture was quenched by addition of water (150 mL) and concentrated to provide a brown mixture. The mixture was extracted with EtOAc (150 mL*2). The combined organic layers were dried over anhydrous $Na_2SO_4$, filtered, and concentrated to provide 5-bromo-2-(4-chloro-2-fluoro-phenyl)-2,3-dihydro-1,4-benzodioxine (13.53 g, crude) as a brown oil.

$^1$H NMR (400 MHZ, $CD_3OD$) δ ppm 7.49 (t, J-8.0 Hz, 1H) 7.26-7.32 (m, 2H) 7.18-7.23 (m, 1H) 7.07-7.17 (m, 2H) 6.95 (dd, J=8.4, 1.2 Hz, 1H) 6.75-6.82 (m, 1H) 5.41 (dd, J=8.4, 2.4 Hz, 1H)$_4$.52 (dd, J=11.2, 2.4 Hz, 1H)$_4$.05-4.14 (m, 1H).

Step H methyl 2-[4-(4,4,5,5-tetramethyl-1,3,2-dioxaborolan-2-yl)phenyl]acetate

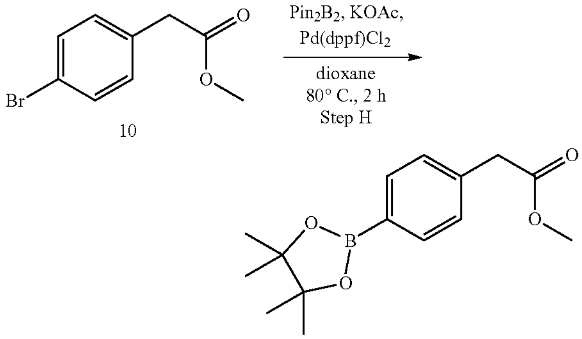

10

4

To a solution of methyl 2-(4-bromophenyl)acetate (1.00 g, 4.37 mmol) and 4,4,5,5-tetramethyl-2-(4,4,5,5-tetramethyl-1,3,2-dioxaborolan-2-yl)-1,3,2-dioxaborolane (1.16 g, 4.58 mmol) in dioxane (12 mL) was added Pd(dppf)$Cl_2$ (159.71 mg, 218.27 umol), KOAc (1.29 g, 13.10 mmol) under $N_2$. The suspension was stirred at 80° C. for 2 h. The dark mixture was diluted with water (10 mL) and extracted with ethyl acetate (10 mL) twice. The organic layer was concentrated to give crude (1.66 g) as a dark gum. The crude was purified by Combi-flash (silica gel, ethyl acetate in petrol ether 0~10%) to give methyl 2-[4-(4,4,5,5-tetramethyl-1,3,2-dioxaborolan-2-yl)phenyl]acetate (980.0 mg, 81.3% yield) as a colorless oil. $^1$H NMR (400 MHZ, $CDCl_3$) δ ppm 7.78-7.79 (m, 2H) 7.27-7.31 (m, 2H) 3.69 (s, 3H) 3.65 (s, 2H) 1.35 (s, 12H).

Step C methyl 2-[4-[2-(4-chloro-2-fluoro-phenyl)-2,3-dihydro-1,4-benzodioxin-5-yl]phenyl]acetate

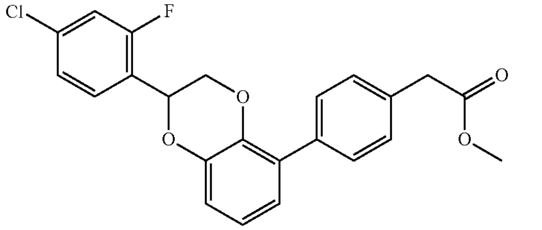 [SMILES: COC(=O)Cc1ccc(-c2cccc3c2OCC(c2ccc(Cl)cc2F)O3)cc1]

To a solution of 5-bromo-2-(4-chloro-2-fluoro-phenyl)-2,3-dihydro-1,4-benzodioxine (360 mg, 1.05 mmol) and methyl 2-[4-(4,4,5,5-tetramethyl-1,3,2-dioxaborolan-2-yl)phenyl]acetate (289.3 mg, 1.05 mmol) in dioxane (4 mL) was added $K_2CO_3$ (434.44 mg, 3.14 mmol), Pd(dppf)$Cl_2$ (76.67 mg, 104.78 umol) and $H_2O$ (1.2 mL) under $N_2$. The mixture was stirred at 80° C. for 1 h. The dark mixture was diluted with water (5 mL) and extracted with ethyl acetate (5 mL) twice. The organic layer was concentrated to give crude (510 mg) as a dark gum. The crude was purified by Combi-flash (silica gel, ethyl acetate in petrol ether 0~15%) to give methyl 2-[4-[2-(4-chloro-2-fluoro-phenyl)-2,3-dihydro-1,4-benzodioxin-5-yl]phenyl]acetate (358.0 mg, 82.7% yield) as a yellow solid.

$^1$H NMR (400 MHZ, $CDCl_3$) δ ppm 7.47-7.57 (m, 3H) 7.33-7.38 (m, 2H) 7.25 (dd, J=8.4, 1.2 Hz, 1H) 7.16 (d, J=10.0 Hz, 1H) 6.95-7.02 (m, 3H) 5.47 (dd, J-8.4, 2.0 Hz, 1H)$_4$.44 (dd, J=11.2, 2.0 Hz, 1H) 3.96 (dd, J=11.2, 8.4 Hz, 1H) 3.72 (s, 3H) 3.68 (s, 2H).

Step D 2-[4-[2-(4-chloro-2-fluoro-phenyl)-2,3-dihydro-1,4-benzodioxin-5-yl]phenyl]acetic acid

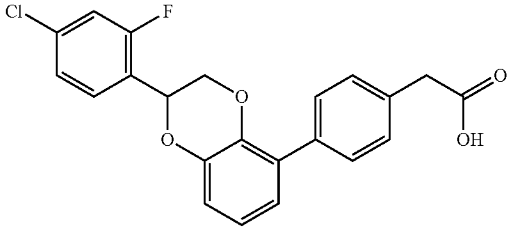 [SMILES: O=C(O)Cc1ccc(-c2cccc3c2OCC(c2ccc(Cl)cc2F)O3)cc1]

To a solution of methyl 2-[4-[2-(4-chloro-2-fluoro-phenyl)-2,3-dihydro-1,4-benzodioxin-5-yl]phenyl]acetate (350.0 mg, 847.79 umol) in MeOH (2 mL) and THF (3 mL) was added LiOH·$H_2O$ (106.73 mg, 2.54 mmol) in $H_2O$ (1 mL). The solution was stirred at 15° C. for 16 h. The colorless solution was treated with 1N HCl to adjust pH to 5. The solution was concentrated to remove MeOH. The white suspension was diluted with water (2 mL) and extracted with ethyl acetate (3 mL) twice. The organic layer was concentrated to give 2-[4-[2-(4-chloro-2-fluoro-phenyl)-2,3-dihydro-1,4-benzodioxin-5-yl]phenyl]acetic acid (340.0 mg, crude) as a white solid.

$^1$H NMR (400 MHZ, DMSO-$d_6$) δ ppm 12.17 (br s, 1H) 7.52-7.60 (m, 2H) 7.43-7.49 (m, 2H) 7.40 (dd, J=8.4, 1.6 Hz, 1H) 7.27-7.33 (m, 2H) 6.92-7.01 (m, 3H) 5.52 (dd, J=8.0, 2.0 Hz, 1H)$_4$.47 (dd, J=11.6, 2.4 Hz, 1H)$_4$.14 (dd, J=11.6, 8.0 Hz, 1H) 3.60 (s, 2H).

Step E 2-[4-[2-(4-chloro-2-fluoro-phenyl)-2,3-dihydro-1,4-benzodioxin-5-yl]phenyl]acetyl chloride

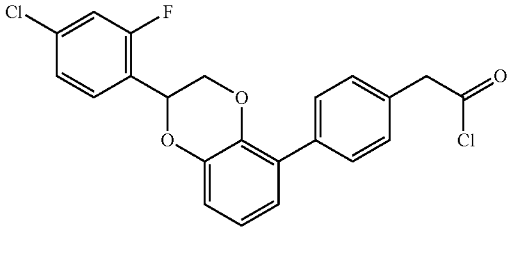 [SMILES: O=C(Cl)Cc1ccc(-c2cccc3c2OCC(c2ccc(Cl)cc2F)O3)cc1]

To a solution of 2-[4-[2-(4-chloro-2-fluoro-phenyl)-2,3-dihydro-1,4-benzodioxin-5-yl]phenyl]acetic acid (170.0 mg, 426.27 umol) in DCM (3 mL) was added oxalyl dichloride (135.26 mg, 1.07 mmol) and one drop of DMF. The solution was stirred at 30° C. for 0.5 h. The yellow solution was concentrated to give 2-[4-[2-(4-chloro-2-fluoro-phenyl)-2,3-dihydro-1,4-benzodioxin-5-yl]phenyl]acetyl chloride (180.0 mg, crude) as a yellow solid.

Step F methyl 5-[[2-[4-[2-(4-chloro-2-fluoro-phenyl)-2,3-dihydro-1,4-benzodioxin-5-yl]phenyl]acetyl]amino]-6-[[(2S)-oxetan-2-yl]methylamino]pyridine-2-carboxylate

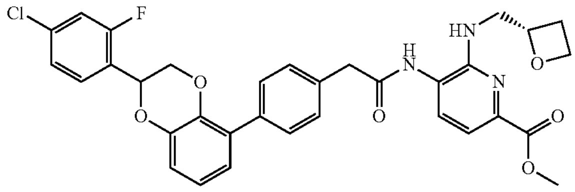 [SMILES: COC(=O)c1ccc(NC(=O)Cc2ccc(-c3cccc4c3OCC(c3ccc(Cl)cc3F)O4)cc2)c(NC[C@@H]2CCO2)n1]

To a solution of methyl 5-amino-6-[[(2S)-oxetan-2-yl]methylamino]pyridine-2-carboxylate (102.35 mg, 431.39 umol) and TEA (218.26 mg, 2.16 mmol) in DCM (1 mL) was added 2-[4-[2-(4-chloro-2-fluoro-phenyl)-2,3-dihydro-1,4-benzodioxin-5-yl]phenyl]acetyl chloride (180.0 mg, 431.39 umol) in DCM (1 mL). The yellow solution was stirred at 25° C. for 16 h. The yellow solution was diluted with MeOH (1 mL) and concentrated to give crude (355 mg) as a yellow gum. The crude was purified by Combi-flash (silica gel, ethyl acetate in petrol ether 50~100%) to give methyl 5-[[2-[4-[2-(4-chloro-2-fluoro-phenyl)-2,3-dihydro-1,4-benzodioxin-5-yl]phenyl]acetyl]amino]-6-[[(2S)-oxetan-2-yl]methylamino]pyridine-2-carboxylate (53.0 mg, 20.2% yield) as a yellow gum.

LCMS m/z 640.1 $(M+Na)^+$.

Step G 2-[[4-[2-(4-chloro-2-fluoro-phenyl)-2,3-dihydro-1,4-benzodioxin-5-yl]phenyl]methyl]-3-(oxetan-2-ylmethyl)imidazo[4,5-b]pyridine-5-carboxylic acid (Compound 107a)

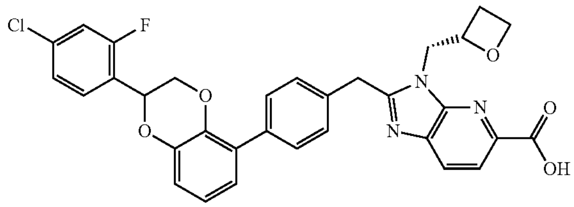

To a suspension of methyl 5-[[2-[4-[2-(4-chloro-2-fluoro-phenyl)-2,3-dihydro-1,4-benzodioxin-5-yl]phenyl]acetyl]amino]-6-[[(2S)-oxetan-2-yl]methylamino]pyridine-2-carboxylate (50.08 mg, 81.03 umol) in i-PrOH (1 mL) was added t-BuOK (18.18 mg, 162.06 umol). The suspension was stirred at 85° C. for 0.5 h under $N_2$. The suspension was treated with 1N HCl to adjust pH to 7 and concentrated to remove the solvent. The crude was purified by prep-HPLC Column: Phenomenex Gemini $C_{18\ 250*50}$ mm*10 um; mobile phase: [water (0.05% ammonia hydroxide v/v)-ACN]; B %: 23%- 43%, 10 min. The fraction was dried by lyophilization to give 2-[[4-[2-(4-chloro-2-fluoro-phenyl)-2,3-dihydro-1,4-benzodioxin-5-yl]phenyl]methyl]-3-(oxetan-2-ylmethyl)imidazo[4,5-b]pyridine-5-carboxylic acid (10.19 mg, 20.2% yield) as a white solid. LC-MS: m/z 586.1 $(M+H)^+$.

$^1$H NMR (400 MHZ, $CD_3OD$) δ ppm 8.05-8.15 (m, 2H) 7.41-7.58 (m, 3H) 7.26-7.34 (m, 4H) 6.90-7.03 (m, 3H) 5.42-5.49 (m, 1H) 5.17-5.26 (m, 0.6H)$_4$.54-4.72 (m, 3.3H)$_4$.37-4.50 (m, 2.3H) 3.98-4.06 (m, 1H) 3.70 (t, J=6.4 Hz, 0.6H) 2.62-2.80 (m, 0.7H)$_2$.42-2.53 (m, 1.3H).

$^{19}$F NMR (377 MHZ, $CD_3OD$) δ ppm-117.932.

Example 4 2-((4-(2-(4-chloro-2-fluorophenyl)-2,3-dihydrobenzo[b][1,4]dioxin-5-yl) piperazin-1-yl) methyl)-3-((S)-oxetan-2-ylmethyl)-3H-imidazo[4,5-b]pyridine-5-carboxylic acid (Compound 108a)
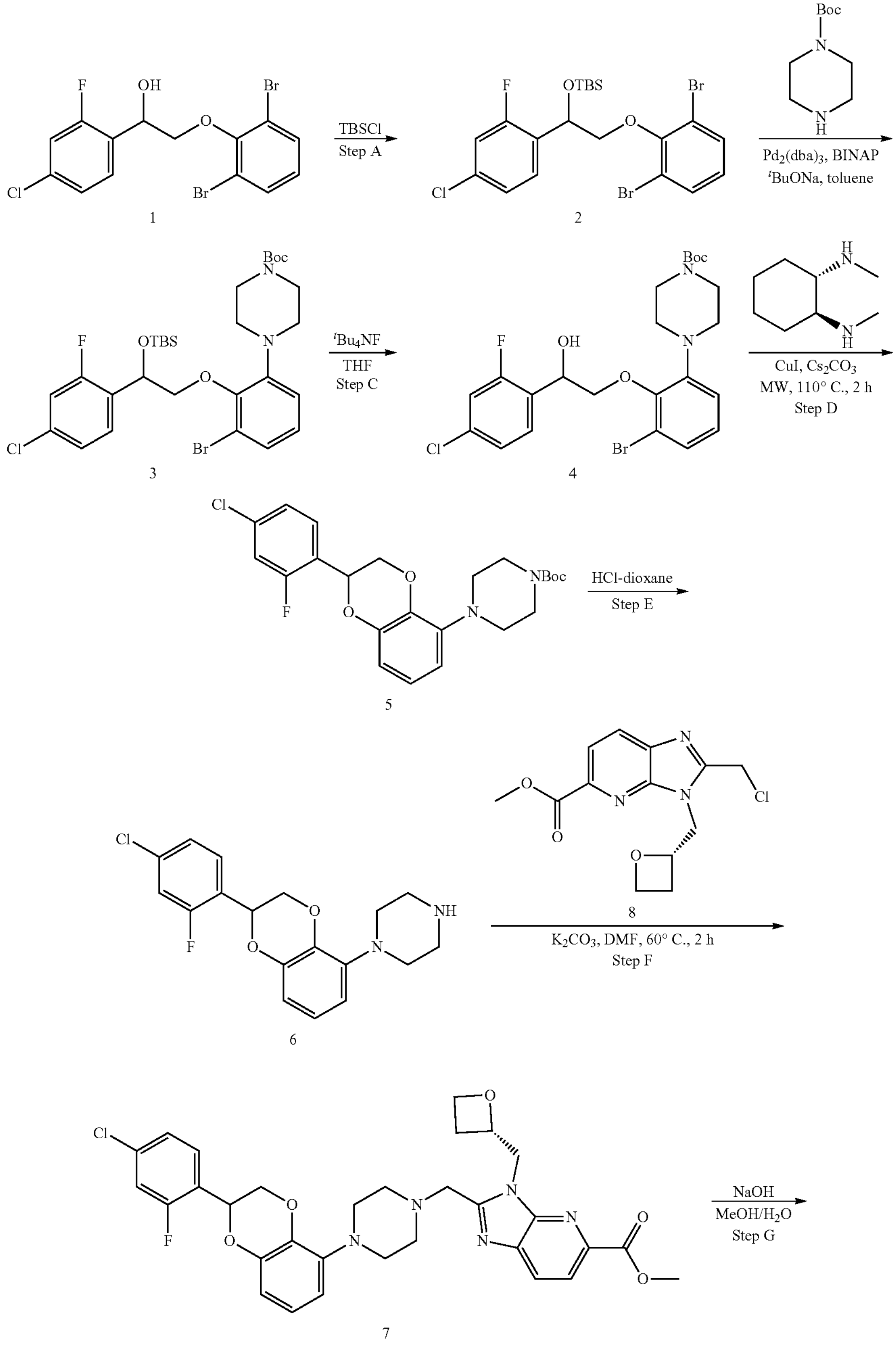
1 2 3 4 5 8 6 7

-continued

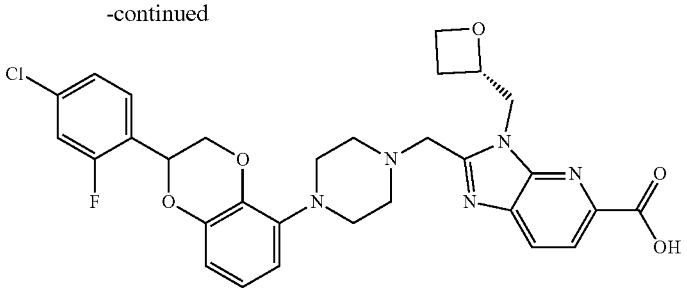

Example 4

Step A: tert-butyl(1-(4-chloro-2-fluorophenyl)-2-(2,6-dibromophenoxy) ethoxy)dimethyl silane

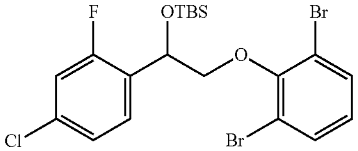 [SMILES: CC(C)(C)[Si](C)(C)OC(COc1c(Br)cccc1Br)c1ccc(Cl)cc1F]

5 A solution of 1-(4-chloro-2-fluorophenyl)-2-(2,6-dibromophenoxy) ethanol (4.20 g, 10.0 mmol), TBSCl (3.75 g, 25.0 mmol) and imidazole (2.04 g, 30.0 mmol) in DCM (100 mL) was stirred at room temperature for 12 hours under $N_2$ atmosphere. Water (150 mL) was added and the mixture was extracted with DCM (3×100 mL). The combined organic phase was washed with brine (80 mL), dried over anhydrous $Na_2SO_4$, filtered and concentrated. The residue was purified by flash chromatography (PE/EtOAc=10/1) to afford the title compound tert-butyl(1-(4-chloro-2-fluorophenyl)-2-(2,6-dibromophenoxy) ethoxy)dimethylsilane (5.00 g, 93% yield) as a colorless oil.

$^1H$ NMR (400 MHZ, $CDCl_3$) δ ppm 7.57 (t, J=8.0 Hz, 1H), 7.45 (d, J=8.0 Hz, 2H), 7.14 (dd, J=8.0, 2.0 Hz, 1H), 7.03 (dd, J=9.6, 2.0 Hz, 1H), 6.81 (t, J=8.0 Hz, 1H), 5.49 (dd, J=7.2, 4.0 Hz, 1H), 4.09 (dd, J=8.8, 7.2 Hz, 1H), 3.91 (dd, J=8.0, 4.0 Hz, 1H), 0.90 (s, 9H), 0.17 (s, 3H), 0.04 (s, 3H).

Step B: tert-butyl 4-(3-bromo-2-(2-((tert-butyldimethylsilyl)oxy)-2-(4-chloro-2-fluorophenyl) ethoxy) phenyl)piperazine-1-carboxylate

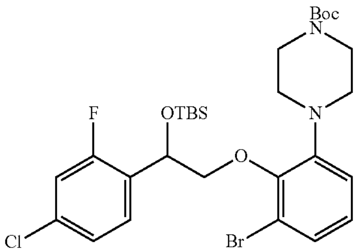 [SMILES: CC(C)(C)OC(=O)N1CCN(c2cccc(Br)c2OCC(O[Si](C)(C)C(C)(C)C)c2ccc(Cl)cc2F)CC1]

A mixture of compound tert-butyl(1-(4-chloro-2-fluorophenyl)-2-(2,6-dibromophenoxy) ethoxy)dimethylsilane (4.90 g, 9.14 mmol), tert-butyl piperazine-1-carboxylate (1.87 g, 10.0 mmol), $Pd_2$ (dba) 3 (833 mg, 0.910 mmol), BINAP (566 mg, 0.910 mmol) and $^t$BuONa (1.75 g, 18.3 mmol) in dry toluene (100 mL) was stirred at 100° C. for 3 hours under $N_2$ atmosphere. The reaction mixture was filtered through celite and washed with EtOAc (100 mL). The organic phase was concentrated and purified by flash chromatography (PE/EtOAc=10/1) to afford the title compound tert-butyl 4-(3-bromo-2-(2-((tert-butyldimethylsilyl)oxy)-2-(4-chloro-2-fluorophenyl) ethoxy)phenyl)piperazine-1-carboxylate (2.60 g, 44% yield) as a yellow oil.

$^1H$ NMR (400 MHZ, $CDCl_3$) δ ppm 7.57 (t, J=8.0 Hz, 1H), 7.15-7.19 (m, 2H), 7.04 (dd, J=9.6, 2.0 Hz, 1H), 6.88 (t, J=8.0 Hz, 1H), 6.80 (dd, J=8.0, 1.6 Hz, 1H), 5.46 (dd, J=8.0, 4.0 Hz, 1H), 4.19 (dd, J=8.4, 8.0 Hz, 1H), 3.85 (dd, J=8.0, 4.0 Hz, 1H), 3.54 (br.s, 4H), 2.99-3.06 (m, 4H), 1.51 (s, 9H), 0.91 (s, 9H), 0.15 (s, 3H), 0.05 (s, 3H).

Step C: tert-butyl 4-(3-bromo-2-(2-(4-chloro-2-fluorophenyl)-2-hydroxyethoxy)phenyl) piperazine-1-carboxylate

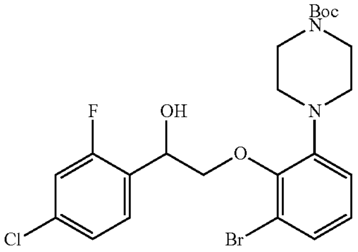 [SMILES: CC(C)(C)OC(=O)N1CCN(c2cccc(Br)c2OCC(O)c2ccc(Cl)cc2F)CC1]

A mixture of compound tert-butyl 4-(3-bromo-2-(2-((tert-butyldimethylsilyl)oxy)-2-(4-chloro-2-fluorophenyl) ethoxy)phenyl)piperazine-1-carboxylate (2.60 g, 4.05 mmol) and $^t$Bu$_4$NF (1 M, 8.10 mL, 8.10 mmol) in THF (20 mL) was stirred at room temperature for 2 h. The reaction mixture was diluted with water (20 mL) and extracted with EtOAc (3×30 mL). The combined organic phase was washed with brine (30 mL), dried over anhydrous $Na_2SO_4$, filtered and concentrated. The residue was purified by flash chromatography (PE/EtOAc=5/1) to afford the title compound tert-butyl 4-(3-bromo-2-(2-(4-chloro-2-fluorophenyl)-2-hydroxyethoxy)phenyl) piperazine-1-carboxylate (1.49 g, 70% yield) as a white solid.

$^1H$ NMR (400 MHZ, $CDCl_3$) δ ppm 7.40 (t, J=8.0 Hz, 1H), 7.23-7.27 (m, 1H), 7.04 (dd, J=8.0, 2.0 Hz, 1H), 6.97 (dd, J=10.0, 2.0 Hz, 1H), 6.92 (d, J=4.0 Hz, 2H), 6.48 (d, J=1.2 Hz, 1H), 5.15 (d, J=9.6 Hz, 1H), 4.63 (dd, J=11.2, 1.6 Hz, 1H), 3.50-3.58 (m, 5H), 3.06-3.11 (m, 2H), 2.83-2.85 (m, 2H), 1.38 (s, 9H).

Step D: tert-butyl 4-(2-(4-chloro-2-fluorophenyl)-2,3-dihydrobenzo[b][1,4]dioxin-5-yl) piperazine-1-carboxylate

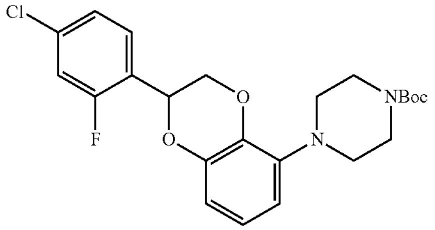

A mixture of compound tert-butyl 4-(3-bromo-2-(2-(4-chloro-2-fluorophenyl)-2-hydroxyethoxy)phenyl) piperazine-1-carboxylate (750 mg, 1.40 mmol), CuI (530 mg, 2.80 mmol), (1S,2S)—$N^1$,$N^2$-dimethylcyclohexane-1,2-diamine (400 mg, 2.80 mmol) and $Cs_2CO_3$ (1.38 g, 4.20 mmol) in dry DMF (10 mL) was stirred at 110° C. via microwave irradiation for 2 h under $N_2$ atmosphere. The reaction mixture was diluted with water (30 mL) and extracted with EtOAc (3x30 mL). The combined organic phase was washed with brine (30 mL), dried over anhydrous $Na_2SO_4$, filtered and concentrated. The residue was purified by flash chromatography (PE/EtOAc=5/1) to afford the title compound tert-butyl 4-(2-(4-chloro-2-fluorophenyl)-2,3-dihydrobenzo[b][1,4]dioxin-5-yl)piperazine-1-carboxylate (360 mg, 58% yield) as a colorless oil.

LC-MS: m/z 449.1 $(M+H)^+$.

Step E: 1-(2-(4-chloro-2-fluorophenyl)-2,3-dihydrobenzo[b][1,4]dioxin-5-yl) piperazine

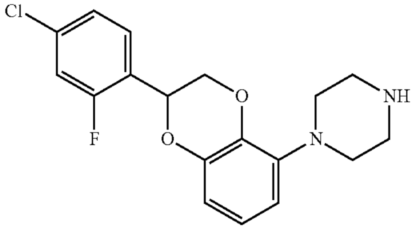 [SMILES: Fc1cc(Cl)ccc1C1COc2c(cccc2N2CCNCC2)O1]

A solution of compound tert-butyl 4-(2-(4-chloro-2-fluorophenyl)-2,3-dihydrobenzo[b][1,4]dioxin-5-yl)piperazine-1-carboxylate (360 mg, 0.800 mmol) in HCl-dioxane (4M, 10 mL) was stirred at 40° C. for 10 mins. The reaction mixture was concentrated afford the title compound 1-(2-(4-chloro-2-fluorophenyl)-2,3- to dihydrobenzo[b][1,4]dioxin-5-yl)piperazine (340 mg, 100% yield) as a white solid, which was used in next step directly.

LC-MS: m/z 349.1 $(M+H)^+$.

Step F: methyl 2-((4-(2-(4-chloro-2-fluorophenyl)-2,3-dihydrobenzo[b][1.4]dioxin-5-yl) piperazin-1-yl) methyl)-3-((S)-oxetan-2-ylmethyl)-3H-imidazo[4,5-b]pyridine-5-carboxylate

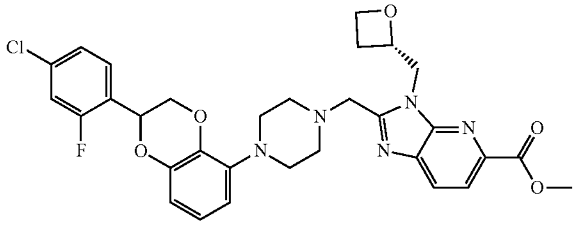 [SMILES: COC(=O)c1ccc2nc(CN3CCN(c4cccc5c4OCC(c4ccc(Cl)cc4F)O5)CC3)n(C[C@@H]3CCO3)c2n1]

A mixture of compound 1-(2-(4-chloro-2-fluorophenyl)-2,3-dihydrobenzo[b][1,4]dioxin-5-yl)piperazine (104 mg, 0.300 mmol), (S)-methyl 2-(chloromethyl)-3-(oxetan-2-ylmethyl)-3H-imidazo[4,5-b]pyridine-5-carboxylate (93.0 mg, 0.300 mmol) and $K_2CO_3$ (85.0 mg, 0.600 mmol) in DMF (2 mL) was stirred at 60° C. for 2 h. The reaction mixture was diluted with water (10 mL) and extracted with EtOAc (3x10 mL). The combined organic phase was washed with brine (10 mL), dried over anhydrous $Na_2SO_4$, filtered and concentrated. The residue was purified by flash chromatography (DCM/MeOH=50/1) to afford the title compound methyl 2-((4-(2-(4-chloro-2-fluorophenyl)-2,3-dihydrobenzo[b][1,4]dioxin-5-yl)piperazin-1-yl)methyl)-3-((S)-oxetan-2-ylmethyl)-3H-imidazo[4,5-b]pyridine-5-carboxylate (80.0 mg, 44% yield) as a colorless oil.

LC-MS: m/z 608.1 $(M+H)^+$.

Step G: 2-((4-(2-(4-chloro-2-fluorophenyl)-2,3-dihydrobenzo[b][1,4]dioxin-5-yl) piperazin-1-yl) methyl)-3-((S)-oxetan-2-ylmethyl)-3H-imidazo[4,5-b]pyridine-5-carboxylic acid (Compound 108a)

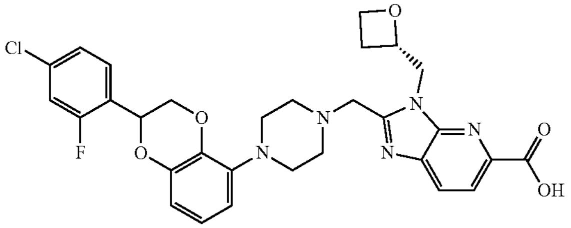 [SMILES: O=C(O)c1ccc2nc(CN3CCN(c4cccc5c4OCC(c4ccc(Cl)cc4F)O5)CC3)n(C[C@@H]3CCO3)c2n1]

A solution of compound methyl 2-((4-(2-(4-chloro-2-fluorophenyl)-2,3-dihydrobenzo[b][1,4]dioxin-5-yl)piperazin-1-yl)methyl)-3-((S)-oxetan-2-ylmethyl)-3H-imidazo[4,5-b]pyridine-5-carboxylate (80.0 mg, 0.130 mmol) and NaOH (52.0 mg, 1.30 mmol) in $MeOH/H_2O$ (5 mL/1 mL) was stirred at 40° C. for 1.5h. The reaction mixture was acidified to pH=5 with HCOOH and concentrated. The residue was purified by prep-HPLC to afford the title compound 2-((4-(2-(4-chloro-2-fluorophenyl)-2,3-dihydrobenzo[b][1,4]dioxin-5-yl)piperazin-1-yl)methyl)-3-((S)oxetan-2-ylmethyl)-3H-imidazo[4,5-b]pyridine-5-carboxylic acid (35.0 mg, 45% yield) as a white solid.

LC-MS: m/z 594.2 $(M+H)^+$.

$^1H$ NMR (400 MHZ, $CDCl_3$) δ ppm 8.21 (s, 2H), 7.46 (t, J=8.0 Hz, 1H), 7.21 (dd, J=8.0, 1.6 Hz, 1H), 7.13 (dd, J=10.0, 2.0 Hz, 1H), 6.83 (t, J=8.0 Hz, 1H), 6.71 (dd, J=8.0, 1.2 Hz, 1H), 6.57 (d, J=8.0 Hz, 1H), 5.39 (dd, J=8.0, 1.6 Hz, 1H), 5.26-5.27 (m, 1H), 4.84-5.00 (m, 2H), 4.62 (dd, J=14.0, 7.2 Hz, 1H), 4.50 (dd, J=11.2, 2.0 Hz, 1H), 4.36-4.42 (m, 1H), 4.14-4.22 (m, 2H), 3.98 (dd, J=11.2, 8.8 Hz, 1H), 3.13 (br.s, 4H), 2.73-2.83 (m, 5H), 2.44-2.52 (m, 1H).

Example 5 2-((4-(2-(4-chlorophenyl)-2-methyl-2,3-dihydrobenzo[b][1,4]dioxin-5-yl) piperidin-1-yl) methyl)-3-((S)-oxetan-2-ylmethyl)-3H-imidazo[4,5-b]pyridine-5-carboxylic acid (Compound 128a)
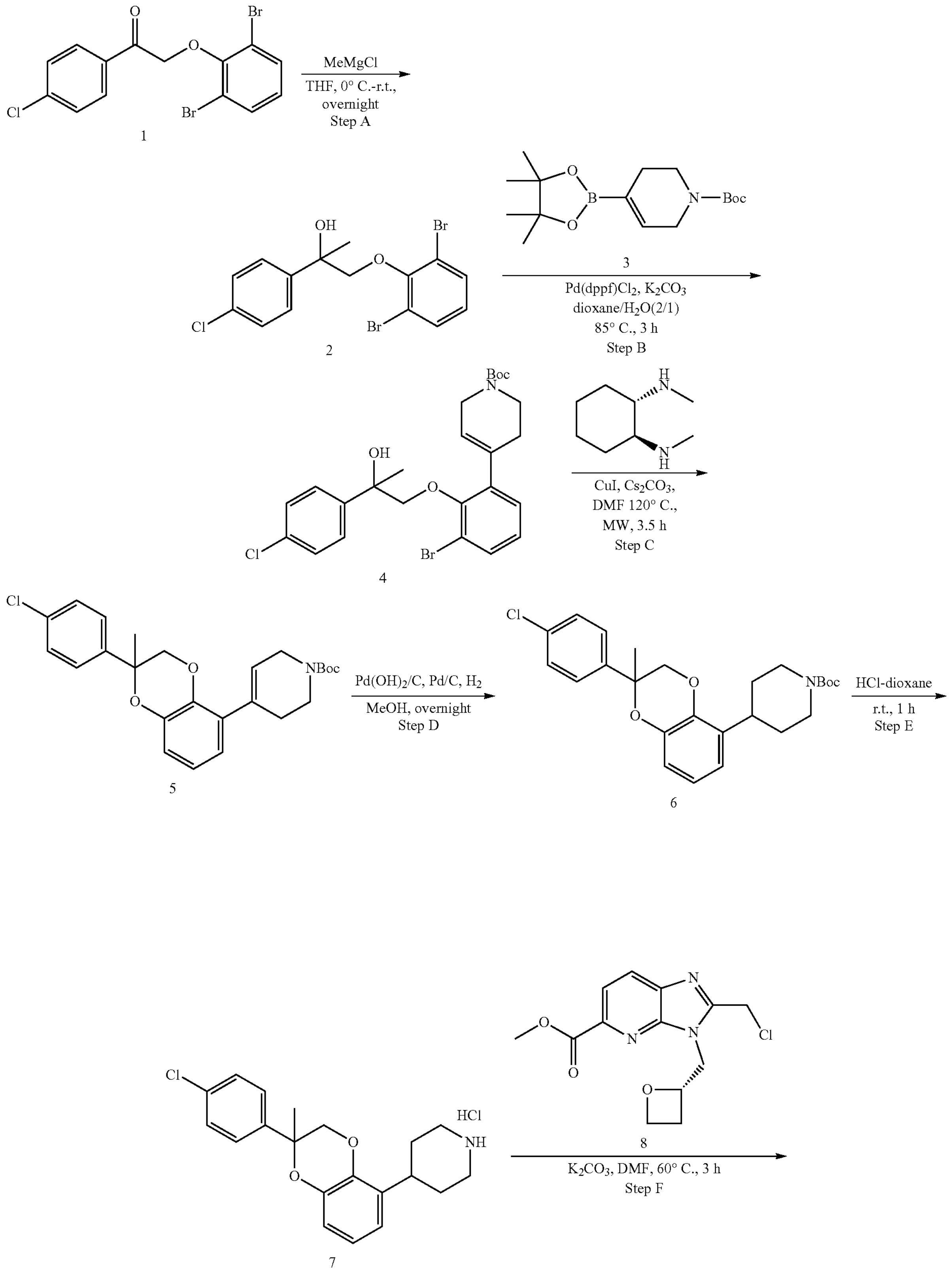

-continued

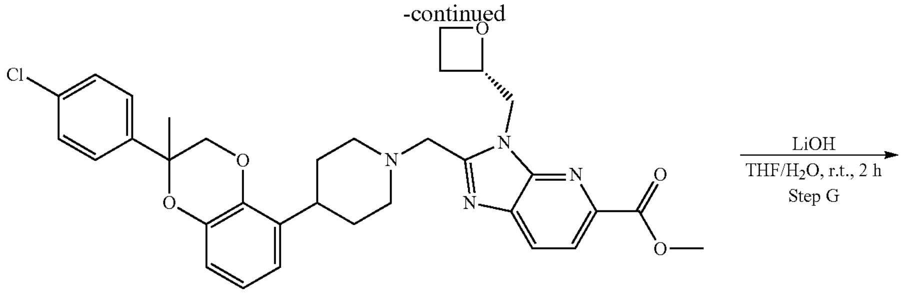

9

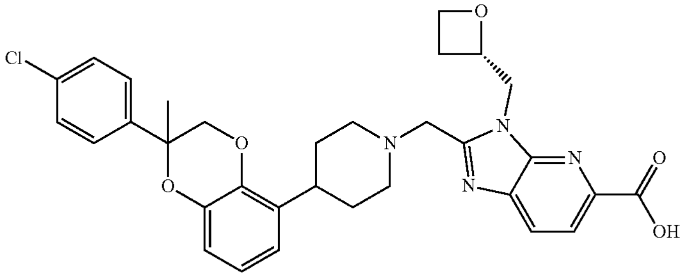

Compound 128a

Step A: 2-(4-chlorophenyl)-1-(2,6-dibromophenoxy) propan-2-ol

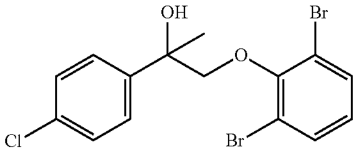 [SMILES: CC(O)(COc1c(Br)cccc1Br)c1ccc(Cl)cc1]

To a solution of 1-(4-chlorophenyl)-2-(2,6-dibromophenoxy) ethanone (1.90 g, 4.69 mmol) in THF (30 mL) was added MeMgCl (3.0 M in THF, 4.7 mL) drop wise at 0° C. under $N_2$ atmosphere. Then the mixture was stirred at room temperature overnight. The reaction mixture was quenched with sat. $NH_4Cl$ aqueous (3 mL) and extracted with EA (3x10 mL). The combined organic layers were washed with water (10 mL) and brine (10 mL), dried over anhydrous $Na_2SO_4$ and concentrated. The residue was purified by flash chromatography (eluted with PE/EtOAc=10/1) to afford the title compound 2-(4-chlorophenyl)-1-(2,6-dibromophenoxy) propan-2-ol (1.77 g, 90% yield) as a white solid. LC-MS: m/z 402.9 $(M-17)^+$ Step B: tert-butyl 4-(3-bromo-2-(2-(4-chlorophenyl)-2-hydroxypropoxy)phenyl)-5,6-dihydropyridine-1 (2H)-carboxylate

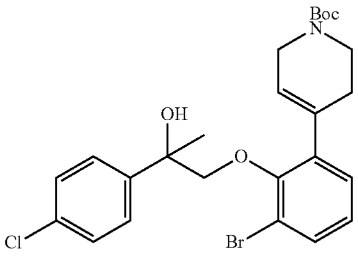 [SMILES: CC(C)(C)OC(=O)N1CC=C(c2cccc(Br)c2OCC(C)(O)c2ccc(Cl)cc2)CC1]

A mixture of 2-(4-chlorophenyl)-1-(2,6-dibromophenoxy) propan-2-ol (700 mg, 1.67 mmol), tert-butyl 4-(4,4,5,5-tetramethyl-1,3,2-dioxaborolan-2-yl)-5,6-dihydropyridine-1 (2H)-carboxylate (566 mg, 1.84 mmol, 1.1 equiv), $Pd(dppf)Cl_2$ (122 mg, 0.167 mmol) and $K_2CO_3$ (460 mg, 3.34 mmol) in dioxane/$H_2O$ (19 mL/1.9 mL) was stirred at 85° C. for 3 hours under $N_2$ atmosphere. The reaction mixture was filtered through celite and the filtrate was concentrated under reduced pressure to give a crude product which was diluted with EtOAc (50 mL). The organic layer was washed with water (2× 20 mL) and brine (20 mL), dried over anhydrous $Na_2SO_4$ and concentrated. The residue was purified by flash chromatography (eluted with PE/EtOAc=10/1) to afford the title compound tert-butyl 4-(3-bromo-2-(2-(4-chlorophenyl)-2-hydroxypropoxy)phenyl)-5,6-dihydropyridine-1 (2H)-carboxylate as a colorless oil (560 mg, 64% yield).

$^1H$ NMR (400 MHZ, $CDCl_3$) δ ppm 7.40-7.49 (m, 3H), 7.29-7.36 (m, 2H), 7.06 (dd, J=7.6, 1.6 Hz, 1H), 6.95 (t, J=7.6 Hz, 1H), 5.73-5.76 (m, 1H), 4.02-4.05 (m, 2H), 3.99 (d, J=8.8 Hz, 1H), 3.86 (d, J=8.8 Hz, 1H), 3.50-3.56 (m, 2H), 2.30-2.34 (m, 2H), 1.61 (s, 3H), 1.52 (s, 9H).

Step C: tert-butyl 4-(2-(4-chlorophenyl)-2-methyl-2,3-dihydrobenzo[b][1,4]dioxin-5-yl) 5,6-dihydropyridine-1 (2H)-carboxylate

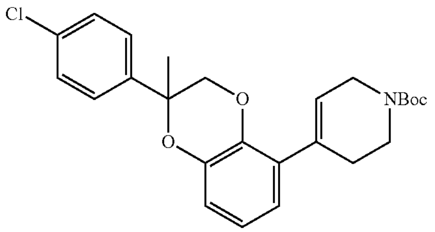 [SMILES: CC(C)(C)OC(=O)N1CC=C(c2cccc3c2OCC(C)(c2ccc(Cl)cc2)O3)CC1]

A mixture of tert-butyl 4-(3-bromo-2-(2-(4-chlorophenyl)-2-hydroxypropoxy)phenyl)-5,6-dihydropyridine-1

(2H)-carboxylate (320 mg, 0.612 mmol), CuI (117 mg, 0.612 mmol), (1S,2S)—$N^1$,$N^2$-dimethylcyclohexane-1,2-diamine (174 mg, 1.23 mmol) and $Cs_2CO_3$ (399 mg, 1.22 mmol) in DMF (7 mL) was stirred at 120° C. via microwave irradiation for 3.5 hours under $N_2$ atmosphere. The reaction mixture was diluted with water (20 mL) and extracted with EtOAc (3x30 mL). The combined organic layers were washed with brine (30 mL), dried over anhydrous $Na_2SO_4$ and concentrated. The residue was purified by flash chromatography (eluted with PE/EtOAc=10/1) to afford the title compound tert-butyl 4-(2-(4-chlorophenyl)-2-methyl-2,3-dihydrobenzo[b][1,4]dioxin-5-yl)-5,6-dihydropyridine-1 (2H)carboxylate as a white solid (120 mg, 45% yield).

$^1$H NMR (400 MHZ, $CDCl_3$) δ ppm 7.37-7.43 (m, 2H), 7.30-7.37 (m, 2H), 6.91 (dd, J=8.0, 2.0 Hz, 1H), 6.84 (t, J=8.0 Hz, 1H), 6.73 (dd, J=7.2, 1.6 Hz, 1H), 5.74-5.79 (m, 1H), 4.21 (d, J=11.6 Hz, 1H), 4.09 (d, J=11.6 Hz, 1H), 3.90-4.04 (m, 2H), 3.54-3.69 (m, 2H), 2.35-2.52 (m, 2H), 1.61 (s, 3H), 1.48 (s, 9H). LC-MS: m/z 386.2 $(M-55)^+$.

Step D: tert-butyl 4-(2-(4-chlorophenyl)-2-methyl-2,3-dihydrobenzo[b][1,4]dioxin-5-yl) piperidine-1-carboxylate

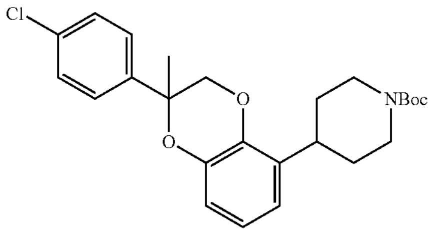

To a solution of tert-butyl 4-(2-(4-chlorophenyl)-2-methyl-2,3-dihydrobenzo[b][1,4]dioxin-5-yl)-5,6-dihydropyridine-1 (2H)-carboxylate (120 mg, 0.270 mmol) in MeOH (10 mL) was added $Pd(OH)_2/C$ (10.0 mg, 10% w/w) and Pd/C (10 mg, 10% w/w) under $N_2$. The resulting mixture was degassed and refilled with $H_2$ for three times. Then the mixture was stirred at room temperature for 12 hours under $H_2$ atmosphere. The reaction mixture was filtered through celite and concentrated to afford the title compound tert-butyl 4-(2-(4-chlorophenyl)-2-methyl-2,3-dihydrobenzo[b][1,4]dioxin-5-yl)piperidine-1-carboxylate (128 mg, 99.8% yield). The title compound was used in next step directly without purification. LC-MS: m/z 388.2 $(M-55)^+$.

Step E: 4-(2-(4-chlorophenyl)-2-methyl-2,3-dihydrobenzo[b][1,4]dioxin-5-yl) piperidine hydrochloride

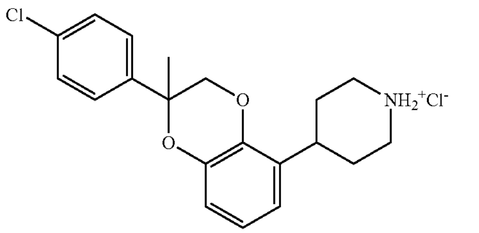

A solution of tert-butyl 4-(2-(4-chlorophenyl)-2-methyl-2,3-dihydrobenzo[b][1,4]dioxin-5-yl)piperidine-1-carboxylate (120 mg, 0.270 mmol) in HCl-dioxane solution (4M, 3 mL) was stirred at room temperature for 1 hour. The reaction mixture was concentrated to dryness to afford the title compound 4-(2-(4-chlorophenyl)-2-methyl-2,3-dihydrobenzo[b][1,4]dioxin-5-yl)piperidine hydrochloride (130 mg) as a white solid. LC-MS: m/z 344.1 $(M+H)^+$.

Step F: methyl 2-((4-(2-(4-chlorophenyl)-2-methyl-2,3-dihydrobenzo[b][1,4]dioxin-5-yl) piperidin-1-yl) methyl)-3-((S)-oxetan-2-ylmethyl)-3H-imidazo[4,5-b]pyridine-5-carboxylate

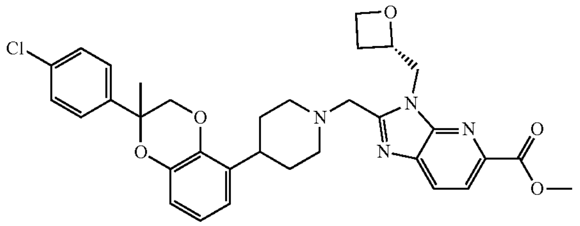 [SMILES: COC(=O)c1ccc2nc(CN3CCC(c4cccc5c4OCC(C)(c4ccc(Cl)cc4)O5)CC3)n(C[C@@H]3CCO3)c2n1]

A mixture of 4-(2-(4-chlorophenyl)-2-methyl-2,3-dihydrobenzo[b][1,4]dioxin-5-yl) piperidine hydrochloride (130 mg, 0.378 mmol), (S)-methyl 2-(chloromethyl)-3-(oxetan-2-ylmethyl)-3H-imidazo[4,5-b]pyridine-5-carboxylate (123 mg, 0.415 mmol) and $K_2CO_3$ (104 mg, 0.756 mmol) in DMF (4 mL) was stirred at 60° C. for 3 hours. The reaction mixture was diluted with water (20 mL) and extracted with EtOAc (3x10 mL). The combined organic phase was washed with brine (10 mL), dried over anhydrous $Na_2SO_4$ and concentrated. The residue was purified by Prep-HPLC to afford the title compound methyl 2-((4-(2-(4-chlorophenyl)-2-methyl-2,3-dihydrobenzo[b][1,4]dioxin-5-yl)piperidin-1-yl)methyl)-3-((S)-oxetan-2-ylmethyl)-3H-imidazo[4,5-b] pyridine-5-carboxylate (70.0 mg, 34% yield) as a white solid.

$^1$H NMR (400 MHZ, $CDCl_3$) δ ppm 8.08 (dd, J=17.2, 8.4 Hz, 2H), 7.39 (d, J=8.4 Hz, 2H), 7.32 (d, J=8.4 Hz, 2H), 6.85 (d, J=4.4 Hz, 2H), 6.75 (t, J=4.4 Hz, 1H), 5.23-5.28 (m, 1H), 4.98 (dd, J=14.4, 8.4 Hz, 1H), 4.89 (dd, J=14.4, 3.2 Hz, 1H), 4.58-4.63 (m, 1H), 4.32-4.44 (m, 1H), 4.18-4.25 (m, 1H), 4.09 (d, J=11.2 Hz, 1H), 4.05 (s, 2H), 4.01 (s, 3H), 2.85-3.00 (m, 3H), 2.74-2.78 (m, 1H), 2.44-2.58 (m, 1H), 2.20-2.38 (m, 2H), 1.78-1.84 (m, 1H), 1.67-1.73 (m, 3H), 1.60 (s, 3H). LC-MS: m/z 603.2 $(M+H)^+$.

Step G: 2-((4-(2-(4-chlorophenyl)-2-methyl-2,3-dihydrobenzo[b][1,4]dioxin-5-yl) piperidin-1-yl) methyl)-3-((S)-oxetan-2-ylmethyl)-3H-imidazo[4,5-b]pyridine-5-carboxylic acid

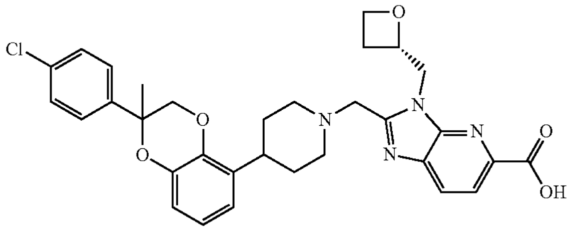 [SMILES: CC1(c2ccc(Cl)cc2)COc2c(cccc2C2CCN(Cc3nc4ccc(C(=O)O)nc4n3C[C@@H]3CCO3)CC2)O1]

To a solution of methyl 2-((4-(2-(4-chlorophenyl)-2-methyl-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylate (70.0 mg, 0.116 mmol) in THF/$H_2O$ (5 mL/1 mL) was added LiOH·$H_2O$ (24.0 mg, 0.580 mmol). The resulting mixture was stirred at room temperature for 2 hours. Then the reaction mixture was adjusted to pH=5~ 6 with HCOOH. The mixture was extracted with EtOAc (3×20 mL). The organic combined layers were washed with water (10 mL) and brine (10 mL), dried over $Na_2SO_4$, concentrated and purified with Prep-HPLC to afford the title compound 2-((4-(2-(4-chlorophenyl)-2-methyl-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylic acid as white solid (44.7 mg, 66% yield).

$^1$H NMR (400 MHZ, DMSO-$d_6$) δ ppm 8.12 (d, J=8.4 Hz, 1H), 7.99 (d, J=8.0 Hz, 1H), 7.51 (d, J=8.8 Hz, 2H), 7.42 (d, J=8.4 Hz, 2H), 6.80-6.86 (m, 2H), 6.73 (dd, J=6.8, 2.4 Hz, 1H), 5.15-5.18 (m, 1H), 4.84 (dd, J=14.4, 6.4 Hz, 1H), 4.71 (dd, J=14.4, 4.0 Hz, 1H), 4.49-4.53 (m, 2H), 4.34-4.38 (m, 1H), 4.18 (d, J=11.6 Hz, 1H), 3.94 (dd, J=28.4, 14.0 Hz, 2H), 2.86-2.96 (m, 2H), 2.65-2.78 (m, 3H), 2.15-2.26 (m, 2H), 1.53-1.76 (m, 4H), 1.52 (s, 3H). LC-MS: m/z 589.2 $(M+H)^+$.

The following compounds were synthesized following the similar methods depicted in Example 5, using the corresponding starting materials.

2-((4-(2-(4-chloro-2-fluorophenyl)-2-methyl-2,3-dihydrobenzo[b][1,4]dioxin-5-yl) piperidin-1-yl)methyl)-3-((S)-oxetan-2-ylmethyl)-3H-imidazo[4,5-b]pyridine-5-carboxylic acid (Compound 127a)

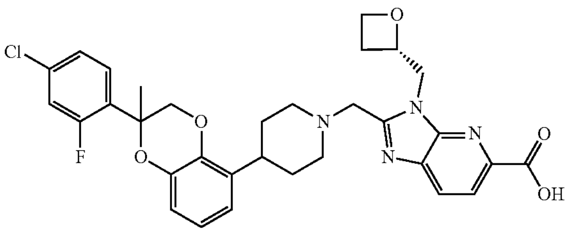 [SMILES: CC1(c2ccc(Cl)cc2F)COc2c(cccc2C2CCN(Cc3nc4ccc(C(=O)O)nc4n3C[C@@H]3CCO3)CC2)O1]

$^1$H NMR (400 MHZ, $CD_3OD$) δ ppm 8.22-8.02 (m, 2H), 7.42 (t, J=8.0 Hz, 1H), 7.24 (dd, J=12.0, 4.0 Hz, 1H), 7.12 (dd, J=8.0, 4.0 Hz, 1H), 6.94-6.82 (m, 2H), 6.77-6.71 (m, 1H), 5.30-5.27 (m, 1H), 5.05-4.95 (m, 1H), 4.85-4.78 (m, 1H), 4.71-4.55 (m, 2H), 4.47-4.42 (m, 1H), 4.34-4.19 (m, 2H), 4.13 (d, J=12.0 Hz, 1H), 3.31-3.16 (m, 2H), 3.01-2.88 (m, 1H), 2.84-2.73 (m, 1H), 2.68-2.45 (m, 3H), 1.92-1.67 (m, 4H), 1.63 (s, 3H). LC-MS: m/z 607.1 $(M+H)^+$. $^{19}$F NMR (377 MHz, $CD_3OD$) δ ppm-112.78.

Example 6 2-((4-((R)-2-(4-chlorophenyl)-2,3-dihydrobenzo[b][1,4]dioxin-5-yl) piperidin-1-yl)methyl)-3-((S)-oxetan-2-ylmethyl)-3H-imidazo[4,5-b]pyridine-5-carboxylic acid (Compound 111b)

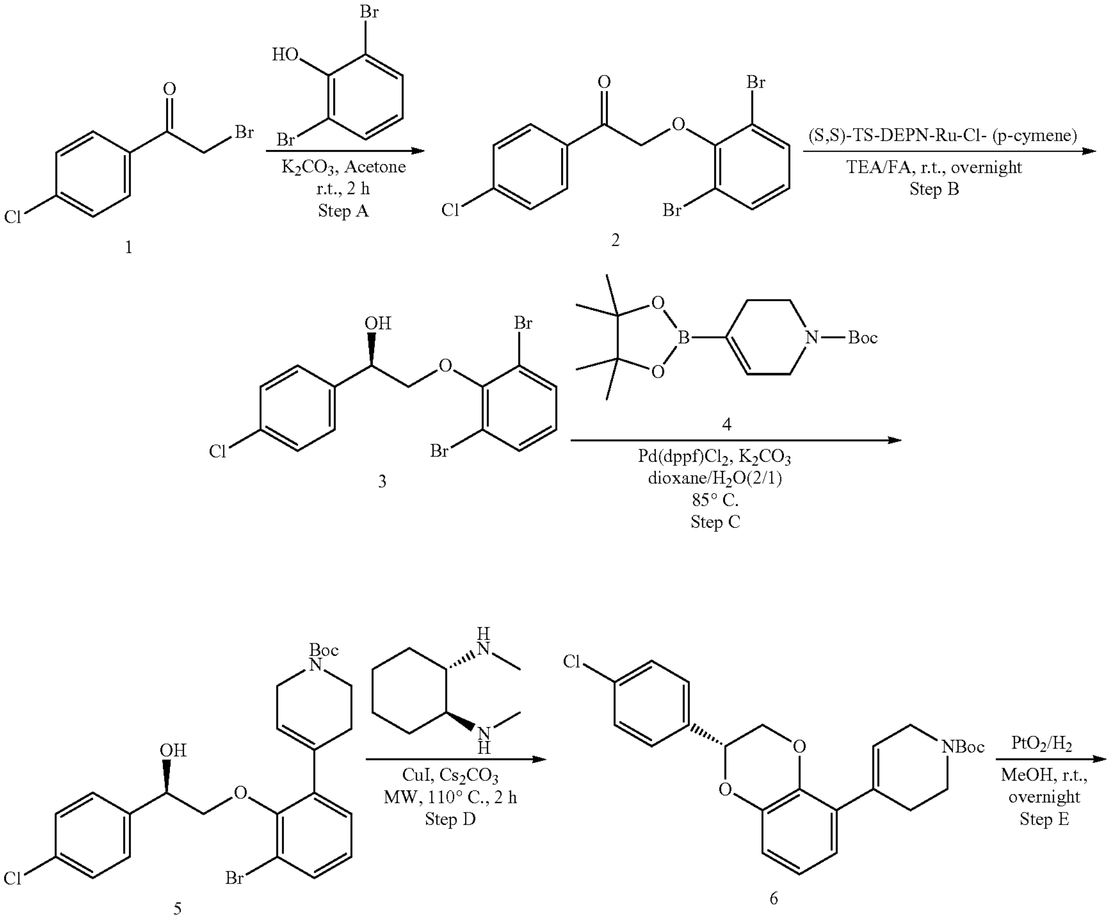

1 2 3 5 6

-continued

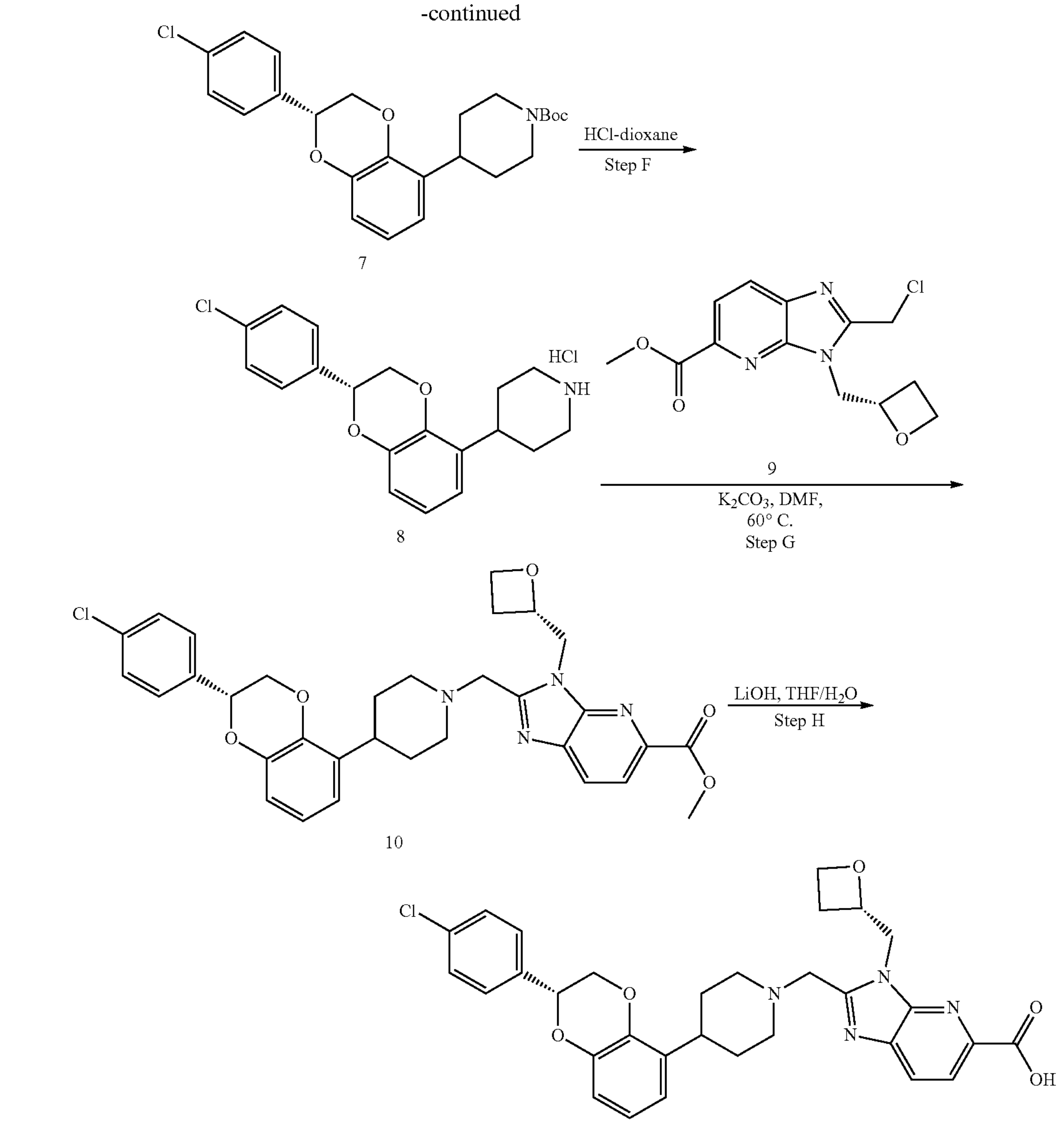

7

8

9

10

Compound 111b

Step A: 1-(4-chlorophenyl)-2-(2,6-dibromophenoxy) ethanone

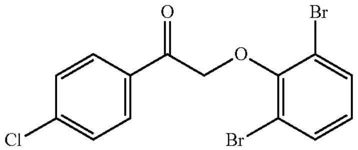 [SMILES: O=C(COc1c(Br)cccc1Br)c1ccc(Cl)cc1]

To a solution of 2-bromo-1-(4-chlorophenyl) ethanone (5.00 g, 21.5 mmol) and 2,6-dibromophenol (5.43 g, 21.5 mmol) in acetone (70 mL) was added $K_2CO_3$ (5.95 g, 43.0 mmol). The resulting mixture was stirred at room temperature for 2 hours under $N^2$ atmosphere. The reaction mixture was quenched with water (140 mL) and lots of solid appeared. The mixture was filtered. The filter cake was washed with water (20 mL) and dried under reduced pressure to give the title compound 1-(4-chlorophenyl)-2-(2,6-dibromophenoxy) ethanone as a white solid (8.00 g, 92.5% yield).

$^1$H NMR (400 MHZ, DMSO-d$_6$) δ ppm 8.02-8.09 (m, 2H), 7.71 (d, J=8.0 Hz, 2H), 7.58-7.67 (m, 2H), 7.10 (t, J=8.0 Hz, 1H), 5.37 (s, 2H).

Step B: (R)-1-(4-chlorophenyl)-2-(2,6-dibromophenoxy) ethanol

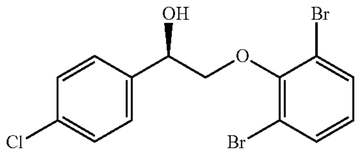 [SMILES: O[C@@H](COc1c(Br)cccc1Br)c1ccc(Cl)cc1]

To a solution of TEA (20 mL) and formic acid (4 mL) was added (S,S)-TS-DEPN—Ru—Cl-(p-cymene) (158 mg, 0.247 mmol) in one portion at rt. Then the mixture was stirred at room temperature for 1 hour. 1-(4-chlorophenyl)-2-(2,6-dibromophenoxy) ethanone (2.00 g, 4.94 mmol) was added. The resulting mixture was stirred at room temperature for 4 hours. The solution was quenched with water (30 mL) and lots of precipitate formed. The mixture was filtered. The filter cake was washed with water (15 mL) and dried under reduced pressure to give crude product, which was purified by flash chromatography (eluted with PE/EtOAc=10/1) to afford the title compound (R)-1-(4-chlorophenyl)-2-(2,6-dibromophenoxy) ethanol (1.90 g, ee % 100%, 95% yield) as a white solid.

$^1H$ NMR (400 MHZ, DMSO-$d_6$) δ ppm 7.64 (d, J=8.0 Hz, 2H), 7.48 (d, J=8.4 Hz, 2H), 7.41 (d, J=8.4 Hz, 2H), 7.02 (t, J=8.0 Hz, 1H), 5.79 (d, J=4.4 Hz, 1H), 5.05 (dd, J=11.2, 5.6 Hz, 1H), 4.06 (dd, J=9.2, 6.8 Hz, 1H), 3.95 (dd, J=9.6, 5.6 Hz, 1H).

Step C: (R)-tert-butyl 4-(3-bromo-2-(2-(4-chlorophenyl)-2-hydroxyethoxy)phenyl)-5,6-dihydropyridine-1 (2H)-carboxylate

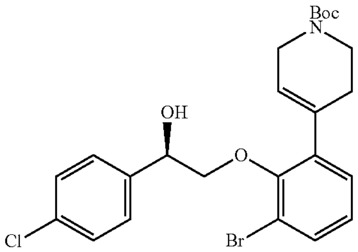 [SMILES: CC(C)(C)OC(=O)N1CC=C(c2cccc(Br)c2OC[C@H](O)c2ccc(Cl)cc2)CC1]

The mixture of (R)-1-(4-chlorophenyl)-2-(2,6-dibromophenoxy) ethanol (1.90 g, 4.70 mmol), tert-butyl 4-(4,4,5,5-tetramethyl-1,3,2-dioxaborolan-2-yl)-5,6-dihydropyridine-1 (2H)-carboxylate (1.75 g, 5.65 mmol), Pd(dppf)$Cl_2$ (344 mg, 0.47 mmol) and $K_2CO_3$ (1.30 g, 9.40 mmol) in dioxane/$H_2O$ (60 mL/8 mL) was stirred at 85° C. for 3 hours under $N_2$ atmosphere. The reaction mixture was filtered through celite and the filtrate was concentrated under reduced pressure. The residue was diluted with EtOAc (50 mL). The organic layer was washed with water (2× 20 mL) and brine (20 mL), dried over anhydrous $Na_2SO_4$ and concentrated. The residue was purified by flash chromatography (eluted with PE/EtOAc=10/1) to afford the title compound (R)-tert-butyl 4-(3-bromo-2-(2-(4-chlorophenyl)-2-hydroxyethoxy)phenyl)-5,6-dihydropyridine-1 (2H)-carboxylate as a colorless oil (1.26 g, 53% yield). $^1H$ NMR (400 MHZ, $CD_3OD$) δ ppm 7.48 (dd, J=8.0, 1.6 Hz, 1H), 7.40 (d, J=8.4 Hz, 2H), 7.36 (d, J=8.4 Hz, 2H), 7.13 (dd, J=7.6, 1.6 Hz, 1H), 6.99 (t, J=8.0 Hz, 1H), 5.78 (brs, 1H), 4.99-5.02 (m, 1H), 3.97-3.98 (m, 2H), 3.93-3.96 (m, 1H), 3.82-3.84 (m, 1H), 3.46-3.53 (m, 2H), 2.29-2.44 (m, 3H), 1.50 (s, 9H).

Step D: (R)-tert-butyl 4-(2-(4-chlorophenyl)-2,3-dihydrobenzo[b][1,4]dioxin-5-yl)-5,6-dihydropyridine-1 (2H)-carboxylate

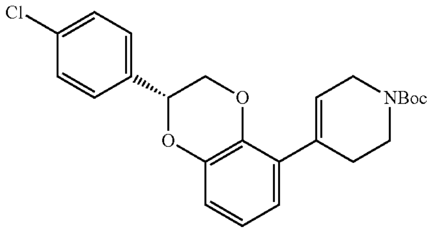

A mixture of (R)-tert-butyl 4-(3-bromo-2-(2-(4-chlorophenyl)-2-hydroxyethoxy)phenyl)-5,6-dihydropyridine-1 (2H)-carboxylate (600 mg, 1.18 mmol), CuI (225 mg, 1.18 mmol), (1S,2S)—$N^1$,$N^2$-dimethylcyclohexane-1,2-diamine (337 mg, 2.37 mmol) and $Cs_2CO_3$ (772 mg, 2.37 mmol) in DMF (15 mL) was stirred at 110° C. via microwave irradiation for 2.5 hours under $N_2$ atmosphere. The reaction mixture was diluted with water (20 mL) and extracted with EtOAc (3×30 mL). The combined organic layers were washed with brine (30 mL), dried over anhydrous $Na_2SO_4$ and concentrated. The residue was purified by flash chromatography (eluted with PE/EtOAc=10/1) to afford the title compound (R)-tert-butyl 4-(2-(4-chlorophenyl)-2,3-dihydrobenzo[b][1,4]dioxin-5-yl)-5,6-dihydropyridine-1 (2H)carboxylate as a yellow oil (640 mg, 100% yield, overweight).

$^1H$ NMR (400 MHZ, $CDCl_3$) δ ppm 7.35-7.42 (m, 4H), 6.92 (dd, J=8.0, 1.6 Hz, 1H), 6.85 (t, J=7.6 Hz, 1H), 6.79 (dd, J=7.6, 1.6 Hz, 1H), 5.84 (brs, 1H), 5.11 (dd, J=8.8, 2.4 Hz, 1H), 4.37 (dd, J=11.6, 2.4 Hz, 1H), 4.04-4.07 (m, 2H), 3.96 (dd, J=11.6, 8.8 Hz, 1H), 3.60-3.63 (m, 2H), 2.49-2.52 (m, 2H), 1.50 (s, 9H).

Step E: (R)-tert-butyl 4-(2-(4-chlorophenyl)-2,3-dihydrobenzo[b][1,4]dioxin-5-yl) piperidine-1-carboxylate

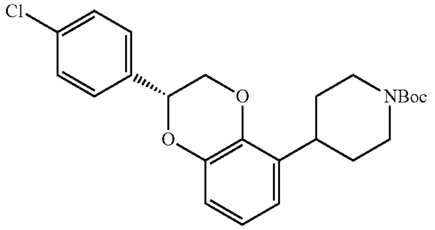 [SMILES: CC(C)(C)OC(=O)N1CCC(c2cccc3c2OC[C@@H](c2ccc(Cl)cc2)O3)CC1]

To a solution of (R)-tert-butyl 4-(2-(4-chlorophenyl)-2,3-dihydrobenzo[b][1,4]dioxin-5-yl)-5,6-dihydropyridine-1 (2H)-carboxylate (640 mg, 1.50 mmol) in MeOH (15 mL) was added $PtO_2$ (34.0 mg) under $N_2$. The resulting mixture was degassed and refilled with $H_2$ for three times. Then the mixture was stirred at room temperature for 12 hours under $H_2$ atmosphere. The reaction mixture was filtered through celite and concentrated to afford the title compound (R)-tert-butyl 4-(2-(4-chlorophenyl)-2,3-dihydrobenzo[b][1,4]dioxin-5-yl)piperidine-1-carboxylate as a white solid (620 mg, 96% yield). The title compound was used in next step directly without purification.

Step F: (R)-4-(2-(4-chlorophenyl)-2,3-dihydrobenzo[b][1,4]dioxin-5-yl)piperidine hydrochloride

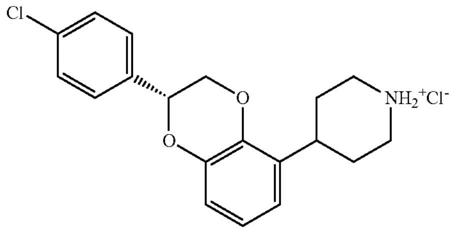

A solution of (R)-tert-butyl 4-(2-(4-chlorophenyl)-2,3-dihydrobenzo[b][1,4]dioxin-5-yl) piperidine-1-carboxylate (600 mg, 1.40 mmol) in HCl-dioxane solution (4M, 10 mL) was stirred at room temperature for 1 hour. The reaction mixture was concentrated to dryness to afford the title compound (R)-4-(2-(4-chlorophenyl)-2,3-dihydrobenzo[b][1,4]dioxin-5-yl)piperidine hydrochloride (500 mg, 98% yield) as a white solid. LC-MS: m/z 330.2 $(M+H)^+$.

Step G: methyl 2-((4-((R)-2-(4-chlorophenyl)-2,3-dihydrobenzo[b][1,4]dioxin-5-yl) piperidin-1-yl) methyl)-3-((S)-oxetan-2-ylmethyl)-3H-imidazo[4,5-b]pyridine-5-carboxylate

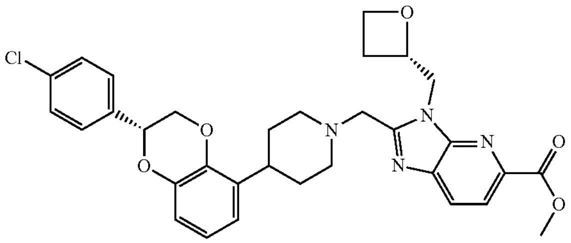 [SMILES: COC(=O)c1ccc2nc(CN3CCC(c4cccc5c4OC[C@@H](c4ccc(Cl)cc4)O5)CC3)n(C[C@@H]3CCO3)c2n1]

A mixture of (R)-4-(2-(4-chlorophenyl)-2,3-dihydrobenzo[b][1,4]dioxin-5-yl) piperidine hydrochloride (500 mg, 1.52 mmol), (S)-methyl 2-(chloromethyl)-3-(oxetan-2-ylmethyl)-3H-imidazo[4,5-b]pyridine-5-carboxylate (494 mg, 1.67 mmol) and K2CO$_3$ (420 mg, 3.04 mmol) in DMF (10 mL) was stirred at 60° C. for 3 hours. The reaction mixture was diluted with water (30 mL) and extracted with EtOAc (3×15 mL). The combined organic phase was washed with brine (10 mL), dried over anhydrous $Na_2SO_4$ and concentrated. The residue was purified by flash chromatography (eluted with DCM/MeOH=50/1) to afford the title compound methyl 2-((4-((R)-2-(4-chlorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylate as a colorless gum (743 mg, 83% yield).

$^1$H NMR (400 MHZ, $CDCl_3$) δ ppm 8.08 (dd, J=16.4, 8.0 Hz, 2H), 7.38 (dd, J=16.0, 8.8 Hz, 4H), 6.81-6.86 (m, 3H), 5.24-5.26 (m, 1H), 5.09 (dd, J=8.8, 2.0 Hz, 1H), 4.89-5.02 (m, 2H), 4.60 (dd, J=14.0, 7.6 Hz, 1H), 4.36-4.40 (m, 2H), 4.07 (s, 2H), 4.01 (s, 3H), 3.95 (dd, J=11.2, 8.8 Hz, 1H), 2.99 (brs, 3H), 2.73-2.81 (m, 1H), 2.47-2.56 (m, 1H), 2.31-2.37 (m, 2H), 1.68-1.92 (m, 4H). LC-MS: m/z 589.2 $(M+H)^+$.

Step H: 2-((4-((R)-2-(4-chlorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylic acid

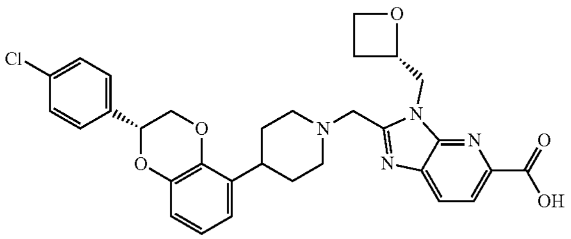 [SMILES: O=C(O)c1ccc2nc(CN3CCC(c4cccc5c4OC[C@@H](c4ccc(Cl)cc4)O5)CC3)n(C[C@@H]3CCO3)c2n1]

To a solution of methyl 2-((4-((R)-2-(4-chlorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylate (743 mg, 1.26 mmol) in THF/$H_2O$ (10 mL/10 mL) was added LiOH·$H_2O$ (284 mg, 6.76 mmol). The resulting mixture was stirred at room temperature for 1 hour. Then the reaction mixture was adjusted to pH=5~6 with HCOOH. The mixture was extracted with EtOAc (3×20 mL). The organic combined layers were washed with water (10 mL) and brine (10 mL), dried over $Na_2SO_4$, concentrated and purified with Prep-HPLC to afford the title compound 2-((4-((R)-2-(4-chlorophenyl)-2,3-dihydrobenzo[b][1,4]dioxin-5-yl)piperidin-1-yl)methyl)-3-((S)-oxetan-2-ylmethyl)-3H-imidazo[4,5-b]pyridine-5-carboxylic acid as white solid (515 mg, 71% yield).

$^1$H NMR (400 MHZ, $CD_3OD$) δ ppm 13.04 (brs, 1H), 8.14 (d, J=8.0 Hz, 1H), 7.99 (d, J=8.0 Hz, 1H), 7.51 (s, 4H), 6.79-6.85 (m, 3H), 5.25 (dd, J=8.4, 2.4 Hz, 1H), 5.17-5.21 (m, 1H), 4.86 (dd, J=14.4, 6.4 Hz, 1H), 4.74 (dd, J=14.8, 4.0 Hz, 1H), 4.48-4.52 (m, 2H), 4.34-4.40 (m, 1H), 4.05 (dd, J=11.6, 8.4 Hz, 1H), 3.96-4.01 (m, 2H), 2.88-2.93 (m, 3H), 2.68-2.72 (m, 1H), 2.22-2.33 (m, 2H), 1.65-1.77 (m, 4H).

LC-MS: m/z 575.2 $(M+H)^+$.

2-((4-((S)-2-(4-chlorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 111c) was synthesized following the methods depicted in Example 6, using N-[(1R,2R)-2-amino-1,2-diphenyl-ethyl]-4-methyl-benzenesulfonamide; chlororuthenium; 1-isopropyl-4-methyl-benzene in step B.

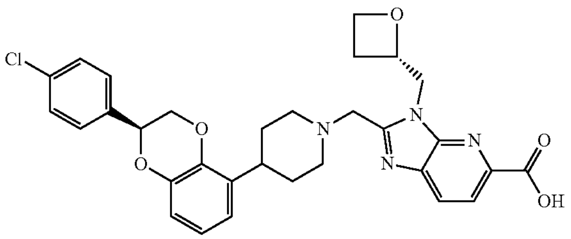 [SMILES: O=C(O)c1ccc2nc(CN3CCC(c4cccc5c4OC[C@H](c4ccc(Cl)cc4)O5)CC3)n(C[C@@H]3CCO3)c2n1]

$^1$H NMR (400 MHZ, DMSO-$d_6$) δ ppm 8.12 (d, J=8.4 Hz, 1H), 7.99 (d, J=8.0 Hz, 1H), 7.47-7.50 (m, 4H), 6.79-6.84 (m, 3H), 5.25 (dd, J=8.0, 2.0 Hz, 1H), 5.14-5.21 (m, 1H), 4.86 (dd, J=14.8, 6.4 Hz, 1H), 4.73 (dd, J=14.8, 4.0 Hz, 1H), 4.48-4.52 (m, 2H), 4.35-4.40 (m, 1H), 4.05 (dd, J=11.2, 8.4 Hz, 1H), 3.99 (d, J=13.6 Hz, 1H), 3.92 (d, J=13.6 Hz, 1H), 2.66-2.99 (m, 5H), 2.20-2.26 (m, 2H), 1.58-1.75 (m, 4H). LC-MS: m/z 575.2 $(M+H)^+$.

2-((4-((R)-2-(4-chloro-2-fluorophenyl)-2,3-dihydrobenzo [b][1,4]dioxin-5-yl) piperidin-1-yl)methyl)-1-((S)-oxetan-2-ylmethyl)-1H-benzo[d]imidazole-6-carboxylic acid (Compound 120b) was synthesized following the methods depicted in Example 6, using 1-(4-chloro-2-fluorophenyl)-2-(2,6-dibromophenoxy) ethenone and N-[(1S,2S)-2-amino-1,2-diphenyl-ethyl]-4-methyl-benzenesulfonamide; chlororuthenium; 1-isopropyl-4-methyl-benzene in step B.

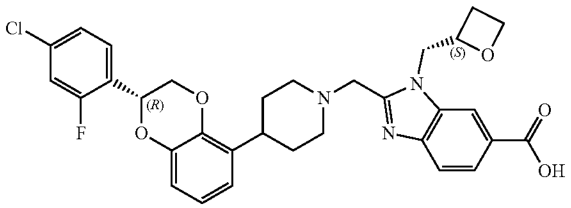

$^1$H NMR (400 MHZ, DMSO-d6) δ ppm 12.70 (brs, 1H), 8.26 (s, 1H), 7.79 (dd, J=8.4, 1.6 Hz, 1H), 7.63 (d, J=8.4 Hz, 1H), 7.57-7.51 (m, 2H), 7.38 (dd, J=8.4, 2.0 Hz, 1H), 6.84-6.78 (m, 3H), 5.43 (dd, J=8.0, 2.2 Hz, 1H), 5.15-5.04 (m, 1H), 4.83-4.77 (m, 1H), 4.69-4.63 (m, 1H), 4.53-4.47 (m, 2H), 4.41-4.33 (m, 1H), 4.13 (dd, J=11.6, 8.2 Hz, 1H), 3.94 (d, J=13.6 Hz, 1H), 3.78 (d, J=13.6 Hz, 1H), 3.00 (d, J=11.2 Hz, 1H), 2.92-2.80 (m, 2H), 2.74-2.69 (m, 1H), 2.47-2.41 (m, 2H), 2.28-2.12 (m, 1H), 1.78-1.57 (m, 4H). LC-MS: m/z 592.2 $(M+H)^+$.

2-((4-((S)-2-(4-chloro-2-fluorophenyl)-2,3-dihydrobenzo [b][1,4]dioxin-5-yl) piperidin-1-yl)methyl)-1-((S)-oxetan-2-ylmethyl)-1H-benzo[d]imidazole-6-carboxylic acid (Compound 120c) was synthesized following the methods depicted in Example 6, using 1-(4-chloro-2-fluorophenyl)-2-(2,6-dibromophenoxy) ethenone and N-[(1R,2R)-2-amino-1,2-diphenyl-ethyl]-4-methyl-benzenesulfonamide; chlororuthenium; 1-isopropyl-4-methyl-benzene in step B.

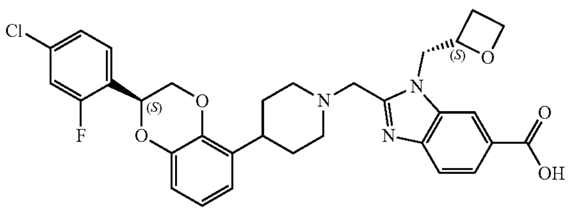

$^1$H NMR (400 MHZ, DMSO-$d_6$) δ ppm 12.75 (brs, 1H), 8.30 (s, 1H), 7.82 (d, J=8.0, 1H), 7.73-7.60 (m, 1H), 7.58-7.50 (m, 2H), 7.39 (dd, J=8.4, 1.8 Hz, 1H), 6.88-6.78 (m, 3H), 5.43 (dd, J=8.0, 1.6 Hz, 1H), 5.12-5.04 (m, 1H), 4.87-4.76 (m, 1H), 4.72-4.63 (m, 1H), 4.56-4.44 (m, 2H), 4.41-4.33 (m, 1H), 4.13 (dd, J=11.2, 8.0 Hz, 1H), 4.04-3.64 (m, 2H), 3.32-3.19 (m, 2H), 3.07-2.85 (m, 2H), 2.78-2.63 (m, 1H), 2.47-2.21 (m, 2H), 1.83-1.63 (m, 4H). LC-MS: m/z 592.1 $(M+H)^+$.

Example 7

2-((4-((R)-2-(4-cyanophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 118b)

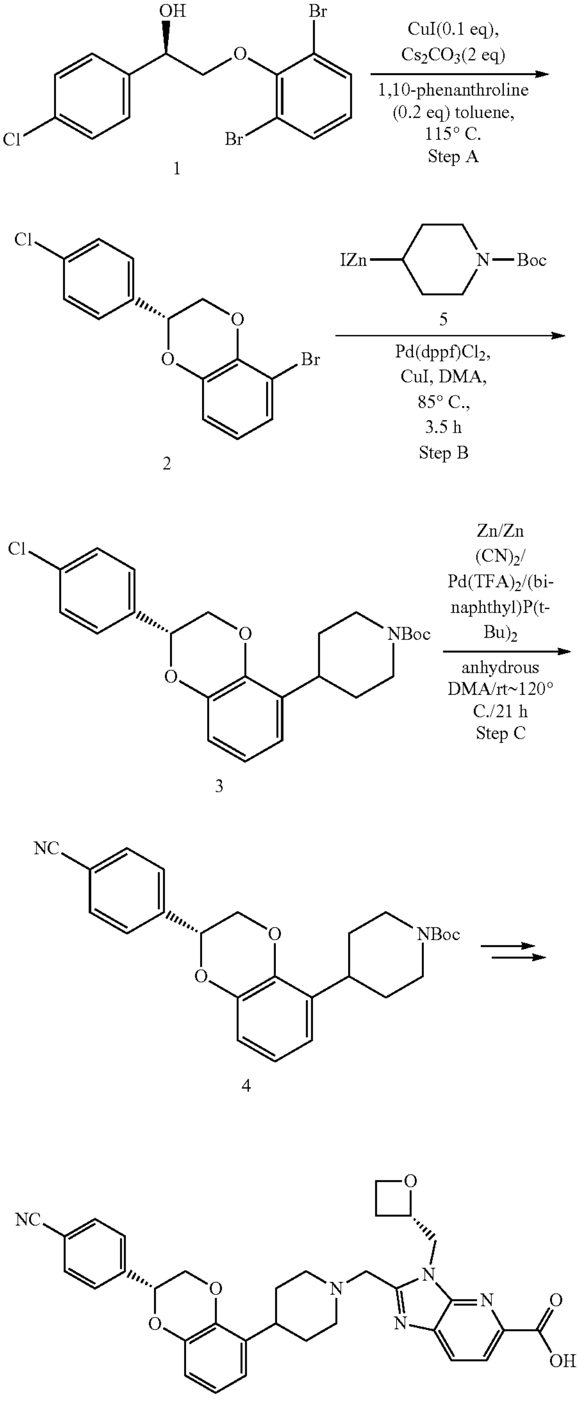

Compound 118b

Step A: (R)-5-bromo-2-(4-chlorophenyl)-2,3-dihydrobenzo[b][1,4]dioxine

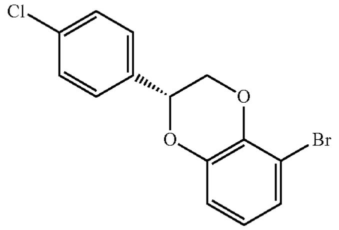 [SMILES: Clc1ccc([C@@H]2COc3c(Br)cccc3O2)cc1]

A mixture of (R)-1-(4-chlorophenyl)-2-(2,6-dibromophenoxy) ethan-1-ol (7.60 g, 18.8 mmol), CuI (359 mg, 1.88 mmol), 1,10'-phenantroline (678 mg, 3.76 mmol) and $Cs_2CO_3$ (12.3 g, 37.6 mmol) in anhydrous toluene (115 mL) was stirred at 120° C. overnight under $N_2$ atmosphere. The reaction mixture was filtered and the filter mass washed with EtOAc (3×30 mL). The combined organic layers was concentrated and purified by flash chromatography (eluted with PE/DCM=10/1) to afford the title compound (R)-5-bromo-2-(4-chlorophenyl)-2,3-dihydrobenzo[b][1,4]dioxine as a white solid (3.39 g, 56% yield).

$^1$H NMR (400 MHZ, DMSO-$d_6$) δ ppm 7.52 (s, 4H), 7.18 (d, J=8.0 Hz, 1H), 7.02 (d, J=8.0 Hz, 1H), 6.84 (t, J=8.0 Hz, 1H), 5.33 (dd, J=8.0, 2.0 Hz, 1H), 4.57 (dd, J=11.6, 2.0 Hz, 1H), 4.19 (dd, J=11.6, 8.0 Hz, 1H).

Step B: tert-butyl (R)-4-(2-(4-chlorophenyl)-2,3-dihydrobenzo[b][1,4]dioxin-5-yl) piperidine-1-carboxylate

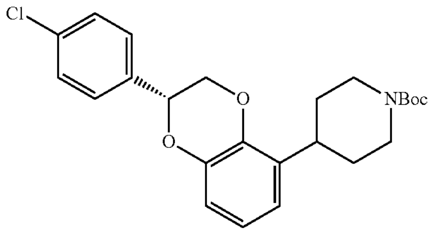 [SMILES: CC(C)(C)OC(=O)N1CCC(c2cccc3c2OC[C@@H](c2ccc(Cl)cc2)O3)CC1]

Zinc dust (11.5 g, 175 mmol) was suspended in DMA (30 mL) and a solution of trimethylsilyl chloride/1,2-dibromoethane (7:5 w/w, 3.1 g) was added via syringe over several minutes. The temperature rose to 60° C. and the mixture was stirred for 15 minutes. After the reaction mixture was cooled back to room temperature, a solution of tert-butyl 4-iodopiperidine-1-carboxylate (5.16 mol, 49.5 g) in DMA (80 mL) was added over 5 minutes. The temperature rose again to 66° C. and the mixture was stirred for another 2 h to give (1-(tert-butoxycarbonyl)piperidin-4-yl) zinc (II) iodide as 1.2 M solution in DMA. To a solution of (R)-5-bromo-2-(4-chlorophenyl)-2,3-dihydrobenzo[b][1,4]dioxine (20.0 g, 61.4 mmol) in DMA (50 mL) were added $PdCl_2$ (dppf) (1.50 g, 1.84 mmol) and CuI (702 mg, 3.68 mmol). The mixture was degassed and refilled with $N_2$ for three tomes. The above zinc reagent was added and the mixture was heated at 90° C. for 4 h. After that, the reaction was cooled and sat. aq. $NH_4Cl$ (250 mL) and EtOAc (250 mL) were added. The mixture was filtered through celite and washed with water (100 mL) and EtOAc (100 mL). The organic layers were separated and the aqueous phase was extracted with EtOAc (200 mL*3). The combined extracts were washed with sat. $NaHCO_3$ solution and brine, dried over $Na_2SO_4$, filtered and concentrated. The resulting oil was purified by flash chromatography on silica gel (EtOAc/Petroleum ether=1/80~1/50) to give tert-butyl (R)-4-(2-(4-chlorophenyl)-2,3-dihydrobenzo[b][1,4]dioxin-5-yl)piperidine-1-carboxylate (21.5 g, 50.0 mmol, 82% yield) as a white solid.

$^1$H NMR (400 MHZ, $CDCl_3$) δ ppm 7.35-7.41 (m, 4H), 6.86 (d, J=4.4 Hz, 2H), 6.75-6.79 (m, 1H), 5.10 (dd, J=8.8, 2.0 Hz, 1H), 4.38 (dd, J=11.2, 2.4 Hz, 1H), 4.24 (d, J=12.4 Hz, 2H), 3.96 (dd, J=11.2, 7.6 Hz, 1H), 3.01-3.07 (m, 1H), 2.82 (t, J=12.8 Hz, 1H), 1.76-1.85 (m, 2H), 1.56-1.68 (m, 3H), 1.48 (s, 9H). LC-MS: m/z 374.2 $(M-55)^+$.

Step C: tert-butyl (R)-4-(2-(4-cyanophenyl)-2,3-dihydrobenzo[b][1,4]dioxin-5-yl) piperidine-1-carboxylate

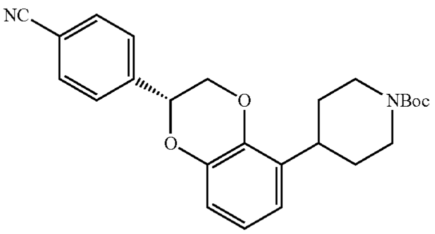 [SMILES: CC(C)(C)OC(=O)N1CCC(c2cccc3c2OC[C@@H](c2ccc(C#N)cc2)O3)CC1]

To a solution of (R)-tert-butyl 4-(2-(4-chlorophenyl)-2,3-dihydrobenzo[b][1,4]dioxin-5-yl)piperidine-1-carboxylate (540 mg, 1.255 mmol, 1.0 equiv) in DMA (4.5 mL) was added Zn powder (32.6 mg, 0.502 mmol), $Zn(CN)_2$ (178 mg, 1.51 mmol), $Pd(TFA)_2$ (42.0 mg, 0.126 mmol) and ditert-butyl-(1-naphthalen-1-yl-naphthalen-2-yl)phosphane (100 mg, 0.251 mmol) at room temperature. The resulting mixture was stirred at 120° C. for 18 h under $N_2$ atmosphere. The reaction mixture was quenched with water (20 mL) and extracted with EA (10 mL×3). The combined organic layers were washed with water (10 mL) and brine (10 mL), dried over $Na_2SO_4$ and filtered. The filtration was concentrated to give a crude product which was purified by flash chromatography (eluted with PE/EtOAc=5/1) to afford the title compound (R)-tert-butyl 4-(2-(4-cyanophenyl)-2,3-dihydrobenzo[b][1,4]dioxin-5-yl)piperidine-1-carboxylate as a white solid (400 mg, 82% yield).

$^1$H NMR (DMSO-$d_6$) δ ppm 7.72 (dd, J=6.8, 2.0 Hz, 2H), 7.55 (d, J=8.0 Hz, 2H), 6.87-6.88 (m, 2H), 6.78-6.80 (m, 1H), 5.18 (dd, J=7.6, 2.0 Hz, 1H), 4.42 (dd, J=11.6, 2.4 Hz, 1H), 4.22-4.25 (m, 2H), 3.97 (dd, J=11.6, 8.4 Hz, 1H), 2.95-3.02 (m, 1H), 2.78-2.85 (m, 2H), 1.74-1.81 (m, 2H), 1.46-1.64 (m, 2H), 1.35 (s, 9H).

2-((4-((R)-2-(4-Cyanophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 118b) was synthesized following the methods depicted in Example 6, using tert-butyl (R)-4-(2-(4-cyanophenyl)-2,3-dihydrobenzo[b][1,4]dioxin-5-yl) piperidine-1-carboxylate in step F.

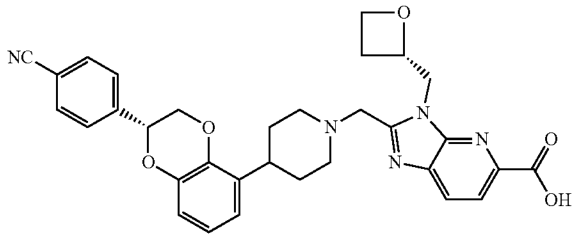 [SMILES: N#Cc1ccc([C@@H]2COc3c(cccc3C3CCN(Cc4nc5ccc(C(=O)O)nc5n4C[C@@H]4CCO4)CC3)O2)cc1]

$^1$H NMR (400 MHZ, DMSO-$d_6$) δ ppm 13.06 (br.s, 1H), 8.14 (d, J=8.0 Hz, 1H), 7.99 (d, J=8.0 Hz, 1H), 7.91 (d, J=8.4 Hz, 2H), 7.68 (d, J=8.4 Hz, 2H), 6.81-6.8 (m, 3H), 5.38 (dd, J=7.6, 1.6 Hz, 1H), 5.11-5.24 (m, 1H), 4.80-4.85 (m, 1H), 4.73 (dd, J=14.8, 3.6 Hz, 1H), 4.44-4.59 (m, 2H), 4.36-4.38 (m, 1H), 4.09 (dd, J=11.2, 8.0 Hz, 1H), 3.96 (dd, J=12, 7.2 Hz, 2H), 2.68-2.99 (m, 5H), 2.15-2.35 (m, 2H), 1.53-1.80 (m, 4H). LC-MS: m/z 566.6 $(M+H)^+$.

2-((4-((R)-2-(4-Cyanophenyl)-2,3-dihydrobenzo[b][1,4]dioxin-5-yl)piperidin-1-yl)methyl)-1-(((S)-oxetan-2-yl)methyl)-1H-benzo[d]imidazole-6-carboxylic acid (Compound 129a) was synthesized following the methods depicted in Example 6, using tert-butyl (R)-4-(2-(4-cyanophenyl)-2,3-dihydrobenzo[b][1,4]dioxin-5-yl) piperidine-1-carboxylate in step F and methyl (S)-2-(chloromethyl)-1-(oxetan-2-ylmethyl)-1H-benzo[d]imidazole-6-carboxylate in step G.

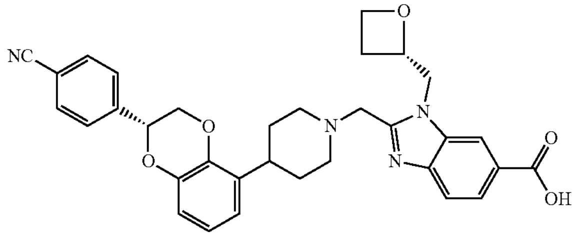 [SMILES: N#Cc1ccc([C@@H]2COc3c(cccc3C3CCN(Cc4nc5ccc(C(=O)O)cc5n4C[C@@H]4CCO4)CC3)O2)cc1]

$^1$H NMR (400 MHZ, DMSO-$d_6$) δ ppm 8.26 (s, 1H), 7.91 (d, J=8.0 Hz, 2H), 7.80 (d, J=8.4 Hz, 1H), 7.68 (d, J=7.6 Hz, 2H), 7.63 (d, J=8.0 Hz, 1H), 6.77-6.92 (m, 3H), 5.38 (d, J=7.2 Hz, 1H), 5.08-5.11 (m, 1H), 4.80 (dd, J=14.8, 6.4 Hz, 1H), 4.66 (d, J=15.6 Hz, 1H), 4.49-4.56 (m, 2H), 4.33-4.42 (m, 1H), 4.05-4.16 (m, 1H), 3.94 (d, J=14.0 Hz, 1H), 3.79 (d, J=14.0 Hz, 1H), 3.00 (d, J=10.0 Hz, 1H), 2.86-2.89 (m, 2H), 2.67-2.74 (m, 1H), 2.40-2.47 (m, 1H), 2.11-2.35 (m, 2H), 1.60-1.78 (m, 4H). LC-MS: m/z 565.6 $(M+H)^+$ Example 8

2-((4-(2-(4-chloro-3-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 113a)

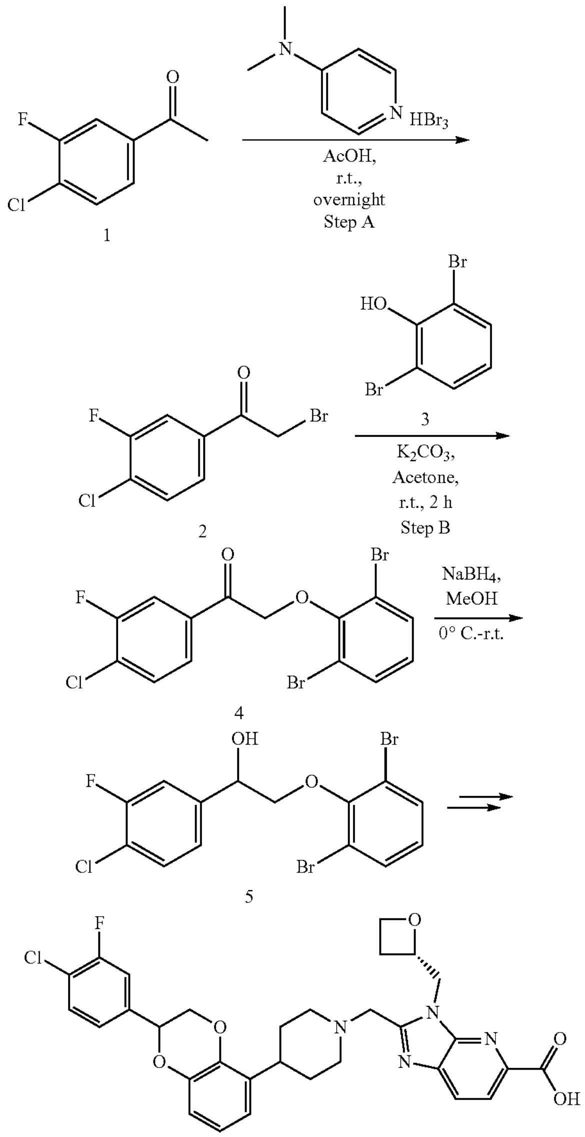

Compound 113a

Step A: 2-bromo-1-(4-chloro-3-fluorophenyl)ethan-1-one

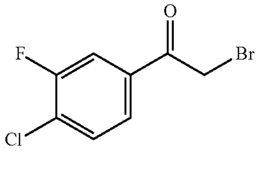 [SMILES: O=C(CBr)c1ccc(Cl)c(F)c1]

To a solution of 1-(4-chloro-3-fluorophenyl) ethan-1-one (3.00 g, 17.4 mmol) in AcOH (30 mL) was added 4-(dimethylamino)pyridine tribromide (6.96 g, 19.2 mmol). The resulting mixture was stirred at room temperature overnight under $N_2$ atmosphere. The reaction mixture was diluted with water (20 mL) and extracted with EtOAc (3×30 mL). The combined organic layers were washed with brine (30 mL), dried over anhydrous $Na_2SO_4$ and concentrated. The residue was purified by flash chromatography (eluted with PE/EtOAc=20/1) to afford the title compound 2-bromo-1-(4-chloro-3-fluorophenyl) ethan-1-one as a white solid (4.30 g, 98% yield,). $^1$H NMR (400 MHZ, DMSO-$d_6$) δ ppm 8.00-8.03 (m, 1H), 7.77-7.89 (m, 2H), 4.96 (s, 2H).

Step B: 1-(4-chloro-3-fluorophenyl)-2-(2,6-dibromophenoxy) ethan-1-one

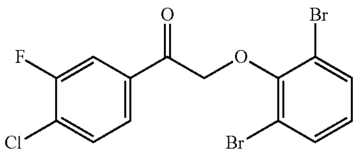 [SMILES: O=C(COc1c(Br)cccc1Br)c1ccc(Cl)c(F)c1]

To a solution of 2-bromo-1-(4-chloro-3-fluorophenyl) ethan-1-one (3.20 g, 12.8 mmol) and 2,6-dibromophenol (3.22 g, 12.8 mmol) in acetone (40 mL) was added $K2CO_3$ (3.50 g, 25.6 mmol). The resulting mixture was stirred at room temperature for 2 hours under $N_2$ atmosphere. The reaction mixture was filtered through celite and the filtrate was concentrated under reduced pressure to give a crude product which was diluted with EtOAc (50 mL). The organic layer was washed with water (2×20 mL) and brine (20 mL), dried over anhydrous $Na_2SO_4$ and concentrated. The residue was purified by flash chromatography (eluted with PE/EtOAc=15/1) to give the title compound 1-(4-chloro-3-fluorophenyl)-2-(2,6-dibromophenoxy) ethan-1-one as a white solid (5.00 g, 92% yield). LC-MS: m/z 420.2 $(M+H)^+$.

Step C: 1-(4-chloro-3-fluorophenyl)-2-(2,6-dibromophenoxy) ethan-1-ol

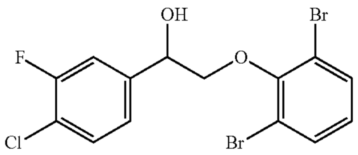 [SMILES: OC(COc1c(Br)cccc1Br)c1ccc(Cl)c(F)c1]

To a solution of 1-(4-chloro-3-fluorophenyl)-2-(2,6-dibromophenoxy) ethan-1-one (5.00 g, 11.8 mmol) was added $NaBH_4$ (896 mg, 23.7 mmol) at 0° C. The resulting mixture was allowed to be warmed to room temperature and stirred for 2 hours. The reaction was quenched with water (30 mL) and extracted with EtOAc (3× 30 mL). The combined organic layers were washed with brine (30 mL), dried over anhydrous $Na_2SO_4$ and concentrated. The residue was purified by flash chromatography (eluted with PE/EtOAc=15/1) to afford the title compound 1-(4-chloro-3-fluorophenyl)-2-(2,6-dibromophenoxy) ethan-1-ol as a white solid (5.00 g, 92% yield).

$^1$H NMR (400 MHZ, $CD_3OD$) δ ppm 7.56 (d, J=8.0 Hz, 2H), 7.45 (t, J=8.0 Hz, 1H), 7.38 (dd, J=10.0, 2.0 Hz, 1H), 7.29 (dd, J=8.4, 2.0 Hz, 1H), 6.95 (t, J=8.0 Hz, 1H), 5.15 (t, J=6.0 Hz, 1H), 4.15 (dd, J=9.2, 6.4 Hz, 1H), 4.04 (dd, J=8.8, 5.2 Hz, 1H).

2-((4-(2-(4-Chloro-3-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 113a) was synthesized following the methods depicted in Example 6, using 1-(4-chloro-3-fluorophenyl)-2-(2,6-dibromophenoxy) ethan-1-ol in step C.

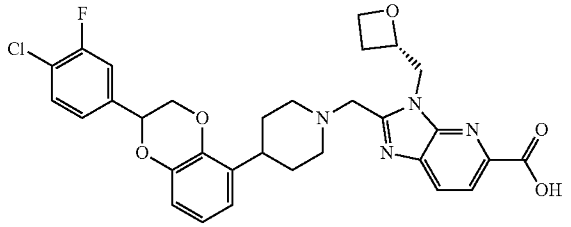 [SMILES: O=C(O)c1ccc2nc(CN3CCC(c4cccc5c4OCC(c4ccc(Cl)c(F)c4)O5)CC3)n(C[C@@H]3CCO3)c2n1]

$^1$H NMR (400 MHz, $CD_3OD$) δ ppm 8.09-8.16 (m, 2H), 7.51 (t, J=8.0 Hz, 1H), 7.37 (dd, J=10.0, 1.6 Hz, 1H), 7.28 (d, J=8.4 Hz, 1H), 6.76-6.91 (m, 3H), 5.25-3.01 (m, 1H), 5.17-5.20 (m, 1H), 4.95-5.00 (m, 1H), 4.87-4.88 (m, 1H), 4.61-4.66 (m, 1H), 4.26-4.49 (m, 5H), 4.01 (dd, J=11.2, 8.0 Hz, 1H), 3.35-3.38 (m, 1H), 3.03-3.06 (m, 1H), 2.76-2.81 (m, 1H), 2.64-2.72 (m, 2H), 2.50-2.55 (m, 1H), 1.89-1.94 (m, 4H). LC-MS: m/z 593.2 $(M+H)^+$.

The following compounds were synthesized following the methods depicted in Example 8, using the corresponding starting materials.

2-((4-(2-(2-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 109a)

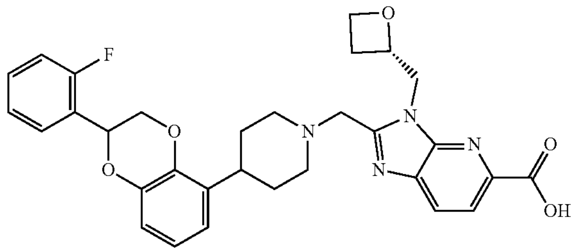 [SMILES: O=C(O)c1ccc2nc(CN3CCC(c4cccc5c4OCC(c4ccccc4F)O5)CC3)n(C[C@@H]3CCO3)c2n1]

$^1$H NMR (400 MHZ, DMSO-$d_6$) δ ppm 8.03 (dd, J=30.8, 8.0 Hz, 2H), 7.44-7.54 (m, 2H), 7.27-7.31 (m, 2H), 6.79-6.86 (m, 3H), 5.43 (dd, J=8.4, 2.0 Hz, 1H), 5.20 (s, 1H), 4.78-4.81 (m, 2H), 4.50-4.54 (m, 2H), 4.32 (s, 1H), 4.13-4.16 (m, 1H), 3.91 (dd, J=34.0, 14.0 Hz, 2H), 2.89-3.01 (m, 4H), 2.67-2.68 (m, 1H), 2.19-2.28 (m, 2H), 1.62-1.75 (m, 4H). LC-MS: m/z 559.2 $(M+H)^+$.

2-((4-(2-(4-chlorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 111a)

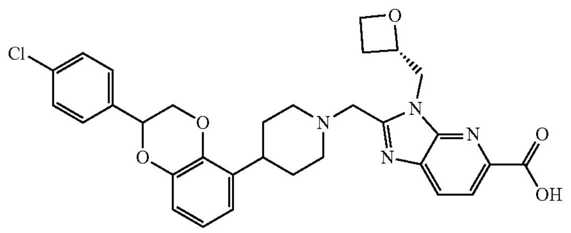 [SMILES: O=C(O)c1ccc2nc(CN3CCC(c4cccc5c4OCC(c4ccc(Cl)cc4)O5)CC3)n(C[C@@H]3CCO3)c2n1]

$^1$H NMR (400 MHZ, DMSO-$d_6$) δ ppm 8.14 (d, J=8.0 Hz, 1H), 7.99 (d, J=8.4 Hz, 1H), 7.48-7.50 (m, 4H), 6.79-6.86 (m, 3H), 5.25 (dd, J=8.0, 2.0 Hz, 1H), 5.16-5.19 (m, 1H), 4.84-4.89 (m, 1H), 4.74 (dd, J=14.8, 3.6 Hz, 1H), 4.48-4.52 (m, 2H), 4.34-4.40 (m, 1H), 4.05 (dd, J=11.6, 8.4 Hz, 1H), 4.00 (dd, J=13.6, 4.0 Hz, 1H), 3.92 (dd, J=13.6, 4.4 kHz, 1H), 2.66-2.99 (m, 5H), 2.20-2.29 (m, 2H), 1.61-1.74 (m, 4H). LC-MS: m/z 575.2 $(M+H)^+$.

3-(((S)-oxetan-2-yl)methyl)-2-((4-(2-(p- tolyl)-2,3-dihydrobenzo[b][1,4]dioxin-5-yl) piperidin-1-yl) methyl)-3H-imidazo[4,5-b]pyridine-5-carboxylic acid (Compound 116a)

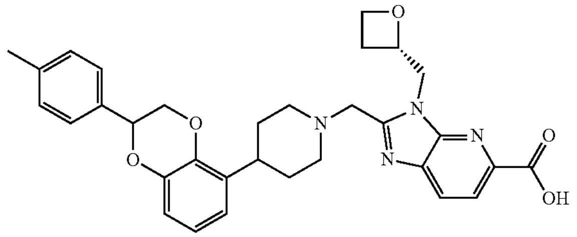 [SMILES: Cc1ccc(C2COc3c(cccc3C3CCN(Cc4nc5ccc(C(=O)O)nc5n4C[C@@H]4CCO4)CC3)O2)cc1]

$^1$H NMR (400 MHZ, $CD_3OD$) δ ppm 8.11-8.15 (m, 2H), 7.32 (d, J=8.0 Hz, 2H), 7.22 (d, J=8.0 Hz, 2H), 6.77-6.86 (m, 3H), 5.25-5.31 (m, 1H), 5.07 (dd, J=8.8, 2.0 Hz, 1H), 4.94-4.99 (m, 1H), 4.85-4.88 (s, 2H), 4.64 (dd, J=14.0, 7.6 Hz, 1H), 4.31-4.46 (m, 4H), 3.99 (dd, J=11.2, 8.4 Hz, 1H), 3.38-3.41 (m, 2H), 3.05-3.08 (m, 1H), 2.76-2.81 (m, 3H), 2.50-2.55 (m, 1H), 2.35 (s, 3H), 1.90-1.94 (m, 4H). LC-MS: m/z 555.2 $(M+H)^+$.

2-((4-(2-(3-chlorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 112a)

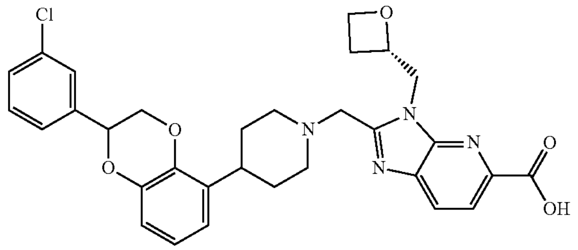 [SMILES: O=C(O)c1ccc2nc(CN3CCC(c4cccc5c4OCC(c4cccc(Cl)c4)O5)CC3)n(C[C@@H]3CCO3)c2n1]

$^1$H NMR (400 MHZ, DMSO-$d_6$) δ ppm 13.04 (s, 1H), 8.06-8.17 (m, 1H), 8.00 (d, J=8.0 Hz, 1H), 7.55 (s, 1H), 7.43-7.46 (m, 3H), 6.79-6.84 (m, 3H), 5.26 (dd, J=8.0, 2.0 Hz, 1H), 5.11-5.22 (m, 1H), 4.78-4.92 (m, 1H), 4.74 (dd, J=14.4, 4.4 Hz, 1H), 4.42-4.56 (m, 2H), 4.33-4.42 (m, 1H), 4.08 (dd, J=11.6, 8.4 Hz, 1H), 3.88-4.03 (m, 2H), 2.68-2.99 (m, 5H), 2.21-2.29 (d, J=13.2 Hz, 2H), 1.53-1.79 (m, 4H). LC-MS: m/z 575.2 $(M+H)^+$.

2-((4-(2-(4-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 117a)

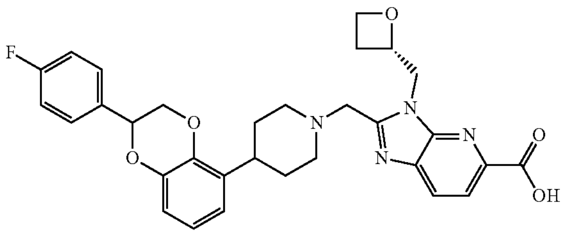 [SMILES: O=C(O)c1ccc2nc(CN3CCC(c4cccc5c4OCC(c4ccc(F)cc4)O5)CC3)n(C[C@@H]3CCO3)c2n1]

$^1$H NMR (400 MHZ, DMSO-$d_6$) δ ppm 13.01 (br.s, 1H), 8.14 (d, J=8.4 Hz, 1H), 7.99 (d, J=8.4 Hz, 1H), 7.53 (dd, J=8.4, 5.6 Hz, 2H), 7.26 (t, J=9.2 Hz, 2H), 6.62-6.92 (m, 3H), 5.13-5.27 (m, 2H), 4.72-4.89 (m, 2H), 4.45-4.54 (m, 2H), 4.33-4.42 (m, 1H), 3.90-4.10 (m, 3H), 2.83-3.01 (m, 3H), 2.66-2.75 (m, 1H), 2.52-2.59 (m, 1H), 2.23-2.33 (m, 2H), 1.61-1.71 (m, 4H). LC-MS: m/z 559.2 $(M+H)^+$.

2-((4-(2-(4-(trifluoromethyl)phenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 119a)

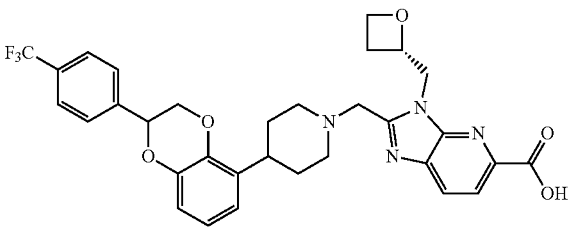 [SMILES: O=C(O)c1ccc2nc(CN3CCC(c4cccc5c4OCC(c4ccc(C(F)(F)F)cc4)O5)CC3)n(C[C@@H]3CCO3)c2n1]

$^1$H NMR (400 MHZ, DMSO-$d_6$) δ ppm 13.12 (br.s, 1H), 8.14 (d, J=8.4 Hz, 1H), 8.00 (d, J=8.4 Hz, 1H), 7.81 (d, J=8.4 Hz, 2H), 7.71 (d, J=8.4 Hz, 2H), 6.80-6.86 (m, 3H), 5.38 (d, J=6.0 Hz, 1H), 5.15-5.19 (m, 1H), 4.80-4.94 (m, 1H), 4.74 (dd, J=14.8, 3.6 Hz, 1H), 4.47-4.57 (m, 2H), 4.29-4.43 (m, 1H), 4.09 (dd, J=11.6, 8.0 Hz, 1H), 3.91-4.15 (m, 2H), 2.79-2.99 (m, 3H), 2.65-2.75 (m, 1H), 2.45-2.55 (m, 1H), 2.21-2.29 (m, 2H), 1.60-1.81 (m, 4H). LC-MS: m/z 609.2 $(M+H)^+$.

2-((4-(2-(4-chlorophenyl)-2,3-dihydrobenzo[b][1,4]dioxin-5-yl)piperidin-1-yl)methyl)-1-(((S)-oxetan-2-yl)methyl)-1H-benzo[d]imidazole-6-carboxylic acid (Compound 115a)

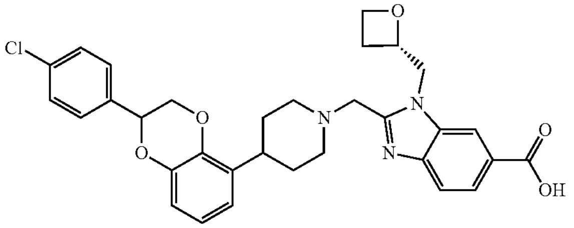 [SMILES: O=C(O)c1ccc2nc(CN3CCC(c4cccc5c4OCC(c4ccc(Cl)cc4)O5)CC3)n(C[C@@H]3CCO3)c2c1]

$^1$H NMR (400 MHZ, DMSO-$d_6$) δ ppm 12.78 (br.s, 1H), 8.27 (s, 1H), 7.80 (dd, J=8.4, 1.6 Hz, 1H), 7.64 (d, J=8.4 Hz, 1H), 7.37-7.56 (m, 4H), 6.64-7.00 (m, 3H), 5.25 (dd, J=8.4, 2.4 Hz, 1H), 5.07-5.14 (m, 1H), 4.81 (dd, J=14.8, 6.4 Hz, 1H), 4.66 (d, J=13.6 Hz, 1H), 4.46-4.53 (m, 2H), 4.35-4.42 (m, 1H), 4.05 (dd, J=11.2, 8.4 Hz, 1H), 3.95 (dd, J=13.6, 5.2 Hz, 1H), 3.79 (dd, J=13.6, 5.2 Hz, 1H), 3.01 (d, J=10.4 Hz, 1H), 2.83-2.88 (m, 2H), 2.66-2.80 (m, 1H), 2.38-2.47 (m, 1H), 2.14-2.26 (m, 2H), 1.46-1.82 (m, 4H). LC-MS: m/z 574.2 $(M+H)^+$.

2-((4-(2-(4-cyanophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 118a)

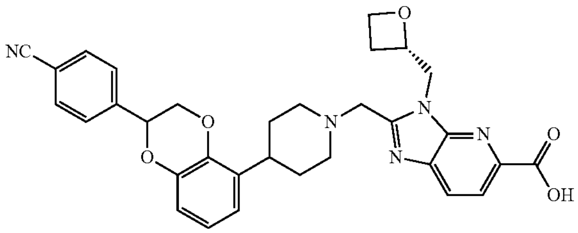 [SMILES: N#Cc1ccc(C2COc3c(cccc3C3CCN(Cc4nc5ccc(C(=O)O)nc5n4C[C@@H]4CCO4)CC3)O2)cc1]

$^1$H NMR (400 MHZ, DMSO-$d_6$) δ ppm 13.06 (br.s, 1H), 8.14 (d, J=8.4 Hz, 1H), 7.99 (d, J=8.4 Hz, 1H), 7.91 (d, J=8.4 Hz, 2H), 7.68 (d, J=8.4 Hz, 2H), 6.80-6.85 (m, 3H), 5.38 (dd, J=7.6, 1.6 Hz, 1H), 5.11-5.24 (m, 1H), 4.80-4.90 (m, 1H), 4.73 (dd, J=14.8, 3.6 Hz, 1H), 4.44-4.59 (m, 2H), 4.36-4.38 (m, 1H), 4.09 (dd, J=11.2, 8.0 Hz, 1H), 3.95 (ddd, J=16.8, 12, 4.8 Hz, 2H), 2.68-2.99 (m, 5H), 2.15-2.35 (m, 2H), 1.53-1.80 (m, 4H). LC-MS: m/z 566.6 $(M+H)^+$.

The (S)-isomer of Compound 118a can be obtained via chiral separation.

2-((4-((S)-2-(4-cyanophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 118c)

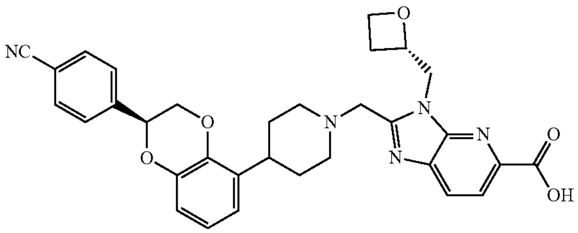 [SMILES: N#Cc1ccc([C@H]2COc3c(cccc3C3CCN(Cc4nc5ccc(C(=O)O)nc5n4C[C@@H]4CCO4)CC3)O2)cc1]

$^1$H NMR (400 MHZ, DMSO-$d_6$) δ ppm 13.06 (br.s, 1H), 8.14 (d, J=8.4 Hz, 1H), 7.99 (d, J=8.4 Hz, 1H), 7.91 (d, J=8.4 Hz, 2H), 7.68 (d, J=8.4 Hz, 2H), 6.81-6.85 (m, 3H), 5.38 (dd, J=7.6, 1.6 Hz, 1H), 5.11-5.24 (m, 1H), 4.80-4.90 (m, 1H), 4.73 (dd, J=14.8, 3.6 Hz, 1H), 4.44-4.59 (m, 2H), 4.36-4.38 (m, 1H), 4.09 (dd, J=11.2, 8.0 Hz, 1H), 3.96 (dd, J=31.6, 13.6 Hz, 2H), 2.68-2.99 (m, 5H), 2.15-2.35 (m, 2H), 1.49-1.80 (m, 4H). LC-MS: m/z 566.6 $(M+H)^+$

Example 9

2-(((2S)-4-(2-(4-chlorophenyl)-2,3-dihydrobenzo[b][1,4]dioxin-5-yl)-2-methylpiperazin-1-yl)methyl)-3-(((S)-oxetan-2-yl)methyl)-3H-imidazo[4,5-b]pyridine-5-carboxylic acid (Compound 114a)

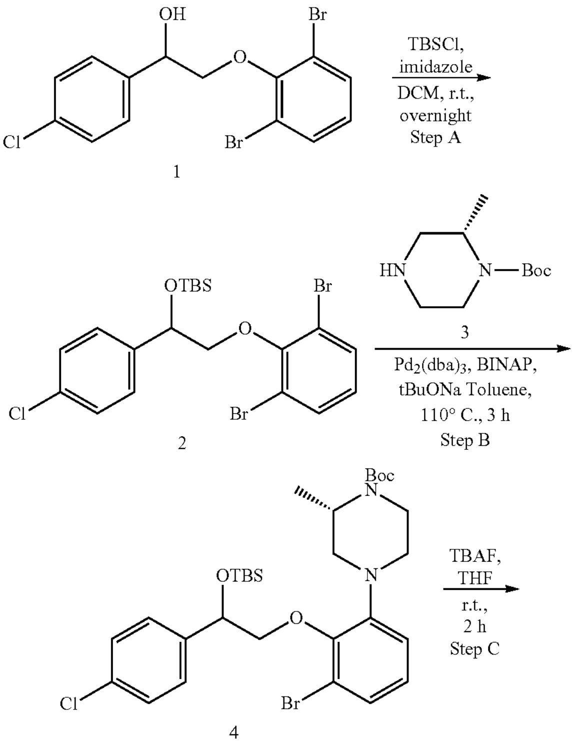

-continued

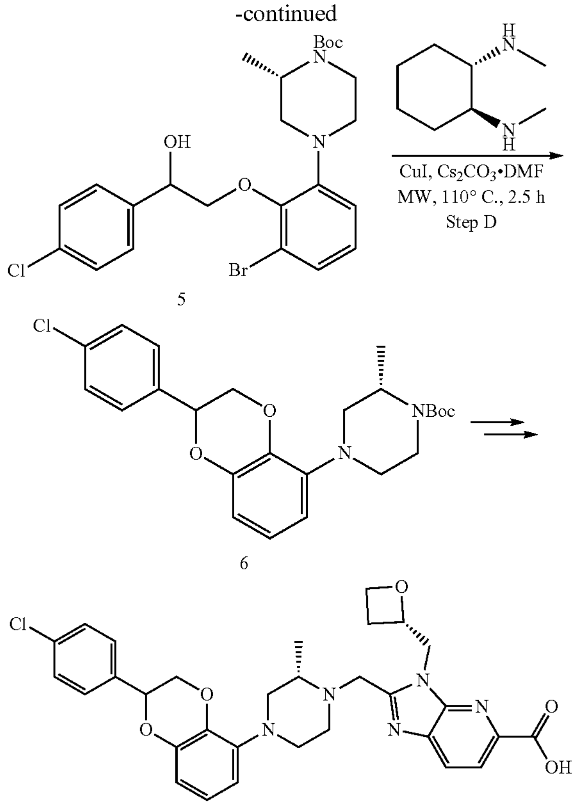

5

6

Compound 114a

Step A: tert-butyl(1-(4-chlorophenyl)-2-(2,6-dibromophenoxy) ethoxy)dimethylsilane

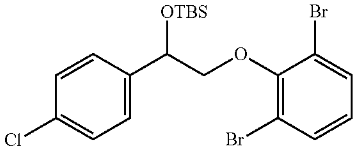 [SMILES: CC(C)(C)[Si](C)(C)OC(COc1c(Br)cccc1Br)c1ccc(Cl)cc1]

A solution of 1-(4-chlorophenyl)-2-(2,6-dibromophenoxy) ethan-1-ol (2.00 g, 4.95 mmol), TBSCl (1.87 g, 12.4 mmol) and imidazole (1.01 g, 14.8 mmol) in DCM (40 mL) was stirred at room temperature for 12 h under $N_2$ atmosphere. Water (100 mL) was added and the mixture was extracted with DCM (3×30 mL). The combined organic phase was washed with brine (80 mL), dried over anhydrous $Na_2SO_4$, filtered and concentrated. The residue was purified by flash chromatography (PE/EtOAc=10/1) to afford the title compound tert-butyl(1-(4-chlorophenyl)-2-(2,6-dibromophenoxy) ethoxy)dimethylsilane (2.80 g, 100% yield, overweight) as a colorless oil. $^1$H NMR (400 MHZ, $CDCl_3$) δ ppm 7.47 (d, J=8.0 Hz, 2H), 7.36-7.39 (m, 2H), 7.25-7.31 (m, 2H), 6.80 (t, J=8.0 Hz, 1H), 5.18 (dd, J=6.8, 4.8 Hz, 1H), 4.09 (dd, J=8.4, 6.8 Hz, 1H), 3.85 (dd, J=8.8, 4.8 Hz, 1H), 0.91 (s, 9H), 0.16 (s, 3H), 0.07 (s, 3H).

Step B: tert-butyl(2S)-4-(3-bromo-2-(2-((tert-butyldimethylsilyl)oxy)-2-(4-chlorophenyl) ethoxy) phenyl)-2-methylpiperazine-1-carboxylate

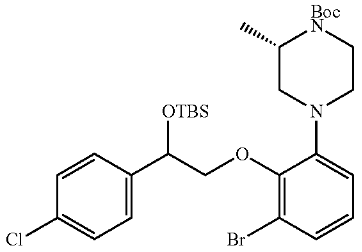 [SMILES: C[C@H]1CN(c2cccc(Br)c2OCC(O[Si](C)(C)C(C)(C)C)c2ccc(Cl)cc2)CCN1C(=O)OC(C)(C)C]

A mixture of tert-butyl(1-(4-chlorophenyl)-2-(2,6-dibromophenoxy) ethoxy)dimethylsilane (840 mg, 1.61 mmol), tert-butyl (S)-2-methylpiperazine-1-carboxylate (355 mg, 1.77 mmol, 1.1 equiv), $Pd_2$ (dba) 3 (147 mg, 0.161 mmol), BINAP (100 mg, 0.160 mmol) and $^t$BuONa (309 g, 3.22 mmol) in dry toluene (20 mL) was stirred at 110° C. for 3 h under $N_2$ atmosphere. The reaction mixture was filtered through celite and diluted with EtOAc (30 mL). The combined organic phase was washed with brine (50 mL), dried over anhydrous $Na_2SO_4$, filtered and concentrated. The residue was purified by flash chromatography (PE/EtOAc=10/1) to afford tertbutyl(2S)-4-(3-bromo-2-(2-((tert-butyldimethylsilyl)oxy)-2-(4-chlorophenyl) ethoxy)pheny)-2-methylpiperazine-1-carboxylate (220 mg, 22% yield) as a yellow oil.

$^1$H NMR (400 MHZ, $CDCl_3$) δ ppm 7.35-7.41 (m, 2H), 7.29-7.32 (m, 2H), 7.20 (dt, J=8.0, 1.2 Hz, 1H), 6.88 (td, J=8.0, 2.4 Hz, 1H), 6.77-6.80 (m, 1H), 5.18 (dd, J=8.0, 3.6 Hz, 0.5H), 5.14 (t, J=6.4 Hz, 0.5H), 4.32-4.36 (m, 1.5H), 4.04 (dd, J=8.4, 6.8 Hz, 0.5H), 3.86-3.92 (m, 1H), 3.65-3.68 (m, 1.5H), 3.26-3.33 (m, 1H), 3.13-3.16 (m, 1H), 3.01-3.03 (m, 1H), 2.88 (dd, J=7.2, 3.6 Hz, 0.5H), 2.76-2.83 (m, 1H), 2.36-2.48 (m, 1H), 1.49 (d, J=2.4 Hz, 9H), 1.29 (d, J=6.8 Hz, 1.5H), 1.20 (d, J=6.8 Hz, 1.5H), 0.89 (s, 9H), 0.11 (s, 2.7H), 0.07 (s, 1.5H), 0.02 (s, 1.2H), 0.11 (s, 0.6H).

Step C: tert-butyl(2S)-4-(3-bromo-2-(2-(4-chlorophenyl)-2-hydroxyethoxy)phenyl)-2-methylpiperazine-1-carboxylate

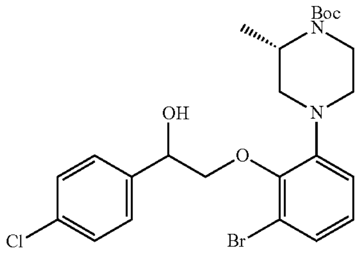 [SMILES: C[C@H]1CN(c2cccc(Br)c2OCC(O)c2ccc(Cl)cc2)CCN1C(=O)OC(C)(C)C]

A mixture of tert-butyl(2S)-4-(3-bromo-2-(2-((tert-butyldimethylsilyl)oxy)-2-(4-chlorophenyl) ethoxy)pheny)-2-methylpiperazine-1-carboxylate (322 mg, 0.500 mmol) and $^t$$Bu_4$NF (1M, 1 mL, 1 mmol) in THF (8 mL) was stirred at room temperature for 2 h. The reaction mixture was diluted with EtOAc (3×10 mL). The combined organic phase was washed with brine (30 mL), dried over anhydrous $Na_2SO_4$, filtered and concentrated. The residue was purified by flash chromatography (PE/EtOAc=5/1) to afford the title compound tert-butyl(2S)-4-(3-bromo-2-(2-(4-chlorophenyl)-2-hydroxyethoxy)phenyl)-2-methylpiperazine-1-carboxylate (260 mg, 97.2% yield) as a yellow oil.

$^1$H NMR (400 MHZ, $CDCl_3$) δ ppm 7.29-7.36 (m, 5H), 6.95-7.02 (m, 2H), 5.04 (dd, J=9.6, 2.4 Hz, 0.5H), 4.90 (dd, J=9.6, 2.4 Hz, 0.5H), 4.62 (dd, J=11.2, 2.8 Hz, 0.5H), 4.58 (dd, J=10.8, 2.4 Hz, 0.5H), 4.33-4.38 (m, 1H), 4.02 (d, J=13.6 Hz, 0.5H), 3.96 (d, J=13.6 Hz, 0.5H), 3.84 (dd, J=10.4, 10.0 Hz, 0.5H), 3.70 (dd, J=11.2, 10.0 Hz, 0.5H), 3.49 (d, J=9.6 Hz, 0.5H), 3.19-3.38 (m, 2.5H), 2.89 (dd, J=11.6, 7.6, 0.5H), 2.80 (dd, J=11.6, 2.8 Hz, 0.5H), 2.75 (dd, J=11.6, 4.0 Hz, 0.5H), 2.61 (td, J=12.0, 3.2 Hz, 0.5H), 1.49 (s, 9H), 1.45 (d, J=7.2 Hz, 1.5H), 1.40 (d, J=6.8 Hz, 1.5H).

Step D: tert-butyl(2S)-4-(2-(4-chlorophenyl)-2,3-dihydrobenzo[b][1,4]dioxin-5-yl)-2-methylpiperazine-1-carboxylate

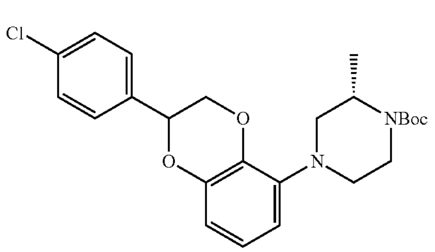 [SMILES: C[C@H]1CN(c2cccc3c2OCC(c2ccc(Cl)cc2)O3)CCN1C(=O)OC(C)(C)C]

A solution of compound tert-butyl(2S)-4-(3-bromo-2-(2-(4-chlorophenyl)-2-hydroxyethoxy)phenyl)-2-methylpiperazine-1-carboxylate (260 mg, 0.480 mmol), CuI (185 mg, 0.970 mmol), (1S,2S)—$N^1$,$N^2$-dimethylcyclohexane-1,2-diamine (138 mg, 0.970 mmol) and $Cs_2CO_3$ (317 mg, 0.970 mmol) in dry DMF (10 mL) was stirred at 110° C. via microwave irradiation for 2.5 h under $N_2$ atmosphere. The reaction mixture was diluted with water (50 mL) and extracted with EtOAc (3×30 mL). The combined organic phase was washed with brine (30 mL), dried over anhydrous $Na_2SO_4$, filtered and concentrated. The residue was purified by flash chromatography (PE/EtOAc=5/1) to afford the title compound tert-butyl(2S)-4-(2-(4-chlorophenyl)-2,3-dihydrobenzo[b][1,4]dioxin-5-yl)-2-methylpiperazine-1-carboxylate (56.4 mg, 26% yield) as a colorless oil. LC-MS: m/z 445.2 $(M+H)^+$.

2-(((2S)-4-(2-(4-Chlorophenyl)-2,3-dihydrobenzo[b][1,4]dioxin-5-yl)-2-methylpiperazin-1-yl)methyl)-3-(((S)-oxetan-2-yl)methyl)-3H-imidazo[4,5-b]pyridine-5-carboxylic acid (Example 9, Compound 114a) was synthesized following the methods depicted in Example 6, using tert-butyl(2S)-4-(3-bromo-2-(2-(4-chlorophenyl)-2-hydroxyethoxy)phenyl)-2-methylpiperazine-1-carboxylate in step F.

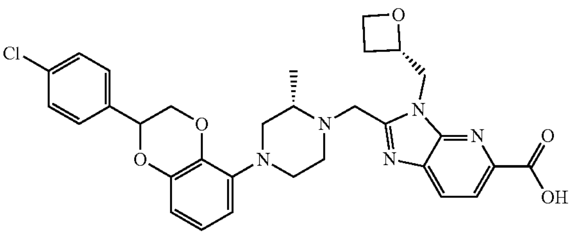 [SMILES: C[C@H]1CN(c2cccc3c2OCC(c2ccc(Cl)cc2)O3)CCN1Cc1nc2ccc(C(=O)O)nc2n1C[C@@H]1CCO1]

$^1$H NMR (400 MHZ, $CD_3OD$) δ ppm 8.12-8.17 (m, 2H), 7.43 (q, J=8.8 Hz, 4H), 6.80 (t, J=8.8 Hz, 1H), 6.66 (dd, J=8.0, 1.6 Hz, 1H), 6.54-6.61 (m, 1H), 5.29-5.34 (m, 1H), 5.15 (td, J=8.4, 2.4 Hz, 1H), 4.97 (d, J=4.0 Hz, 2H), 4.72 (d, J=14.0 Hz, 1H), 4.59 (dd, J=13.2, 8.0 Hz, 1H), 4.41-4.51 (m, 1H), 4.26-4.31 (m, 1H), 3.96-4.02 (m, 1H), 3.83-3.86 (m, 1H), 3.39-3.42 (m, 1H), 3.17-3.23 (m, 1H), 2.87-2.89 (m, 2H), 2.71-2.83 (m, 2H), 2.64-2.67 (m, 2H), 2.45-2.52 (m, 1H), 1.23-1.29 (m, 3H). LC-MS: m/z 590.2 $(M+H)^+$.

Example 10

2-((4-(2-(4-chloro-2-fluorophenyl) chroman-5-yl) piperazin-1-yl)methyl)-3-((S)oxetan-2-ylmethyl)-3H-imidazo[4,5-b]pyridine-5-carboxylic acid (Compound 123a)

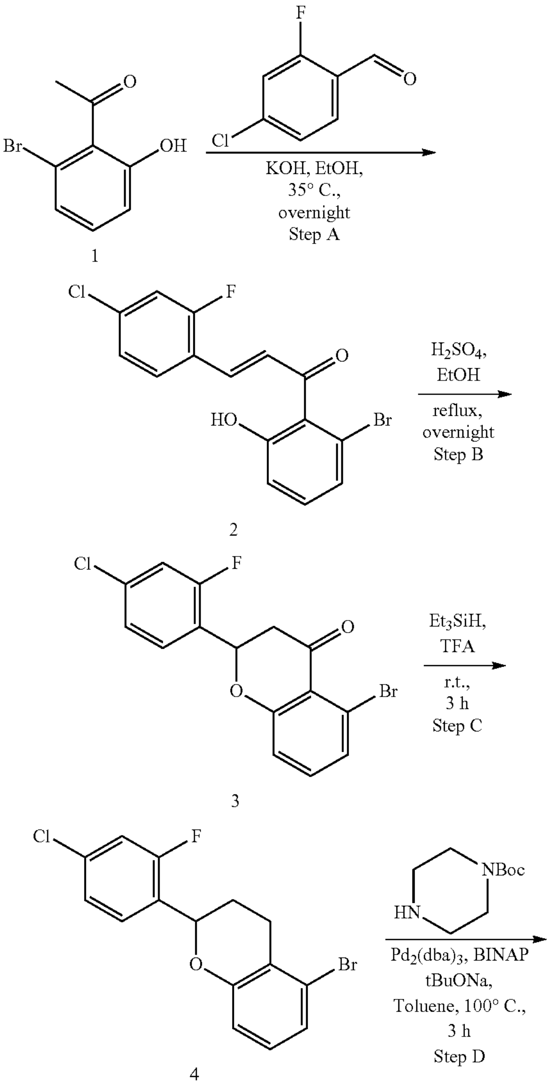

-continued

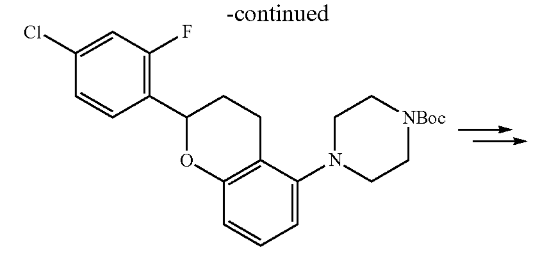

5

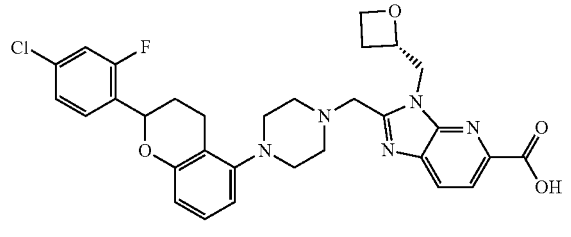

123a

Step A: (E)-1-(2-bromo-6-hydroxyphenyl)-3-(4-chloro-2-fluorophenyl) prop-2-en-1-one

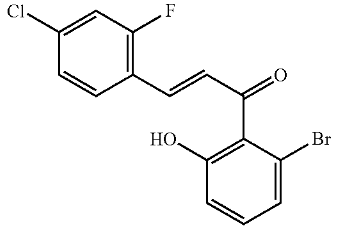 [SMILES: O=C(/C=C/c1ccc(Cl)cc1F)c1c(O)cccc1Br]

A solution of 1-(2-bromo-6-hydroxyphenyl) ethanone (950 mg, 4.42 mmol), 4-chloro-2-fluorobenzaldehyde (1.05 g, 6.63 mmol), KOH (1.12 g, 20.0 mmol) in EtOH (7 mL) was stirred at 35° C. overnight. The mixture was acidified with HCOOH and extracted with DCM (50 mL*3). The organic layers were washed with brine, dried over anhydrous $Na_2SO_4$ and concentrated. The residue was purified by flash chromatography on silica gel (eluted with PE/EtOAc=19/1) to give (E)-1-(2-bromo-6-hydroxyphenyl)-3-(4-chloro-2-fluorophenyl) prop-2-en-1-one (1.26 g, 75% yield) as a yellow solid.

$^1$H NMR (400 MHZ, $CDCl_3$) δ ppm 10.58 (s, 1H), 7.82 (d, J=15.6 Hz, 1H), 7.69 (d, J=15.6 Hz, 1H), 7.58 (t, J=8.0 Hz, 1H), 7.14-7.25 (m, 4H), 6.99 (dd, J=7.6, 2.0 Hz, 1H).

Step B: 5-bromo-2-(4-chloro-2-fluorophenyl) chroman-4-one

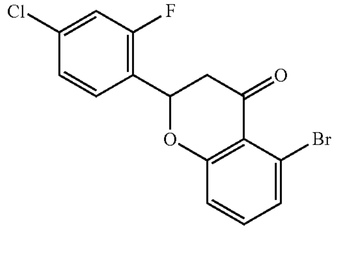 [SMILES: O=C1CC(c2ccc(Cl)cc2F)Oc2cccc(Br)c21]

A solution of (E)-1-(2-bromo-6-hydroxyphenyl)-3-(4-chloro-2-fluorophenyl) prop-2-en-1-one (1.2 g, 3.2 mmol, 1.0 equiv), $H_2SO_4$ (3 mL) in EtOH (15 mL) was stirred at 80° C. overnight. The mixture was extracted with DCM (50 mL*3), washed with brine, dried over anhydrous $Na_2SO_4$ and concentrated. The residue was purified by flash chromatography on silica gel (eluted with PE/EtOAc=97/3) to give the 5-bromo-2-(4-chloro-2-fluorophenyl) chroman-4-one (570 mg, 47% yield) as a yellow solid.

$^1$H NMR (400 MHZ, $CDCl_3$) δ ppm 7.55 (t, J=8.0 Hz, 1H), 7.34 (dd, J=7.6, 1.2 Hz, 1H), 7.29 (d, J=8.0 Hz, 1H), 7.22-7.26 (m, 1H), 7.15 (dd, J=10.0, 2.0 Hz, 1H), 7.04 (dd, J=8.0, 1.2 Hz, 1H), 5.72 (dd, J=12.8, 3.2 Hz, 1H), 3.06 (dd, J=16.4, 12.8 Hz, 1H), 2.96 (dd, J=16.4, 3.2 Hz, 1H).

Step C: 5-bromo-2-(4-chloro-2-fluorophenyl) chroman

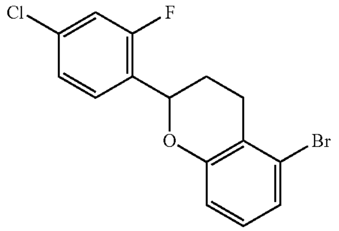 [SMILES: Fc1cc(Cl)ccc1C1CCc2c(Br)cccc2O1]

A solution of 5-bromo-2-(4-chloro-2-fluorophenyl) chroman-4-one (35.0 mg, 0.0980 mmol), $Et_3SiH$ (46.0 mg, 0.393 mmol) in TFA (5 mL) was stirred at room temperature for 3 hours. The mixture was filtered and concentrated. The residue was purified by flash chromatography on silica gel (eluted with 100% PE) to give 5-bromo-2-(4-chloro-2-fluorophenyl) chroman (30.0 mg, 90% yield) as a colorless oil.

$^1$H NMR (400 MHZ, $CDCl_3$) δ ppm 7.45 (t, J=8.0 Hz, 1H), 7.15-7.20 (m, 2H), 7.11 (dd, J=10.0, 2.0 Hz, 1H), 7.00 (t, J=8.0 Hz, 1H), 6.86 (dd, J=8.4, 1.2 Hz, 1H), 5.25 (dd, J=10.4, 2.4 Hz, 1H), 2.81-2.91 (m, 2H), 2.24-2.34 (m, 1H), 1.94-2.05 (m, 1H).

Step D: tert-butyl 4-(2-(4-chloro-2-fluorophenyl) chroman-5-yl) piperazine-1-carboxylate

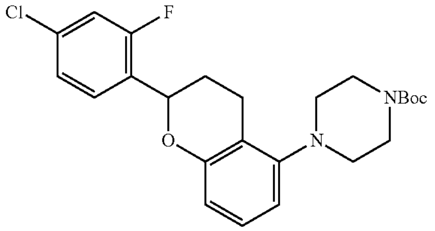 [SMILES: CC(C)(C)OC(=O)N1CCN(c2cccc3c2CCC(c2ccc(Cl)cc2F)O3)CC1]

A mixture of 5-bromo-2-(4-chloro-2-fluorophenyl) chroman (200 mg, 0.590 mmol), tert-butyl piperazine-1-carboxylate (121 mg, 0.650 mmol), $Pd_2$ (dba) 3 (54.0 mg, 0.0590 mmol), BINAP (37.0 mg, 0.0590 mmol) and tBuONa (113 mg, 1.18 mmol) in dry toluene (5 mL) was stirred at 100° C. for 3 hours under $N_2$. The reaction mixture was concentrated under vacuum. The residue was purified by flash chromatography on silica gel (PE/EtOAc=93/7) to give tert-butyl 4-(2-(4-chloro-2-fluorophenyl) chroman-5-yl)piperazine-1-carboxylate (130 mg, 50% yield) as a colorless oil.

$^1$H NMR (400 MHZ, $CDCl_3$) δ ppm 7.46 (t, J=8.0 Hz, 1H), 7.06-7.18 (m, 3H), 6.70 (dd, J=8.4, 1.2 Hz, 1H), 6.62 (dd, J=8.0, 1.2 Hz, 1H), 5.35 (dd, J=10.0, 2.4 Hz, 1H), 3.46-3.64 (m, 4H), 2.86-3.02 (m, 3H), 2.70-2.83 (m, 3H), 2.21-2.30 (m, 1H), 1.86-1.98 (m, 1H).

2-((4-(2-(4-Chloro-2-fluorophenyl) chroman-5-yl)piperazin-1-yl)methyl)-3-((S)oxetan-2-ylmethyl)-3H-imidazo[4,5-b]pyridine-5-carboxylic acid (Example 10, Compound 123a) was synthesized following the methods depicted in Example 6, using tert-butyl 4-(2-(4-chloro-2-fluorophenyl) chroman-5-yl)piperazine-1-carboxylate in step F.

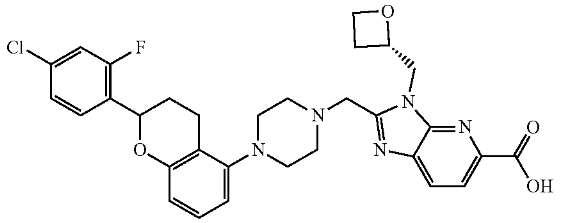 [SMILES: O=C(O)c1ccc2nc(CN3CCN(c4cccc5c4CCC(c4ccc(Cl)cc4F)O5)CC3)n(C[C@@H]3CCO3)c2n1]

$^1$H NMR (400 MHZ, $CDCl_3$) δ ppm 8.18-8.25 (m, 2H), 7.46 (t, J=8.0 Hz, 1H), 7.16 (dd, J=8.4, 2.0 Hz, 1H), 7.08-7.14 (m, 3H), 6.66 (dd, J=20.4, 8.0 Hz, 2H), 5.35 (dd, J=10.0, 2.4 Hz, 2H), 5.22-5.30 (m, 1H), 4.80-5.01 (m, 2H), 4.61-4.69 (m, 1H), 4.34-4.44 (m, 1H), 4.14 (br.s, 2H), 3.07 (s, 2H), 2.63-2.95 (m, 9H), 2.42-2.53 (m, 1H), 2.20-2.30 (m, 1H), 1.87-1.95 (m, 1H). LC-MS: m/z 592.2 $(M+H)^+$.

2-((4-(2-(4-chloro-2-fluorophenyl) chroman-5-yl)piperidin-1-yl)methyl)-3-(((S)oxetan-2-yl)methyl)-3H-imidazo[4,5-b]pyridine-5-carboxylic acid (Compound 105a) was synthesized following the methods depicted in Example 6, using tert-butyl 4-(2-(4-chloro-2-fluorophenyl) chroman-5-yl)piperazine-1-carboxylate in step F.

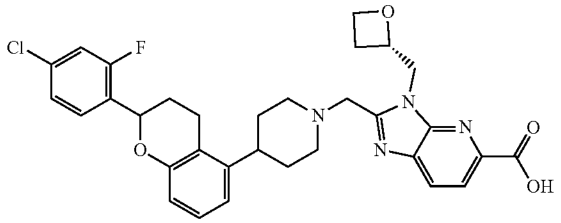 [SMILES: O=C(O)c1ccc2nc(CN3CCC(c4cccc5c4CCC(c4ccc(Cl)cc4F)O5)CC3)n(C[C@@H]3CCO3)c2n1]

$^1$H NMR (400 MHZ, $CDCl_3$) δ ppm 8.19 (dd, J=10.8, 8.4 Hz, 2H), 7.47 (t, J=8.0 Hz, 1H), 7.08-7.18 (m, 3H), 6.86 (dd, J=7.6, 1.2 Hz, 1H), 6.78 (dd, J=8.4, 1.2 Hz, 1H), 5.24-5.29 (m, 2H), 4.99 (dd, J=15.2, 6.4 Hz, 1H), 4.86 (dd, J=14.8, 3.2 Hz, 1H), 4.60-4.65 (m, 1H), 4.38-4.43 (m, 1H), 4.16 (dd, J=20.4, 14.0 Hz, 2H), 3.10-3.16 (m, 2H), 2.68-2.94 (m, 4H), 2.26-2.53 (m, 4H), 1.75-2.04 (m, 5H). LC-MS: m/z=519.2 $(M+H)^+$.

Example 11

2-((4-(3-(4-chloro-2-fluorophenyl)-3,4-dihydro-2H-benzo[b][1,4]oxazin-8-yl) piperidin-1-yl)methyl)-3-(((S)-oxetan-2-yl)methyl)-3H-imidazo[4,5-b]pyridine-5-carboxylic acid (Compound 124a)

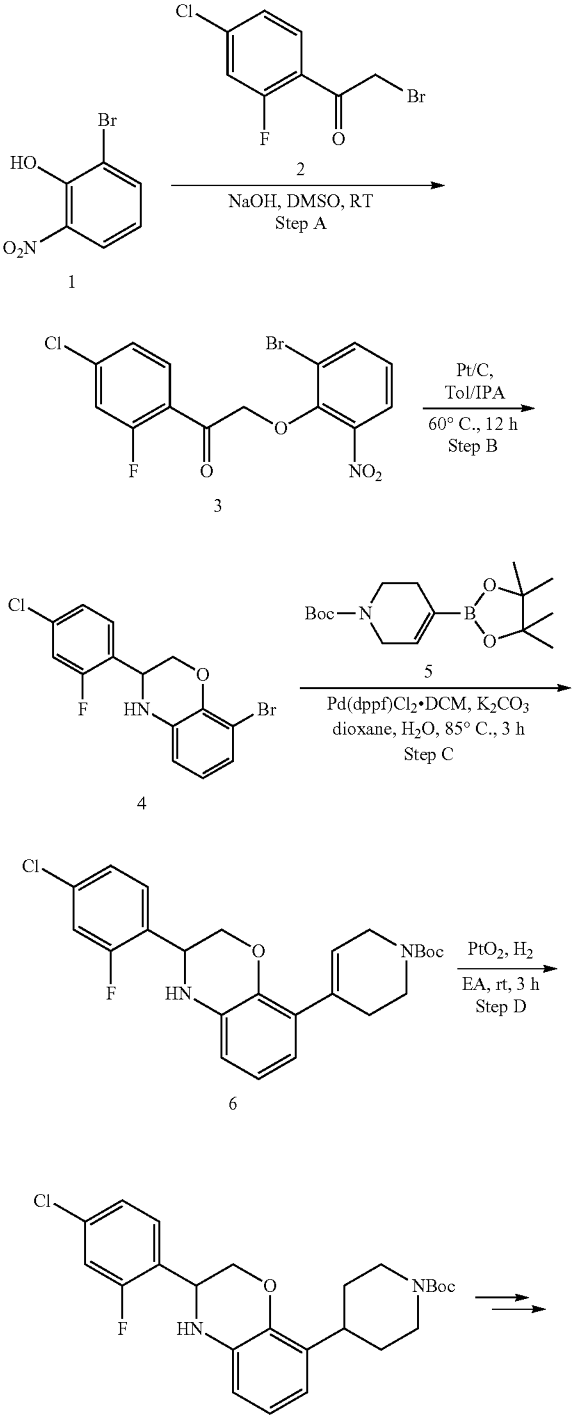

-continued

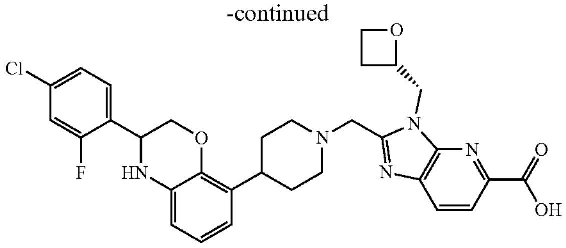

Compound 124a

Step A: 2-(2-bromo-6-nitrophenoxy)-1-(4-chloro-2-fluorophenyl) ethan-1-one

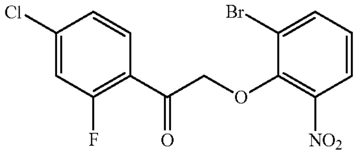 [SMILES: O=C(COc1c(Br)cccc1[N+](=O)[O-])c1ccc(Cl)cc1F]

A mixture of 2-bromo-6-nitrophenol (1.09 g, 5.00 mmol), 2-bromo-1-(4-chloro-2-fluorophenyl) ethan-1-one (1.38 g, 5.50 mmol), NaOH (202 mg, 5.50 mmol) in DMSO (5 mL) was stirred at 20° C. for 3 h. LCMS showed the reaction was completed. The mixture was diluted with ethyl acetate (50 mL) and washed with water (50 mL). The organic layer was dried and concentrated. The residue was purified with silica gel column chromatography (PE/EA=5:1) to give 2-(2-bromo-6-nitrophenoxy)-1-(4-chloro-2-fluorophenyl) ethan-1-one (1.28 g, 3.30 mmol, 66% yield) as a yellow solid. $^1H$ NMR (400 MHZ, $CDCl_3$) δ ppm 8.01-8.10 (m, 1H), 7.83 (d, J=8.0 Hz, 2H), 7.31 (dd, J=8.4, 1.6 Hz, 1H), 7.15-7.24 (m, 2H), 5.39 (d, J=3.6 Hz, 2H). LC-MS: m/z=388.0, 390.0 $(M+H)^+$.

Step B: 8-bromo-3-(4-chloro-2-fluorophenyl)-3.4-dihydro-2H-benzo[b][1,4]oxazine

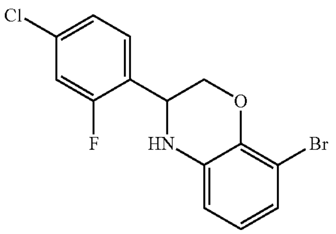 [SMILES: Fc1cc(Cl)ccc1C1COc2c(Br)cccc2N1]

To a solution of 2-(2-bromo-6-nitrophenoxy)-1-(4-chloro-2-fluorophenyl) ethan-1-one (1.04 g, 2.67 mmol) in toluene (9 mL) and isopropanol (6 mL) was added Pt/C (5% Pt, 104 mg). The mixture was heated at 60° C. for 12 h. LCMS showed the starting material was consumed. The mixture was filtered. The filtrate was concentrated and purified with silica gel column chromatography (PE/EA=20:1) to give 8-bromo-3-(4-chloro-2-fluorophenyl)-3,4-dihydro-2H-benzo[b][1,4]oxazine (765 mg, 2.23 mmol, 84% yield) as a yellow solid.

$^1H$ NMR (400 MHZ, $CDCl_3$) δ ppm 7.38 (t, J=8.0 Hz, 1H), 7.03-7.21 (m, 2H), 6.95 (dd, J=7.6, 1.6 Hz, 1H), 6.70 (t, J=8.0 Hz, 1H), 6.63 (dd, J=8.0, 1.6 Hz, 1H), 4.81-4.95 (m, 1H), 4.43 (dd, J=10.8, 2.8 Hz, 1H), 4.11 (dd, J=10.8, 7.2 Hz, 1H). LC-MS: m/z=342.0, 344.0 $(M+H)^+$.

Step C: tert-butyl 4-(3-(4-chloro-2-fluorophenyl)-3,4-dihydro-2H-benzo[b][1,4]oxazin-8-yl)-3,6-dihydropyridine-1 (2H)-carboxylate

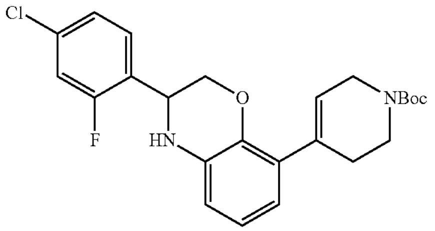

A mixture of 8-bromo-3-(4-chloro-2-fluorophenyl)-3,4-dihydro-2Hbenzo[b][1,4]oxazine (665 mg, 1.94 mmol), tert-butyl 4-(4,4,5,5-tetramethyl-1,3,2-dioxaborolan-2-yl)-3,6-dihydropyridine-1 (2H)-carboxylate (905 mg, 2.92 mmol), $Pd(dppf)Cl_2{\cdot}CH_2Cl_2$ (159 mg, 0.194 mmol) and $K_2CO_3$ (805 mg, 5.83 mmol) in 10 mL of 1,4-dioxane and 3 mL of $H_2O$ was stirred at 85° C. for 3 h under an atmosphere of argon. LCMS showed the reaction was completed. The mixture was diluted with ethyl acetate (30 mL) and washed with water (30 mL). The organic layer was dried and concentrated. The residue was purified with silica gel column chromatography (PE/EA=5:1) to give tert-butyl 4-(3-(4-chloro-2-fluorophenyl)-3,4-dihydro-2Hbenzo[b][1,4]oxazin-8-yl)-3,6-dihydropyridine-1 (2H)-carboxylate (842 mg, 1.89 mmol, 98% yield) as a yellow solid.

$^1H$ NMR 00 MHZ, $CDCl_3$) δ ppm 7.41 (t, J=7.8 Hz, 1H), 7.10-7.17 (m, 2H), 6.78 (t, J=7.8 Hz, 1H), 6.55-6.67 (m, 2H), 5.78 (br.s, 1H), 4.87 (dd, J=6.4, 3.02 Hz, 1H), 4.33 (dd, J=10.8, 3.2 Hz, 1H), 4.00-4.05 (m, 3H), 3.58 (br.s, 2H), 2.48 (br.s, 2H), 1.48 (s, 9H). LC-MS: m/z=445.2 $(M+H)^+$.

Step D: tert-butyl 4-(3-(4-chloro-2-fluorophenyl)-3,4-dihydro-2H-benzo[b][1,4]oxazin-8-yl)piperidine-1-carboxylate

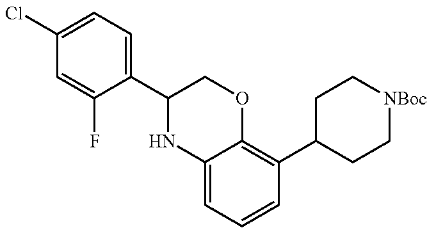 [SMILES: CC(C)(C)OC(=O)N1CCC(c2cccc3c2OCC(c2ccc(Cl)cc2F)N3)CC1]

To a solution of tert-butyl 4-(3-(4-chloro-2-fluorophenyl)-3,4-dihydro-2Hbenzo[b][1,4]oxazin-8-yl)-3,6-dihydropyridine-1 (2H)-carboxylate (250 mg, 0.560 mmol) in ethyl acetate (3 mL) was added $PtO_2$ (5% Pt, 46.0 mg). The mixture was stirred at room temperature for 3 h under an atmosphere of $H_2$. LCMS showed the reaction was completed. The mixture was filtered. The filtrate was concentrated and purified with silica gel column chromatography (PE/EA=5:1) to give tert-butyl 4-(3-(4-chloro-2-fluorophenyl)-3,4-dihydro-2H-benzo[b][1,4]oxazin-8-yl)piperidine- 1-carboxylate (247 mg, 0.497 mmol, 88.7% yield) as a yellow solid. LC-MS: m/z=391.2 $(M-55)^+$.

2-((4-(3-(4-Chloro-2-fluorophenyl)-3,4-dihydro-2H-benzo[b][1,4]oxazin-8-yl) piperidin-1-yl)methyl)-3-(((S)-oxetan-2-yl)methyl)-3H-imidazo[4,5-b]pyridine-5-carboxylic acid (Compound 124a) was synthesized following the methods depicted in Example 6, using tert-butyl 4-(3-(4-chloro-2-fluorophenyl)-3,4-dihydro-2Hbenzo[b][1,4] oxazin-8-yl)piperidine-1-carboxylate in step F.

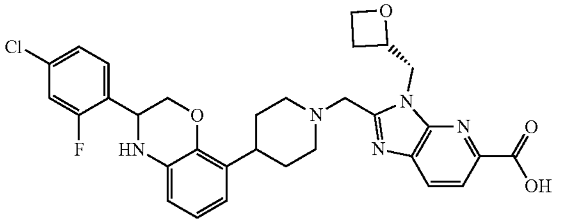

$^1$H NMR (400 MHZ, $CDCl_3$) δ ppm 8.20 (dd, J=13.6, 8.0 Hz, 2H), 7.40 (t, J=8.0 Hz, 1H), 7.09-7.17 (m, 2H), 6.79 (t, J=7.6 Hz, 1H), 6.64 (dd, J=7.6, 1.2 Hz, 1H), 6.57 (dd, J=7.6, 1.2 Hz, 1H), 5.21-5.30 (m, 1H), 4.97 (dd, J=14.8, 6.4 Hz, 1H), 4.79-4.91 (m, 2H), 4.64 (m, 1H), 4.42 (m, 1H), 4.34 (dd, J=10.4, 2.8 Hz, 1H), 4.09 (s, 2H), 4.02 (dd, J=10.4, 6.8 Hz, 1H), 2.90-3.08 (m, 3H), 2.72-2.86 (m, 1H), 2.43-2.54 (m, 1H), 2.28-2.43 (m, 2H), 1.70-1.91 (m, 4H). LC-MS: m/z=592.2 $(M+H)^+$.

Example 12

2-((4-(3-(2-fluorophenyl)-3,4-dihydro-2H-benzo[b][1,4]oxazin-8-yl)piperidin-1-yl)methyl)-3-(((S)-oxetan-2-yl)methyl)-3H-imidazo[4,5-b]pyridine-5-carboxylic acid (Compound 125a)

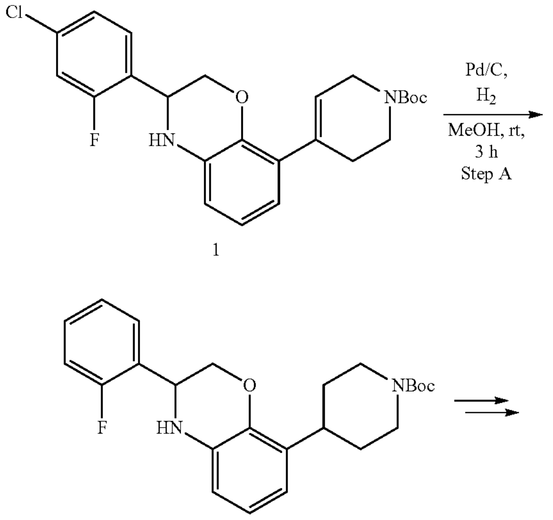

1

2

-continued

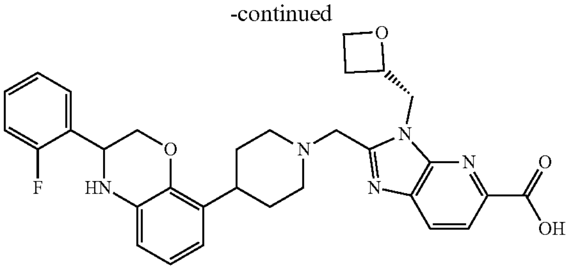

Compound 125a

Step A: tert-butyl 4-(3-(2-fluorophenyl)-3.4-dihydro-2H-benzo[b][1,4]oxazin-8-yl) piperidine-1-carboxylate

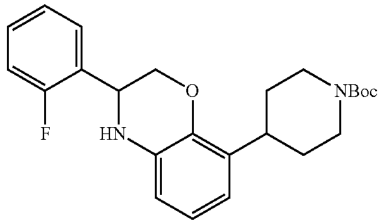 [SMILES: CC(C)(C)OC(=O)N1CCC(c2cccc3c2OCC(c2ccccc2F)N3)CC1]

To a solution of tert-butyl 4-(3-(4-chloro-2-fluorophenyl)-3,4-dihydro-2Hbenzo[b][1,4]oxazin-8-yl)-3,6-dihydropyridine-1 (2H)-carboxylate (100 mg, 0.225 mmol) in methanol (2 mL) was added Pd/C (5% Pd, 14.0 mg). The mixture was stirred at room temperature for 3 h under an atmosphere of $H_2$. LCMS showed the reaction was completed. The mixture was filtered. The filtrate was concentrated and purified with silica gel column chromatography (PE/EA=5:1) to give tert-butyl 4-(3-(2-fluorophenyl)-3,4-dihydro-2H-benzo[b][1,4]oxazin-8-yl)piperidine-1-carboxylate (84.0 mg, 0.188 mmol, 84% yield) as a yellow solid. LC-MS: m/z=357.2 $(M-56)^+$ 2-((4-(3-(2-Fluorophenyl)-3,4-dihydro-2H-benzo[b][1,4] oxazin-8-yl)piperidin-1-yl)methyl)-3-(((S)-oxetan-2-yl) methyl)-3H-imidazo[4,5-b]pyridine-5-carboxylic acid (Compound 125a) was synthesized following the methods depicted in Example 6, using tert-butyl 4-(3-(2-fluorophenyl)-3,4-dihydro-2H-benzo[b][1,4]oxazin-8-yl) piperidine-1-carboxylate in step F.

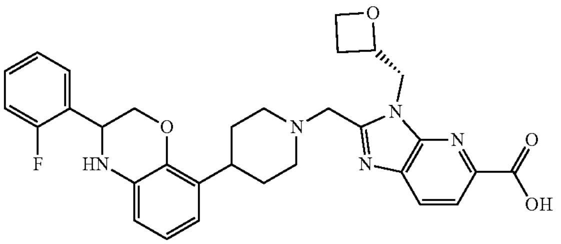

$^1$H NMR (400 MHZ, $CDCl_3$) δ ppm 8.20 (dd, J=13.2, 8.0 Hz, 2H), 7.43-7.49 (m, 1H), 7.27-7.33 (m, 1H), 7.12-7.19 (m, 1H), 7.04-7.12 (m, 1H), 6.79 (t, J=7.6 Hz, 1H), 6.63 (dd, J=7.6, 1.2 Hz, 1H), 6.57 (dd, J=7.6, 1.2 Hz, 1H), 5.20-5.30 (m, 1H), 4.80-5.05 (m, 3H), 4.58-4.69 (m, 1H), 4.33-4.47

(m, 2H), 4.10 (s, 2H), 4.04 (dd, J=10.4, 7.2 Hz, 1H), 2.89-3.12 (m, 3H), 2.73-2.87 (m, 1H), 2.25-2.58 (m, 3H), 1.62-2.00 (m, 4H). LC-MS: m/z=558.2 $(M+H)^+$.

Example 13 2-((4-(3-(4-chloro-2-fluorophenyl) chroman-8-yl)piperidin-1-yl)methyl)-3-(((S)-oxetan-2-yl)methyl)-3H-imidazo[4,5-b]pyridine-5-carboxylic acid (Compound 106a)

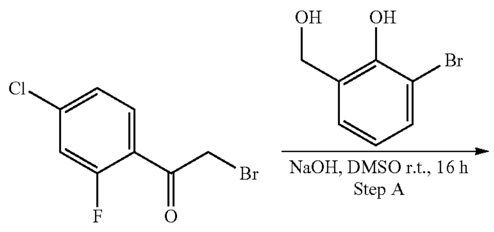

1

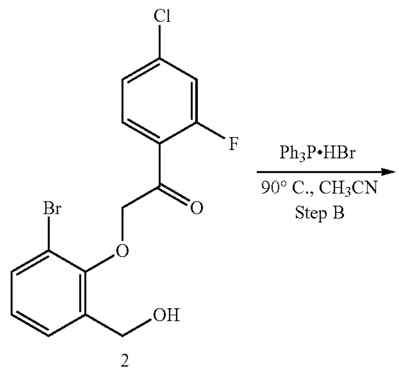

2

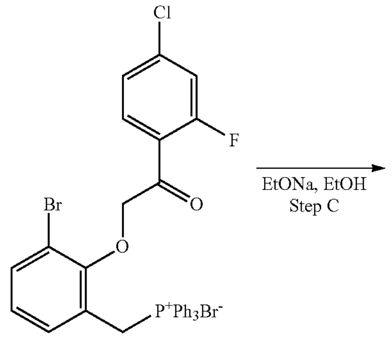

3

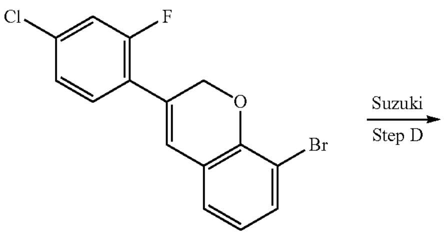

4

-continued

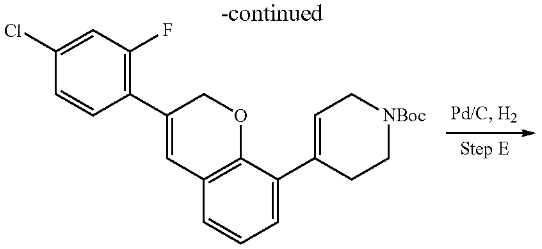

5

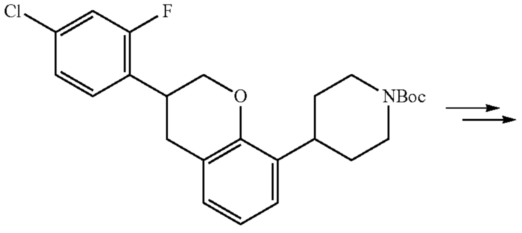

6

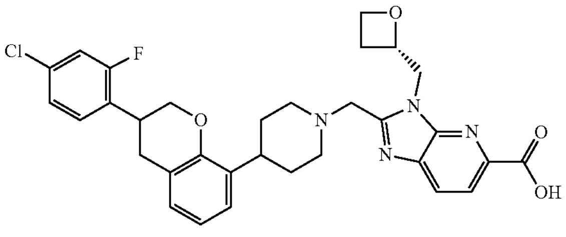

106a

Step A: 2-(2-bromo-6-(hydroxymethyl) phenoxy)-1-(4-chloro-2-fluorophenyl) ethan-1-one

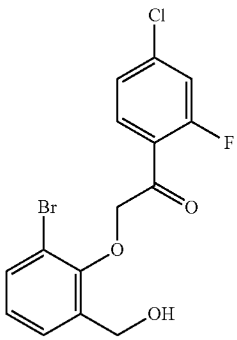 [SMILES: O=C(COc1c(Br)cccc1CO)c1ccc(Cl)cc1F]

To a solution of 2-bromo-1-(4-chloro-2-fluorophenyl) ethan-1-one (3.22 g, 12.8 mmol, synthesized following step A of Example 8) in DMSO (60 ml) was added NaOH (564 mg, 14.1 mmol) and 2-bromo-6-(hydroxymethyl) phenol (2.60 g, 12.8 mmol). The resulting mixture was stirred at room temperature for 16 hours. The solution was diluted with water (40 ml) and extracted with EtOAc (3×50 ml). The combined organic layers were washed with brine (50 mL), dried over anhydrous $Na_2SO_4$, filtered and concentrated. The residue was purified by flash chromatography (eluted with PE/EtOAc=7/1-4/1) to afford the title compound 2-(2-bromo-6-(hydroxymethyl) phenoxy)-1-(4-chloro-2-fluorophenyl) ethan-1-one as a white solid (2.75 g, 57% yield).

$^1H$ NMR (400 MHZ, DMSO-$d_6$) δ ppm 7.97 (t, J=8.4 Hz, 1H), 7.66 (dd, J=11.2, 1.6 Hz, 1H), 7.54 (d, J=7.6 Hz, 1H), 7.49 (dd, J=8.4, 1.6 Hz, 1H), 7.45 (d, J=6.4 Hz, 1H), 7.13 (t, J=7.6 Hz, 1H), 5.20-5.23 (m, 2H), 4.55-4.59 (m, 2H).

Step B: (3-bromo-2-(2-(4-chloro-2-fluorophenyl)-2-oxoethoxy)benzyl)triphenyl phosphonium bromide

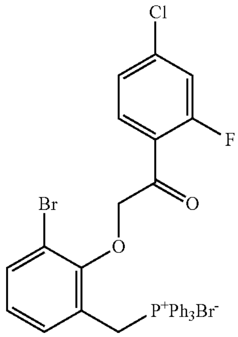

The mixture of 2-(2-bromo-6-(hydroxymethyl) phenoxy)-1-(4-chloro-2-fluorophenyl) ethan-1-one (2.75 g, 7.35 mmol) and Ph3P·HBr (2.52 g, 7.35 mmol) in $CH_3CN$ (95 ml) was stirred at 90° C. for 16 hours under $N_2$ atmosphere. The reaction mixture was filtered through celite and the filtrate was concentrated under reduced pressure to give a crude product which was purified by flash chromatography (eluted with DCM/MeOH=6/1~5/1) to afford the title compound (3-bromo-2-(2-(4-chloro-2-fluorophenyl)-2-oxoethoxy)benzyl)triphenylphosphonium bromide as a yellow solid (2.02 g, 39% yield).

$^1$H NMR (400 MHZ, $CDCl_3$) δ ppm 7.96 (t, J=8.0 Hz, 1H), 7.75-7.85 (m, 9H), 7.61-7.66 (m, 6H), 7.49-7.51 (m, 1H), 7.43-7.46 (m, 1H), 7.30 (dd, J=8.4, 2.0 Hz, 1H), 7.19 (dd, J=10.8, 2.0 Hz, 1H), 6.89 (d, J=8.0 Hz, 1H), 5.81 (d, J=14.8 Hz, 2H), 5.08 (d, J=3.2 Hz, 2H).

Step C: 8-bromo-3-(4-chloro-2-fluorophenyl)-2H-chromene

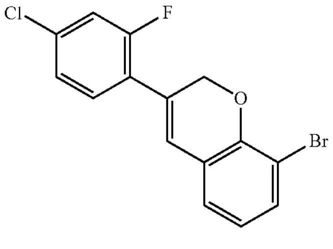 [SMILES: Fc1cc(Cl)ccc1C1=Cc2cccc(Br)c2OC1]

To a solution of (3-bromo-2-(2-(4-chloro-2-fluorophenyl)-2-oxoethoxy)benzyl)triphenylphosphonium bromide (2.02 mg, 2.89 mmol) in EtOH (40 mL) was added 1M solution of EtONa in EtOH (3.18 ml, 3.18 mmol). The reaction was stirred at room temperature for 16 hours under $N_2$ atmosphere. The reaction mixture was quenched with water (50 mL) and extracted with EtOAc (3× 40 mL). The combined organic layers were washed with brine (60 mL), dried over anhydrous $Na_2SO_4$ and concentrated. The residue was purified by flash chromatography (eluted with PE/EtOAc=10/1~6/1) to afford the title compound 8-bromo-3-(4-chloro-2-fluorophenyl)-2H-chromene as a yellow solid (815 mg, 83% yield).

$^1$H NMR (400 MHZ, DMSO-$d_6$) δ ppm 7.53-7.60 (m, 2H), 7.45 (dd, J=8.0, 1.2 Hz, 1H), 7.38 (dd, J=8.4, 2.0 Hz, 1H), 7.24 (dd, J=7.2, 1.2 Hz, 1H), 6.99 (s, 1H), 6.91 (t, J=7.6 Hz, 1H), 5.18 (s, 2H).

2-((4-(3-(4-Chloro-2-fluorophenyl) chroman-8-yl)piperidin-1-yl)methyl)-3-(((S)oxetan-2-yl)methyl)-3H-imidazo[4,5-b]pyridine-5-carboxylic acid (Compound 106a) was synthesized following the methods depicted in Example 11, using 8-bromo-3-(4-chloro-2-fluorophenyl)-2H-chromene in step C.

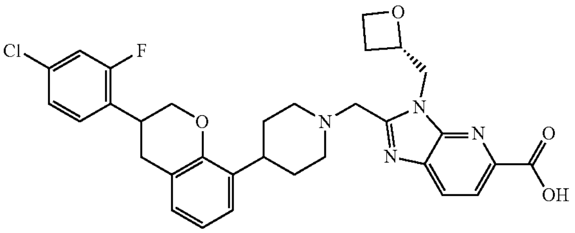 [SMILES: O=C(O)c1ccc2nc(CN3CCC(c4cccc5c4OCC(c4ccc(Cl)cc4F)C5)CC3)n(C[C@@H]3CCO3)c2n1]

$^1$H NMR (400 MHZ, DMSO-$d_6$) δ ppm 8.10 (d, J=8.0 Hz, 1H), 7.97 (d, J=8.4 Hz, 1H), 7.45 (dd, J=10.4, 2.0 Hz, 1H), 7.38 (t, J=8.4 Hz, 1H), 7.28 (dd, J=8.4, 2.0 Hz, 1H), 7.03 (d, J=7.6 Hz, 1H), 6.96 (d, J=7.2 Hz, 1H), 6.83 (t, J=7.6 Hz, 1H), 5.14-5.19 (m, 1H), 4.85 (dd, J=14.8, 6.4 Hz, 1H), 4.73 (dd, J=14.8, 4.0 Hz, 1H), 4.67-4.52 (m, 1H), 4.28-4.43 (m, 2H), 4.12 (t, J=10.0 Hz, 1H), 3.94 (dd, J=29.6, 13.6 Hz, 2H), 3.40-3.46 (m, 1H), 2.65-3.09 (m, 5H), 2.20-2.28 (m, 2H), 1.52-1.77 (m, 4H). LC-MS: m/z 591.2 $(M+H)^+$.

2-((4-(3-(2-fluorophenyl) Chroman-8-yl)piperidin-1-yl)methyl)-3-(((S)-oxetan-2-yl)methyl)-3H-imidazo[4,5-b]pyridine-5-carboxylic acid (Compound 122a) was synthesized following the methods depicted in Example 13, above.

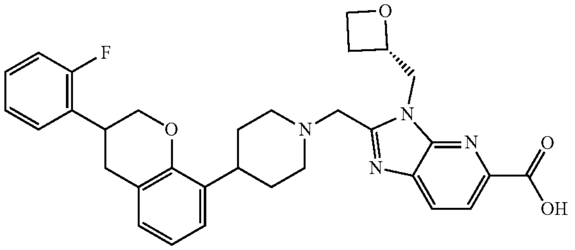 [SMILES: O=C(O)c1ccc2nc(CN3CCC(c4cccc5c4OCC(c4ccccc4F)C5)CC3)n(C[C@@H]3CCO3)c2n1]

$^1$H NMR (400 MHZ, DMSO-$d_6$) δ ppm 13.03 (s, 1H), 8.14 (d, J=8.0 Hz, 1H), 8.00 (d, J=8.0 Hz, 1H), 7.29-7.40 (m, 2H), 7.15-7.26 (m, 2H), 7.03 (d, J=7.2 Hz, 1H), 6.96 (d, J=7.2 Hz, 1H), 6.82 (t, J=7.6 Hz, 1H), 5.13-5.24 (m, 1H), 4.87 (dd, J=14.4, 6.4 Hz, 1H), 4.74 (dd, J=14.8, 4.4 Hz, 1H), 4.47-4.52 (m, 1H), 4.32-4.42 (m, 2H), 4.13 (t, J=10.0 Hz, 1H), 3.97 (q, J=13.8 Hz, 2H), 3.44-3.48 (m, 1H), 2.66-3.11 (m, 7H), 2.19-2.34 (m, 2H), 1.65-1.71 (m, 4H). LC-MS: m/z 557.2 $(M+H)^+$.

Example 14

2-((4-(2-(3-chlorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 121a)

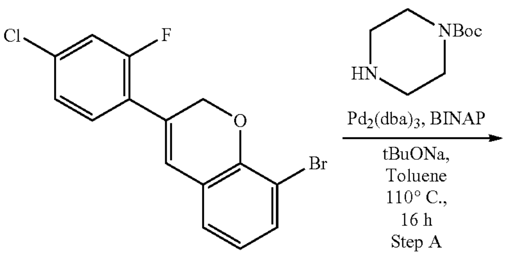

1

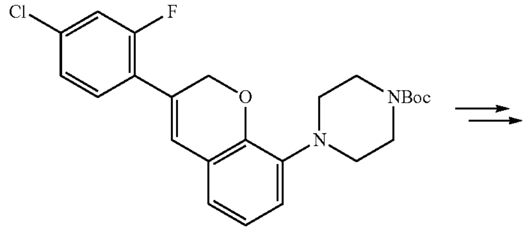

2

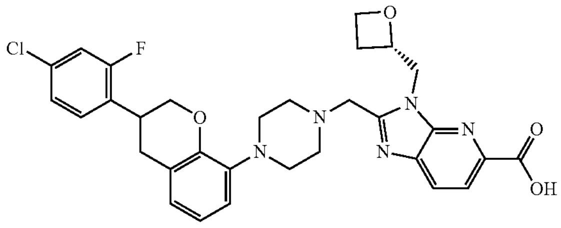

Compound 121a

Step A: tert-butyl 4-(3-(4-chloro-2-fluorophenyl)-2H-chromen-8-yl)piperazine-1-carboxylate

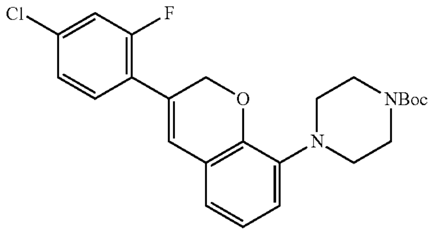 [SMILES: CC(C)(C)OC(=O)N1CCN(c2cccc3c2OCC(c2ccc(Cl)cc2F)=C3)CC1]

To a solution of 8-bromo-3-(4-chloro-2-fluorophenyl)-2H-chromene (230 mg, 0.680 mmol) in toluene (8 ml) were added tert-butyl piperazine-1-carboxylate (252 mg, 1.36 mmol), t-BuONa (130 mg, 1.36 mmol), BINAP (96.0 mg, 0.160 mmol) and $Pd_2$ (dba) 3 (72.0 mg, 0.0800 mmol). The mixture was stirred at 110° C. for 16 hours under $N_2$ atmosphere. The mixture was diluted with water (30 mL) and extracted with EtOAc (3× 20 mL). The combined organic layers were washed with brine (30 mL), dried over anhydrous $Na_2SO_4$, filtered and concentrated. The residue was purified by flash chromatography (eluted with PE/EtOAc=10/1-4/1) to afford the title compound tertbutyl 4-(3-(4-chloro-2-fluorophenyl)-2H-chromen-8-yl)piperazine-1-carboxylate as a white solid (220 mg, 73% yield).

$^1$H NMR (400 MHZ, DMSO-$d_6$) δ ppm 7.56 (t, J=7.6 Hz, 1H), 7.52 (dd, J=11.6, 2.4 Hz, 2H), 7.35 (dd, J=8.4, 2.0 Hz, 1H), 6.95 (s, 1H), 6.79-6.92 (m, 3H), 5.04 (s, 2H), 3.46 (t, J=9.6 Hz, 4H), 2.93 (t, J=9.6 Hz, 4H), 1.42 (s, 9H).

2-((4-(3-(4-Chloro-2-fluorophenyl) chroman-8-yl)piperazin-1-yl)methyl)-3-(((S)oxetan-2-yl)methyl)-3H-imidazo[4,5-b]pyridine-5-carboxylic acid (Compound 121a) was synthesized following the methods depicted in Example 6, using tert-butyl 4-(3-(4-chloro-2-fluorophenyl)-2H-chromen-8-yl)piperazine-1-carboxylate in step F.

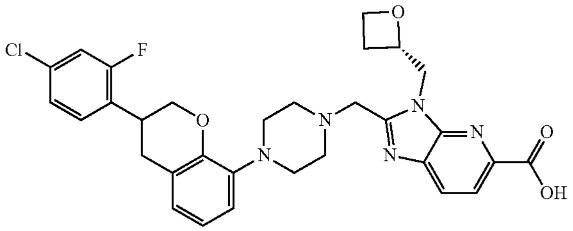 [SMILES: O=C(O)c1ccc2nc(CN3CCN(c4cccc5c4OCC(c4ccc(Cl)cc4F)C5)CC3)n(C[C@@H]3CCO3)c2n1]

$^1$H NMR (400 MHZ, DMSO-$d_6$) δ ppm 8.13 (d, J=8.0 Hz, 1H), 7.99 (d, J=8.0 Hz, 1H), 7.45 (dd, J=10.2, 2.0 Hz, 1H), 7.37 (t, J=8.4 Hz, 1H), 7.28 (dd, J=8.0, 2.0 Hz, 1H), 6.73-6.81 (m, 3H), 5.11-5.22 (m, 1H), 4.85 (dd, J=14.4, 4.4 Hz, 1H), 4.72 (dd, J=14.4, 3.6 Hz, 1H), 4.46-4.51 (m, 1H), 4.32-4.37 (m, 3H), 4.10 (t, J=9.6 Hz, 1H), 3.94-4.05 (m, 2H), 3.40-3.46 (m, 2H), 2.91-3.06 (m, 6H), 2.63-2.77 (m, 4H). LC-MS: m/z 592.2 (M+H)$^+$.

Example 15

(S)-2-((4-(2-(4-chlorophenyl)-1,2,3,4-tetrahydroisoquinolin-5-yl)piperidin-1-yl)methyl)-3-(oxetan-2-ylmethyl)-3H-imidazo[4,5-b]pyridine-5-carboxylic acid

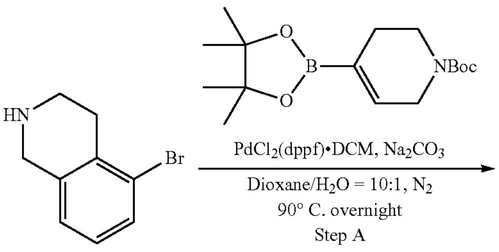

1

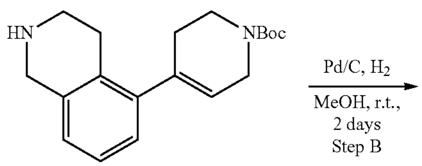

2

-continued

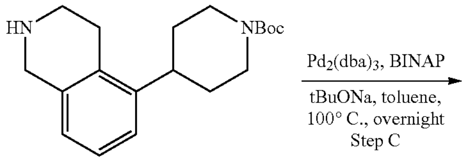

3

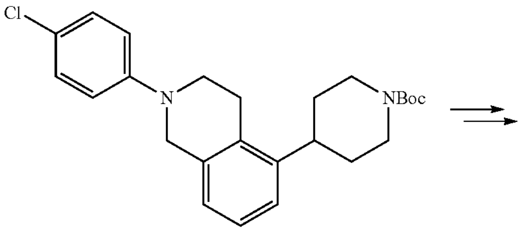

4

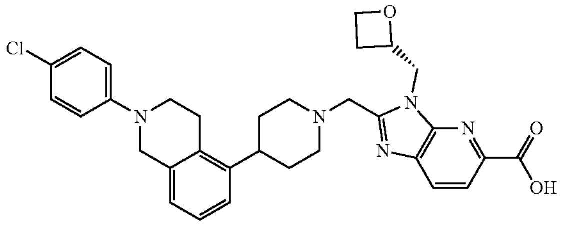

Compound 126a

Step A: tert-butyl 4-(1,2,3,4-tetrahydroisoquinolin-5-yl)-3,6-dihydropyridine-1 (2H)carboxylate

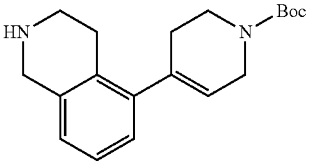 [SMILES: CC(C)(C)OC(=O)N1CC=C(c2cccc3c2CCNC3)CC1]

To the mixture of 5-bromo-1,2,3,4-tetrahydroisoquinoline (1.00 g, 4.71 mmol), Pd(dppf)$Cl_2$·DCM (385 mg, 0.471 mmol) and $Na_2CO_3$ (1.00 g, 9.43 mmol) in dioxane (20 mL) and $H_2O$ (2 mL) was added tert-butyl 4-(4,4,5,5-tetramethyl-1,3,2-dioxaborolan-2-yl)-3,6-dihydropyridine-1 (2H)-carboxylate (1.70 g, 5.50 mmol). The mixture was purged with $N_2$ and stirred at 90° C. overnight. The mixture was diluted with water (40 mL) and extracted with EtOAc (3×40 mL). The combined organic phase was washed with brine (30 mL), dried over anhydrous $Na_2SO_4$, concentrated and purified by flash chromatography to afford tert-butyl 4-(1,2,3,4-tetrahydroisoquinolin-5-yl)-3,6-dihydropyridine-1 (2H)-carboxylate as a brown solid (940 mg, 63% yield). $^1$H NMR (400 MHZ, DMSO-$d_6$) δ ppm 7.09 (t, J=7.6 Hz, 1H), 6.94 (d, J=7.6 Hz, 1H), 6.90 (d, J=7.6 Hz, 1H), 5.52 (s, 1H), 3.94 (s, 2H), 3.90 (s, 2H), 3.52 (t, J=5.6 Hz, 2H), 2.94 (t, J=5.6 Hz, 2H), 2.61 (t, J=5.6 Hz, 2H), 2.24 (br.s, 2H), 1.42 (s, 9H). LC-MS: m/z 315.2 $(M+H)^+$.

Step B: tert-butyl 4-(1,2,3,4-tetrahydroisoquinolin-5-yl)piperidine-1-carboxylate

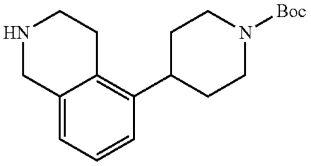 [SMILES: CC(C)(C)OC(=O)N1CCC(c2cccc3c2CCNC3)CC1]

To a solution of tert-butyl 4-(1,2,3,4-tetrahydroisoquinolin-5-yl)-3,6-dihydropyridine-1 (2H)-carboxylate (940 mg, 2.99 mmol) in MeOH (50 mL) was added Pd/C (5% Pd, 940 mg). The mixture was stirred at room temperature under $H_2$ for 2 days. The mixture was filtrated and concentrated to afford the title compound tert-butyl 4-(1,2,3,4-tetrahydroisoquinolin-5-yl)piperidine-1-carboxylate as a brown solid (629 mg, 67% yield).

$^1$H NMR (400 MHZ, DMSO-$d_6$) δ ppm 7.04-7.10 (m, 2H), 6.87-6.90 (m, 1H), 4.07 (d, J=10.8 Hz, 2H), 3.35 (br.s, 2H), 3.05 (t, J=6.0 Hz, 2H), 2.81-2.87 (m, 3H), 2.73 (t, J=6.0 Hz, 2H), 1.61-1.64 (m, 2H), 1.46-1.49 (m, 2H), 1.42 (s, 9H). LC-MS:

m/z 317.2 $(M+H)^+$

Step C: tert-butyl 4-(2-(4-chloro-2-fluorophenyl)-1,2,3,4-tetrahydroisoquinolin-5-yl) piperidine-1-carboxylate

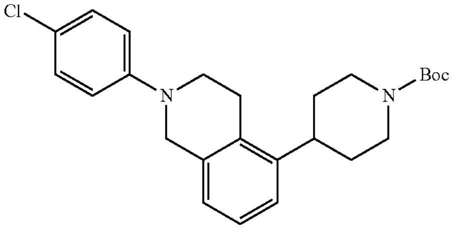 [SMILES: CC(C)(C)OC(=O)N1CCC(c2cccc3c2CCN(c2ccc(Cl)cc2)C3)CC1]

To the mixture of tert-butyl 4-(1,2,3,4-tetrahydroisoquinolin-5-yl)piperidine-1-carboxylate (629 mg, 1.99 mmol), $Pd_2$ (dba) 3 (182 mg, 0.20 mmol), BINAP (248 mg, 0.40 mmol) and t-BuONa (382 mg, 3.98 mmol) in toluene (20 mL) was added 1-bromo-4-chlorobenzene (570 mg, 2.98 mmol). The mixture was purged with $N_2$ and stirred at 110° C. overnight. The mixture was filtrated and concentrated. The residue was purified by flash chromatography to afford the title compound tert-butyl 4-(2-(4-chloro-2-fluorophenyl)-1,2,3,4-tetrahydroisoquinolin-5-yl)piperidine-1-carboxylate as a brown solid (321 mg, 39% yield).

$^1$H NMR (400 MHZ, DMSO-$d_6$) δ ppm 7.24 (d, J=8.8 Hz, 2H), 7.14 (d, J=7.6 Hz, 1H), 7.05-7.10 (m, 2H), 7.00 (d, J=8.8 Hz, 2H), 4.37 (s, 2H), 4.08 (d, J=10.4 Hz, 2H), 3.54 (t, J=5.6 Hz, 2H), 2.83-2.93 (m, 5H), 1.64-1.68 (m, 2H), 1.44-1.51 (m, 2H), 1.42 (s, 9H). LC-MS: m/z 371.2 $(M-55)^+$.

(S)-2-((4-(2-(4-Chlorophenyl)-1,2,3,4-tetrahydroisoquinolin-5-yl)piperidin-1-yl)methyl)-3-(oxetan-2-ylmethyl)-3H-imidazo[4,5-b]pyridine-5-carboxylic acid was synthesized following the route of example 6, using tert-butyl 4-(2-(4-chlorophenyl)-1,2,3,4-tetrahydroisoquinolin-5-yl) piperidine-1-carboxylate in step F.

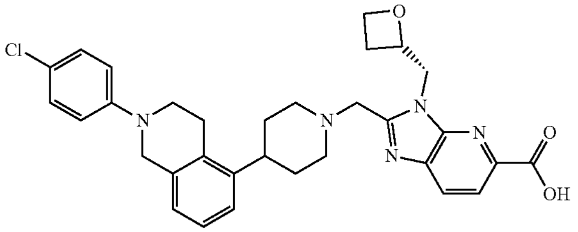

$^1$H NMR (400 MHZ, DMSO-$d_6$) δ ppm 8.14 (d, J=8.0 Hz, 1H), 7.99 (d, J=8.4 Hz, 1H), 7.23 (d, J=8.4 Hz, 2H), 7.11-7.18 (m, 2H), 7.05 (d, J=15.2 Hz, 1H), 6.99 (d, J=8.8 Hz, 2H), 5.16-5.19 (m, 1H), 4.87 (dd, J=14.4, 6.4 Hz, 1H), 4.74 (dd, J=14.4, 4.0 Hz, 1H), 4.47-4.51 (m, 1H), 4.36-4.39 (m, 3H), 3.98 (q, J=14.4 Hz, 2H), 3.48-3.54 (m, 2H), 2.89-3.01 (m, 4H), 2.66-2.75 (m, 2H), 2.55-2.60 (m, 1H), 2.24-2.33 (m, 2H), 1.66-1.68 (m, 4H). LCMS: m/z=572.6 $(M+H)^+$.

Example 16

3-(((S)-oxetan-2-yl)methyl)-2-((4-(2-phenylchroman-5-yl)piperidin-1-yl)methyl)-3Himidazo[4,5-b]pyridine-5-carboxylic acid (Compound 102a)

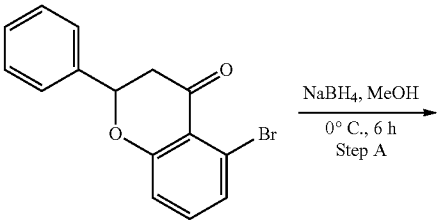

1

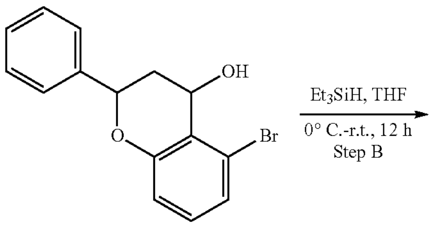

2

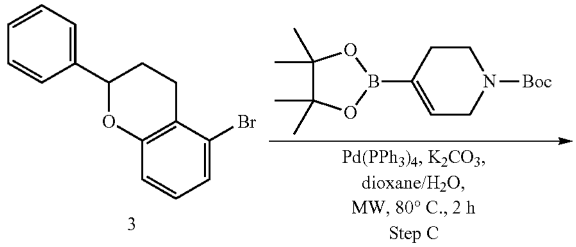

3

-continued

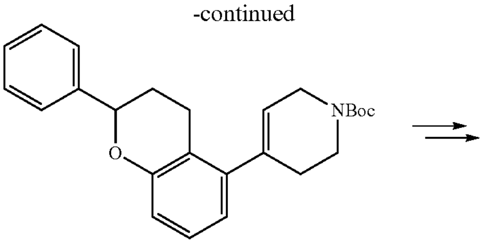

5

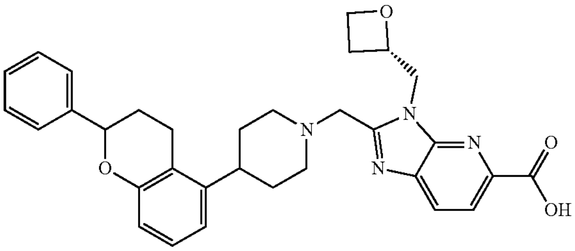

Compound 102a

Step A: 5-bromo-2-phenylchroman-4-ol

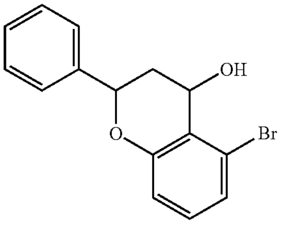 [SMILES: OC1CC(c2ccccc2)Oc2cccc(Br)c21]

5-Bromo-2-phenylchroman-4-one (820 mg, 2.71 mmol) (which was synthesized following the methods depicted in Example 10 using benzaldehyde in step A) was dissolved in 15 mL MeOH and $NaBH_4$ (206 mg, 5.42 mmol) was added slowly at 0° C. The reaction mixture was stirred at room temperature for 6 hours. MeOH was removed and the residue was diluted with water (10 mL) and extracted with EtOAc (10 mL×3). The organic layer was dried over $Na_2SO_4$, concentrated and purified by flash chromatography on silica gel (eluted with PE/EtOAc=10/1) to afford the title compound 5-bromo-2-phenylchroman-4-ol (764 mg, 92% yield) as a white solid. $^1$H NMR (400 MHZ, $CDCl_3$) δ ppm 7.31-7.50 (m, 5H), 7.18-7.26 (m, 1H), 7.06-7.14 (m, 1H), 6.93-6.96 (m, 1H), 5.00-5.31 (m, 2H), 2.94 (s, 1H), 2.56-2.66 (m, 1H), 2.30-2.56 (m, 1H).

Step B: 5-bromo-2-phenylchromane

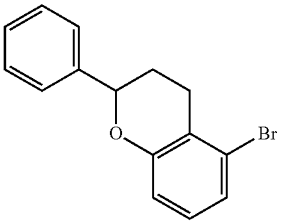 [SMILES: Brc1cccc2c1CCC(c1ccccc1)O2]

To a solution of 5-bromo-2-phenylchroman-4-ol (764 mg, 2.50 mmol) in THF (2 mL) at 0° C. was added $Et_3SiH$ (1 mL). The solution was stirred at room temperature for 12 hours. The solvent was removed under reduced pressure and the residue was purified by flash chromatography on silica gel (eluted with heptane/EtOAc=20/1) to afford the title compound 5-bromo-2-phenylchromane (530 mg, 73% yield) as a yellow oil. $^1$H NMR (400 MHZ, $CDCl_3$) δ ppm 7.26-7.43 (m, 5H), 7.16 (dd, J=8.0, 1.2 Hz, 1H), 7.00 (t, J=8.0 Hz, 1H), 6.94 (t, J=8.4 Hz, 1H), 5.00 (dd, J=10.4, 2.4 Hz, 1H), 2.85-2.90 (m, 2H), 2.22-2.30 (m, 1H), 2.04-2.14 (m, 1H).

Step C: tert-butyl 4-(2-phenylchroman-5-yl)-3,6-dihydropyridine-1 (2H)-carboxylate

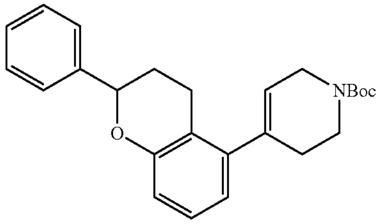 [SMILES: CC(C)(C)OC(=O)N1CC=C(c2cccc3c2CCC(c2ccccc2)O3)CC1]

A solution of 5-bromo-2-phenylchromane (200 mg, 0.692 mmol) and tert-butyl 4-(4,4,5,5-tetramethyl-1,3,2-dioxaborolan-2-yl)-3,6-dihydropyridine-1 (2H)-carboxylate 428 mg, 1.38 mmol) in dioxane/$H_2O$ (3 mL/0.2 mL) were added $Pd(PPh_3)_4$ (80.0 mg, 0.0692 mmol) and $K_2CO_3$ (191 mg, 1.38 mmol). The mixture was degassed and refilled with $N_2$ for three times. The reaction mixture was stirred at 80° C. for 2 hours in a microwave reactor. After cooling down and concentrated in vacuo, the mixture was purified by flash chromatography on silica gel (eluted with heptane/EtOAc=20/1 to 3/2) to afford the title compound tert-butyl 4-(2-phenylchroman-5-yl)-3,6-dihydropyridine-1 (2H)-carboxylate (240 mg, 88% yield) as a yellow solid. LC-MS: m/z 336.2 $(M-55)^+$.

3-(((S)-oxetan-2-yl)methyl)-2-((4-(2-phenylchroman-5-yl)piperidin-1-yl)methyl)-3Himidazo[4,5-b]pyridine-5-carboxylic acid (Compound 102a) was then synthesized following the methods depicted in Example 13 using tert-butyl 4-(2-phenylchroman-5-yl)-3,6-dihydropyridine-1 (2H)-carboxylate in step E.

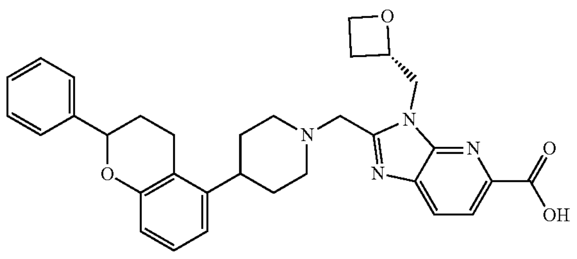 [SMILES: O=C(O)c1ccc2nc(CN3CCC(c4cccc5c4CCC(c4ccccc4)O5)CC3)n(C[C@@H]3CCO3)c2n1]

$^1$H NMR (400 MHZ, DMSO-$d_6$) δ ppm 13.06 (br.s, 1H), 8.11-8.17 (m, 1H), 8.00 (d, J=8.0 Hz, 1H), 7.37-7.44 (m, 4H), 7.31-7.34 (m, 1H), 7.07 (t, J=8.0 Hz, 1H), 6.82 (d, J=7.2 Hz, 1H), 6.68 (d, J=7.6 Hz, 1H), 5.15-5.21 (m, 1H), 5.03 (d, J=8.4 Hz, 1H), 4.87 (dd, J=14.8, 6.4 Hz, 1H), 4.75 (dd, J=14.4, 8.0 Hz, 1H), 4.50 (dd, J=13.6, 7.6 Hz, 1H), 4.38 (dd, J=14.8, 6.0 Hz, 1H), 3.92-4.03 (m, 2H), 2.93-3.00 (m, 2H), 2.78-2.87 (m, 2H), 2.67-2.73 (m, 2H), 2.53-2.55 (m, 1H), 2.19-2.32 (m, 3H), 1.91-2.04 (m, 1H), 1.61-1.71 (m, 4H). LC-MS: m/z 539.2 $(M+H)^+$.

3-(((S)-oxetan-2-yl)methyl)-2-((4-(3-phenylchroman-8-yl)piperidin-1-yl)methyl)-3Himidazo[4,5-b]pyridine-5-carboxylic acid (Compound 103a) was synthesized following the methods depicted in Example 13 using 2-bromo-1-phenylethan-1-one in step A.

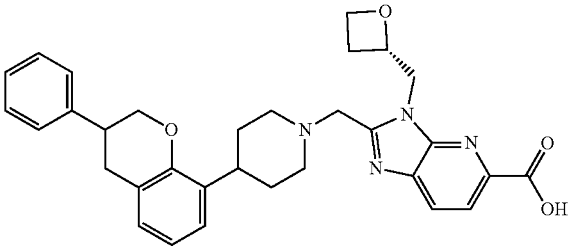 [SMILES: O=C(O)c1ccc2nc(CN3CCC(c4cccc5c4OCC(c4ccccc4)C5)CC3)n(C[C@@H]3CCO3)c2n1]

$^1$H NMR (400 MHZ, DMSO-$d_6$) δ ppm 8.14 (d, J=8.0 Hz, 1H), 7.99 (d, J=8.4 Hz, 1H), 7.34 (d, J=4.4 Hz, 4H), 7.23-7.30 (m, 1H), 7.02 (d, J=7.2 Hz, 1H), 6.95 (d, J=6.8 Hz, 1H), 6.81 (t, J=7.6 Hz, 1H), 5.10-5.24 (m, 1H), 4.86 (dd, J=14.8, 6.4 Hz, 1H), 4.74 (dd, J=14.8, 4.4 Hz, 1H), 4.45-4.57 (m, 1H), 4.30-4.42 (m, 2H), 4.07 (t, J=10.0 Hz, 1H), 3.96 (q, J=14.0 Hz, 2H), 3.13-3.24 (m, 2H), 3.01-3.11 (m, 1H), 2.82-3.00 (m, 4H), 2.63-2.76 (m, 1H), 2.17-2.31 (m, 2H), 1.53-1.80 (m, 4H).

LC-MS: m/z 539.2 $(M+H)^+$.

Example 17

2-((4-(3-(4-chloro-2-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylic acid (Compound 130a)

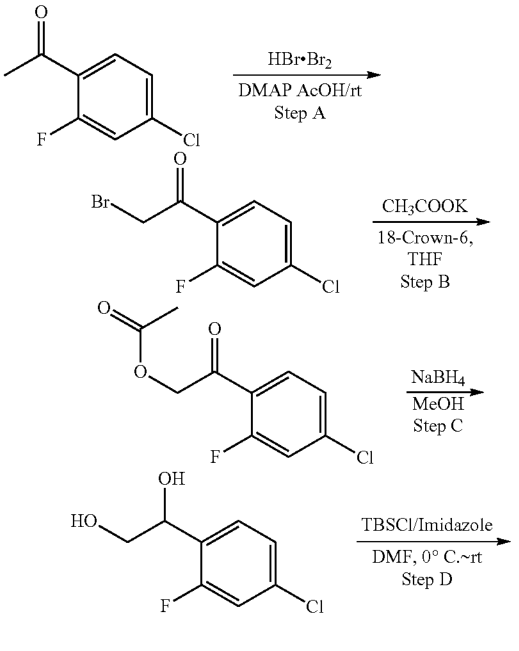

-continued

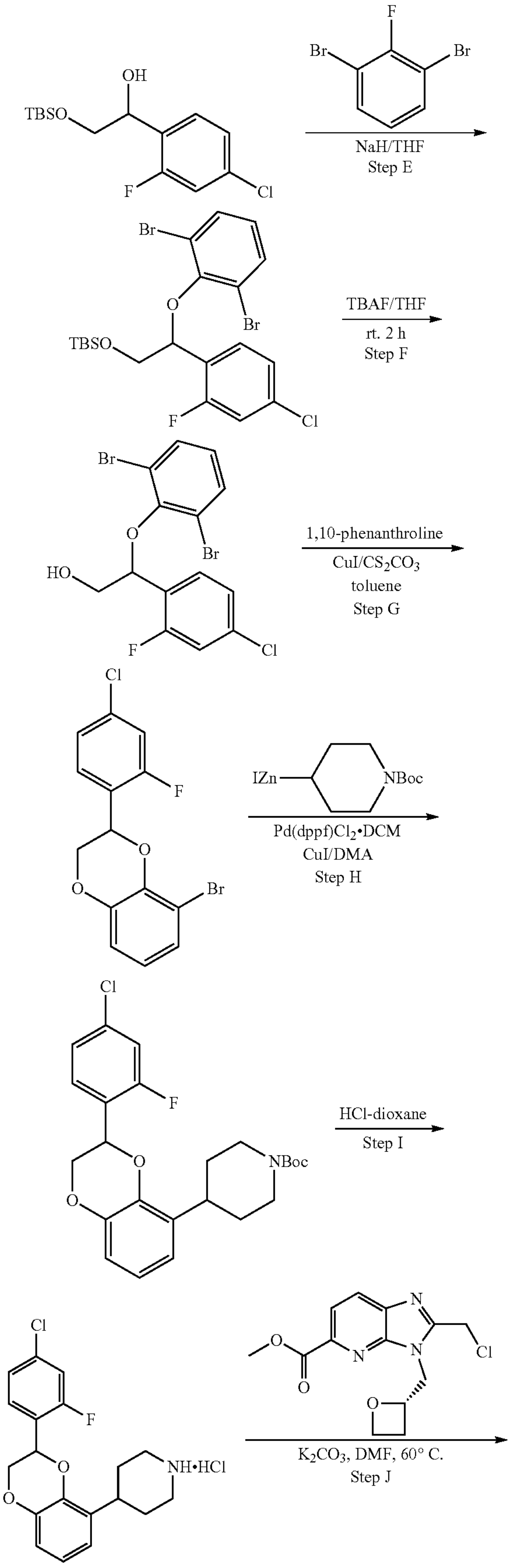

-continued

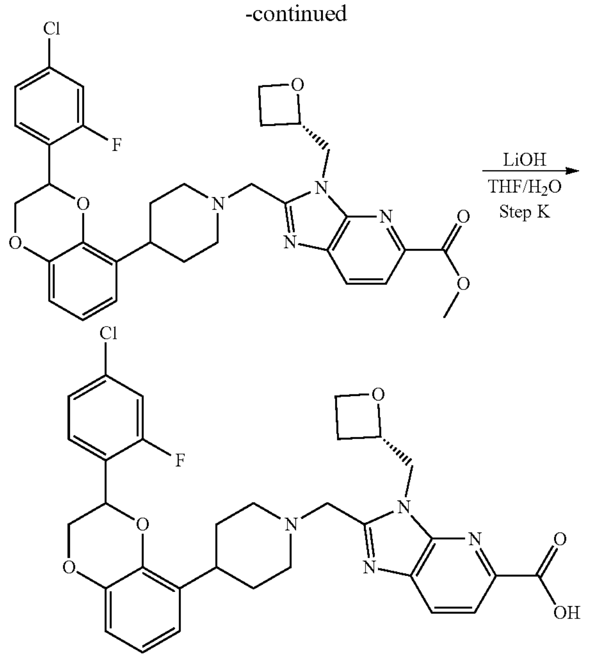

Compound 130a

Step A: 2-bromo-1-(4-chloro-2-fluorophenyl) ethan-1-one To a solution of 1-(4-chloro-2-fluorophenyl) ethan-1-one (1.73 g, 10.0 mmol) in AcOH (10 ml) was added 4-(dimethylamino)pyridine tribromide (4.00 g, 11.0 mmol). The reaction mixture was stirred at room temperature for 40 hours. Water (50 mL) was added, and the mixture was filtered. The filter cake was washed with water and then dried in vacuo to afford the title compound 2-bromo-1-(4-chloro-2-fluorophenyl) ethan-1-one (2.30 g, 92% yield) as a white solid.

$^1$H NMR (400 MHZ, $CDCl_3$) δ ppm 7.91 (t, J=8.0 Hz, 1H), 7.28 (dd, J=8.4, 1.6 Hz, 1H), 7.22 (dd, J=10.8, 2.0 Hz, 1H), 4.48 (d, J=2.4 Hz, 2H).

Step B: 2-(4-chloro-2-fluorophenyl)-2-oxoethyl acetate

To a solution of 2-bromo-1-(4-chloro-2-fluorophenyl) ethan-1-one (2.00 g, 8.00 mmol,) in THF (30 mL, dry) were added $CH_3COOK$ (1.57 g, 16.0 mmol) and 18-crown-6 (1.06 g, 4.00 mmol). The mixture was stirred at 60° C. for 2 hours. The solvent was removed and the residue was purified by flash chromatography on silica gel (eluted with PE/EtOAc=20/1) to afford the title compound 2-(4-chloro-2-fluorophenyl)-2-oxoethyl acetate (1.00 g, 56% yield) as a yellow liquid.

$^1$H NMR (400 MHZ, DMSO-$d_6$) δ ppm 7.90 (t, J=8.0 Hz, 1H), 7.70 (dd, J=10.8, 1.6 Hz, 1H), 7.49 (dd, J=8.8, 2.0 Hz, 1H), 5.25 (d, J=3.2 Hz, 2H), 2.14 (s, 3H).

Step C: 1-(4-chloro-2-fluorophenyl) ethane-1,2-diol

To a solution of 2-(4-chloro-2-fluorophenyl)-2-oxoethyl acetate (810 mg, 3.52 mmol) in MeOH (15 mL) was added $NaBH_4$ (200 mg, 5.28 mmol) at 0° C. The mixture was stirred at room temperature for 2 hours. The mixture was quenched with $H_2O$ (10 mL) at 0° C. and extracted with EtOAc (50 mL×3). The organic layers were washed with brine, dried over $Na_2SO_4$, concentrated, and purified by flash chromatography on silica gel (eluted with PE/EtOAc=30/1) to afford the title compound 1-(4-chloro-2-fluorophenyl) ethane-1,2-diol (610 mg, 91% yield) as a yellow liquid.

$^1$H NMR (400 MHZ, DMSO-$d_6$) δ ppm 7.50 (t, J=8.0 Hz, 1H), 7.33 (dd, J=10.4, 2.0 Hz, 1H), 7.27 (dd, J=8.8, 2.0 Hz, 1H), 5.46 (d, J=4.8 Hz, 1H), 4.75-4.84 (m, 2H), 3.41-3.47 (m, 2H).

Step D: 2-((tert-butyldimethylsilyl)oxy)-1-(4-chloro-2-fluorophenyl) ethan-1-ol

To a solution of 1-(4-chloro-2-fluorophenyl) ethane-1,2-diol (1.70 g, 9.04 mmol) in DMF (20 mL) were added TBSCl (1.64 g, 10.9 mmol) and imidazole (923 mg, 13.6 mmol) at 0° C. The mixture was stirred at room temperature overnight. Water (50 mL) was added, and the mixture was extracted with EtOAc (50 mL×3). The organic layers were washed with water, brine, dried over $Na_2SO_4$, concentrated, and purified by flash chromatography on silica gel (eluted with PE/EtOAc=10/1) to afford the title compound 2-((tert-butyldimethylsilyl)oxy)-1-(4-chloro-2-fluorophenyl) ethan-1-ol (2.10 g, 78% yield) as a yellow liquid.

$^1$H NMR (400 MHZ, DMSO-$d_6$) δ ppm 7.50 (t, J=8.4 Hz, 1H), 7.33 (dd, J=10.4, 2.0 Hz, 1H), 7.28 (dd, J=8.8, 2.0 Hz, 1H), 5.52 (d, J=4.8 Hz, 1H), 4.83 (q, J=5.6 Hz, 1H), 3.68 (dd, J=10.4, 6.0 Hz, 1H), 3.58 (dd, J=10.4, 5.6 Hz, 1H), 0.78 (s, 9H), −0.06 (s, 3H), −0.09 (s, 3H).

Step E: tert-butyl(2-(4-chloro-2-fluorophenyl)-2-(2,6-dibromophenoxy) ethoxy)di methylsilane To a solution of 2-((tert-butyldimethylsilyl)oxy)-1-(4-chloro-2-fluorophenyl) ethan-1-ol (500 mg, 1.65 mmol in THF (5 mL) was added NaH (264 mg, 6.60 mmol) at −10° C. After 30 mins, 1,3-dibromo-2-fluorobenzene (419 mg, 1.65 mmol) was added. The mixture was stirred at room temperature overnight. The mixture was diluted with water (10 mL) and extracted with EtOAc (50 mL×3). The organic layers were dried over $Na_2SO_4$, concentrated, and purified by flash chromatography on silica gel (eluted with PE) to afford the title compound tert-butyl(2-(4-chloro-2-fluorophenyl)-2-(2,6-dibromophenoxy) ethoxy)dimethylsilane (406 mg, 46% yield) as a yellow liquid.

$^1$H NMR (400 MHZ, DMSO-$d_6$) δ ppm 7.72 (t, J=8.4 Hz, 1H), 7.64 (d, J=8.0 Hz, 2H), 7.45 (dd, J=10.4, 2.0 Hz, 1H), 7.37 (dd, J=8.4, 2.0 Hz, 1H), 7.00 (t, J=8.0 Hz, 1H), 5.68 (t, J=5.6 Hz, 1H), 4.16 (dd, J=10.4, 6.4 Hz, 1H), 3.91-3.95 (m, 1H), 0.68 (s, 9H), −0.09 (s, 3H), −0.12 (s, 3H).

Step F: 2-(4-chloro-2-fluorophenyl)-2-(2,6-dibromophenoxy) ethan-1-ol

To a solution of tert-butyl(2-(4-chloro-2-fluorophenyl)-2-(2,6-dibromophenoxy) ethoxy)dimethylsilane (400 mg, 0.750 mmol) in THF (3 mL) was added TBAF (254 mg, 0.970 mmol). The reaction mixture was stirred at room temperature for 3 hours. The solvent was removed, and the residue was purified by flash chromatography on silica gel (eluted with PE/EtOAc=20/1) to afford the title compound 2-(4-chloro-2-fluorophenyl)-2-(2,6-dibromophenoxy) ethan-1-ol (241 mg, 76% yield) as a yellow oil.

$^1$H NMR (400 MHZ, DMSO-$d_6$) δ ppm 7.68 (t, J=8.4 Hz, 1H), 7.63 (d, J=8.0 Hz, 2H), 7.40 (dd, J=10.4, 2.0 Hz, 1H), 7.35 (dd, J=8.4, 2.0 Hz, 1H), 6.99 (t, J=8.0 Hz, 1H), 5.59 (dd, J=6.8, 5.6 Hz, 1H), 5.02 (t, J=5.6 Hz, 1H), 4.05-3.97 (m, 1H), 3.89-3.82 (m, 1H).

Step G: 8-bromo-2-(4-chloro-2-fluorophenyl)-2,3-dihydrobenzo[b][1,4]dioxine

A mixture of 2-(4-chloro-2-fluorophenyl)-2-(2,6-dibromophenoxy) ethan-1-ol (241 mg, 0.568 mmol), 1,10-phenanthroline (24.0 mg, 0.113 mmol), CuI (12.0 mg, 0.0570 mmol) and $Cs_2CO_3$ (556 mg, 1.70 mmol) in toluene (3 mL) was stirred at 115° C. overnight under $N_2$. The suspension was filtered, and the filtrate was concentrated under vacuum. The residue was purified by prep-TLC (PE) to afford the title compound 8-bromo-2-(4-chloro-2-fluorophenyl)-2,3-dihydrobenzo[b][1,4]dioxine (140 mg, 72% yield) as a yellow oil.

$^1$H NMR (400 MHZ, DMSO-$d_6$) δ ppm 7.52-7.59 (m, 2H), 7.43 (dd, J=8.4, 2.0 Hz, 1H), 7.19 (dd, J=8.0, 1.6 Hz, 1H), 6.98 (dd, J=8.4, 1.6 Hz, 1H), 6.85 (t, J=8.4 Hz, 1H), 5.59 (dd, J=8.0, 2.4 Hz, 1H), 4.51 (dd, J=11.6, 2.4 Hz, 1H), 4.20 (dd, J=11.6, 8.0 Hz, 1H).

Step H: tert-butyl 4-(3-(4-chloro-2-fluorophenyl)-2,3-dihydrobenzo[b][1,4]dioxin-5-yl) piperidine-1-carboxylate To a solution of 8-bromo-2-(4-chloro-2-fluorophenyl)-2,3-dihydrobenzo[b][1,4]dioxine (50.0 mg, 0.147 mmol), Pd(dppf)$Cl_2$ DCM (4.00 mg, 5.00 umol) and CuI (2.00 mg, 9.00 umol) in DMA (1.5 mL) was added (1-(tert-butoxycarbonyl)piperidin-4-yl) zinc (II) iodide (1.2 M in DMA) (0.500 ml, 0.590 mmol) under $N_2$. The reaction mixture was stirred at 90° C. overnight. The reaction was quenched with sat. $NH_4Cl$ (aq.) and extracted with EtOAc (15 mL×3). The combined organic layer was washed with water (10 mL), brine (10 mL), dried over $Na_2SO_4$, concentrated, and purified by Prep-TLC (PE/EA=20/1) to afford the title compound tert-butyl 4-(3-(4-chloro-2-fluorophenyl)-2,3-dihydrobenzo[b][1,4]dioxin-5-yl)piperidine-1-carboxylate (45.0 mg, 70% yield) as a yellow oil.

$^1$H NMR (400 MHZ, $CDCl_3$) δ ppm 7.41 (t, J=8.0 Hz, 1H), 7.24 (dd, J=8.4, 1.6 Hz, 1H), 7.16 (dd, J=10.0, 2.0 Hz, 1H), 6.77-6.89 (m, 3H), 5.42 (dd, J=8.4, 2.4 Hz, 1H), 4.41 (dd, J=11.2, 2.4 Hz, 1H), 4.22 (s, 2H), 3.97 (dd, J=11.2, 8.4 Hz, 1H), 3.11-3.00 (m, 1H), 2.74-2.84 (m, 2H), 1.86 (d, J=12.8 Hz, 1H), 1.79 (d, J=12.8 Hz, 1H), 1.61-1.66 (m, 2H), 1.46 (s, 9H). LC-MS: m/z 392 [M+H-56]*.

Step I: 4-(3-(4-chloro-2-fluorophenyl)-2,3-dihydrobenzo[b][1,4]dioxin-5-yl) piperidine HCl salt To a solution of tert-butyl 4-(3-(4-chloro-2-fluorophenyl)-2,3-dihydrobenzo[b][1,4]dioxin-5-yl)piperidine-1-carboxylate (45.0 mg, 0.1 mmol) in 1,4-dioxane (2 mL) was added HCl-1,4-dioxane solution (4 M, 2 mL). The mixture was stirred at room temperature for 3 hours. The reaction mixture was concentrated to afford the title compound 4-(3-(4-chloro-2-fluorophenyl)-2,3-dihydrobenzo[b][1,4]dioxin-5-yl) piperidine HCl salt (crude, 35.0 mg, 90% yield) as a white solid. LC-MS: m/z 348 $[M+H]^+$.

Step J: methyl 2-((4-(3-(4-chloro-2-fluorophenyl)-2,3-dihydrobenzo[b][1,4]dioxin-5-yl) piperidin-1-yl)methyl)-3-(((S)-oxetan-2-yl)methyl)-3H-imidazo[4,5-b]pyridine-5-carboxylate To a solution of 4-(3-(4-chloro-2-fluorophenyl)-2,3-dihydrobenzo[b][1,4]dioxin-5-yl) piperidinehydrochloride (35.0 mg, 0.100 mmol) in DMF (2 mL) was added methyl (S)-2-(chloromethyl)-3-(oxetan-2-ylmethyl)-3H-imidazo[4,5-b]pyridine-5-carboxylate (30.0 mg, 0.100 mmol) and $K_2CO_3$ (28.0 mg, 0.200 mmol). The resulting mixture was stirred at 60° C. for 3 hours. The reaction was quenched with water (5 mL) and extracted with EtOAc (10 mL×3). The combined organic phase was washed with water (10 mL), brine (10 mL), dried over $Na_2SO_4$ and concentrated. The residue was purified by prep-TLC (PE/EA=1/1) to afford the title compound methyl 2-((4-(3-(4-chloro-2-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylate (50.0 mg, 83% yield) as a white solid. LC-MS: m/z 607 [M+H]$^+$.

Step K: 2-((4-(3-(4-chloro-2-fluorophenyl)-2,3-dihydrobenzo[b][1,4]dioxin-5-yl) piperidin-1-yl)methyl)-3-(((S)-oxetan-2-yl)methyl)-3H-imidazo[4,5-b]pyridine-5-carboxylic acid (Compound 130a)

To a solution of methyl 2-((4-(3-(4-chloro-2-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylate (50.0 mg, 0.0830 mmol) in THF/$H_2O$ (2 mL/0.5 mL) was added LiOH $H_2O$ (10.0 mg, 0.420 mmol). The resulting mixture was stirred at room temperature overnight. Then the reaction mixture was adjusted to pH=5 with HCOOH and concentrated. The residue was purified by prep-HPLC to afford the title compound 2-((4-(3-(4-chloro-2-fluorophenyl)-2,3-dihydrobenzo[b][1,4]dioxin-5-yl) piperidin-1-yl)methyl)-3-(((S)-oxetan-2-yl)methyl)-3H-imidazo[4,5-b]pyridine-5-carboxylic acid (29.8 mg, 68% yield) as a white solid.

$^1$H NMR (400 MHZ, DMSO-$d_6$) δ 13.04 (br. s, 1H), 8.13 (d, J=8.4 Hz, 1H), 7.99 (d, J=8.4 Hz, 1H), 7.50-7.58 (m, 2H), 7.42 (dd, J=8.4, 2.0 Hz, 1H), 6.77-6.86 (m, 3H), 5.47 (dd, J=7.6, 2.4 Hz, 1H), 5.11-5.20 (m, 1H), 4.81-4.87 (m, 1H), 4.71 (dt, J=14.4, 3.6 Hz, 1H), 4.41-4.51 (m, 2H), 4.31-4.40 (m, 1H), 4.10 (dd, J=11.6, 7.6 Hz, 1H), 3.88-4.00 (m, 2H), 2.84-2.97 (m, 3H), 2.62-2.73 (m, 1H), 2.42-2.48 (m, 1H), 2.13-2.27 (m, 2H), 1.63-1.79 (m, 4H). LC-MS: m/z 593.2 [M+H]$^+$.

The compound methyl 2-((4-(3-(4-chloro-2-fluorophenyl)-2,3-dihydrobenzo[b][1,4]dioxin-5-yl)piperidin-1-yl)methyl)-3-(((S)-oxetan-2-yl)methyl)-3H-imidazo[4,5-b]pyridine-5-carboxylate was purified by SFC (column: CHIRALCEL OJ-H, elution: 100% MeOH; Flow rate: 60 mL/min; Temperature: 38° C.) to afford the ester diastereomer 1 (retention time: 7.8 min) and ester diastereomer 2 (retention time: 11.2 min) and then followed by hydrolysis at step K to afford the two diastereomers Compound 130b and Compound 130c.

Diastereomer 1 (Compound 130b)

$^1$HNMR (400 MHZ, DMSO-$d_6$) δ ppm 12.98 (br.s, 1H), 8.12-8.14 (m, 1H), 7.99 (d, J=8.4 Hz, 1H), 7.50-7.58 (m, 2H), 7.42 (dd, J=8.4, 1.6 Hz, 1H), 6.77-6.84 (m, 3H), 5.45-5.47 (m, 1H), 5.11-5.19 (m, 1H), 4.85 (dd, J=14.4, 6.4 Hz, 1H), 4.71 (dd, J=14.4, 4.4 Hz, 1H), 4.41-4.52 (m, 2H), 4.37 (dt, J=9.0, 6.0 Hz, 1H), 4.10 (dd, J=11.2, 7.6 Hz, 1H), 3.99 (d, J=13.6 Hz, 1H), 3.90 (d, J=13.6 Hz, 1H), 2.85-2.97 (m, 3H), 2.63-2.74 (m, 1H), 2.41-2.46 (m, 1H), 2.18-2.23 (m, 2H), 1.57-1.79 (m, 4H). LC-MS: m/z 593.2 [M+H]$^+$.

Diastereomer 2 (Compound 130c)

$^1$HNMR (400 MHZ, DMSO-$d_6$) δ ppm 13.01 (br.s, 1H), 8.13 (d, J=8.4 Hz, 1H), 7.99 (d, J=8.4 Hz, 1H), 7.50-7.58 (m, 2H), 7.42 (dd, J=8.4, 1.6 Hz, 1H), 6.77-6.84 (m, 3H), 5.43-5.50 (m, 1H), 5.11-5.20 (m, 1H), 4.84 (dd, J=14.4, 6.4 Hz, 1H), 4.71 (dd, J=14.4, 4.0 Hz, 1H), 4.42-4.48 (m, 2H), 4.35 (dt, J=9.2, 6.4 Hz, 1H), 4.10 (dd, J=11.2, 7.6 Hz, 1H), 3.94 (dd, J=19.2, 13.6 Hz, 2H), 2.81-2.96 (m, 3H), 2.64-2.72 (m, 1H), 2.42-2.47 (m, 1H), 2.16-2.26 (m, 2H), 1.78-1.82 (m, 1H), 1.61-1.72 (m, 3H). LC-MS: m/z 593.2 [M+H]$^+$.

Example A: CAMP Assays

Activation of GLP-1 receptor is known to stimulate cyclic AMP (cAMP) production in cells which indicates primary coupling to the $G_{\alpha s}$ subunit of the G protein heterotrimeric complex. Evidence suggests signaling through $G_{\alpha s}$ induced CAMP stimulation elicits the desired pharmacological response regarding insulin release from pancreatic β-cells.

To optimize functional activity directed toward $G_{\alpha s}$ coupling, a HEK293/CRELuc cell line developed by HDB stably expressing the GLP-1 Receptor was used. 200× concentration of compound working solutions were prepared (Agilent Technologies Bravo) with 1/2 log serial dilution in 384-well Echo LDV plate (Labcyte, Cat #LP-0200). 50 nL/well 200× concentration of compound working solutions were moved to 384-well white low volume plate (Greiner, Cat #784075) using Labcyte ECHO550. 1×10$^5$ cells/mL HEK293/GLP1R/CRE-LUC (HD Biosciences) cell suspensions prepared with assay buffer [DPBS containing 0.5 mM IBMX (Sigma,Cat #I5879) and 0.1% BSA (GENVIEW, Cat #FA016-100 g)], 10 uL cell suspensions were added to each well of previous generated assay plate which already contains 50 nl compound at 200× concentration using ThermoFisher Multidrop Combi (1000cells/well). Seal the plate and incubate at 37° C. with 5% $CO_2$ for 30 min.

After incubation the CAMP assay signal was generated using cAMP dynamic 2 Kit (Cisbio). 5 μL cAMP-$d_2$ working solution was added to each well, followed with 5 μL Anti-cAMP antibody-cryptate working solution added to each well using ThermoFisher Multidrop Combi. Incubate at room temperature for 1 hour protected from light. Read the fluorescence at 665 and 615 nm with Reader PerkinElmer En Vision.

$$\% \text{ Activity} = 100\% \times (\text{mean } RLU \text{ of test sample} - \text{mean } RLU \text{ of vehicle control}) / (\text{mean } RLU \text{ of MAX control} - \text{mean } RLU \text{ of vehicle control})$$

TABLE 1 shows the biological activity of compounds in GLP-1R agonist cAMP stimulation assay ($EC_{50}$)

| Compound Number | GLP1R cAMP Stimulation DR: $EC_{50}$ (nM) |
|---|---|
| 101a | B |
| 102a | D |
| 103a | B |
| 104a | B |
| 104b | B |
| 104c | C |
| 105a | D |
| 106a | B |
| 107a | C |
| 108a | B |
| 109a | C |
| 111a | A |
| 111b | A |
| 111c | C |
| 112a | B |
| 113a | B |
| 114a | B |

TABLE 1-continued

| shows the biological activity of compounds in GLP-1R agonist cAMP stimulation assay ($EC_{50}$) | |
|---|---|
| Compound Number | GLP1R cAMP Stimulation DR: $EC_{50}$ (nM) |
| 115a | A |
| 116a | A |
| 117a | B |
| 118a | A |
| 118b | A |
| 118c | C |
| 119a | A |
| 120b | B |
| 120c | C |
| 121a | C |
| 122a | C |
| 123a | C |
| 124a | B |
| 125a | C |
| 126a | D |
| 127a | B |
| 128a | B |
| 129a | A |
| 130a | A |
| 130b | A |
| 130c | B |

$EC_{50}$ ranges:
A ≤ 0.2 nM;
0.2 < B ≤ 20 nM;
20 < C ≤ 200 nM;
D > 200 nM

Example B: Nonhuman primate (NHP) Pharmacokinetics (PK) studies

Pharmacokinetics (PK) study was conducted on male NHP (e.g. cynomolgus monkey) by two delivery routes intravenous (IV) and/or oral gavage (PO). NHP in IV route (n=3) were free access to food and water. NHP in PO route (n=3) were fasted overnight and fed at 4 hrs post dosing. Test article was formulated in solution for IV route and solution or suspension for PO route, respectively.

On the day of experiment, test article was administered via vein (e.g. cephalic vein) injection (commonly at 0.2 to 1 mg/kg and 1 to 2 mL/kg) for IV route or via oral gavage (commonly at 1 to 100 mg/kg and 2 to 10 mL/kg) for PO route, respectively.

Blood samples were collected via serial bleeding at ~8 time points from 0.083 to 24 hours post dose. Approximate 500 μL of blood/time point was collected into EDTA-K2 tube via cephalic or saphenous vein. Blood samples were put on wet ice and centrifuged to obtain plasma samples and plasma samples were submitted to LCMS/MS for sample analysis.

Pharmacokinetics parameters, including maximum plasma concentration ($C_{max}$), time to reach maximum plasma concentration ($T_{max}$), area under the curve ($AUC_{0-4}$) and oral bioavailability (F%), etc., were calculated by non-compartmental model using WinNonlin.

Exemplary compounds of Formula I (e.g., certain compounds of Formula IB (e.g., Formula IB-1)) were tested using the protocol above. Reference compound REF1 was tested as a control compound.

Compound REF1

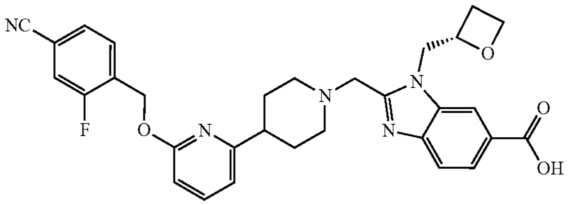

The pharmacokinetic data for reference compound REF1 is provided below:

| | Oral dose (arbitrary unit) | $C_{max}$ (arbitrary unit) | $T_{max}$ (hr) | $AUC_{0-24h}$ (arbitrary unit) | F % |
|---|---|---|---|---|---|
| REF1 | Dose 1 | 36.0 | 5.33 | 362 | 3.14 |

In some embodiments, compared to reference compound REF1, compounds of Formula I (e.g., compounds of Formula IB (e.g., Formula IB-1)) exhibited a $C_{max}$ value of between 2000 and 5000 units (e.g., between 3000 and 5000 units (e.g., between 3500 and 4500 units)) at Dose 1.

In some embodiments, compounds of Formula I (e.g., compounds of Formula IB (e.g., Formula IB-1)) exhibited a $T_{max}$ value of between 5 and 10 hours (e.g., between 6 and 10 hours (e.g., between 7 and 9 hours (e.g., between 7.5 and 8.5 hours))

In some embodiments, compared to reference compound REF1, compounds of Formula I (e.g., compounds of Formula IB (e.g., Formula IB-1)) exhibited an AUC0-24h value of between 30000 and 70000 units (e.g., between 30000 to 40000 (e.g., between 32000 to 38000); or between 60000 to 70000 (e.g., between 62500 to 67500)) at Dose 1.

In some embodiments, compounds of Formula I (e.g., compounds of Formula IB (e.g., Formula IB-1)) exhibited an F % value of between 10% and 70% (e.g., between 10% and 65% (e.g., between 20% and 40% (e.g., between 30% and 40%); or between 50% and 65% (e.g., between 57.5% and 62.5%).

In some embodiments, compared to reference compound REF1, compounds of Formula I (e.g., compounds of Formula IB (e.g., Formula IB-1)) exhibited:

(a) $C_{max}$ value of between 2000 and 5000 units (e.g., between 3000 and 5000 units (e.g., between 3500 and 4500 units)) at Dose 1;

(b) $T_{max}$ value of between 5 and 10 hours (e.g., between 6 and 10 hours (e.g., between 7 and 9 hours (e.g., between 6 and 8 hours (e.g., between 7.5 and 8.5 hours)));

(c) $AUC_{0-24h}$ value of between 30000 and 70000 units (e.g., between 30000 to 40000 (e.g., between 32000 to 38000); or between 60000 to 70000 (e.g., between 62500 to 67500)) at Dose 1; and (d) F % value of between 10% and 70% (e.g., between 10% and 65% (e.g., between 20% and 40% (e.g., between 30% and 40%); or between 50% and 65% (e.g., between 57.5% and 62.5%).

Accordingly, it can be seen based on the data above that: in some embodiments, compounds of Formula I (e.g., compounds of Formula IB (e.g., Formula IB-1)) exhibited improved pharmacokinetic property (e.g., oral pharmacokinetic property) compared to reference compound REF1. In some embodiments, concentrations of orally administered compounds of Formula I (e.g., compounds of Formula IB (e.g., Formula IB-1)) decreased more gradually over the course of 24 hours compared to reference compound REF1. In some embodiments, compounds of Formula I (e.g., compounds of Formula IB (e.g., Formula IB-1)) exhibited enhanced oral bioavailability (e.g., based on F %) compared to reference compound REF1.

Example C: Glucose tolerance test in Non-human primate (NHP)

Cynomolgus monkeys (2.5-6.0 kg) were individually housed in stainless steel cages for the duration of the study under a controlled environment that was set to maintain a temperature of 18-26° C. and relative humidity of 30-70%, a minimum of 10 air changes/hour. A time-controlled lighting system was used (light 7:00 AM-7:00 PM) to provide a regular 12-hour light/12-hour dark diurnal cycle.

The monkeys were provided with 3 meals per day consisting of 100 g of proprietary normal diet in the morning 9:00-10:00, one regular fruit (150 g) in the afternoon 14:00-15:00, and 100 g of proprietary normal diet in the afternoon 16:00-17:00. Drinking water was provided ad libitum. All animals were subjected to baseline ivGTT, and selected animals were assigned into pre-set groups based on the baseline ivGTT insulin AUC and their body weights.

The general study outline is presented in the table below:

| Day: | | | | | | | | | | | | | | | |
|---|---|---|---|---|---|---|---|---|---|---|---|---|---|---|---|
| −7 | −6 | −5 | −4 | −3 | −2 | −1 | 1 | 2 | 3 | 4 | 5 | 6 | 7 | 8 | 9 |
| Acclimation Phase | | | | | | | Treatment Phase | | | | | | | | |

Prior to the start of the study, animals were acclimatized for 1 week. On day 1, all animals were dosed with vehicle via IV injection for 5 minutes prior to IV glucose challenge. On day 9, all animals were dosed with either vehicle or test compound via IV injection for 5 minutes prior to IV glucose challenge.

The ivGTT was conducted on day 1 and day 9, respectively. The overnight fasted animals were anaesthetized (Zoletil 50, intramuscularly, 5 mg/kg initial dose, and followed by maintenance dose at 2.5-5 mg/kg if needed). 5 minutes after the test compound or vehicle dosing, the animals were intravenously injected with 50% glucose at a dose of 0.5 g/kg (1 mL/kg) for 30 seconds via the saphenous vein or the appropriate peripheral vein. The whole blood samples (1.2 mL) were collected into EDTA-K2 tubes from a peripheral vein at the following time-points: −6 (prior to compound dosing) and 1, 3, 5, 10, 20, 40 and 60 minutes after glucose challenge.

The collected blood samples were stored under wet-ice and then centrifuged at 3500 rpm, 4° C. for 10 min within 60 min. The collected plasma samples (0.5 mL each) were stored in a freezer set to maintain −80° C. until analysis for glucose, insulin and C-peptide.

For test compound groups, approximately 1.0 mL of whole blood was collected into EDTA-K2 tubes from saphenous or cephalic vein at each time point of ivGTT on day 9. The collected blood samples were maintained on wet ice until centrifugation. Plasma was separated by centrifugation at 3500 rpm, 4° C. for 10 minutes within 60 minutes of collection. Statistical analysis of the data was completed using GraphPad Prism (version 9, GraphPad Software Inc, La Jolla, CA).

Exemplary compounds of Formula I (e.g., certain compounds of Formula IB (e.g., Formula IB-1)) were tested using the protocol above. Exemplary compounds of Formula I (e.g., certain compounds of Formula IB (e.g., Formula IB-1)) were iv injected into healthy NHPs at the dose selected from 0.1 to 1.0 mg/kg (e.g., 0.1 mg/Kg, 0.3 mg/Kg, or 1.0 mg/Kg). Following the procedures described above, a robust insulin secretion was induced in ivGTT, and a significantly enhanced glucose clearance was observed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I:

Formula I

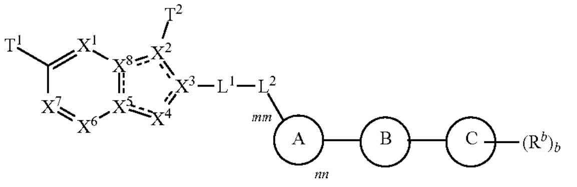

or a pharmaceutically acceptable salt or solvate thereof, wherein:

 indicates an optional single or double bond, as allowed by valence;

$X^8$, $X^5$, and $X^3$ are C; $X^2$ and $X^4$ are N; $X^7$ is CH; and $X^1$ and $X^6$ are independently CH or N;

$T^1$ is C(═O) OH;

$T^2$ is

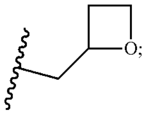 [SMILES: *CC1CCO1]

$L^1$ is $CH_2$;

$L^2$ is a bond;

Ring A is selected from the group consisting of:

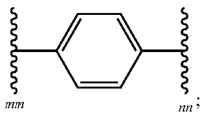

and

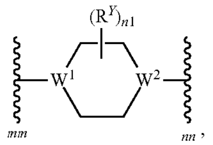

wherein n1 is 0, 1, or 2; $W^1$ is $CR^{Y1}$ or N; and $W^2$ is $CR^{Y2}$ or N;

wherein mm represents the point of attachment to $L^2$, and nn represents the point of attachment to Ring B; and each occurrence of $R^Y$ is independently selected from the group consisting of halogen, cyano, —OH, oxo, $(C_1\text{-}C_6)$alkyl, $(C_1\text{-}C_3)$haloalkyl, $(C_1\text{-}C_3)$alkoxy, and $(C_1\text{-}C_3)$haloalkoxy;

$R^{Y1}$ and $R^{Y2}$ are each independently selected from the group consisting of hydrogen, halogen, cyano, —OH, $(C_1\text{-}C_6)$alkyl, $(C_1\text{-}C_3)$haloalkyl, $(C_1\text{-}C_3)$alkoxy, and $(C_1\text{-}C_3)$haloalkoxy; or when $W^1$ is $CR^{Y1}$ and $W^2$ is $CR^{Y2}$, the $R^{Y1}$ and $R^{Y2}$ groups taken together can form $(C_1\text{-}C_4)$alkylene, wherein one of the $CH_2$ units of the $(C_1\text{-}C_4)$alkylene is optionally replaced by a heteroatom selected from the group consisting of O, S, NH, and $N(C_{1-3})$alkyl;

Ring B is selected from the group consisting of (B-I) and (B-II):

(B-I)

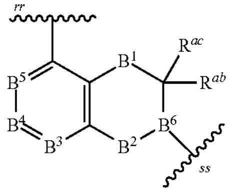

and (B-II)

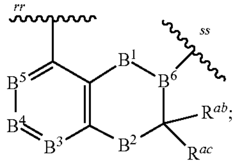

wherein rr represents the point of attachment to Ring A; and ss represents the point of attachment to Ring C;

$B^1$ and $B^2$ are independently selected from the group consisting of: —O—, —$NR^N$—, and —$C(R^1)_2$—;

$B^6$ is N or $CR^{aa}$;

each $R^1$ is independently selected from the group consisting of: hydrogen, $(C_1\text{-}C_6)$alkyl, $(C_1\text{-}C_6)$haloalkyl, and halogen;

$R^N$ is selected from the group consisting of: hydrogen, $(C_1\text{-}C_6)$alkyl, $(C_1\text{-}C_6)$haloalkyl, C(=O) $(C_1\text{-}C_6)$alkyl, $S(O)_2$ $(C_1\text{-}C_6)$alkyl, and C(=O) $O(C_1\text{-}C_6)$alkyl;

$B^3$, $B^4$, and $B^5$ are independently selected from the group consisting of CH, $CR^a$, and N;

each $R^a$ is independently selected from the group consisting of: halogen, $(C_1\text{-}C_6)$alkyl, $(C_1\text{-}C_3)$alkyl $(C_3\text{-}C_6)$ cycloalkyl, $(C_1\text{-}C_3)$alkyl (3- to 5-membered heterocycloalkyl), —$C(O)NR^2R^3$, and $(C_1\text{-}C_6)$ fluoroalkyl;

each $R^2$ and $R^3$ is independently selected from the group consisting of H and $(C_1\text{-}C_6)$alkyl;

$R^{aa}$, $R^{ab}$, and $R^{ac}$ are each independently selected from the group consisting of H, $(C_1\text{-}C_6)$alkyl, and $(C_1\text{-}C_6)$ haloalkyl;

Ring C is phenyl;

each $R^b$ is independently selected from the group consisting of $(C_1\text{-}C_6)$alkyl, $(C_1\text{-}C_6)$haloalkyl, $(C_1\text{-}C_6)$alkoxy, halogen, $(C_3\text{-}C_6)$ cycloalkyl, and CN; and b is an integer selected from 0-3.

2. The compound of claim 1, wherein:

i) $X^1$ and $X^6$ are CH; or ii) $X^1$ is N; and $X^6$ is CH; or iii) $X^1$ is CH; and $X^6$ is N.

3. The compound of claim 1, wherein the stereocenter in

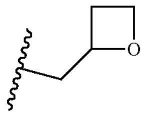 [SMILES: *CC1CCO1]

of $T^2$ has (S)-configuration.

4. The compound of claim 1, wherein Ring A is

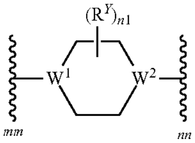

5. The compound of claim 4, wherein $W^1$ is N; and $W^2$ is $CR^{Y2}$.

6. The compound of claim 5, wherein $R^{Y2}$ is hydrogen.

7. The compound of claim 4, wherein n1 is 0 or 1.

8. The compound of claim 4, wherein $W^1$ is N; and $W^2$ is N.

9. The compound of claim 1, wherein Ring A is

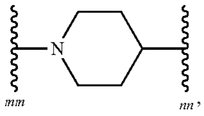

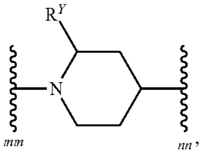

or

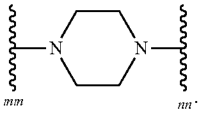

10. The compound of claim 1, wherein Ring B is (B-Ia)

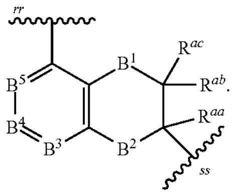

11. The compound of claim 1, wherein Ring B is (B-IIa)

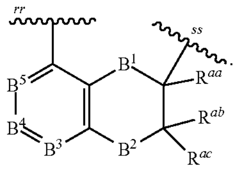

12. The compound of claim 1, wherein $B^1$ is —O-; and $B^2$ is —O-.

13. The compound of claim 1, wherein $R^{aa}$ is H or $(C_1$-$C_3)$alkyl; $R^{ab}$ is H;

and $R^{ac}$ is H.

14. The compound of claim 1, wherein $B^3$, $B^4$, and $B^5$ are independently CH or $CR^a$.

15. The compound of claim 1, wherein Ring B is selected from the group consisting of:

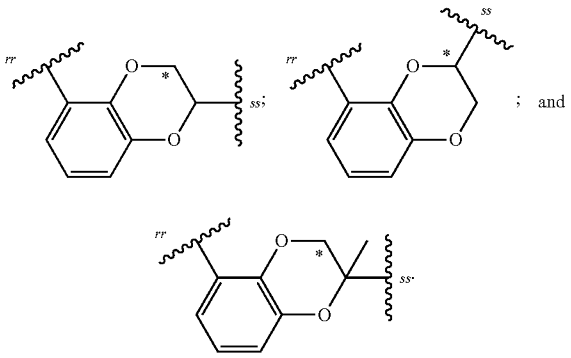

16. The compound of claim 1, wherein b is 0, 1, or 2.

17. The compound of claim 1, wherein each occurrence of $R^b$ is independently selected from the group consisting of—F, -Cl,—$CH_3$,—$CF_3$, and CN.

18. The compound of claim 1, wherein the compound is of Formula IB:

Formula IB

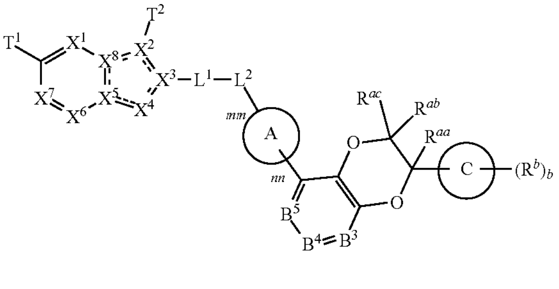

or a pharmaceutically acceptable salt thereof, or the compound is of Formula IC:

Formula IC

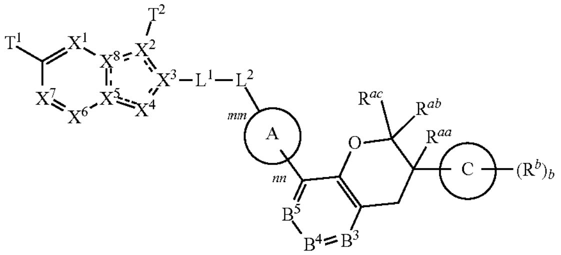

or a pharmaceutically acceptable salt thereof; or the compound is of Formula ID:

Formula ID

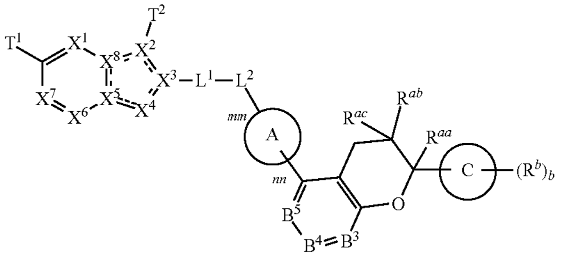

or a pharmaceutically acceptable salt thereof; or the compound is of Formula IE:

Formula IE

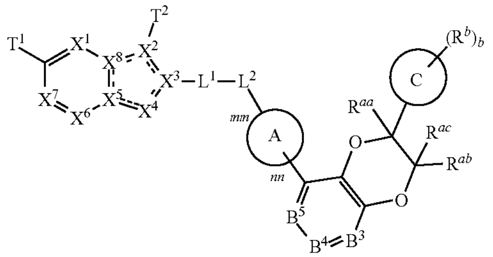

or a pharmaceutically acceptable salt thereof.

19. A pharmaceutical composition comprising a compound claim 1, or a pharmaceutically acceptable salt or solvate thereof, and a pharmaceutically acceptable excipient.

20. A method of treating type 2 diabetes mellitus in a patient in need thereof, the method comprising administering to the patient a therapeutically effective amount of a compound of claim 1, or a pharmaceutically acceptable salt or solvate thereof.

21. The method of claim 20, wherein the compound, or the pharmaceutically acceptable salt or solvate thereof, is administered orally.

22. A method for modulating insulin levels or glucose levels in a patient in need of such modulating, the method comprising administering to the patient an effective amount of a compound of claim 1, or a pharmaceutically acceptable salt or solvate thereof.

23. A method for treating a GLP-1 associated disease, disorder, or condition, the method comprising administering to a patient in need thereof an effective amount of a compound of claim 1.

24. The method of claim 23, wherein the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, idiopathic intracranial hypertension, Wolfram syndrome, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof.

25. The method of claim 23, wherein the disease, disorder, or condition is selected from the group consisting of type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), idiopathic intracranial hypertension, Wolfram syndrome, or any combination thereof.

26. The method of claim 23, wherein the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, idiopathic intracranial hypertension, Wolfram syndrome, or any combination thereof.

27. A method for treating obesity, the method comprising administering to a patient in need thereof a therapeutically effective amount of a compound of claim 1, or the pharmaceutically acceptable salt or solvate thereof.

* * * * *